(12) United States Patent
Gelfand et al.

(10) Patent No.: US 9,283,033 B2
(45) Date of Patent: Mar. 15, 2016

(54) CAROTID BODY ABLATION VIA DIRECTED ENERGY

(71) Applicant: Cibiem, Inc., Los Altos, CA (US)

(72) Inventors: Mark Gelfand, New York, NY (US); Charles Lennox, Hudson, NH (US); Ary Chernomorsky, Walnut Creek, CA (US); Howard Levin, Teaneck, NJ (US); Veijo T. Suorsa, Sunnyvale, CA (US); Kenneth M. Martin, Woodside, CA (US); Yegor D. Sinelnikov, Port Jefferson, NY (US)

(73) Assignee: CIBIEM, INC., Los Altos, CA (US)

( * ) Notice: Subject to any disclaimer, the term of this patent is extended or adjusted under 35 U.S.C. 154(b) by 0 days.

(21) Appl. No.: 13/933,023

(22) Filed: Jul. 1, 2013

(65) Prior Publication Data
US 2014/0005706 A1    Jan. 2, 2014

Related U.S. Application Data

(60) Provisional application No. 61/666,804, filed on Jun. 30, 2012, provisional application No. 61/667,991, filed on Jul. 4, 2012, provisional application No. 61/667,996, filed on Jul. 4, 2012, provisional
(Continued)

(51) Int. Cl.
*A61N 7/02* (2006.01)
*A61B 18/00* (2006.01)
(Continued)

(52) U.S. Cl.
CPC ......... *A61B 18/1492* (2013.01); *A61B 17/2202* (2013.01); *A61B 17/320092* (2013.01); *A61N 7/022* (2013.01); *A61B 18/24* (2013.01); *A61B 2017/003* (2013.01); *A61B 2017/00256* (2013.01); *A61B 2017/22024* (2013.01); *A61B 2017/22028* (2013.01); *A61B 2017/22058* (2013.01); *A61B 2017/22062* (2013.01); *A61B 2017/22069* (2013.01); *A61B 2017/320044* (2013.01); *A61B 2018/00404* (2013.01);
(Continued)

(58) Field of Classification Search
CPC ........... A61B 2018/00005; A61B 2018/00011; A61B 2018/00023; A61B 2018/00041; A61B 2018/00404; A61B 2018/0293
See application file for complete search history.

(56) References Cited

U.S. PATENT DOCUMENTS

| 3,650,277 A | 3/1972 | Sjostrand et al. |
| 4,011,872 A | 3/1977 | Komiya |

(Continued)

FOREIGN PATENT DOCUMENTS

| CN | 1440256 A | 9/2003 |
| DE | 10151797 A1 | 5/2003 |

(Continued)

OTHER PUBLICATIONS
Abboud, F.; In search of autonomic balance: the good, the bad, and the ugly; Am J Physiol Regul Integr Comp Physiol; 298; pp. R1449-R1467; Jun. 2010.
(Continued)

*Primary Examiner* — Ronald Hupczey, Jr.
(74) *Attorney, Agent, or Firm* — Shay Glenn LLP

(57) ABSTRACT

Methods and devices for assessing, and treating patients having sympathetically mediated disease, involving augmented peripheral chemoreflex and heightened sympathetic tone by reducing chemosensor input to the nervous system via carotid body ablation.

46 Claims, 55 Drawing Sheets

Related U.S. Application Data application No. 61/667,998, filed on Jul. 4, 2012, provisional application No. 61/682,034, filed on Aug. 10, 2012, provisional application No. 61/768,101, filed on Feb. 22, 2013, provisional application No. 61/791,769, filed on Mar. 15, 2013, provisional application No. 61/791,420, filed on Mar. 15, 2013, provisional application No. 61/792,214, filed on Mar. 15, 2013, provisional application No. 61/792,741, filed on Mar. 15, 2013, provisional application No. 61/793,267, filed on Mar. 15, 2013, provisional application No. 61/794,667, filed on Mar. 15, 2013, provisional application No. 61/810,639, filed on Apr. 10, 2013, provisional application No. 61/836,100, filed on Jun. 17, 2013.

(51) Int. Cl.
| | | |
|---|---|---|
| *A61B 18/14* | (2006.01) | |
| *A61B 17/22* | (2006.01) | |
| *A61B 17/32* | (2006.01) | |
| *A61B 18/24* | (2006.01) | |
| *A61B 17/00* | (2006.01) | |
| *A61B 19/00* | (2006.01) | |

(52) U.S. Cl.
CPC . *A61B2018/1425* (2013.01); *A61B 2018/1475* (2013.01); *A61B 2019/528* (2013.01)

(56) References Cited

U.S. PATENT DOCUMENTS

| | | | |
|---|---|---|---|
| 4,201,219 | A | 5/1980 | Bozal |
| 4,791,931 | A | 12/1988 | Slate |
| 4,960,133 | A | 10/1990 | Hewson |
| 5,139,496 | A | 8/1992 | Hed et al. |
| 5,325,860 | A | 7/1994 | Seward et al. |
| 5,345,940 | A | 9/1994 | Seward et al. |
| 5,354,271 | A | 10/1994 | Voda |
| 5,476,495 | A | 12/1995 | Kordis et al. |
| 5,817,021 | A | 10/1998 | Reichenberger |
| 5,893,863 | A | 4/1999 | Yoon |
| 5,906,580 | A | 5/1999 | Kline-Schoder et al. |
| 5,916,213 | A | 6/1999 | Haissaguerre et al. |
| 5,919,187 | A | 7/1999 | Guglielmi et al. |
| 5,957,882 | A | 9/1999 | Nita et al. |
| 6,004,269 | A | 12/1999 | Crowley et al. |
| 6,068,629 | A | 5/2000 | Haissaguerre et al. |
| 6,071,279 | A | 6/2000 | Whayne et al. |
| 6,125,857 | A | 10/2000 | Silber |
| 6,129,359 | A | 10/2000 | Haas et al. |
| 6,182,666 | B1 | 2/2001 | Dobak, III |
| 6,217,576 | B1 | 4/2001 | Tu et al. |
| 6,228,082 | B1 | 5/2001 | Baker et al. |
| 6,235,024 | B1 | 5/2001 | Tu |
| 6,402,746 | B1 | 6/2002 | Whayne et al. |
| 6,411,852 | B1 | 6/2002 | Danek et al. |
| 6,497,705 | B2 | 12/2002 | Comben |
| 6,522,926 | B1 | 2/2003 | Kieval et al. |
| 6,533,726 | B1 | 3/2003 | Lizzi et al. |
| 6,544,187 | B2 | 4/2003 | Seward |
| 6,556,695 | B1 | 4/2003 | Packer et al. |
| 6,656,136 | B1 | 12/2003 | Weng et al. |
| 6,660,013 | B2 | 12/2003 | Rabiner et al. |
| 6,673,066 | B2 | 1/2004 | Werneth |
| 6,905,497 | B2 | 6/2005 | Truckai et al. |
| 6,937,903 | B2 | 8/2005 | Schuler et al. |
| 7,097,641 | B1 | 8/2006 | Arless et al. |
| 7,137,963 | B2 | 11/2006 | Nita et al. |
| 7,149,574 | B2 | 12/2006 | Yun et al. |
| 7,155,284 | B1 | 12/2006 | Whitehurst et al. |
| 7,162,303 | B2 | 1/2007 | Levin et al. |
| 7,207,989 | B2 | 4/2007 | Pike et al. |
| 7,363,076 | B2 | 4/2008 | Yun et al. |
| 7,617,005 | B2 | 11/2009 | Demarais et al. |
| 7,628,785 | B2 | 12/2009 | Hadjicostis et al. |
| 7,736,317 | B2 | 6/2010 | Stephens et al. |
| 7,736,360 | B2 | 6/2010 | Mody et al. |
| 7,738,952 | B2 | 6/2010 | Yun et al. |
| 7,766,961 | B2 | 8/2010 | Patel et al. |
| 7,853,333 | B2 | 12/2010 | Demarais |
| 7,901,450 | B2 | 3/2011 | Johnson et al. |
| 7,922,663 | B2 | 4/2011 | Tran et al. |
| 7,925,352 | B2 | 4/2011 | Stack et al. |
| 7,959,628 | B2 | 6/2011 | Schaer et al. |
| 8,002,728 | B2 | 8/2011 | Chang |
| 8,060,206 | B2 | 11/2011 | Kieval et al. |
| 8,075,554 | B2 | 12/2011 | Malecki et al. |
| 8,116,883 | B2 | 2/2012 | Williams et al. |
| 8,157,760 | B2 | 4/2012 | Criado et al. |
| 8,167,805 | B2 | 5/2012 | Emery et al. |
| 8,192,425 | B2 | 6/2012 | Mirza et al. |
| 8,192,760 | B2 | 6/2012 | Hossainy et al. |
| 8,292,879 | B2 | 10/2012 | Manwaring et al. |
| 8,295,912 | B2 | 10/2012 | Gertner |
| 8,308,709 | B2 | 11/2012 | Chang |
| 8,326,429 | B2 | 12/2012 | Wenzel et al. |
| 8,364,237 | B2 | 1/2013 | Stone et al. |
| 8,374,674 | B2 | 2/2013 | Gertner |
| 8,396,548 | B2 | 3/2013 | Perry et al. |
| 8,409,200 | B2 | 4/2013 | Holcomb et al. |
| 8,433,423 | B2 | 4/2013 | Demarais |
| 8,465,752 | B2 | 6/2013 | Seward |
| 8,469,904 | B2 | 6/2013 | Gertner |
| 8,568,399 | B2 | 10/2013 | Azamian et al. |
| 8,620,423 | B2 | 12/2013 | Demarais et al. |
| 9,060,784 | B2 | 6/2015 | Coe et al. |
| 9,089,541 | B2 | 7/2015 | Azamian |
| 2001/0041890 | A1 | 11/2001 | Hassett et al. |
| 2002/0087151 | A1 | 7/2002 | Mody et al. |
| 2002/0128639 | A1 | 9/2002 | Pless et al. |
| 2003/0009125 | A1 | 1/2003 | Nita et al. |
| 2004/0116921 | A1 | 6/2004 | Sherman et al. |
| 2004/0210239 | A1 | 10/2004 | Nash et al. |
| 2005/0096642 | A1 | 5/2005 | Appling et al. |
| 2005/0096710 | A1 | 5/2005 | Kieval |
| 2005/0143378 | A1 | 6/2005 | Yun et al. |
| 2005/0153885 | A1 | 7/2005 | Yun et al. |
| 2005/0288656 | A1 | 12/2005 | Koerner et al. |
| 2006/0064137 | A1 | 3/2006 | Stone |
| 2006/0135962 | A1 | 6/2006 | Kick et al. |
| 2006/0195149 | A1 | 8/2006 | Hopper et al. |
| 2006/0224110 | A1 | 10/2006 | Scott et al. |
| 2006/0253161 | A1 | 11/2006 | Libbus et al. |
| 2006/0259084 | A1 | 11/2006 | Zhang et al. |
| 2006/0282131 | A1 | 12/2006 | Caparso et al. |
| 2006/0287679 | A1 | 12/2006 | Stone |
| 2007/0015006 | A1 | 1/2007 | Lee et al. |
| 2007/0073135 | A1 | 3/2007 | Lee et al. |
| 2007/0112327 | A1 | 5/2007 | Yun et al. |
| 2007/0135875 | A1* | 6/2007 | Demarais et al. ............... 607/96 |
| 2007/0150006 | A1 | 6/2007 | Libbus et al. |
| 2007/0156179 | A1 | 7/2007 | S.E. |
| 2007/0265609 | A1 | 11/2007 | Thapliyal et al. |
| 2007/0299476 | A1 | 12/2007 | Park et al. |
| 2008/0009916 | A1 | 1/2008 | Rossing et al. |
| 2008/0009917 | A1 | 1/2008 | Rossing et al. |
| 2008/0045936 | A1 | 2/2008 | Vaska et al. |
| 2008/0058871 | A1 | 3/2008 | Libbus et al. |
| 2008/0086181 | A1 | 4/2008 | Amurthur et al. |
| 2009/0299362 | A1 | 12/2009 | Long et al. |
| 2010/0023088 | A1* | 1/2010 | Stack et al. ..................... 607/44 |
| 2010/0063564 | A1* | 3/2010 | Libbus et al. ................... 607/62 |
| 2010/0070004 | A1 | 3/2010 | Hlavka |
| 2010/0152590 | A1 | 6/2010 | Moore et al. |
| 2010/0168731 | A1 | 7/2010 | Wu et al. |
| 2010/0168739 | A1 | 7/2010 | Wu et al. |
| 2010/0217151 | A1 | 8/2010 | Gostout et al. |
| 2010/0262013 | A1 | 10/2010 | Smith et al. |
| 2010/0268307 | A1 | 10/2010 | Demarais et al. |
| 2010/0274219 | A1 | 10/2010 | Wenzel et al. |
| 2011/0009854 | A1 | 1/2011 | Babkin et al. |
| 2011/0040297 | A1 | 2/2011 | Babkin et al. |
| 2011/0066085 | A1 | 3/2011 | Weng et al. |

(56) References Cited

U.S. PATENT DOCUMENTS

| | | |
|---|---|---|
| 2011/0098699 A1 | 4/2011 | Pachon et al. |
| 2011/0104060 A1 | 5/2011 | Seward |
| 2011/0118598 A1 | 5/2011 | Gertner |
| 2011/0118600 A1 | 5/2011 | Gertner |
| 2011/0130708 A1 | 6/2011 | Perry et al. |
| 2011/0172529 A1 | 7/2011 | Gertner |
| 2011/0208096 A1 | 8/2011 | Demarais et al. |
| 2011/0208174 A1 | 8/2011 | Baust |
| 2011/0208175 A1 | 8/2011 | Sobotka et al. |
| 2011/0251487 A1 | 10/2011 | Magnin et al. |
| 2011/0251607 A1 | 10/2011 | Kruecker et al. |
| 2011/0257561 A1 | 10/2011 | Gertner et al. |
| 2011/0257562 A1* | 10/2011 | Schaer .............................. 601/2 |
| 2011/0301587 A1 | 12/2011 | Deem et al. |
| 2012/0016226 A1 | 1/2012 | Gertner |
| 2012/0059437 A1* | 3/2012 | Shalev ............................. 607/62 |
| 2012/0065492 A1 | 3/2012 | Gertner et al. |
| 2012/0065494 A1 | 3/2012 | Gertner et al. |
| 2012/0078248 A1 | 3/2012 | Worrell et al. |
| 2012/0095335 A1 | 4/2012 | Sverdlik et al. |
| 2012/0095371 A1 | 4/2012 | Sverdlik et al. |
| 2012/0095372 A1 | 4/2012 | Sverdlik et al. |
| 2012/0095461 A1 | 4/2012 | Herscher et al. |
| 2012/0101018 A1* | 4/2012 | Miracle et al. ................ 510/324 |
| 2012/0109018 A1 | 5/2012 | Gertner et al. |
| 2012/0130368 A1 | 5/2012 | Jenson |
| 2012/0157992 A1 | 6/2012 | Smith et al. |
| 2012/0157993 A1 | 6/2012 | Jenson et al. |
| 2012/0172680 A1 | 7/2012 | Gelfand et al. |
| 2012/0172723 A1 | 7/2012 | Gertner |
| 2012/0184952 A1 | 7/2012 | Jenson et al. |
| 2012/0199616 A1 | 8/2012 | Lamb et al. |
| 2012/0232436 A1 | 9/2012 | Warnking |
| 2012/0238918 A1 | 9/2012 | Gertner |
| 2012/0245494 A1 | 9/2012 | Gertner |
| 2012/0265227 A1 | 10/2012 | Sverdlik et al. |
| 2012/0277763 A1 | 11/2012 | Greenblatt et al. |
| 2012/0302877 A1 | 11/2012 | Harks et al. |
| 2013/0066316 A1 | 3/2013 | Steinke et al. |
| 2013/0123625 A1 | 5/2013 | Hastings et al. |
| 2013/0123778 A1 | 5/2013 | Richardson et al. |
| 2013/0131668 A1 | 5/2013 | Schaer |
| 2013/0137980 A1 | 5/2013 | Waters et al. |
| 2013/0197555 A1 | 8/2013 | Schaer |
| 2013/0197614 A1 | 8/2013 | Gustus et al. |
| 2014/0180034 A1 | 6/2014 | Hoseit et al. |
| 2014/0243809 A1 | 8/2014 | Gelfand et al. |
| 2014/0249042 A1 | 9/2014 | Cai et al. |
| 2014/0276771 A1 | 9/2014 | Miller et al. |
| 2014/0288015 A1 | 9/2014 | Venkateswara-Rao et al. |
| 2014/0350401 A1 | 11/2014 | Sinelnikov |
| 2015/0045675 A1 | 2/2015 | Chernomorsky |
| 2015/0328452 A1 | 11/2015 | Hlavka et al. |

FOREIGN PATENT DOCUMENTS

| | | |
|---|---|---|
| EP | 0819014 B1 | 2/2003 |
| EP | 2008600 A2 | 12/2008 |
| EP | 2488250 A | 8/2012 |
| EP | 1299035 B1 | 2/2013 |
| WO | WO97/25916 A1 | 7/1997 |
| WO | WO98/43701 A1 | 10/1998 |
| WO | WO00/25685 A1 | 5/2000 |
| WO | WO03/076008 A1 | 9/2003 |
| WO | WO2004/105807 A2 | 12/2004 |
| WO | WO2007/092330 A1 | 8/2007 |
| WO | WO2007/146834 A2 | 12/2007 |
| WO | WO2008/025855 A2 | 3/2008 |
| WO | WO2009/120953 A1 | 10/2009 |
| WO | WO2010/093603 A1 | 8/2010 |
| WO | WO2010/124120 A1 | 10/2010 |
| WO | WO2010/132703 A1 | 11/2010 |
| WO | WO2011/082278 A1 | 7/2011 |
| WO | WO2011/130531 A2 | 10/2011 |
| WO | WO2012/015720 A1 | 2/2012 |
| WO | WO2012/015721 A1 | 2/2012 |
| WO | WO2012/015722 A1 | 2/2012 |
| WO | WO2012/016135 A1 | 2/2012 |
| WO | WO2012/112165 A1 | 8/2012 |
| WO | WO2012/125172 A1 | 9/2012 |
| WO | WO2013/018083 A2 | 2/2013 |
| WO | WO2013/074813 A1 | 5/2013 |
| WO | WO2013/157011 A2 | 10/2013 |
| WO | WO2015/103539 A1 | 7/2015 |

OTHER PUBLICATIONS

Abdala et al; Hypertension is critically dependent on the carotid body input in the spontaneously hypertensive rat; J Physiol; 590(17); pp. 4269-4277; Sep. 2012.

Abdala et al; Peripheral chemoreceptor inputs contribute to the development of high blood pressure in spontaneously hypertensive rats(proceeding abstract); Proc Physiol Soc 23; PC22; Oxford, England; Jul. 2011 (printed Sep. 24, 2013 from: http://www.physoc.org/proceedings/abstract/Proc%20Physiol%20Soc%2023PC22).

Al-Rawi et al.; Effect of lignocaine injection in carotid sinus on baroreceptor sensitivity during carotid endarterectomy; J Vasc Surg; 39(6); pp. 1288-1294; Jun. 2004.

Anand et al.; Management of the internal carotid artery during carotid body tumor surgery; Laryngoscope; 105; pp. 231-235; Mar. 1995.

Anderson et al. (executive committee); Carotid body resection; J. Allergy Clin. Immunol.; 78(2); pp. 273-275; Aug. 1986.

Arena et al.; Prognostic value of resting end-tidal carbon dioxide in patients with heart failure; Int J Cardiol; 109(3); pp. 351-358; May 2006.

Banzett et al.; Dyspnea and pain: similarities and contrasts between two very unpleasant sensations; APS Bulletin; 11(1); 6 pgs.; Mar./Apr. 2001.

Bencini et al.; The carotid bodies in bronchial asthma; Histopathology; 18; pp. 195-200; Mar. 1991.

Bencini, A.; Reduction of reflex bronchotropic impulses as a result of carotid body surgery; International Surgery; 54(6); pp. 415-423; Dec. 1970.

Bernstein et al.; Current status of glomectomy; (The Amer. Acad. of Allergy, Abstracts of papers given at Ann. Meeting, Feb. 3-7, 1978, Boston MA; J. Allergy; 41(2); pp. 88-89; Feb. 1968.

Bishop, Jr. et al.; Paragangliomas of the neck; Arch Surg.; 127; pp. 1441-1445; Dec. 1992.

Braunwald et al.; Carotid sinus nerve stimulation for the treatment of intractable angina pectoris: surgical technic; Annals of Surgery; 172(5); pp. 870-876; Nov. 1970.

Braunwald et al.; Carotid sinus nerve stimulation in the treatment of angina pectoris and supraventricular tachycardia; The Western Journal of Medicine; 112(3); pp. 41-50; Mar. 1970.

Capps et al.; The late effects of bilateral carotid sinus denervation in man; J Clin Invest; 17(4); pp. 385-389; Jul. 1938.

Chang et al.; Impaired response to hypoxia after bilateral carotid body resection for treatment of bronchial asthma; Chest; 73; pp. 667-669; May 1978.

Curran et al.; Glomectomy for severe bronchial asthma. A double-blind study; Am Rev Respir Dis; 93(1); pp. 84-89; Jan. 1966.

Davidson et al.; Role of the carotid bodies in breath-holding; N Engl J Med; 290(15); pp. 819-822; Apr. 1974.

de Weerd et al.; Prevalence of asymptomatic carotid artery stenosis according to age and sex: Systematic review and metaregression analysis; Stroke; 40(4); pp. 1105-1113; Apr. 2009.

Dickinson et al.; Carotid body tumour: 30 years experience; Br. J. Surg.; 73(1); pp. 14-16; Jan. 1986.

Ding et al.; Role of blood flow in carotid body chemoreflex function in heart failure; J Physiol; 589(1); pp. 245-258; Jan. 2011.

Doumas et al.; Benefits from treatment and control of patients with resistant hypertension; Int. J Hypertension; 8 pgs; Dec. 2011.

Fletcher, Jr. et al.; The surgical treatment of bronchial asthma by excision of the carotid body; J Christ Med Assoc India; 38; pp. 492-496; Sep. 1963.

Gain et al.; Anaesthesia for glomectomy in the asthmatic patient; Can Aneas Soc J; 11(4); pp. 417-424; Jul. 1964.

(56) References Cited

OTHER PUBLICATIONS

Giannoni et al.; Combined increased chemosensitiviy to hypoxia and hypercapnia as a prognosticator in heart failure; JACC; 53(21); pp. 1975-1980; May 2009.
Grassi, G.; Renal denervation in cardiometabolic disease: Concepts, achievements and perspectives; Nutr Metab Cardiovasc Dis; 23(2); pp. 77-83; Feb. 2013 (Epub Nov. 10, 2012).
Green, M.; Observations on glomectomized asthmatic patients; Annals of Allergy; 23(5); pp. 213-219; May 1965.
Gudovsky et al.; Surgical treatment of bronchial asthma (with translation); Khirurgiia; 7; pp. 14-18; 2002 (year of pub. sufficiently earlier than effective US filing date and any foreign priority date).
Guz et al.; Peripheral chemoreceptor block in man; Respiration Physiology; 1; pp. 38-40; 1966 (year of pub. sufficiently earlier than effective US filing date and any foreign priority date).
Gwon et al.; Risk factors for stroke during surgery for carotid body tumors; World J Surg; 35(9); pp. 2154-2158; Sep. 2011.
Handelsman, H.; Bilateral carotid body resection as a treatment for chronic intractable bronchospastic diseases; Health Technology Assessment Series: Health Technology Assessment Report; No. 12; 13 pgs.; 1985 (year of pub. sufficiently earlier than effective US filing date and any foreign priority date).
Hickey et al.; Bilateral carotid endarterectomy with attempted preservation of the carotid body function; Ann. Surg.; 175(2); pp. 268-273; Feb. 1972.
Honda et al.; Hypoxic chemosensitivity in asthmatic patients two decades after carotid body resection; J Appl Physiol.; 46(4); pp. 632-638; Apr. 1979.
Honda, Y.; Respiratory and circulatory activities in carotid body-resected humans; J Appl Physiol; 73(1); pp. 1-8; Jul. 1992.
Karashurov et al.; Radiofrequency electrostimulation of synocarotid for the treatment of bronchial asthma (with translation); Khirurgiia (Mosk); 12; pp. 4-6; 1999 (year of pub. sufficiently earlier than effective US filing date and any foreign priority date).
Keim, W. F.; Carotid glomectomy in bronchial asthma; Archives of Otolaryngology; 79; pp. 225-228; Mar. 1964.
Kim et al.; Carotid artery-hypoglossal nerve relationships in the neck: an anatomical work; Neurol Res; 31; pp. 895-899; Nov. 2009.
Kline et al.; Cervical glomectomy for bronchial asthma; Journal of the Medical Society of New Jersey; 61(5); pp. 176-178; May 1964.
Leggate, J. M.; Treatment of asthma by excision of the carotid body; Postgraduate Med. Journal; 26(292)pp. 71-77; Feb. 1950.
Lesske et al.; Hypertension caused by chronic intermittent hypoxia—influence of chemoreceptors and sympathetic nervous system; J Hypertens; 15(12); pp. 1593-1603; Dec. 1997.
Lo et al.; Anatomical variations of the common carotid artery bifurcation; ANZ J. Surg.; 76(11); pp. 970-972; Nov. 2006.
Lugliani et al.; A role for the carotid body in cardiovascular control in man; Chest; 63(5); pp. 744-750; May 1973.
Lugliani et al.; Effect of bilateral carotid-body resection on ventilatory control at rest and during exercise in man; New England J Med; 285(20); pp. 1105-1111; Nov. 1971.
Lusiani et al.; Prevalence of atherosclerotic involvement of the internal carotid artery in hypertensive patients; Int J Cardiol; 17; pp. 51-56; Oct. 1987.
Lyons et al.; Anatomical variants of the cervical sympathetic chain to be considered during neck dissection; Br J Oral Maxillofac Surg; 36(3); pp. 180-182; Jun. 1998.
Ma et al.; A retrospective study in management of carotid body tumour; Br J Oral Maxillofac Surg; 47(6); pp. 461-465; Sep. 2009.
MacGowan, W.; Removal of the carotid body for asthma: A report of 19 treated patients; Dis Chest; 51(3); pp. 278-281; Mar. 1967.
Marschke et al.; Carotid-body removal in asthma; JAMA; 191(5); p. 397; Feb. 1965.
Marshall, J.; Peripheral chemoreceptors and cardiovascular regulation; Physiological Reviews; 74(3); pp. 543-594; Jul. 1994.
Meyerson, Sheldon; A histological study of the morphology of the cervical carotid bifurcation, including descriptions of intramural neural elements (Thesis); Ohio State University; 47 pgs.; 1968 (year of pub. sufficiently earlier than effective US filing date and any foreign priority date).
Myers et al.; End-tidal CO2 pressure and cardiac performance during exercise in heart failure; Med Sci Sports Exerc; 41(1); pp. 18-24; Jan. 2009.
Nadel et al.; Effect of changes in blood gas tensions and carotid sinus pressure on tracheal volume and total lung resistance to airflow; J Physiol; 163(1); pp. 13-33; Aug. 1962.
Nakayama, K.; Surgical removal of the carotid body for bronchial asthma; Chest; 40(6); pp. 595-604; Dec. 1961.
Nakayama, K.; Surgical removal of the carotid body for bronchial asthma; The Australian and the New Zealand Journal of Surgery; 31(3); pp. 214-221; Feb. 1962.
Nakayama, K.; The surgical significance of the carotid body in relation to bronchial asthma; Thoracic Surgery; Journal of the International College of Surgeons; 39(4); pp. 374-389; Apr. 1963.
Nespoulet et al.; Altitude illness is related to low hypoxic chemoresponse and low oxygenation during sleep; Eur Respir J; 40(3); pp. 673-680; Sep. 2012 (ERJ Express; epub Apr. 20, 2012).
Nguyen et al.; Carotid body detection on CT angiography; Am J Neuroradiol; 32; pp. 1096-1099; Jun.-Jul. 2011.
O'Donnell et al.; Pathophysiology of dyspnea in chronic obstructive pulmonary disease: a rountable; Proc Am Thorac Soc; 4(2); pp. 145-168; May 2007.
O'Rourke et al.; Removal of the carotid body for asthma: A preliminary report of 40 cases; The Medical Journal of Australia; 2; pp. 1040-1043; Dec. 1963.
O'Rourke et al.; Removal of the carotid body for asthma: An appraisal of results; The Medical Journal of Australia; 2; pp. 869-870; Nov. 1964.
Overholt et al.; Hidden or unsuspected brochiectasis in the asthmatic patient; JAMA; 150(5); pp. 438-441; Oct. 1952.
Overholt, R.; Glomectomy for asthma; Chest; 40; pp. 605-610; Dec. 1961.
Paliwoda et al.; Surgical removal of the carotid body and denervation of the carotid sinus for bronchial asthma; East African Medical Journal; 44(7); pp. 285-287; Jul. 1967.
Paton et al.; the carotid body as a therapeutic target for the treatment of sympathetically mediated diseases; Hypertension; 61; pp. 5-13; Jan. 2013.
Perret et al.; High prevalence of peripheral atherosclerosis in a rapidly developing country; Atherosclerosis; 153(1); pp. 9-21; Nov. 2000.
Phillips et al.; Results of glomectomy in chronic obstructive pulmonary disease: A four year follow-up report of 57 cases; Chest; 58(4); pp. 358-362; Oct. 1970.
Phillips, J.; Removal of the carotid body for asthma and emphysema; Southern Medical Journal; 57; pp. 1278-1281; Nov. 1964.
Phillips, J.; Treatment of obstructive bronchial diseases; Geriatrics; 21(7); pp. 137-143; Jul. 1966.
Ponikowski et al.; Peripheral chemoreceptor hypersensitivity; Circulation; 101; pp. 544-549; Jul. 2001.
Rabl et al.; Diagnosis and treatment of carotid body tumors; Thorac Cardiovasc Surg.; 41(6); pp. 340-343; Dec. 1993.
Sanghvi et al.; Carotid body tumors; Journal of Surgical Oncology; 54(3); pp. 190-192; Nov. 1993.
Sedwitz et al.; Should the carotid body be removed in the treatment of asthma and emphysema?; International Surgery; 57(6); pp. 467-469; Jun. 1972.
Sedwitz et al.; Unilateral excision of the carotid body in the treatment of 500 asthma patients; Vascular Diseases; 2; pp. 91-98; Mar. 1965.
Sedwitz, J.; Unilateral carotid body resectin for asthma; Jounal of the National Medical Association; 55(5); pp. 384-388; Sep. 1963.
Segal et al.; Glomectomy in the treatment of chronic bronchial asthma; NEJM; 272(2); pp. 57-63; Jan. 1965.
Segal, M.; Glomectomy for chronic bronchial asthma: A three phase study; Annals of Allergy; 23; pp. 377-384; Aug. 1965.
Severinghaus, J.; Carotid body resection for COPD?; Chest; 95(5); pp. 1128-1129; May 1989.
Shalev, Alon; U.S. Appl. No. 61/178,049 entitled "Endovascular systems for performing interventions during ischemic conditions of

(56) References Cited

OTHER PUBLICATIONS the CNS by utilizing the carotid baroreceptors and chemoreceptors and methods for using same," filed May 14, 2009.
Shamblin et al.; Carotid Body Tumor; Am J Surg; 122; pp. 732-739; Dec. 1971.
Shek, J.; Excision of carotid body for advanced emphysema; Michigan State Medical Society Journal; 63; pp. 211-212; Mar. 1964.
Silva et al.; Welcome the carotid chemoreflex to the 'neural control of the circulation during exercise' club; J Physiol; 590(Pt 12) ; pp. 2835-2836; Jun. 2012.
Somfay et al.; Dose-response effect of oxygen on hyperinflation and exercise endurance in non-hypoxaemic COPD patients; European Respiratory Journal 18; pp. 77-84; Jul. 2001.
Somfay et al.; Effect of hyperoxia on gas exchange and lactate kinetics following exercise on set in nonhypoxemic COPD patients; Chest; 121(2); pp. 393-400; Feb. 2002.
Stickland et al.; Distribution during exercise in health and chronic heart failure; Circ Res; 100; pp. 1371-1378; May 2007.
Streian et al.; Glomectomy in carotid sinus syncope and associated arrythmias: Symptomatic bradycardia, atrial flutter and atrial fibrillation; Rom J Intern Med; 44(2); pp. 153-163; 2006 (year of pub. sufficiently earlier than effective US filing date and any foreign priority date).
Streian et al.; Glomectomy in carotid sinus syncope; Rev. Roum. Med.—Med. Int.; 26(1); pp. 47-52; Jan.-Mar. 1988.
Syed et al.; Percutaneous superficial temporal artery access for carotid artery stenting in patients with a hostile aortic arch; J Endovasc Ther; 18(5); pp. 729-733; Oct. 2011.
Tamura et al.; A morphometric study of the carotid sinus nerve in patients with diabetes mellitus and chronic alchoholism; Journal of the Autonomic Nervous System; 23; pp. 9-15; Jun. 1988.
Tchibukmacher, N.; Surgical anatomy of carotid sinus nerve and intercarotid ganglion; Surgery, Gynecology and Obstetrics; 67; pp. 740-745; 1938 (year of pub. sufficiently earlier than effective US filing date and any foreign priority date).
Timmers et al.; Denervation of carotid baro—and chemoreceptors in humans; J Physiol; 553(1); pp. 3-11; Nov. 2003.
Toorop et al.; Anatomy of the carotid sinus nerve and surgical implications in carotid sinus syndrome; J Vasc Surg; 50; pp. 177-182; Jul. 2009.
Toorop et al.; Effective surgical treatment of the carotid sinus syndrome; J Cardiovasc Surg.; 50; pp. 683-686; Oct. 2009.
Tubbs et al.; Anatomic landmarks for nerves of the neck: a vade mecum for neurosurgeons; Operative Neurosurgery; 56(ONS Suppl 2); pp. ONS256-ONS260; Apr. 2005.
Van Der Mey et al.; Management of carotid body tumors; Otolaryngol Clin North Am.; 34(5); pp. 907-924; Oct. 2001.
Vermeire et al.; Carotid body resection in patients with severe chronic airflow limitation; Bull Eur Physiopathol Respir; 23 Suppl 11; pp. 165s-166s; Aug. 1987.
Ward et al.; Embolization: An adjunctive measure for removal of carotid body tumors; Laryngoscope; 98; pp. 1287-1291; Dec. 1988.
Wasserman et al.; Effect of carotid body resection on ventilatory and acid-base control during exercise; Journal of Applied Physiology; 39(3); pp. 354-358; Aug. 1975.
Wasserman et al.; Ventilation during exercise in chronic heart failure; Basic Res Cardiol; 91(suppl. 1); pp. 1-11; 1996 (year of pub. sufficiently earlier than effective US filing date and any foreign priority date).
Whipp et al.; Physiologic changes following bilateral carotid-body resection in patients with chronic obstructive pulmonary disease; Chest; 101(3); pp. 656-661; Mar. 1992.
Whipp, B.J.; Carotid bodies and breathing in humans; Thorax; 49(11); pp. 1081-1084; Nov. 1994.
Williams et al.; Carotid body tumor; Arch Surg.; 127; pp. 963-968; Aug. 1992.
Winter et al.; Immediate effects of bilateral carotid body resection on total respiratory resistance and compliance in humans; Adv Exp Med Biol; 551; pp. 15-21; 2005 (year of pub. sufficiently earlier than effective US filing date and any foreign priority date).
Winter, B.; Bilateral carotid body resection for asthma and emphysema; International Surgery; 57(6); pp. 458-466; Jun. 1972.
Winter, B.; Carotid body resection in chronic obstructive pulmonary disease; Chest; 100(3); p. 883; Sep. 1991.
Winter, B.; Carotid body resection: Controversy—confusion—conflict; Ann thorac Surg.; 16(6); pp. 648-659; Dec. 1973.
Wood et al.; Bilateral removal of carotid bodies for asthma; thorax; 20(6); pp. 570-573; Nov. 1965.
Gelfand et al.; U.S. Appl. No. 13/852,895 entitled "Carotid Body Modulation Planning and Assessment," filed Mar. 28, 2013.
Gelfand et al.; U.S. Appl. No. 13/869,765 entitled "Endovascular Catheters and Methods for Carotid Body Ablation," filed Apr. 24, 2013.
Engelman et al.; U.S. Appl. No. 13/936,121 entitled "Devices and Systems for Carotid Body Ablation," filed Jul. 5, 2013.
Leung et al.; U.S. Appl. No. 13/908,853 entitled "Methods and Devices for Cryogenic Carotid Body Ablation," filed Jun. 3, 2013.
Leung et al.; U.S. Appl. No. 13/908,995 entitled "Percutaneous Methods and Devices for Carotid Body Ablation," filed Jun. 3, 2013.
Giannoni et al.; Clinical significance of chemosensitivity in chronic heart failure: influence on neurohormonal derangement, cheyne-strokes respiration and arrhythmias; Clinical Science (London); 114 (7); pp. 489-497; Apr. 2008.
Pennes; Analysis of tissue and arterial blood temperatures in the resting human forearm; J. Appl. Physiol.; 1(2); pp. 93-122; Aug. 1948.
Sehirli et al.; The diameters of common carotid artery and its branches in newborns; Surg. Radiol. Anat.; 27(4); pp. 292-296; Nov. 2005.
Sinelnikov et al.; U.S. Appl. No. 14/656,635 entitled "Carotid body ablation with a transvenous ultrasound imaging and ablation catheter," filed Mar. 12, 2015.
Sapareto et al.; Thermal dose determination in cancer therapy; Int. J. Radiat. Biol. Phys.; 10(6); pp. 787-800; Jun. 1984.
Lennox et al.; U.S. Appl. No. 14/769,515 entitled "Endovascular catheters for carotid body ablation utilizing an ionic lquid stream," filed Aug. 21, 2015.
Holton et al.; The effects of bilateral removal of the carotid bodies and denervation of the carotid sinuses in two human subjects; J. Physiol.; 181(2); pp. 365-378; Nov. 1965.
Petersen et al.; Lesion dimensions during temperature-controlled radiofrequency catheter ablation of left ventricular porcine myocardium impact of ablation site; electrode size, and convective cooling; Circulation; 99(2); pp. 319-325; Jan. 1999.
Wittkampf et al.; Control of radiofrequency lesion size by power regulation; Circulation; 80(4); pp. 962-968; Oct. 1989.

\* cited by examiner

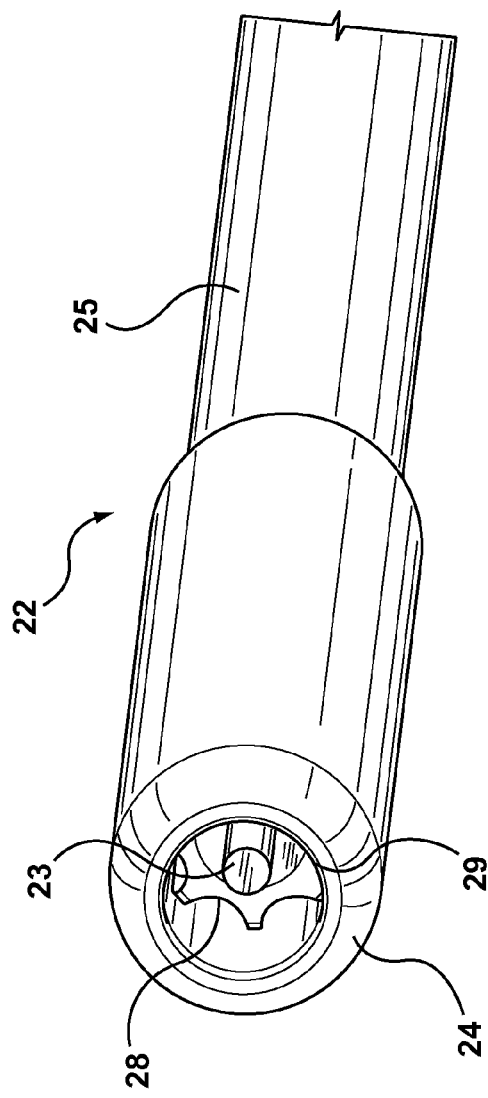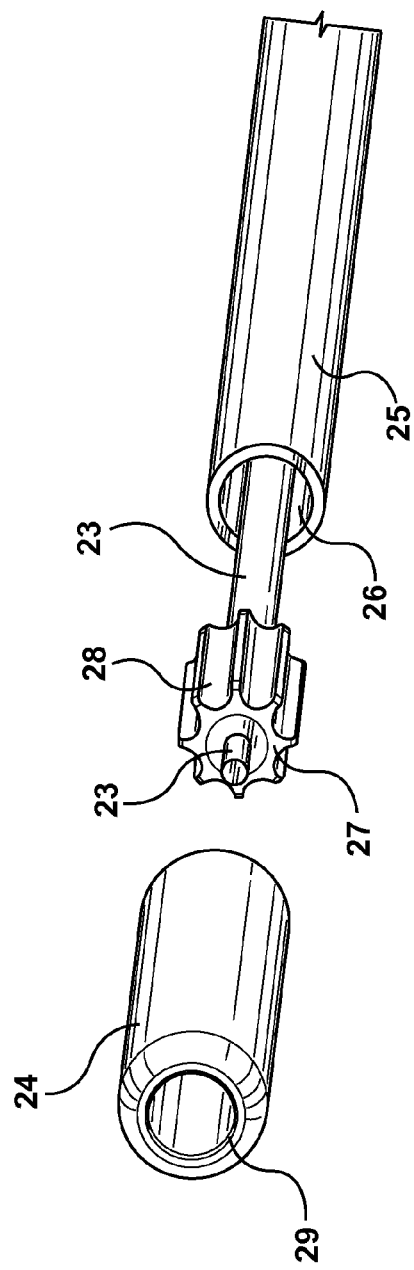
FIG. 4A
FIG. 4B

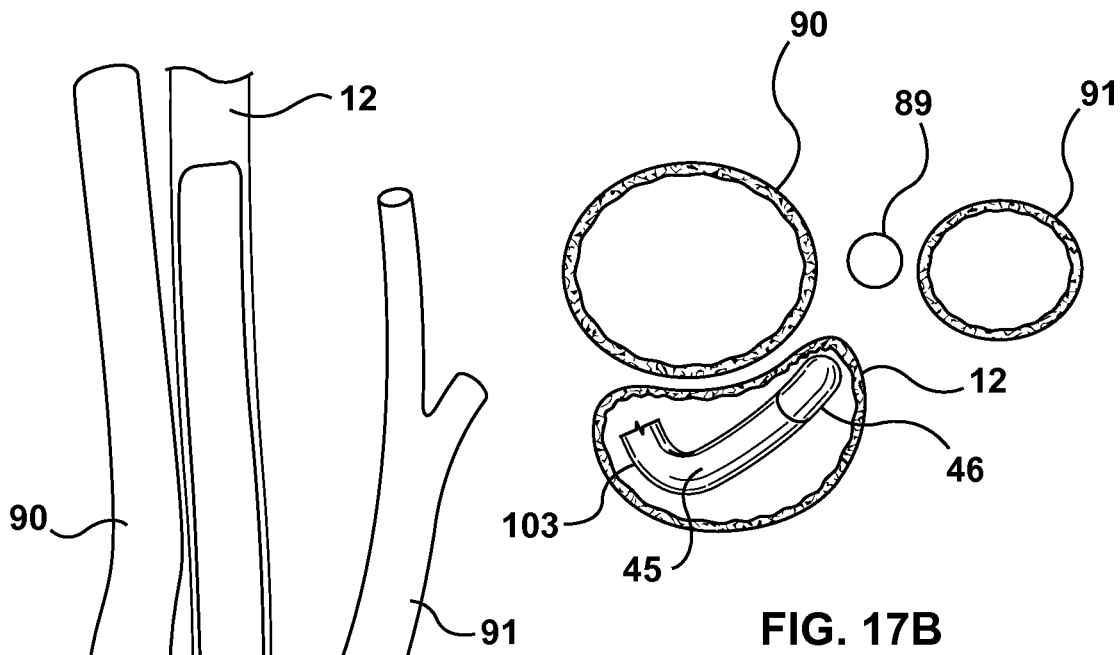
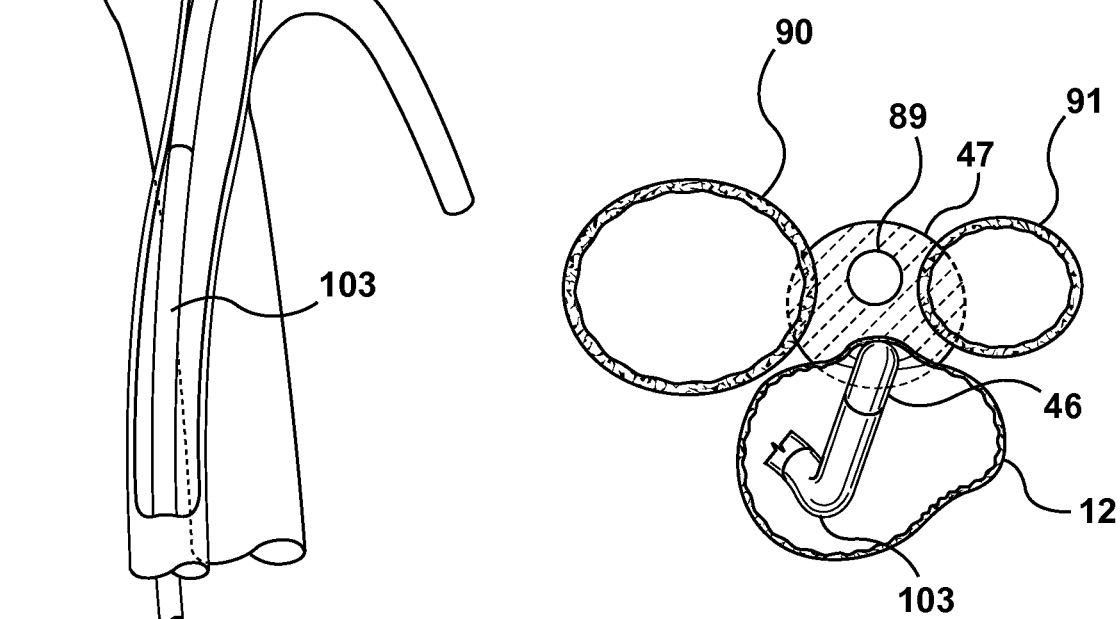
FIG. 17A
FIG. 17B
FIG. 17C

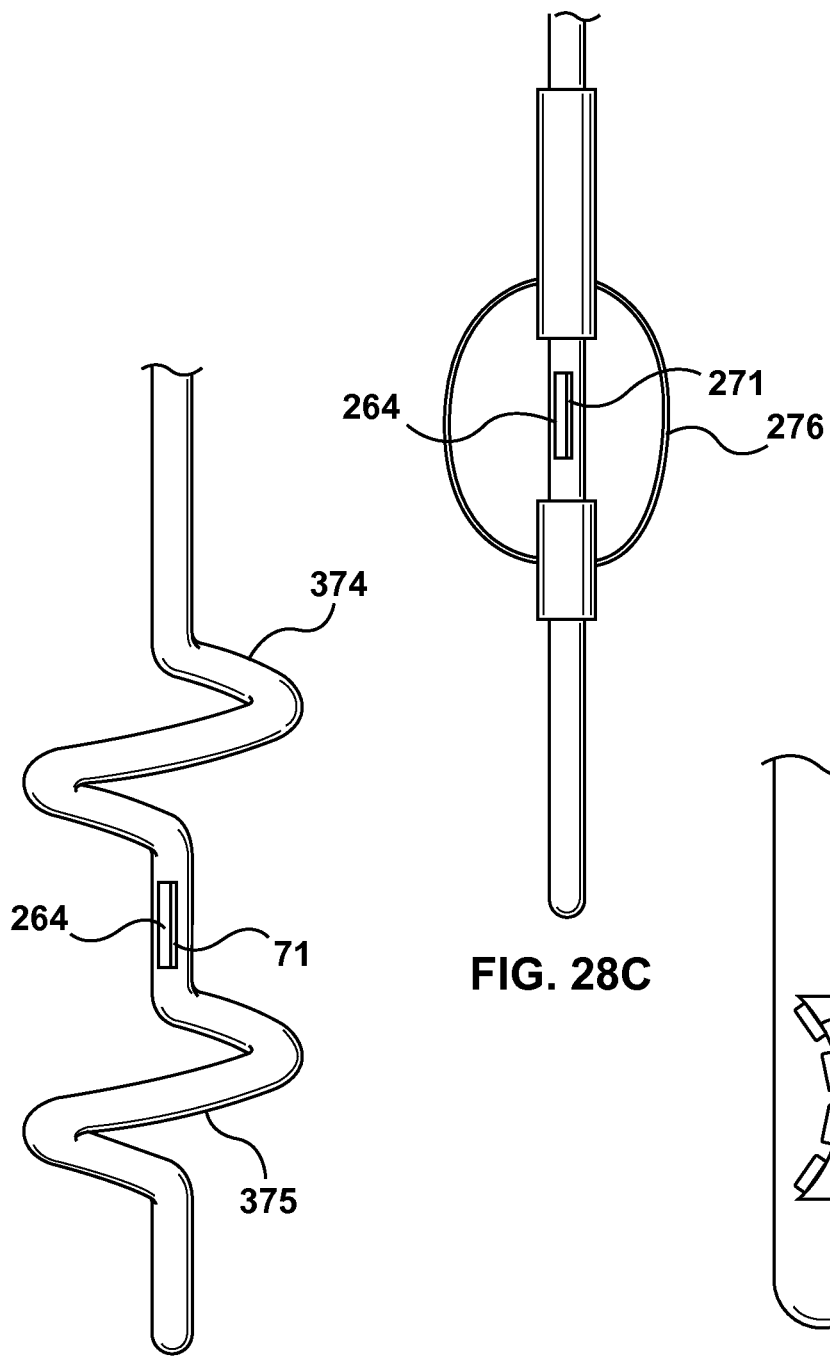

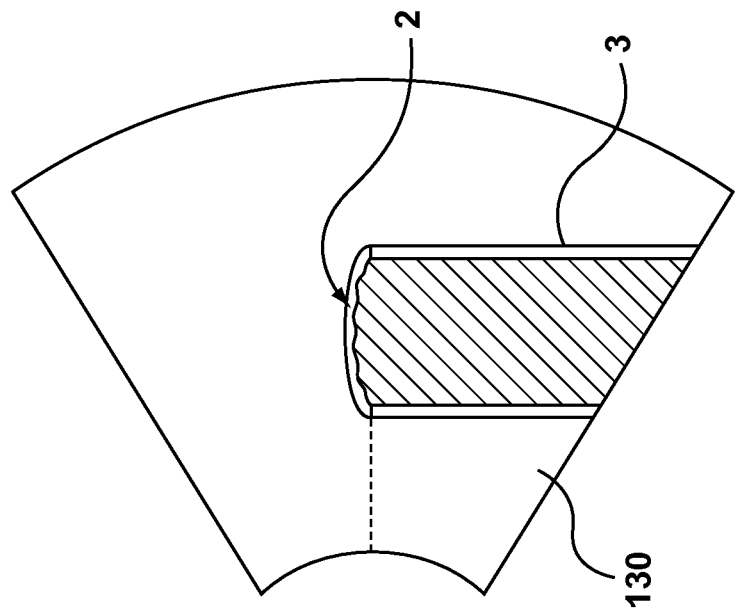
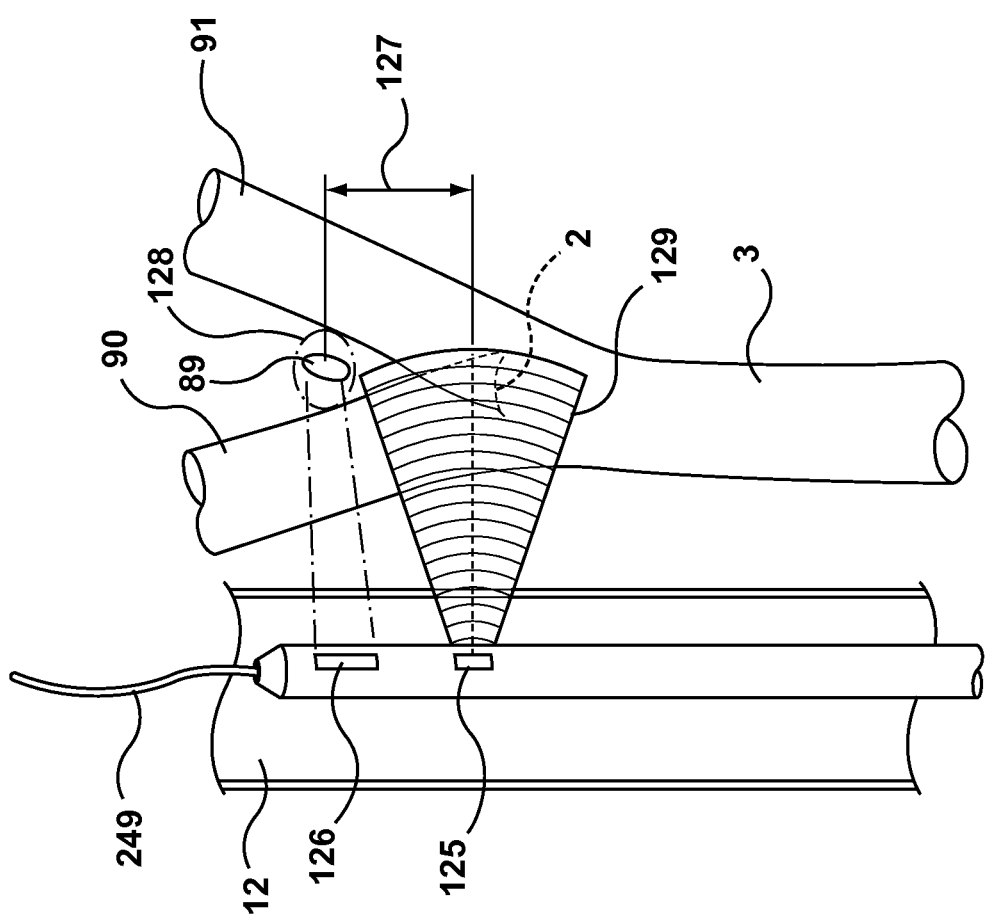
FIG. 31B
FIG. 31A

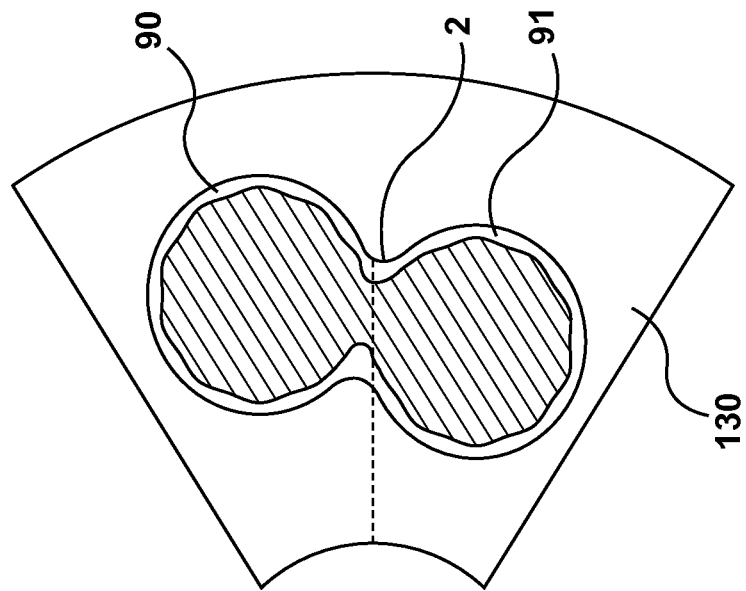
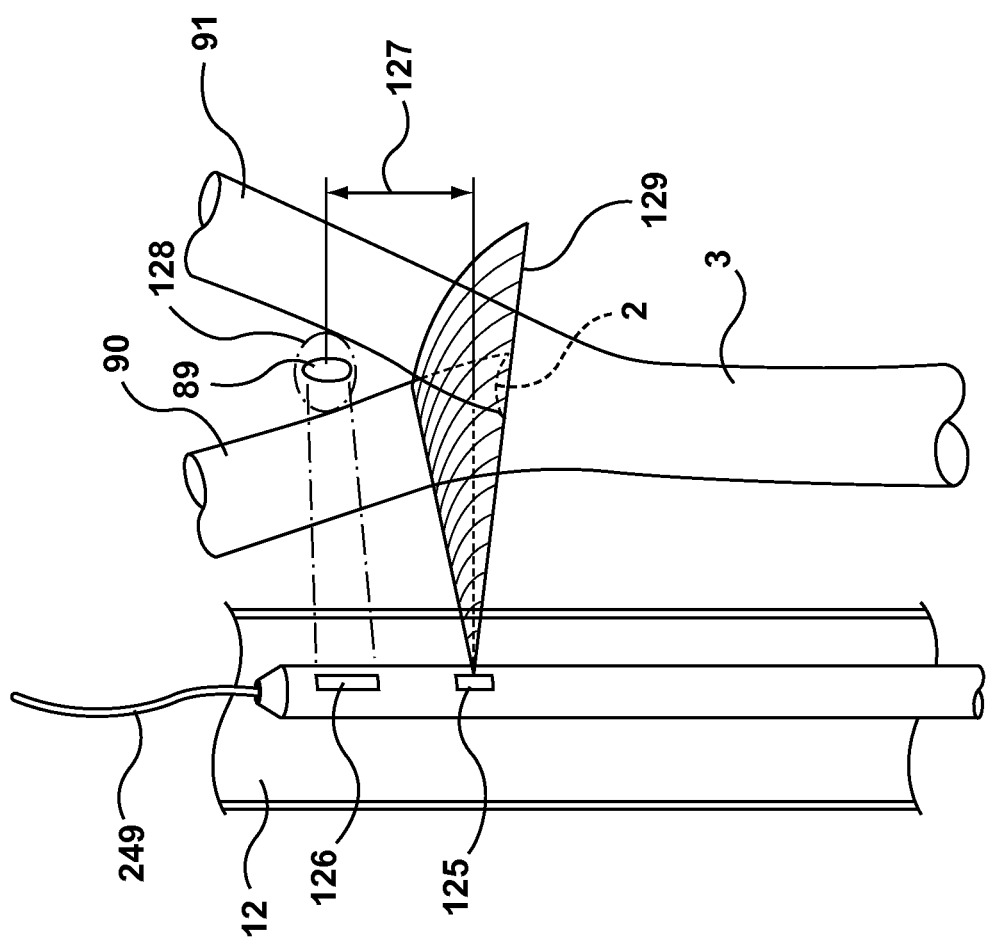
FIG. 32B
FIG. 32A

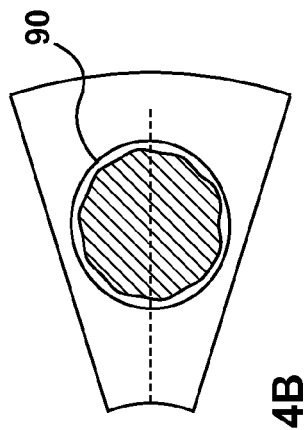
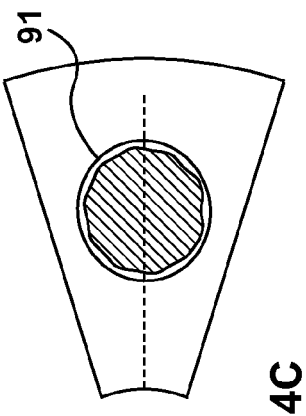
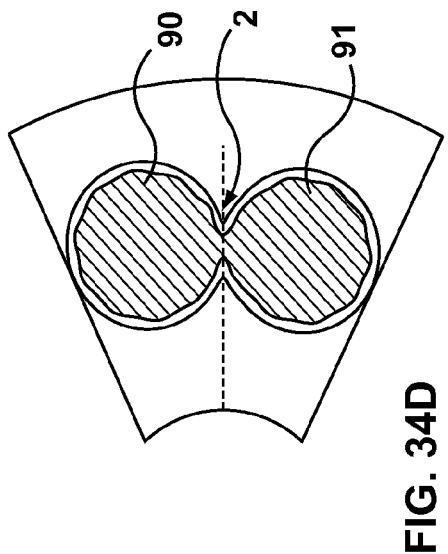
FIG. 34B
FIG. 34C
FIG. 34D
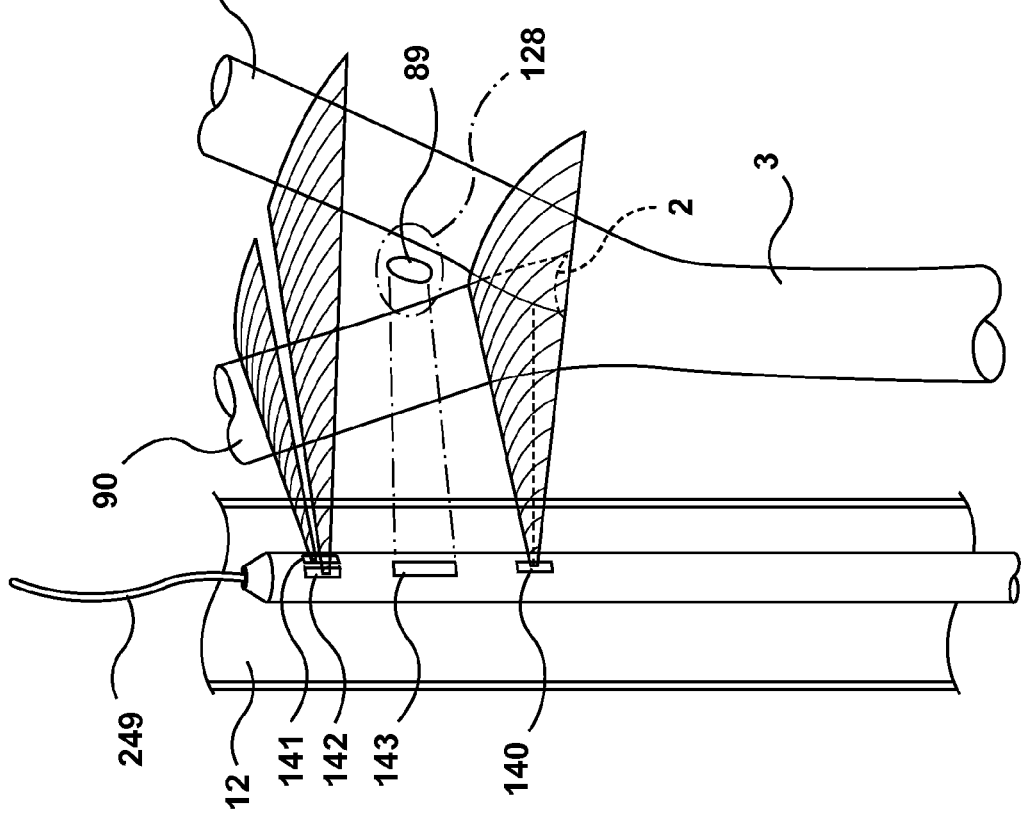
FIG. 34A

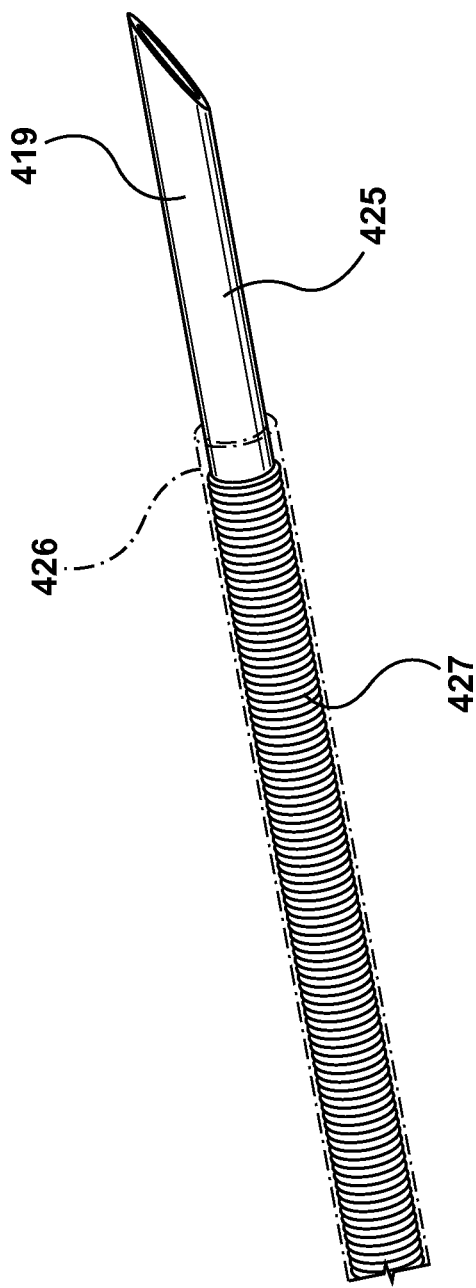
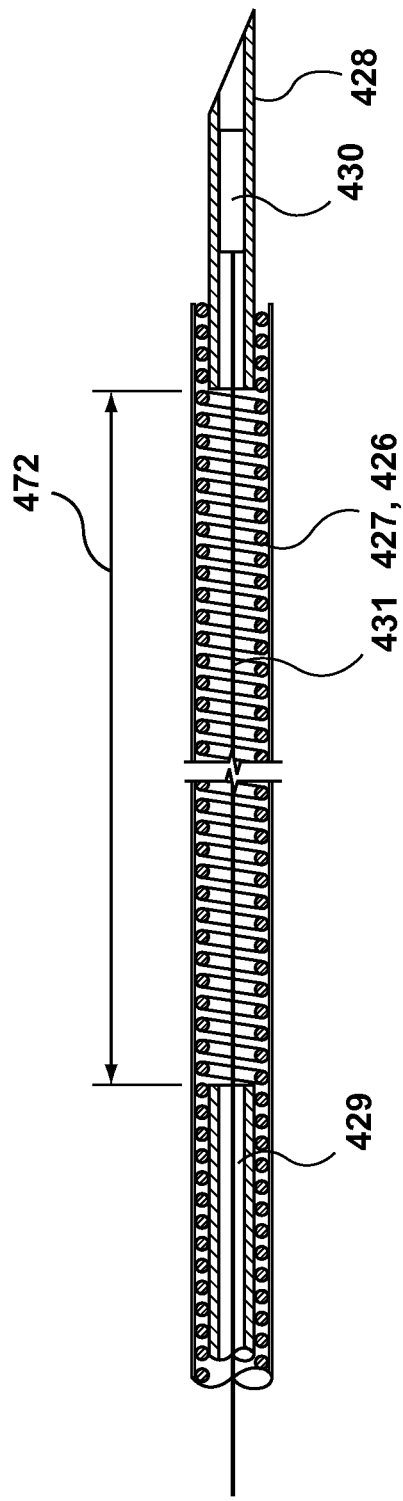
FIG. 44A
FIG. 44B

CAROTID BODY ABLATION VIA DIRECTED ENERGY

CROSS REFERENCE TO RELATED APPLICATIONS

This application claims priority to the following U.S. Provisional Applications, the disclosures of which are incorporated by reference herein in their entireties: U.S. Prov. App. No. 61/666,804, filed Jun. 30, 2012; U.S. Prov. App. No. 61/667,991, filed Jul. 4, 2012; U.S. Prov. App. No. 61/667,996, filed Jul. 4, 2012; U.S. Prov. App. No. 61/667,998, filed Jul. 4, 2012; U.S. Prov. App. No. 61/682,034, filed Aug. 10, 2012; U.S. Prov. App. No. 61/768,101, filed Feb. 22, 2013; U.S. Prov. App. No. 61/791,769, filed Mar. 15, 2013; U.S. Prov. App. No. 61/791,420, filed Mar. 15, 2013; U.S. Prov. App. No. 61/792,214, filed Mar. 15, 2013; U.S. Prov. App. No. 61/792,741, filed Mar. 15, 2013; U.S. Prov. App. No. 61/793,267, filed Mar. 15, 2013; U.S. Prov. App. No. 61/794,667, filed Mar. 15, 2013; U.S. Prov. App. No. 61/810,639, filed Apr. 10, 2013; and U.S. Prov. App. No. 61/836,100, filed Jun. 17, 2013.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

The present disclosure is directed generally to systems and methods for treating patients having sympathetically mediated disease associated at least in part with augmented peripheral chemoreflex or heightened sympathetic activation by ablating at least one of peripheral chemoreceptor (e.g., carotid body) and a nerve associated therewith.

BACKGROUND

It is known that an imbalance of the autonomic nervous system is associated with several disease states. Restoration of autonomic balance has been a target of several medical treatments including modalities such as pharmacological, device-based, and electrical stimulation. For example, beta blockers are a class of drugs used to reduce sympathetic activity to treat cardiac arrhythmias and hypertension; Gelfand and Levin (U.S. Pat. No. 7,162,303) describe a device-based treatment used to decrease renal sympathetic activity to treat heart failure, hypertension, and renal failure; Yun and Yuarn-Bor (U.S. Pat. No. 7,149,574; U.S. Pat. No. 7,363,076; U.S. Pat. No. 7,738,952) describe a method of restoring autonomic balance by increasing parasympathetic activity to treat disease associated with parasympathetic attrition; Kieval, Burns and Serdar (U.S. Pat. No. 8,060,206) describe an electrical pulse generator that stimulates a baroreceptor, increasing parasympathetic activity, in response to high blood pressure; Hlavka and Elliott (US 2010/0070004) describe an implantable electrical stimulator in communication with an afferent neural pathway of a carotid body chemoreceptor to control dyspnea via electrical neuromodulation. More recently, Carotid Body Ablation (CBA) has been conceived for treating sympathetically mediated diseases.

SUMMARY

This disclosure is related to methods, devices, and systems for reducing afferent signaling between a peripheral chemoreceptor and the central nervous system. The disclosure includes methods, devices, and systems for directed energy ablation of a carotid body and/or its associated nerves. Directed energy ablation of a carotid body generally refers to delivering a device with a directed energy emitter in the region of its distal tip through a patient's body proximate to a peripheral chemosensor (e.g., carotid body) and/or an associated nerve(s) of the patient and then activating the directed energy emitter to ablate the tissue proximate to the directed energy emitter resulting in carotid body ablation. When ablation of a "carotid body" is described herein, it should be interpreted to include ablation of a carotid body and/or an associated nerve(s) unless the disclosure indicates to the contrary.

A carotid body may be ablated by placing a directed energy emitter within or against the wall of a carotid artery adjacent to the carotid body of interest, then aiming and activating the directed energy emitter thereby raising the temperature of the periarterial space containing the carotid body to an extent and duration sufficient to ablate the carotid body.

A carotid body may also be ablated by placing a directed energy emitter within or against the wall of an internal jugular vein or one of its tributaries adjacent to the carotid body of interest, then aiming and activating the directed energy emitter thereby raising the temperature of the perivenous space containing the carotid body or its nerves to an extent and duration sufficient to ablate the carotid body and/or its nerves.

A carotid body may also be ablated by placing a directed energy emitter within or against the wall of a facial vein adjacent to the carotid body of interest, then activating the directed energy emitter thereby raising the temperature of the perivenous space containing the carotid body or its nerves to an extent and duration sufficient to ablate the carotid body and/or its nerves.

A carotid body may also be ablated by placing a directed energy emitter within an extravascular space proximate to a carotid body of interest, then activating the directed energy emitter thereby raising the temperature of the extravascular space containing the carotid body or its to an extent and duration sufficient to ablate the carotid body and/or its nerves.

In another exemplary procedure a location of periarterial space associated with a carotid body is identified, then a directed energy emitter is placed against or within the interior wall of a carotid artery adjacent to the identified location, then directed energy ablation parameters are selected and the directed energy emitter is activated thereby ablating the carotid body, whereby the position of the directed energy emitter and the selection of directed energy ablation parameters provides for ablation of the carotid body without substantial collateral damage to adjacent functional structures.

In a further exemplary procedure a location of perivenous space associated with a carotid body is identified, then a directed energy emitter is placed against or within the interior wall of an internal jugular vein adjacent to the identified location, then directed energy ablation parameters are selected and the directed energy emitter is activated thereby ablating the carotid body, whereby the orientation and position of the directed energy emitter and the selection of directed energy ablation parameters provides for ablation of the carotid body without substantial collateral damage to adjacent functional structures.

In a further exemplary procedure a location of extravascular space associated with a carotid body is identified, then a directed energy emitter is placed proximate to the identified location, then directed energy ablation parameters are selected and the directed energy emitter is activated thereby ablating the carotid body, whereby the position of the directed energy emitter and the selection of directed energy ablation parameters provides for ablation of the carotid body without substantial collateral damage to adjacent functional structures.

In a further example the location of the periarterial space associated with a carotid body is identified, as well as the location of important non-target structures not associated with the carotid body, then a directed energy emitter is placed against or within the interior wall of a carotid artery adjacent to the identified location, directed energy ablation parameters are selected and the directed energy emitter is then activated thereby ablating the carotid body, whereby the position of the directed energy emitter and the selection of directed energy ablation parameters provides for ablation of the target carotid body without substantial collateral damage to important non-target structures in the vicinity of the carotid body.

In another example the location of the perivenous space associated with a carotid body is identified, as well as the location of important non-target structures not associated with the carotid body, then a directed energy emitter is placed against or within the interior wall of an internal jugular vein, or alternatively a facial vein adjacent to the identified location, directed energy ablation parameters are selected and the directed energy emitter is then activated thereby ablating the carotid body, whereby the position of the directed energy emitter and the selection of directed energy ablation parameters provides for ablation of the target carotid body without substantial collateral damage to important non-target structures in the vicinity of the carotid body.

In another example the location of the extravascular space associated with a carotid body is identified, as well as the location of important non-target structures not associated with the carotid body, then a directed energy emitter is placed within or adjacent to the identified location, directed energy ablation parameters are selected and the directed energy emitter is then activated thereby ablating the carotid body, whereby the position of the directed energy emitter and the selection of directed energy ablation parameters provides for ablation of the target carotid body without substantial collateral damage to important non-target structures in the vicinity of the carotid body.

Selectable carotid body directed energy ablation parameters include directed energy wavelength or frequency, power, duration of activation, numerical aperture, energy modality (optical or ultrasonic), number of directed energy emitter activations, and directed energy emitter position or orientation within a patient as well as contrast agent injection, volume, and time since injection.

The location of the perivascular space associated with a carotid body is determined by means of a non-fluoroscopic imaging procedure prior to carotid body directed energy ablation, where the non-fluoroscopic location information is translated to a coordinate system based on fluoroscopically identifiable anatomical and/or artificial landmarks.

A function of a carotid body is stimulated and at least one physiological parameter is recorded prior to and during the stimulation, then the carotid body is ablated, and the stimulation is repeated, whereby the change in recorded physiological parameter(s) prior to and after directed energy ablation is an indication of the effectiveness of the directed energy ablation.

A function of a carotid body is blocked and at least one physiological parameter(s) is recorded prior to and during the blockade, then the carotid body is ablated, and the blockade is repeated, whereby the change in recorded physiological parameter(s) prior to and after directed energy ablation is an indication of the effectiveness of the directed energy ablation.

A device configured to prevent embolic debris from entering the brain is deployed in an internal carotid artery associated with a carotid body, then a directed energy emitter is placed proximate with the carotid body, the directed energy emitter is activated resulting in carotid body ablation, the directed energy emitter is then withdrawn from the proximate location, then the embolic prevention device is withdrawn from the internal carotid artery, whereby the device in the internal carotid artery prevents debris resulting from the use of the directed energy emitter from entering the brain.

A method has been conceived in which the location of the perivascular space associated with a carotid body is identified, then a directed energy emitter is placed in a predetermined location within or against the interior wall of a vessel adjacent to the identified location, then directed energy ablation parameters are selected and the directed energy emitter is activated and then deactivated, the directed energy emitter is then repositioned in at least one additional predetermine location within or against the same interior wall and the directed energy emitter is then reactivated using the same or different directed energy ablation parameters, whereby the positions of the directed energy emitter and the selection of directed energy ablation parameters provides for ablation of the carotid body without substantial collateral damage to adjacent functional structures.

A method has been conceived in which the location of the extravascular space associated with a carotid body is identified, then a directed energy emitter is placed within the extravascular location or adjacent to the extravascular location, then directed energy ablation parameters are selected and the directed energy emitter is activated and then deactivated, the directed energy emitter is then repositioned in at least one additional location and the directed energy emitter is then reactivated using the same or different directed energy ablation parameters, whereby the positions of the directed energy emitter and the selection of directed energy ablation parameters provides for ablation of the carotid body without substantial collateral damage to adjacent functional structures.

A system has been conceived comprising a vascular catheter configured with a directed energy emitter in the vicinity of the distal end, and a connection between the directed energy emitter and a source of ablation energy at the proximal end, whereby the distal end of the catheter is constructed to be inserted into a peripheral artery of a patient and then maneuvered into an internal or external carotid artery using standard fluoroscopic guidance techniques.

A system has been conceived comprising a catheter configured with a directed energy emitter in the vicinity of the distal end, and a means to connect the ablation emitter to a source of ablation energy at the proximal end, whereby the distal end of the catheter is constructed to be inserted into a peripheral vein of a patient and then maneuvered into an internal jugular vein, or alternately a facial vein using standard fluoroscopic guidance techniques.

A system has been conceived comprising a vascular catheter configured with a directed energy emitter in the vicinity of the distal end configured for carotid body directed energy ablation and further configured for at least one of the following: neural stimulation, neural blockade, carotid body stimulation and carotid body blockade; and a connection between the directed energy emitter and a source of ablation energy, and stimulation energy and/or blockade energy.

A system has been conceived comprising a vascular catheter configured with a directed energy emitter and at least one electrode configured for at least one of the following: neural stimulation, neural blockade, carotid body stimulation and carotid body blockade; and a connection between the directed energy emitter to a source of ablation energy, and a connection between the directed energy emitter and/or electrode(s) to a source of stimulation energy and/or blockade energy.

A vascular directed energy ablation catheter has been conceived with a user deflectable segment in the vicinity of the distal end and a non-deflectable segment proximal to the deflectable segment, where the deflection of the distal segment is facilitated by a pull wire within the catheter in communication between the distal segment and a handle containing a deflection actuator at the proximal end, and a directed energy emitter mounted in the vicinity of the distal end, whereby the deflection mechanism is configured to provide the user with a means for orienting the directed energy emitter within or against the wall of a vessel adjacent to a carotid body.

A vascular directed energy ablation catheter has been conceived with a directed energy emitter in the vicinity of the distal end, with an energy transparent balloon encompassing the directed energy emitter, a means to inflate the balloon with an energy transparent fluid, an energy conduit between the directed energy emitter and a source of ablation energy, and a fluid conduit between the interior of the balloon and a balloon inflating means, wherein the vascular catheter is configured for: insertion into the vasculature, positioning of the distal region proximate to a carotid body, inflation of the balloon in the proximate position, and aiming the directed energy emitter in the direction of the carotid body.

A vascular directed energy ablation catheter has been conceived with a directed optical energy emitter in the vicinity of the distal end, with an optically transparent balloon encompassing the directed optical energy emitter, a means to inflate the balloon with an optically transparent fluid, an optical energy conduit between the directed optical energy emitter and a source of optical ablation energy, and a fluid conduit between the interior of the balloon and a balloon inflating means, wherein the vascular catheter is configured for: insertion into the vasculature of a patient, positioning of the distal region proximate to a carotid body, inflation of the balloon in the proximate position, and aiming the directed optical energy emitter in the direction of the carotid body.

A vascular directed energy ablation catheter has been conceived with a directed ultrasonic energy emitter in the vicinity of the distal end, with an ultrasonically transparent balloon encompassing the directed ultrasonic energy emitter, a means to inflate the balloon with an ultrasonically transparent fluid, an ultrasonic energy conduit between the directed ultrasonic energy emitter and a source of ultrasonic ablation energy, and a fluid conduit between the interior of the balloon and a balloon inflating means, wherein the vascular catheter is configured for: insertion into the vasculature of a patient, positioning of the distal region proximate to a carotid body, inflation of the balloon in the proximate position, and aiming the directed ultrasonic energy emitter in the direction of the carotid body.

A method has been conceived for preferential directed energy ablation of a carotid body comprising positioning a directed energy emitter proximate to and oriented towards a carotid body, selecting directed energy ablation parameters configured for substantially selective absorption by a carotid body or its associated nerves, activating the directed energy emitter thereby ablating the function of the carotid body, whereby the selective energy absorption by the carotid body or its associated nerves provides effective carotid body ablation while avoiding damage to adjacent important non-target anatomical structures.

A method has been conceived for preferential directed energy ablation of a carotid body comprising positioning a directed optical energy emitter proximate to and oriented towards a carotid body, selecting directed optical energy ablation parameters comprising green optical energy between 500 nm and 550 nm configured for substantially selective absorption by hemoglobin, activating the directed energy emitter thereby selectively heating the hemoglobin component of blood circulating through the capillary bed surrounding the carotid body to a level sufficient to substantially ablate the function of the carotid body, whereby the selective optical energy absorption by the hemoglobin provides effective carotid body ablation while avoiding damage to adjacent important non-target anatomical structures.

A method has been conceived for preferential directed energy ablation of a carotid body comprising positioning a directed optical energy emitter proximate to and oriented towards a carotid body, selecting directed optical energy ablation parameters comprising red or infrared optical energy between 700 nm and 1100 nm configured for substantially selective absorption by nervous structures, activating the directed energy emitter thereby selectively heating the nerves associated with the carotid body to a level sufficient to substantially ablate the function of the carotid body, whereby the selective optical energy absorption by the nerves provides effective carotid body ablation while avoiding damage to adjacent important non-target anatomical structures.

A method has been conceived for preferential directed energy ablation of a carotid body comprising positioning a directed ultrasonic energy emitter proximate to and oriented towards a carotid body, selecting directed ultrasonic energy ablation parameters comprising ultrasonic energy between 1 mHz and 6 mHz configured for substantially selective absorption by nervous structures, activating the directed energy emitter thereby selectively heating the nerves associated with the carotid body to a level sufficient to substantially ablate the function of the carotid body, whereby the selective ultrasonic energy absorption by the nerves provides effective carotid body ablation while avoiding damage to adjacent important non-target anatomical structures. Alternatively, an energy frequency range of about 10 to about 20 MHz can be chosen to create uniform heating of tissue to the desired depth.

A method has been conceived for preferential directed energy ablation of a carotid body comprising positioning a directed ultrasonic energy emitter proximate to and oriented towards a carotid body, selecting directed ultrasonic energy ablation parameters comprising ultrasonic energy between 500 kHz and 6 mHz configured for substantially selective absorption by fluorocarbon gas bubbles in a size range of 2 to 8 micron diameter, injecting a solution of fluorocarbon gas bubbles into the patient's vasculature in a volume sufficient to make the capillary bed associated with a carotid body substantially ultrasonically opaque, then activating the directed energy emitter upon arrival of the fluorocarbon bubbles within the capillary bed, thereby selectively heating the capillary bed associated with the carotid body to a level sufficient to substantially ablate the function of the carotid body, whereby the selective ultrasonic energy absorption by the fluorocarbon bubbles provides effective carotid body ablation while avoiding damage to adjacent important non-target anatomical structures.

A method has been conceived for ablating the function of a carotid body using an ultrasonic system comprising a multifunctional extracorporeal probe and a display capable of: ultrasonic imaging of the region containing a carotid body, measuring blood flow velocity in the region, overlaying the measured blood flow velocity on the ultrasonic imaging display, ablating tissue in the region using focused ultrasonic ablation energy, and overlaying the focus of the ultrasonic energy on the imaging display, with the method comprising the steps of placing the extracorporeal probe on the neck of the patient, using the ultrasonic imaging and Doppler flow velocity information to focus the ultrasonic ablation energy on the location of a carotid body, then injecting a solution into the patient's vasculature comprising micro bubbles, then activating the focused ultrasonic ablation energy upon arrival of the micro bubbles in the capillary bed surrounding the carotid body, whereby the micro bubbles absorb the ultrasonic energy resulting in an elevation in temperature of the capillary bed sufficient to substantially ablate the function of the carotid body while leaving adjacent important non-target anatomical structures unaffected.

A system for endovascular directed energy ablation of a carotid body has been conceived comprising an endovascular catheter with a directed energy emitter mounted in the vicinity of the distal end, a means for positioning the directed energy emitter at a specific location, a means for providing the user with a substantially unambiguous fluoroscopic determination of the position of the directed energy emitter, a means for connecting the directed energy emitter to a source of ablation energy mounted in the vicinity of the proximal end, and a console comprising a source of ablation energy, a means for controlling the ablation energy, a user interface configured to provide the user with a selection of directed energy ablation parameters, indications of the status of the console and the status of the directed energy ablation activity, a means to activate and deactivate a directed energy ablation, and an umbilical to provide a means for connecting the catheter to the console.

A method has been conceived to reduce or inhibit chemoreflex function generated by a carotid body in a human patient, to reduce afferent nerve sympathetic activity of carotid body nerves to treat a sympathetically mediated disease, the method comprising: positioning a catheter comprising a directed energy emitter in the vicinity of the distal end in a vascular system of the patient such that a distal section of the catheter is in a lumen proximate to the carotid body of the patient; positioning the directed energy emitter within a vascular lumen adjacent to the carotid body, orienting to the directed energy emitter towards the carotid body; activating the directed energy emitter to ablate tissue proximate to or included in the carotid body; and removing the directed energy ablation device from the patient; wherein a carotid body chemoreflex function is inhibited or sympathetic afferent nerve activity of carotid body nerves is reduced due to the ablation.

The disclosure also includes methods, devices, and systems for ablating a target site (e.g., a carotid body, a portion of a carotid body, one or more carotid body nerves, and an intercarotid septum) by positioning an ablation needle within a lumen of a vein adjacent to the target site, inserting the needle through the vein and into perivascular space containing the target site, delivering an ablation agent into the perivascular space by using the needle, and withdrawing the needle from the perivascular space back into the vein.

In some embodiments a location of perivascular space associated with the target site (e.g., a carotid body, portion of a carotid body, carotid body nerves, intercarotid septum) is identified.

In some embodiments electrosurgical current is provided at the tip of the needle to facilitate insertion, and heat is applied to the needle tract prior to withdrawal to prevent bleeding.

In some embodiments ablation parameters are selected, and an ablation needle is placed into a lumen of a vein in proximity of the target site, then the needle is inserted into the perivascular space containing the target site, then an ablation agent is delivered into the perivascular space by means of the needle, then the needle is withdrawn from the perivascular space back into the vein, whereby the position of the ablation needle within the perivascular space and selection of ablation parameters provides for ablation of the target site without substantial collateral damage to adjacent functional structures.

A location of perivascular space associated with a target site (e.g., a carotid body, portion of a carotid body, carotid body nerves, intercarotid septum) is identified, as well as the location of important non-target structures not associated with the target site, and ablation parameters are selected, then an ablation needle is placed into a lumen of a vein in proximity of the target site, then the needle is inserted into the perivascular space containing the target site, then an ablation agent is delivered into the perivascular space by means of the needle, then the needle is withdrawn from the perivascular space back into the vein, whereby position of the ablation needle within the perivascular space and selection of ablation parameters provides for ablation of the target site without substantial collateral damage to adjacent functional structures.

Ablation agents for needle delivery into perivascular space comprising a carotid body may include chemicals selected for thrombogenic properties, chemicals selected for sympathetic neural toxicity, chemicals selected for glomus cell toxicity, tissue heating energies including radiofrequency energy, microwave energy, ultrasonic energy, laser energy, and resistive element heating.

Selectable carotid body ablation parameters include ablation needle temperature, duration of ablation agent delivery, ablation energy power, ablation needle position within perivascular space, ablation needle size, type of ablation agent delivered, volume of ablation agent delivered, and ablation needle insertion tract.

A location of perivascular space associated with a target site (e.g., a carotid body, portion of a carotid body, carotid body nerves, intercarotid septum) may be determined by means of a non-fluoroscopic imaging procedure (e.g., CTA, DSA, MRI, sonography) prior to carotid body ablation, where non-fluoroscopic location information is translated to a coordinate system based on fluoroscopically identifiable anatomical and/or artificial landmarks.

An angiographic catheter is placed into a proximal common carotid artery, then a fluoroscopic contrast agent in injected into the proximal common carotid through the catheter and a fluoroscopic image of a vicinity of a carotid bifurcation is recorded in at least one plane, whereby the recorded image is subsequently used to guide insertion of a needle into perivascular space associated with a target site (e.g., a carotid body, portion of a carotid body, carotid body nerves, intercarotid septum).

A function of a carotid body is stimulated and at least one physiological parameter is recorded prior to and during the stimulation, then a target site (e.g., a carotid body, portion of a carotid body, carotid body nerves, intercarotid septum) associated with the stimulated carotid body is ablated, and stimulation is repeated, whereby a change in recorded physiological parameter(s) prior to and after ablation is an indication of effectiveness of the ablation.

A function of a carotid body is blocked and at least one physiological parameter(s) is recorded prior to and during the blockade, then a target site (e.g., a carotid body, portion of a carotid body, carotid body nerves, intercarotid septum) associated with the blocked carotid body is ablated, and the blockade is repeated, whereby a change in recorded physiological parameter(s) prior to and after ablation is an indication of effectiveness of the ablation.

A location of perivascular space associated with a target site (e.g., a carotid body, portion of a carotid body, carotid body nerves, intercarotid septum) is identified, then an ablation needle is inserted into a predetermined location within the perivascular space from a vein, then ablation parameters are selected and an ablation agent is delivered into the perivascular space with the needle in accordance with the selected parameters, the ablation needle is then withdrawn into the vein and then reinserted into perivascular space in at least one additional predetermined location, then an ablation agent is delivered using the same or different ablation parameters, whereby the positions of the ablation needle within the perivascular space and the selection of ablation parameters provides for ablation of the target site without substantial collateral damage to adjacent functional structures.

A catheter device is configured with an ablation needle in vicinity of a distal end, and a means to connect the ablation needle to a source of an ablation agent at a proximal end, whereby the distal end of the catheter is constructed to be inserted into a peripheral vein of a patient and then maneuvered into a vein proximate to a carotid artery using standard fluoroscopic guidance techniques.

A carotid artery catheter is configured with an ablation needle in vicinity of a distal end configured for carotid body ablation and further configured for at least one of the following: neural stimulation, neural blockade, carotid body stimulation and carotid body blockade; and a means to connect the ablation needle to a source of an ablation agent, stimulation agent and/or blockade agent located in vicinity of a proximal end.

Stimulation agents include chemicals that stimulate nerves, chemicals that stimulate carotid body function, electrical energy configured for nerve stimulation, and electrical energy configured for carotid body stimulation.

Blockade agents include chemicals that blockade nerve function, chemicals that blockade carotid body function, electrical energy configured for blockade of nerve function, and electrical energy configured for blockade of carotid body function.

A venous catheter configured with an ablation needle in vicinity of a distal end is inserted into a peripheral vein of a patient and then maneuvered into a neck vein (e.g., internal jugular vein, facial vein, etc.) at the level of the perivascular space associated with a carotid body, then a wall of the vein is deformed by the catheter in a manner that facilitates needle insertion into the perivascular space while avoiding important non-target anatomical structures.

A venous catheter is configured with an ablation needle and at least one electrode configured for at least one of the following: neural stimulation, neural blockade, carotid body stimulation, and carotid body blockade at the distal end; and at the proximal end a means for connecting the ablation needle to a source of an ablation agent, and a means for connecting the ablation needle and/or electrode(s) to a source of stimulation energy and/or blockade energy.

A venous catheter is configured with an ablation needle, configured for insertion into perivascular space associated with a target site (e.g., a carotid body, portion of a carotid body, carotid body nerves, intercarotid septum) in a substantially normal angle to a wall of a vein.

A venous catheter is configured with an ablation needle in vicinity of a distal end, a mechanism configured to apply radial elongation of a vein, and a shaft configured to transmit torque from a vicinity of a proximal end to the vicinity of the distal end of the catheter.

A venous catheter is configured with an ablation needle in vicinity of a distal end, a mechanism configured to apply radial elongation of a vein, and a shaft configured to transmit torque from a vicinity of a proximal end to the vicinity of the distal end of the catheter, at least a single axis ultrasound imaging transducer configured to guide insertion of the needle into perivascular space associated with a target site (e.g., a carotid body, portion of a carotid body, carotid body nerves, intercarotid septum), a connection between the ablation needle and an ablation agent source, and a connection between the ultrasonic imaging transducer(s) and an ultrasonic imaging console.

A system comprising a venous catheter with an ablation needle mounted in vicinity of a distal end configured for tissue heating, whereby, the ablation needle comprises at least one ablation electrode and at least one temperature sensor, and a means for connecting the ablation needle electrode(s) and temperature sensor(s) to an ablation energy source mounted in vicinity of a proximal end, with the ablation energy source being configured to maintain the ablation needle electrode at a temperature in the range of 40 to 100 degrees centigrade during ablation using signals received from the temperature sensor(s).

A system comprising a venous catheter with an ablation element needle in vicinity of a distal end configured for tissue heating, whereby, the ablation needle comprises at least one ablation electrode and at least one temperature sensor and at least one irrigation channel, and a means for connecting the ablation needle electrode(s) and temperature sensor(s) and irrigation channel(s) to an ablation energy source mounted in vicinity of a proximal end, with the ablation energy source being configured to maintain the ablation needle electrode at a temperature in the range of 40 to 100 degrees centigrade during ablation using signals received from the temperature sensor(s) and by providing irrigation to the vicinity of the ablation needle electrode.

A venous catheter comprising an inner sheath configured to house an ablation needle assembly, and an outer sheath configured to house the inner sheath in a slidable manner, a fenestration in the outer sheath in vicinity of a distal end, and a hinge mechanism between the inner sheath and the outer sheath in the vicinity of the distal end, an actuator in vicinity of a proximal end configured to slide the inner sheath within the outer sheath, whereby when the inner sheath is slid in a distal direction the hinge mechanism and the configuration of the fenestration causes the inner sheath to mechanically buckle through the fenestration in the outer sheath causing a deformation in a wall of a vein, whereby the deformation facilitates needle insertion into a perivascular space associated with a target site (e.g., a carotid body, portion of a carotid body, carotid body nerves, intercarotid septum).

A venous catheter with a structure configured for user actuated radial expansion in vicinity of a distal end, a radiopaque ablation needle mounted on one side of the structure and at least one radiopaque element mounted on an opposite side of the structure, whereby the structure provides the user with a means for positioning the ablation needle for insertion into perivascular space comprising a target site (e.g., a carotid body, portion of a carotid body, carotid body nerves, intercarotid septum), where a combination of the radiopaque ablation needle and the radiopaque element provide the user with a substantially unambiguous fluoroscopic determination of the location of the ablation needle within the vein or the perivascular space.

A system for trans-venous interstitial ablation of a carotid body comprising a venous catheter with an ablation needle mounted in vicinity of a distal end, a means for positioning the ablation needle within a vein at a specific location, a means to provide a user with a substantially unambiguous fluoroscopic determination of the location of the ablation needle within the vein, a means for inserting the ablation needle into a perivascular space comprising a target site (e.g., a carotid body, portion of a carotid body, carotid body nerves, intercarotid septum) to predetermined depth, a means for connecting the ablation needle to a source of an ablation agent mounted in vicinity of a proximal end, and a console comprising a source of an ablation agent, a means for controlling delivery of the ablation agent, a user interface configured to provide the user with a selection of ablation parameters, indications of a status of the console and a status of ablation activity, a means to activate and deactivate an ablation, and an umbilical to provide a means for connecting the catheter to the console. The methods and systems disclosed herein may be applied to satisfy clinical needs related to treating cardiac, metabolic, and pulmonary diseases associated, at least in part, with enhanced or augmented chemoreflex (e.g., high chemosensor sensitivity or high chemosensor activity) and related sympathetic activation. The treatments disclosed herein may be used to restore autonomic balance by reducing sympathetic activity, as opposed to increasing parasympathetic activity. It is understood that parasympathetic activity can increase as a result of the reduction of sympathetic activity (e.g., sympathetic withdrawal) and normalization of autonomic balance. Furthermore, the treatments may be used to reduce sympathetic activity by modulating a peripheral chemoreflex. Furthermore, the treatments may be used to reduce afferent neural stimulus, conducted via afferent carotid body nerves, from a carotid body to the central nervous system. Enhanced peripheral and central chemoreflex is implicated in several pathologies including hypertension, cardiac tachyarrhythmias, sleep apnea, dyspnea, chronic obstructive pulmonary disease (COPD), diabetes and insulin resistance, and CHF. Mechanisms by which these diseases progress may be different, but they may commonly include contribution from increased afferent neural signals from a carotid body. Central sympathetic nervous system activation is common to all these progressive and debilitating diseases. Peripheral chemoreflex may be modulated, for example, by modulating carotid body activity. The carotid body is the sensing element of the afferent limb of the peripheral chemoreflex. Carotid body activity may be modulated, for example, by ablating a carotid body or afferent nerves emerging from the carotid body. Such nerves can be found in a carotid body itself, in a carotid plexus, in an intercarotid septum, in periarterial space of a carotid bifurcation and internal and external carotid arteries, and internal jugular vein, or facial vein. Therefore, a therapeutic method has been conceived that comprises a goal of restoring or partially restoring autonomic balance by reducing or removing carotid body input into the central nervous system.

BRIEF DESCRIPTION OF THE DRAWINGS

FIGS. 4A and 4B depict a distal end of an axial directed optical energy ablation device.

FIGS. 17A, 17B, and 17C depict a steerable axial directed ultrasonic energy ablation catheter for ablation of a carotid body from within an internal jugular vein.

FIGS. 28A, 28B, 28C, 28D are schematic illustrations of ultrasound ablation catheters configured to position an emitter in an external carotid artery while avoiding contact with a vessel wall.

FIGS. 31A, 31B, 32A, 32B, 33A, 33B, 33C, 34A, 34B, 34C, and 34D are schematic illustrations of an ultrasound CBA catheter having one or more diagnostic catheters used to align with vascular landmarks delivered to an internal jugular vein.

FIGS. 44A and 44B are schematic illustrations of an RF ablation needle assembly.

FIG. 46A depicts the TVICBA catheter residing in an internal jugular vein prior to outer sheath retraction. FIG. 46B depicts the TVICBA catheter with the ablation needle deployed, and forces exerted by the TVICBA catheter of the internal jugular vein to provide in-line needle access to the carotid body.

DETAILED DESCRIPTION

Figure 1:
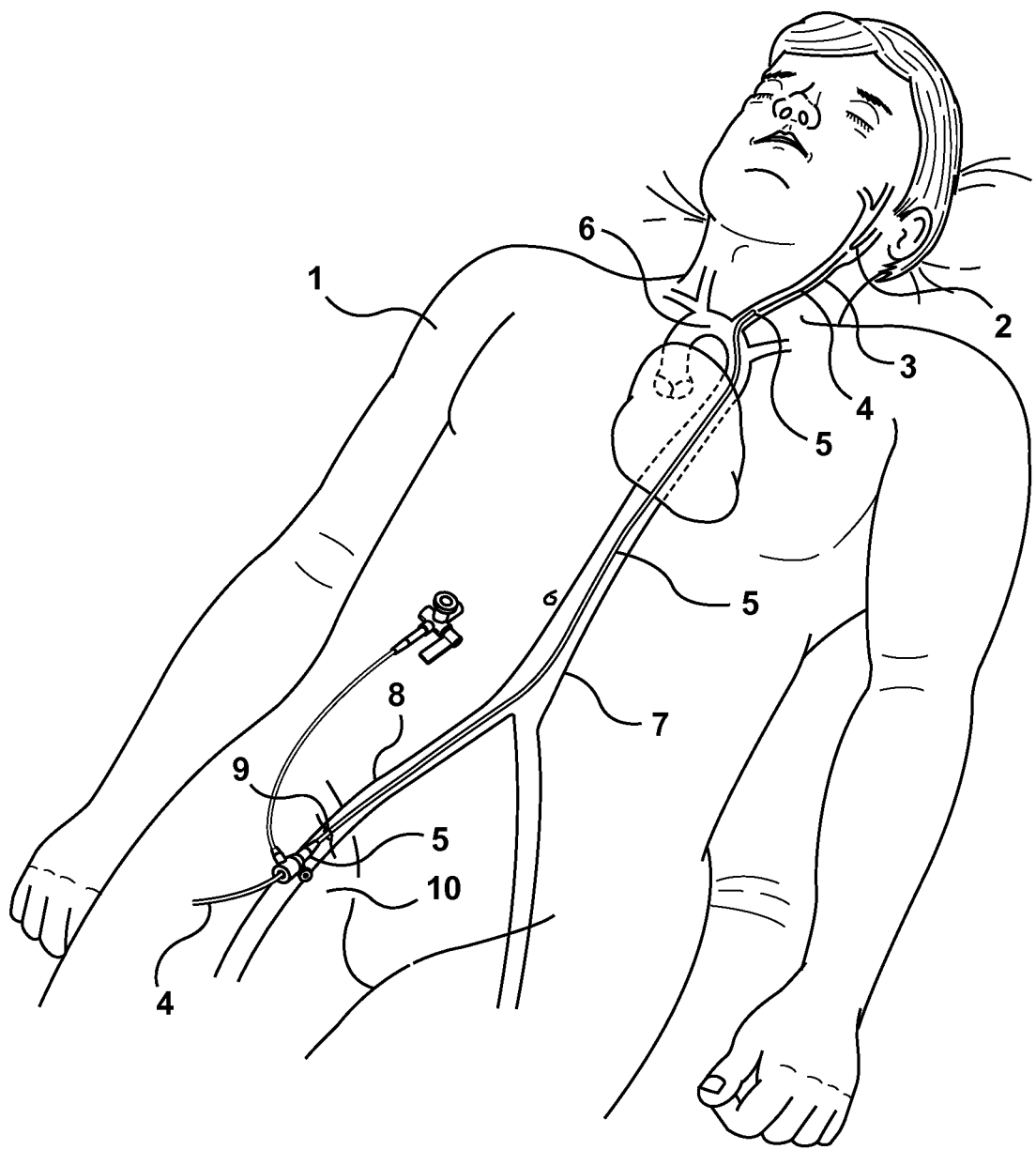
FIG. 1 depicts in simplified form a placement of a carotid access sheath into a patient.

The disclosure herein is related to systems, devices, and methods for carotid body ablation to treat patients having a sympathetically mediated disease (e.g., cardiac, renal, metabolic, or pulmonary disease such as hypertension, CHF, sleep apnea, sleep disordered breathing, diabetes, insulin resistance) at least partially resulting from augmented peripheral chemoreflex (e.g., peripheral chemoreceptor hypersensitivity, peripheral chemosensor hyperactivity) or heightened sympathetic activation. Carotid body ablation as used herein refers generally to completely or partially ablating one or both carotid bodies, carotid body nerves, intercarotid septums, or peripheral chemoreceptors. A main therapy pathway is a reduction of peripheral chemoreflex or reduction of afferent nerve signaling from a carotid body (CB), which results in a reduction of central sympathetic tone. Higher than normal chronic or intermittent activity of afferent carotid body nerves is considered enhanced chemoreflex for the purpose of this application regardless of its cause. Other important benefits such as increase of parasympathetic tone, vagal tone and specifically baroreflex and baroreceptor activity reduction of dyspnea, hyperventilation and breathing rate may be expected in some patients. Secondary to reduction of breathing rate additional increase of parasympathetic tone may be expected in some cases. Augmented peripheral chemoreflex (e.g., carotid body activation) leads to increases in sympathetic nervous system activity, which is in turn primarily responsible for the progression of chronic disease as well as debilitating symptoms and adverse events seen in the intended patient populations. Carotid bodies contain cells that are sensitive to oxygen and carbon dioxide. Carotid bodies also respond to blood flow, pH acidity, blood glucose level and possibly other variables. Thus carotid body ablation may be a treatment for patients, for example having hypertension, heart disease or diabetes, even if chemosensitive cells are not activated.

Targets:

To inhibit or suppress a peripheral chemoreflex, anatomical targets for ablation (also referred to as targeted tissue, target ablation sites, or target sites) may include at least a portion of at least one carotid body, an aortic body, nerves associated with a peripheral chemoreceptor (e.g., carotid body nerves, carotid sinus nerve, carotid plexus), small blood vessels feeding a peripheral chemoreceptor, carotid body parenchyma, chemosensitive cells (e.g., glomus cells), tissue in a location where a carotid body is suspected to reside (e.g., a location based on pre-operative imaging or anatomical likelihood), an intercarotid septum, a portion of an intercarotid septum, a substantial part of an intercarotid septum or a combination thereof. As used herein, ablation of a carotid body may refer to ablation of any of these target ablation sites.

An intercarotid septum, which is also referred to herein as a carotid septum, is herein defined as a wedge or triangular segment of tissue with the following boundaries: a saddle of a carotid bifurcation defines a caudal aspect (i.e., an apex) of a carotid septum; facing walls of internal and external carotid arteries define two sides of the carotid septum; a cranial boundary of a carotid septum extends between these arteries and may be defined as cranial to a carotid body but caudal to any important non-target nerve structures (e.g., a hypoglossal nerve) that might be in the region, for example a cranial boundary may be about 10 mm to about 15 mm from the saddle of the carotid bifurcation; medial and lateral walls of the carotid septum are generally defined by planes approximately tangent to the internal and external carotid arteries; one of the planes is tangent to the lateral walls of the internal and external carotid arteries and the other plane is tangent to the medial walls of these arteries. An intercarotid septum is disposed between the medial and lateral walls. An intercarotid septum may contain, completely or partially, a carotid body and may be absent of important non-target structures such as a vagus nerve or sympathetic nerves or a hypoglossal nerve. An intercarotid septum may include some baroreceptors or baroreceptor nerves. An intercarotid septum may also include intercarotid plexus nerves, small blood vessels and fat.

Carotid body nerves are anatomically defined herein as carotid plexus nerves and carotid sinus nerves. Carotid body nerves are functionally defined herein as nerves that conduct information from a carotid body to a central nervous system. Carotid body nerves can be referred to herein as one or more nerves that are associated with the carotid body.

An ablation may be focused exclusively on targeted tissue, or be focused on the targeted tissue while safely ablating tissue proximate to the targeted tissue (e.g., to ensure the targeted tissue is ablated or as an approach to gain access to the targeted tissue). An ablation region may be as big as a peripheral chemoreceptor (e.g., carotid body or aortic body) itself, somewhat smaller, or bigger and can include one or more tissues surrounding the chemoreceptor such as blood vessels, adventitia, fascia, small blood vessels perfusing the chemoreceptor, and nerves connected to and innervating the glomus cells. An intercarotid plexus or carotid sinus nerve may be a target of ablation with an understanding that some baroreceptor nerves will be ablated together with carotid body nerves. Baroreceptors are distributed in the human arteries and have a high degree of redundancy.

Tissue may be ablated to inhibit or suppress a chemoreflex of only one of a patient's two carotid bodies. Other embodiments include ablating tissue to inhibit or suppress a chemoreflex of both of a patient's carotid bodies. In some embodiments an ablation is performed on a first carotid body, and an assessment is then performed to determine if the other carotid body should be ablated. For example, a therapeutic method may include ablation of one carotid body, measurement of resulting chemosensitivity, sympathetic activity, respiration or other parameter related to carotid body hyperactivity, and ablation of the second carotid body can be performed if desired to further reduce chemosensitivity following the unilateral ablation.

An embodiment of a therapy may substantially reduce chemoreflex without excessively reducing the baroreflex of the patient. The proposed ablation procedure may be targeted to substantially spare the carotid sinus, baroreceptors distributed in the walls of carotid arteries, particularly internal carotid arteries, and at least some of the carotid sinus nerves that conduct signals from said baroreceptors. For example, the baroreflex may be substantially spared by targeting a limited volume of ablated tissue possibly enclosing the carotid body, tissues containing a substantial number of carotid body nerves, tissues located in periadventitial space of a medial segment of a carotid bifurcation, or tissue located at the attachment of a carotid body to an artery. Said targeted ablation is enabled by visualization of the area or carotid body itself, for example by CT, CT angiography, MRI, ultrasound sonography, fluoroscopy, blood flow visualization, or injection of contrast, and positioning of an instrument in the carotid body or in close proximity while avoiding excessive damage (e.g., perforation, stenosis, thrombosis) to carotid arteries, baroreceptors, carotid sinus nerves or other important non-target nerves such as a vagus nerve or sympathetic nerves located primarily outside of the carotid septum. Thus imaging a carotid body before ablation may be instrumental in (a) selecting candidates if a carotid body is present, large enough and identified and (b) guiding therapy by providing a landmark map for an operator to guide an ablation instrument to the carotid septum, center of the carotid septum, carotid body nerves, the area of a blood vessel proximate to a carotid body, or to an area where carotid body itself or carotid body nerves may be anticipated. It may also help exclude patients in whom the carotid body is located substantially outside of the carotid septum in a position close to a vagus nerve, hypoglossal nerve, jugular vein or some other structure that can be endangered by ablation. In one embodiment only patients with a carotid body substantially located within the intercarotid septum are selected for ablation therapy.

Once a carotid body is ablated, removed or denervated, the carotid body function (e.g., carotid body chemoreflex) does not substantially return in humans, partly because in humans aortic chemoreceptors are considered undeveloped. To the contrary, once a carotid sinus baroreflex is removed it is generally compensated, after weeks or months, by the aortic or other arterial baroreceptor baroreflex. Thus, if both the carotid chemoreflex and baroreflex are removed or substantially reduced, for example by interruption of the carotid sinus nerve or intercarotid plexus nerves, the baroreflex may eventually be restored while the chemoreflex may not. The consequences of temporary removal or reduction of the baroreflex can be in some cases relatively severe and require hospitalization and management with drugs, but they generally are not life threatening, terminal or permanent. Thus, it is understood that while selective removal of carotid body chemoreflex with baroreflex preservation may be desired, it may not be absolutely necessary in some cases.

Ablation:

The term "ablation" may refer to the act of altering a tissue to suppress or inhibit its biological function or ability to respond to stimulation permanently or for an extended period of time (e.g., greater than 3 weeks, greater than 6 months, greater than a year, for several years, or for the remainder of the patient's life). Selective denervation may involve, for example, interruption of afferent nerves from a carotid body while substantially preserving nerves from a carotid sinus, which conduct baroreceptor signals, and other adjacent nerves such as hypoglossal, laryngeal, and vagal nerves. Another example of selective denervation may involve interruption of a carotid sinus nerve, or intercarotid plexus which is in communication with both a carotid body and some baroreceptors wherein chemoreflex from the carotid body is reduced permanently or for an extended period of time (e.g., years) and baroreflex is substantially restored in a short period of time (e.g., days or weeks). As used herein, the term "ablate" or a derivative thereof refers to interventions that suppress or inhibit natural chemoreceptor or afferent nerve functioning, which is in contrast to electrically neuromodulating or reversibly deactivating and reactivating chemoreceptor functioning.

Carotid Body Ablation ("CBA") as used herein refers to ablation of a target tissue wherein the desired effect is to reduce or remove the afferent neural signaling from a chemosensor (e.g., carotid body) or reducing a chemoreflex. Chemoreflex or afferent nerve activity cannot be directly measured in a practical way, thus indices of chemoreflex such as chemosensitivity can sometimes be used instead. Chemoreflex reduction is generally indicated by a reduction of blood pressure, a reduction of an increase of ventilation and ventilation effort per unit of blood gas concentration, saturation or partial pressure change or by a reduction of central sympathetic nerve activity that can be measured indirectly. Sympathetic nerve activity can be assessed by reduction of blood pressure, measuring activity of peripheral nerves leading to muscles (MSNA), heart rate (HR), heart rate variability (HRV), production of hormones such as renin, epinephrine and angiotensin, and peripheral vascular resistance. All these parameters are measurable and can lead directly to the health improvements. In the case of CHF, a patient's blood pH, blood $PCO_2$, degree of hyperventilation and metabolic exercise test parameters such as peak $VO_2$, and $VE/VCO_2$ slope are also important. It is believed that patients with heightened chemoreflex have low $VO_2$ and high $VE/VCO_2$ slope (index of respiratory efficiency) as a result of, for example, tachypnea and low blood $CO_2$. These parameters are also related to exercise limitations that further speed up a patient's status deterioration towards morbidity and death. It is understood that all these indices are indirect and imperfect and intended to direct therapy to patients that are most likely to benefit or to acquire an indication of technical success of ablation rather than to prove an exact measurement of effect or guarantee a success. It has been observed that some tachyarrhythmias in cardiac patients are sympathetically mediated. Thus carotid body ablation may be instrumental in treating reversible atrial fibrillation and ventricular tachycardia.

Carotid body ablation may include methods and systems for the thermal ablation of tissue via thermal heating or cooling mechanisms. Thermal ablation may be achieved due to a direct effect on tissues and structures that are induced by the thermal stress. Additionally or alternatively, the thermal disruption may at least in part be due to alteration of vascular or perivascular structures (e.g., arteries, arterioles, capillaries or veins), which perfuse the carotid body and neural fibers surrounding and innervating the carotid body (e.g., nerves that transmit afferent information from carotid body chemoreceptors to the brain). Additionally or alternatively thermal disruption may be due to a healing process, fibrosis, or scarring of tissue following thermal injury, particularly when prevention of regrowth and regeneration of active tissue is desired. As used herein, thermal mechanisms for ablation may include both thermal necrosis or thermal injury or damage (e.g., via sustained heating, convective heating, resistive heating, or any combination thereof). Thermal heating mechanisms may include raising the temperature of target tissue, such as neural fibers, chemosensitive cells, all or a substantial number of carotid body cells, and small blood vessels perfusing the carotid body or its nerves, above a desired threshold, for example, above a body temperature of about 37° C. e.g., to achieve thermal injury or damage, or above a temperature of about 45° C. (e.g., above about 60° C.) to achieve thermal necrosis for a duration of time known to induce substantially irreversible ablation at the resulting temperature. Thermal-cooling mechanisms for ablation may include reducing the temperature of target neural fibers below a desired threshold (e.g., to achieve freezing thermal injury). It is generally accepted that temperatures below −40° C. applied over a minute or two results in irreversible necrosis of tissue and scar formation. It is recognized that tissue ablation by cold involves mechanisms of necrosis and apoptosis. At a low cooling rate freeze, tissue is destroyed by cellular dehydration and at high cooling rate freeze by intracellular ice formation and lethal rupture of plasma membrane.

In addition to raising or lowering temperature during thermal ablation, a length of exposure to thermal stimuli may be specified to affect an extent or degree of efficacy of the thermal ablation. In some embodiments the length of exposure to thermal stimuli is between about 1 and about 60 seconds, such as between about 5 and about 30 seconds. In some embodiments the length of exposure to thermal stimuli can be, longer than or equal to about 30 seconds, or even longer than or equal to about 2 minutes. Furthermore, the length of exposure can be less than or equal to about 10 minutes, though this should not be construed as the upper limit of the exposure period. A temperature threshold, or thermal dosage, may be determined as a function of the duration of exposure to thermal stimuli. Additionally or alternatively, the length of exposure may be determined as a function of the desired temperature threshold. These and other parameters may be specified or calculated to achieve and control desired thermal ablation. In some embodiments, ablation of carotid body or carotid body nerves may be achieved via direct application of ablative energy to target tissue. For example, an ablation element may be applied at least proximate to the target, or an ablation element may be placed in a vicinity of a chemosensor (e.g., carotid body). In other embodiments, thermally-induced ablation may be achieved via indirect generation or application of thermal energy to the target tissue, such as neural fibers, chemosensitive cells, and all or a substantial number of carotid body cells, such as through application of an electric field (e.g., radiofrequency, alternating current, and direct current), high-intensity focused ultrasound (HIFU), partially focused ultrasound, directed ultrasound, laser irradiation, or microwave radiation, to the target neural fibers. For example, thermally induced ablation may be achieved via delivery of a pulsed or continuous thermal electric field to the target tissue such as alternating current and in some embodiments alternated current in RF frequency range and pulsed RF, the electric field being of sufficient magnitude or duration to thermally induce ablation of the target tissue (e.g., to heat or thermally ablate or cause necrosis of the targeted tissue). Additional and alternative methods and apparatuses may be utilized to achieve ablation, as described hereinafter.

Directed Energy Embodiments

FIG. 1 depicts in simplified schematic form the placement of a carotid access sheath 5 into a patient 1. The sheath is depicted in position for insertion of an endovascular directed energy ablation catheter 4 into the vicinity of the left carotid artery bifurcation 2 through the central lumen of the carotid access sheath 5. The distal end of the sheath is shown residing in the left common carotid artery 3. The proximal end of the sheath 5 is shown residing outside of the patient 1, with the sheath's entry point into the patient 9 being in the vicinity of the groin 10. From the sheath's entry point 9, the sheath enters a peripheral artery 8, and traverses the abdominal aorta 7, the aortic arch 6, and into the left common carotid artery 3. The carotid access sheath 5 may be commercially available, or may be configured specifically for endovascular directed energy ablation of a carotid body. Techniques for placing a carotid access sheath 5 into position as depicted are known to those skilled in the art of endovascular carotid procedures.

Figure 2:
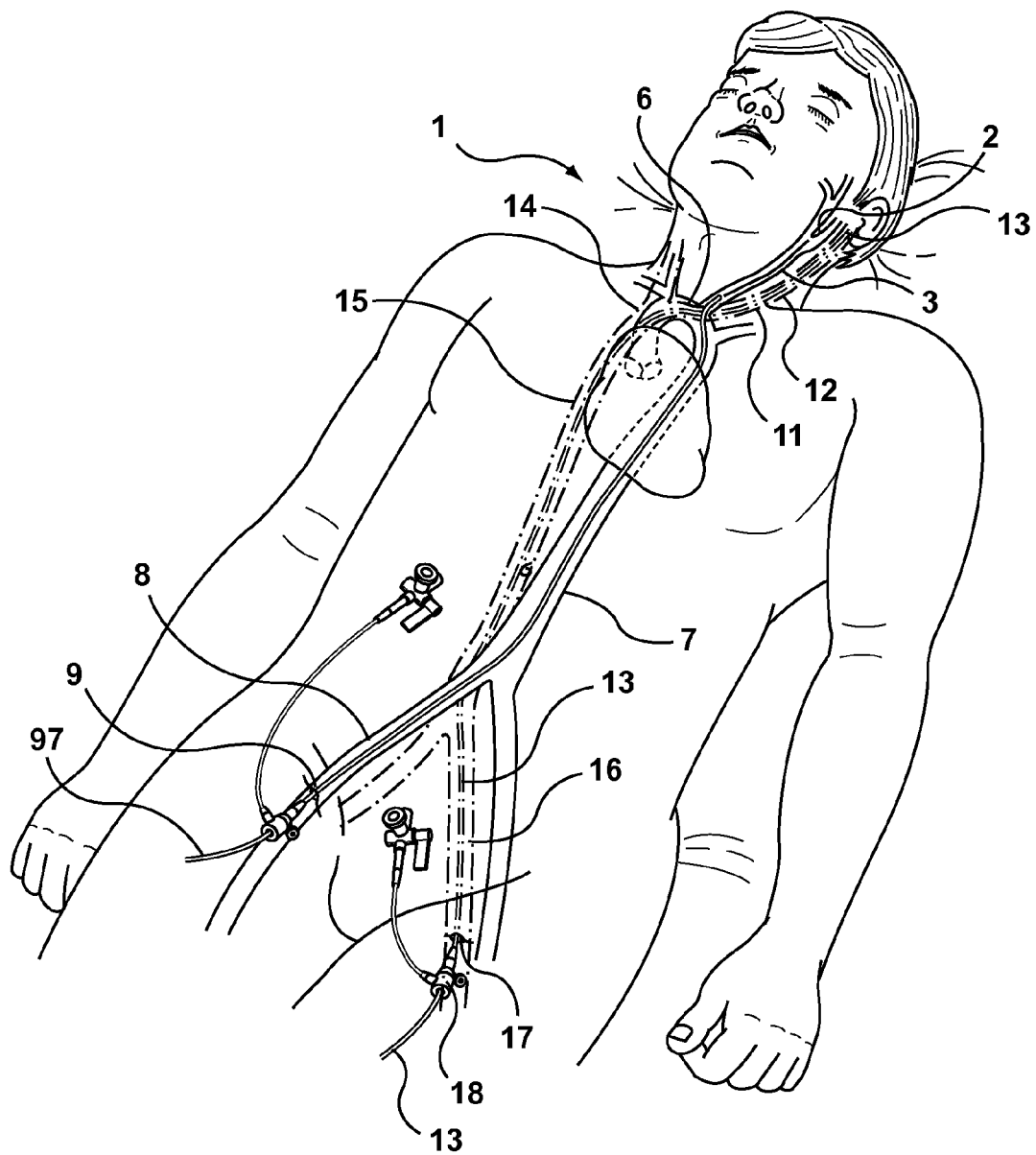
FIG. 2 depicts in simplified schematic form a placement of an endovascular directed energy ablation catheter into a patient via a femoral vein puncture.

FIG. 2 depicts in simplified schematic form an alternative embodiment of a placement of an endovascular directed energy ablation catheter 13 into a patient 1 via an endovascular approach with a femoral vein puncture 17. The distal end of the endovascular directed energy ablation catheter 13 (shown in phantom) is depicted in the left internal jugular vein 12 (shown in phantom) at the level of the left carotid artery bifurcation 2 positioned for directed energy ablation of a carotid artery. As depicted the endovascular directed energy ablation catheter 13 is inserted into the patient at insertion site 17 in the vicinity of the groin into a femoral vein 16 and advanced through the inferior vena cava 15, superior vena cava 14, left common jugular vein 11 and into the left internal jugular vein 12. Alternatively, the insertion site may be selected to gain venous access through a brachial vein, a subclavian vein, a common jugular vein 11, or any suitable peripheral vein. Furthermore, the distal end of the endovascular directed energy ablation catheter 13 may be positioned for carotid body ablation in other than the internal jugular vein 12 or one of its tributaries (e.g., a facial vein, not shown) depending on the particular vascular and neural anatomy of patient 1. Also depicted is an optional angiographic catheter 97 positioned in the common carotid artery 3 for the purpose of creating an arterial angiographic image of the region of the carotid bifurcation 2 to allow for visualization of the region and for guiding directed energy ablation of the carotid body from the internal jugular vein 12. As depicted, angiographic catheter 97 is inserted into a femoral artery 8 through insertion site 9 in the groin, then advanced through the abdominal aorta 7, the aortic arch 6 and into the left common carotid artery 3 using standard angiographic techniques. It would be understood to those skilled in the art of endovascular interventions that means other than carotid artery angiography may be used to guide trans-venous directed energy ablation of a carotid body. For example, extracorporeal ultrasonic imaging of the neck may be used, as well as intra-vascular ultrasound, computed tomography angiography, and other known modalities alone or in combination. It should also be understood that while FIGS. 1 and 2 illustrates a left-side carotid body ablation, a right side carotid artery ablation or bilateral carotid artery ablations can be carried out in any of the embodiments herein.

Figure 3:
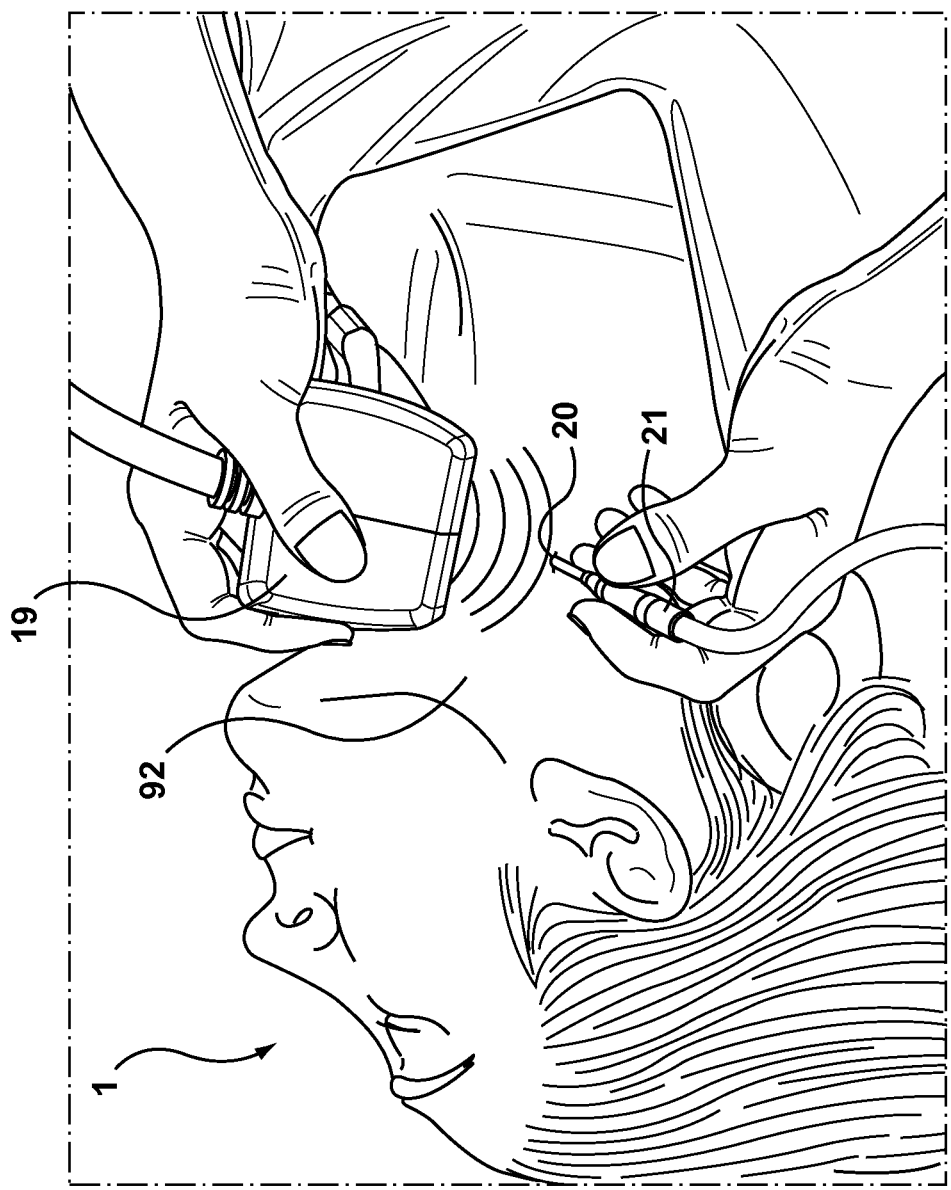
FIG. 3 is an illustration of a procedure for direct percutaneous access to a region comprising a carotid body for the purpose of directed energy carotid body ablation.

FIG. 3 is an illustration of an exemplary procedure for percutaneous access to the target carotid body directed energy ablation zone showing an extracorporeal ultrasonic imaging transducer 19 guiding the insertion of percutaneous directed energy ablation probe 21 through insertion location 20 in the neck 92 of patient 1.

Sonography can be instrumental in guiding both percutaneous and endovascular procedures. Sonography can be performed from the surface of the skin, such as the neck, from inside the vasculature, or from a natural orifice such as the esophagus.

A trans-esophageal sonography can be used as an alternative way to perform sonographic imaging of carotid arteries, a carotid septum, and ablation instruments. A specialized probe containing an ultrasound transducer at its tip can be passed into the patient's esophagus. This allows image and Doppler evaluation which can be recorded or used in real-time to guide placement of percutaneous or endovascular instruments and ablation of carotid body.

An exemplary advantage of trans-esophageal sonography may be clearer images, especially of structures that are difficult to view through the skin and muscles of the neck. This can largely be due to the close proximity of the carotid bifurcation and esophagus, leaving only tens of millimeters that the ultrasound beam has to travel. This reduces the attenuation of the ultrasound signal, generating a stronger return signal, ultimately enhancing image and Doppler quality. Comparatively, external ultrasound must first traverse skin, fat, and muscle layers before reflecting off the carotids and back to the probe before an image can be created. All these structures, along with the increased distance the beam must travel, may weaken the ultrasound signal thus degrading the image and Doppler quality.

A directed energy device as used herein refers to an elongate device with an energy emitter configured to emit energy, and wherein the device is configured to deliver directed energy into target tissue. In some embodiments the device includes a directed energy emitter, or transducer, which can be in a distal region of the device. In some embodiments the device includes an energy emitter, and the catheter is configured to direct the energy into target tissue. In methods of use, the device can be positioned in a patient's body proximate to a peripheral chemosensor (e.g., carotid body) and/or an associated nerve(s) of the patient. The energy emitter is then activated and directed energy is delivered to the target tissue, ablating the target tissue, such as a carotid body. As used herein, "directed energy" generally refers to energy that is directed into tissue in a general direction relative to and by the elongate directed energy device, rather than energy that is delivered into tissue in all directions, circumferentially, or in multiple directions relative to the axis of the elongate device. For example without limitation, directed energy can be considered to be axially directed relative to an elongate directed energy device, or laterally directed relative to the elongate directed energy device. Directed energy is not limited to these particular directions relative to the elongate directed energy device, and are only included herein as examples. For example, energy can be directed in any general direction relative the elongate directed energy device, such as at about 45 degrees, or about 135 degrees, relative to the elongate device. Directed energy can be expected generally to penetrate tissue in a way that causes substantially simultaneous volumic heating of a volume of tissue in the direction in which the energy is emitted. It is expected that as the distance from the emitter increases, the directed energy is deposited, converted into heat and deformation of tissue, and thus attenuated. There is a boundary or distance beyond which the directed energy will not penetrate in a biologically significant way because of attenuation in tissue. Volumic heating of target tissue, which occurs when using high frequency ultrasound ablation energy as described herein, is different than conductive heating of tissue, which requires heating from the contact point, through intervening tissue, and to the target tissue. As an example, conductive heating occurs when using RF energy to ablate tissue. There may be, however, some degree of conductive heating that accompanies volumic heating. With directed energy, however, it is intended that volumic heating is the primary means by which the target tissue is heated. Additionally, directed energy such as high intensity ultrasound energy does not require intimate contact with the target to be effectively delivered. Ultrasound can be transmitted through blood with approximately ten times lower absorption than in the carotid body area, for example, allowing the energy to be delivered without intimate carotid artery or jugular vein wall contact, or even without serious regard to the distance from emitter to that wall. This can be important where a vessel wall is irregular or vulnerable.

In some embodiments herein the directed energy emitter is a directed ultrasound energy emitter. Ultrasonic acoustic energy is produced by an ultrasonic transducer by electrically exciting the ultrasonic emitter, which is disposed on or about the elongate device (e.g., a catheter). In some embodiments ultrasonic transducers may be energized to produce directed acoustic energy from the transducer surface in a range from about 10 MHz to about 30 MHz. The transducer can be energized at a duty cycle, such as in the range from about 10% to about 100%. Focused ultrasound may have much higher energy densities localized to a small focal volume, but will typically use shorter exposure times and/or duty cycles. In the case of heating the tissue, the transducer will usually be energized under conditions which cause a temperature rise in the tissue to a tissue temperature of greater than about 45 degrees C. In such instances, it can be desirable to cool the luminal surface in which the elongate device is positioned, in order to reduce the risk of injury.

Figure 10:
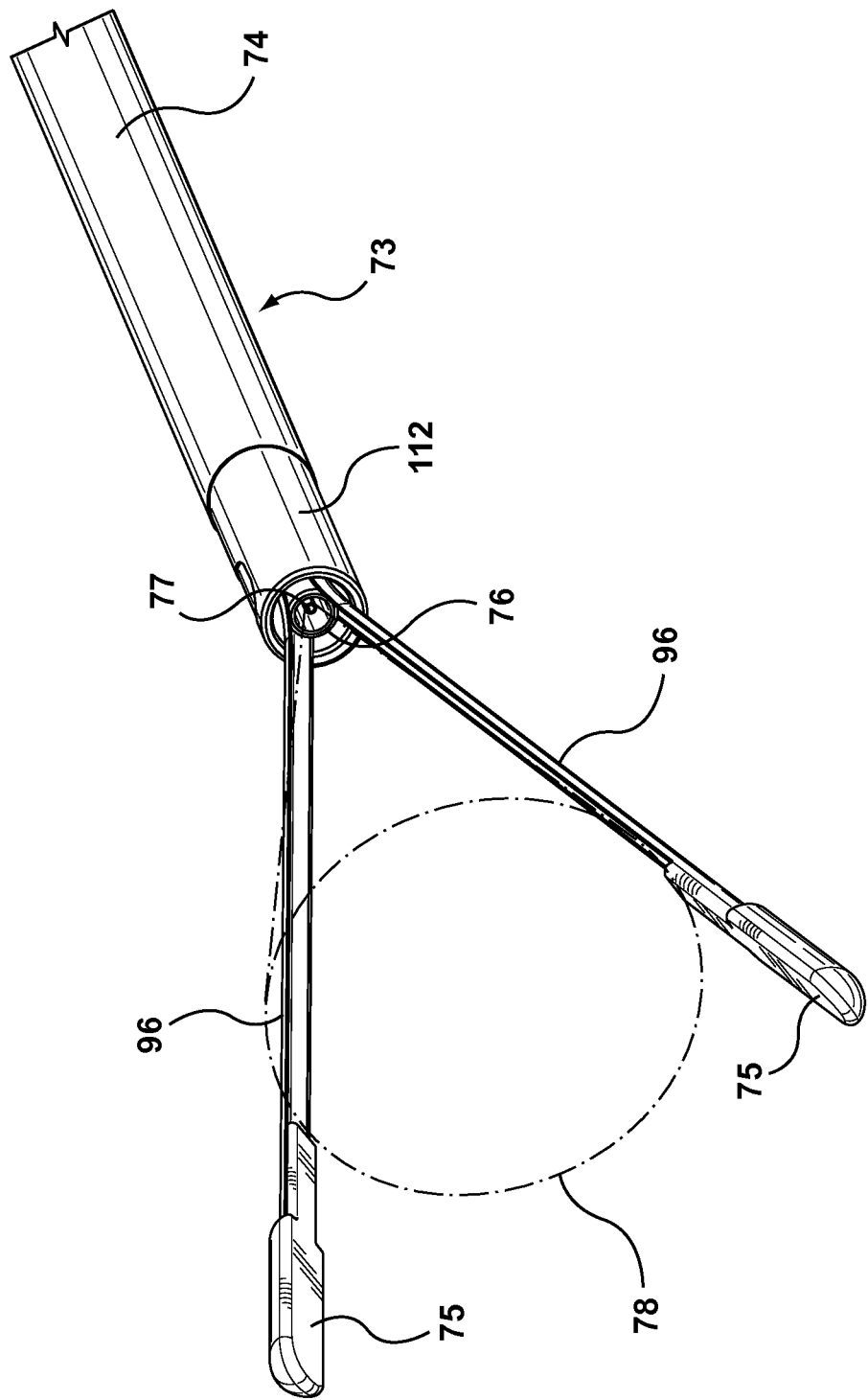
FIG. 10 depicts an axial directed energy device used from within a bifurcation forceps catheter.

FIGS. 4A and 4B illustrate a portion of an exemplary directed energy device. FIG. 4A depicts the distal end of an Axial Directed Optical Energy Ablation (ADOEA) device 22 where the optical energy is directed in an axial direction. FIG. 4B depicts in exploded view the construction details of ADOEA device 22. FIGS. 4A and 4B depict in general an axial directed optical energy device, which may be configured as an endovascular catheter, steerable, or used over a guide wire, for use through an endovascular catheter or sheath, or as a rigid percutaneous probe. ADOEA device 22 comprises shaft 25 defining central lumen 26, optical fiber 23, optical fiber mounting ferrule 27, and distal housing 24. Shaft 25 maybe a polymeric catheter shaft, or may be a rigid shaft made from hypodermic tubing. Central lumen 26 runs the length of shaft 25 and is terminated at the proximal end of shaft 25 with a fluid port, and a Tuohy Borst seal around the optical fiber 23, which extends to make connection with an optical energy source not shown. Optical fiber 23 is terminated with a polished surface, and bonded to optical fiber mounting ferrule 27 as shown with adhesive. Fluid channels 28 allow fluid to flow past optical fiber mounting ferrule 27 and out through aperture 29 in distal housing 24 providing a means to displace blood from the optical energy pathway and to cool a vessel wall that the optical energy is directed towards. Optical fiber 23 can be a step index glass fiber with a numerical aperture greater than 2, and has a core diameter between 200 and 1000 microns. The caliber of ADOEA device 22 is dependent on the particular configuration for use. The same basic construction can be used for small caliber probes on the order of 3 French and used within the central lumen of an endovascular catheter or sheath, as depicted in FIG. 10, or may be of a larger caliber and used as a standalone device. Additional lumens and functions may also be incorporated. In use, optical energy can be transmitted down optical fiber 23 and emitted axially from the distal end of the fiber 23.

Figure 5A:
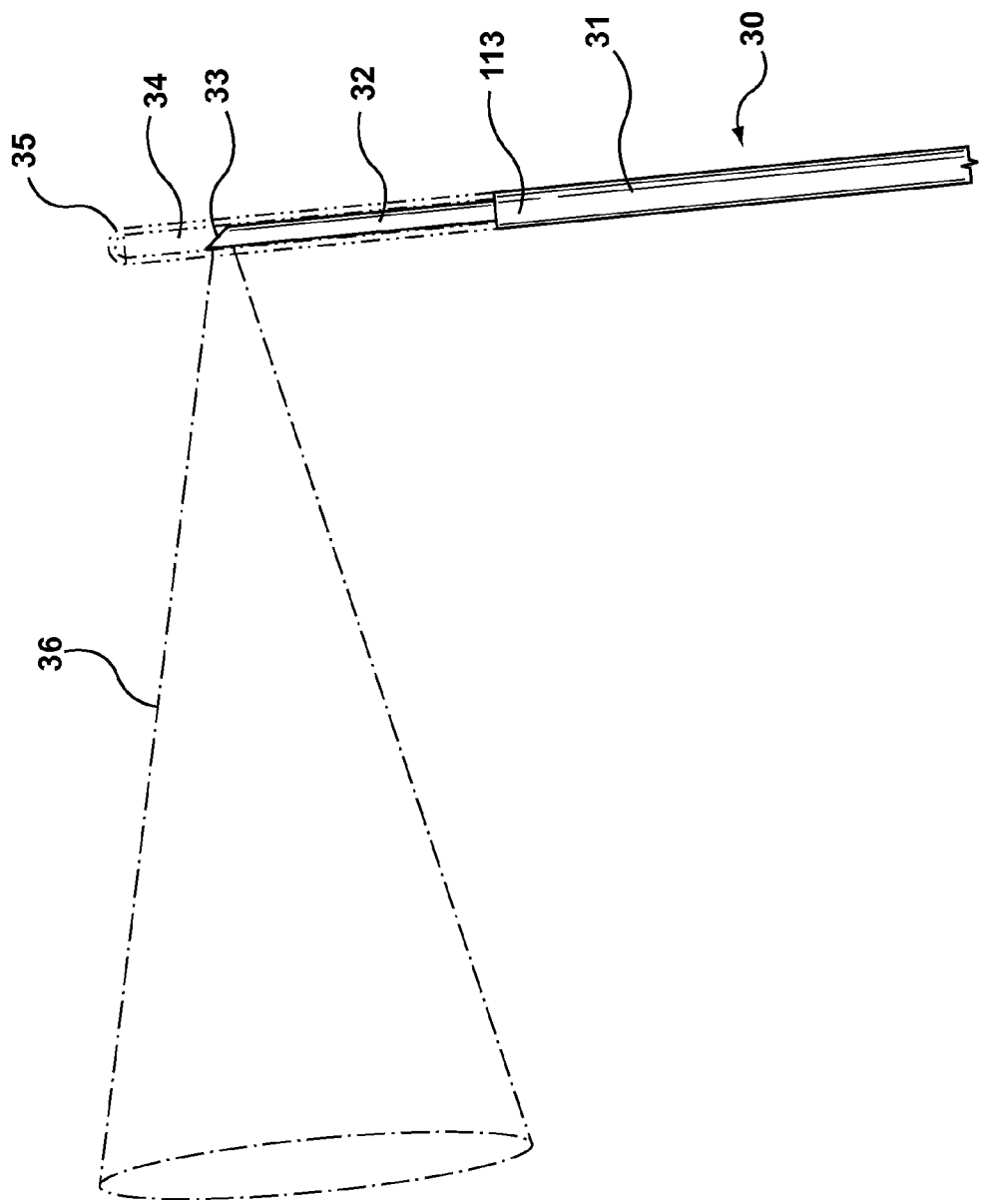
FIGS. 5A, 5B, and 5C depict a distal end of a lateral directed optical energy ablation device.
Figure 5B:
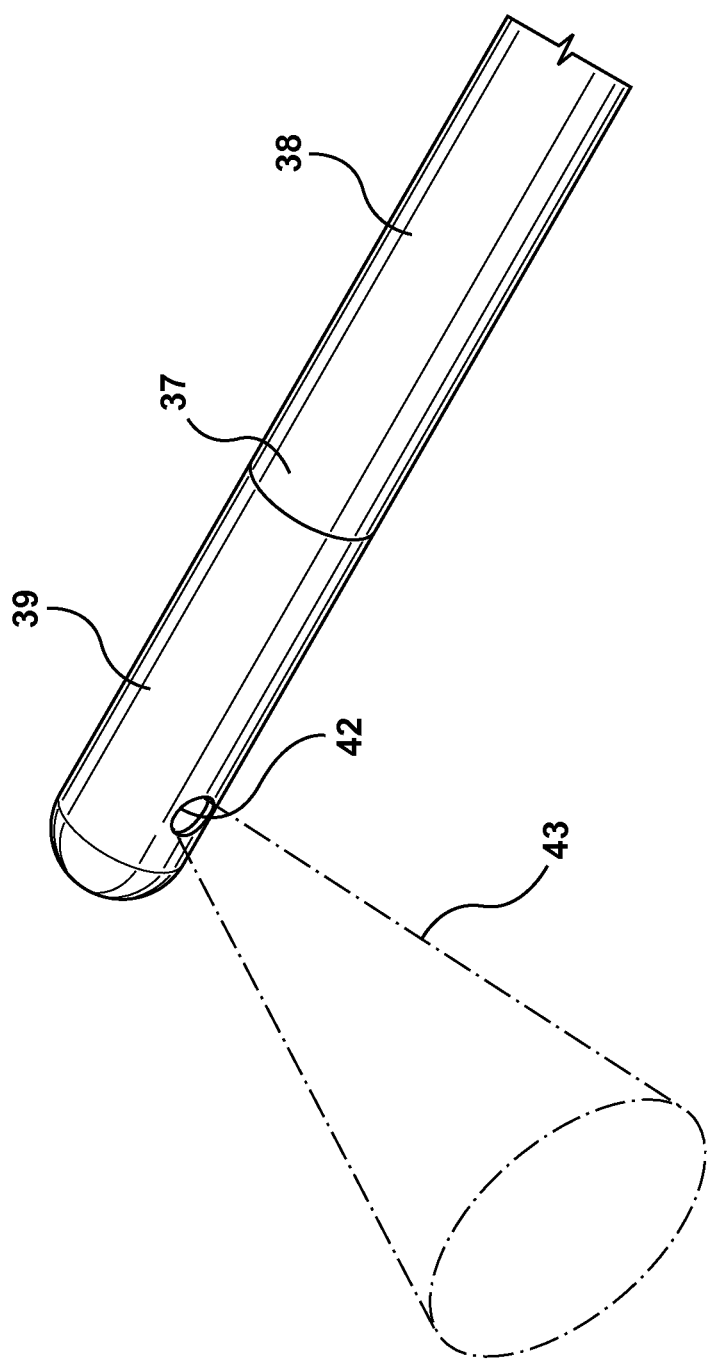
Figure 5C:
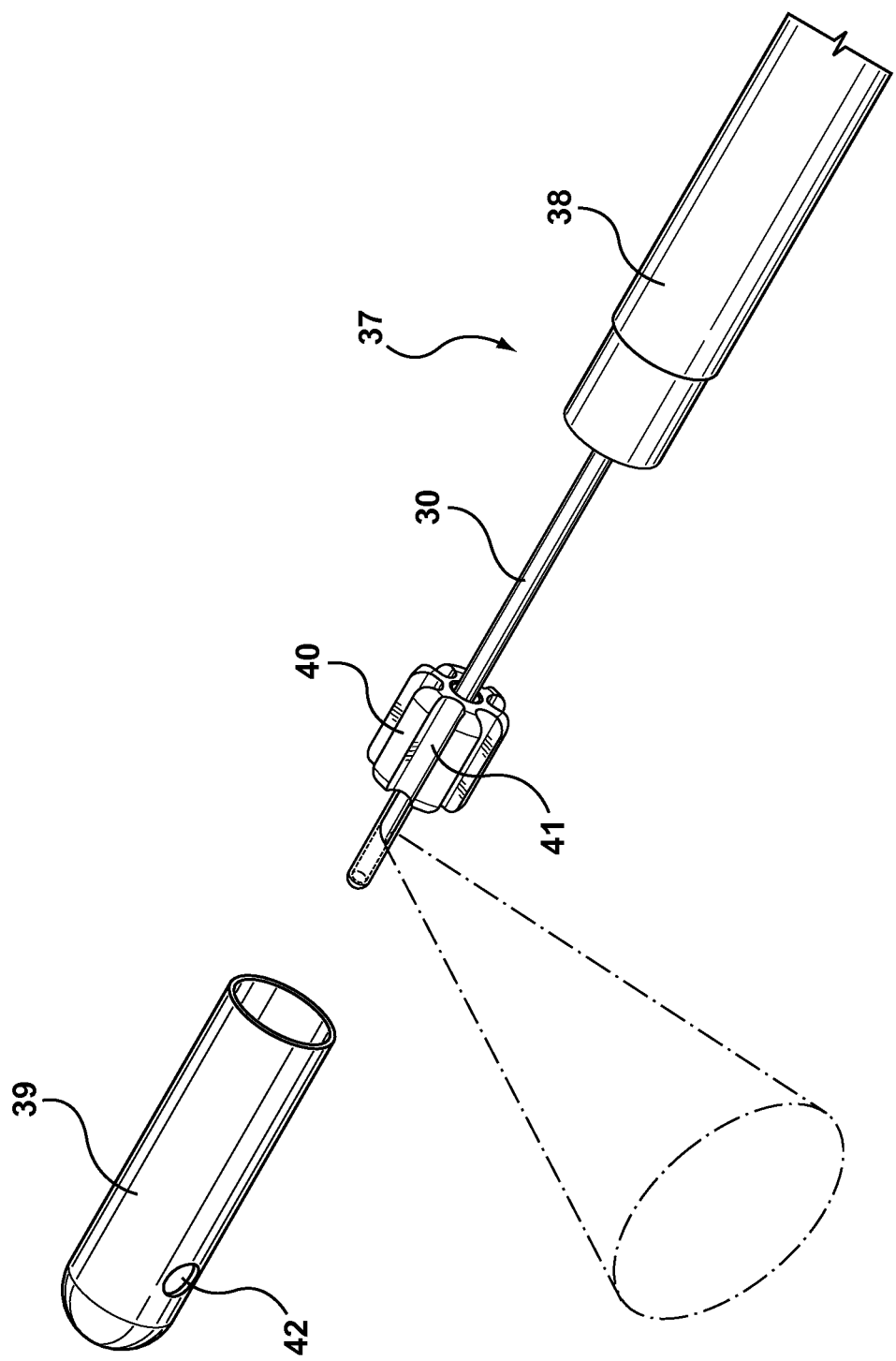

FIGS. 5A, 5B and 5C depict a Lateral Directed Optical Energy Ablation (LDOEA) device. FIGS. 5A, 5B and 5C depicts in general a lateral directed optical energy device, which may be configured as an endovascular catheter, steerable, or used over a guide wire, for use through an endovascular catheter or sheath, or as a percutaneous probe. FIG. 5A depicts the construction of a lateral optical energy deflecting assembly 30 used in multiple LDOEA device embodiments. The assembly may comprise optical fiber 113, and a closed ended glass of quartz tube 35. Optical fiber 113 comprises a glass core and cladding 32, and polymeric buffer 31. To fabricate the assembly 30, buffer 31 is removed from the distal end for 2 mm to 5 mm. The distal tip of optical fiber 113 is then polished at a bevel 33 at approximately 45 degrees as shown, and glass quartz closed ended tube 35 is bonded to core/cladding 32 using either an adhesive or thermal welding technique. Resulting air space 34 works in conjunction with beveled surface 33 to effect a prism where all optical energy is deflected in the lateral direction as depicted by optical emission cone 36 due to "total internal reflection". Optical finer 113 is preferably a step index fiber with a numerical aperture greater than 2, and a core diameter between 200 and 1000 microns. FIG. 5B depicts the distal tip of LDOEA device 37 showing shaft 38, distal housing 39, aperture 42, and optical emission cone 43. FIG. 5C depicts in exploded view LDOEA device 37, showing shaft 38 comprising a central lumen, lateral optical energy deflecting assembly 30, lateral optical energy deflecting assembly mounting ferrule 40, and distal housing 39. Lateral optical energy deflecting assembly 30 is bonded to lateral optical energy deflecting assembly ferrule 40 as shown. Lateral optical energy deflecting assembly mounting ferrule 40 comprise fluid channels 41 to allow fluid to exit aperture 42 to displace blood from the optical pathway, and to provide cooling to the wall of the vessel that the optical energy is being directed. Other aspects of LDOEA device 37 are similar in form and function to the ADOEA device 22 depicted in FIGS. 4A and 4B.

Figure 6A:
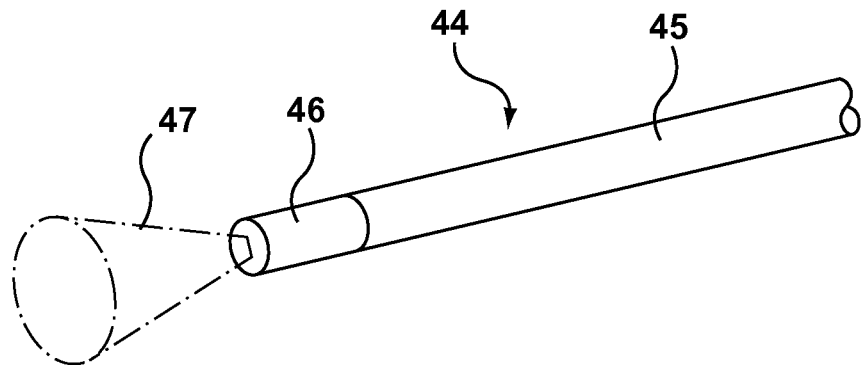
FIG. 6A depicts a distal end of an axial directed ultrasonic energy ablation device.
Figure 6B:
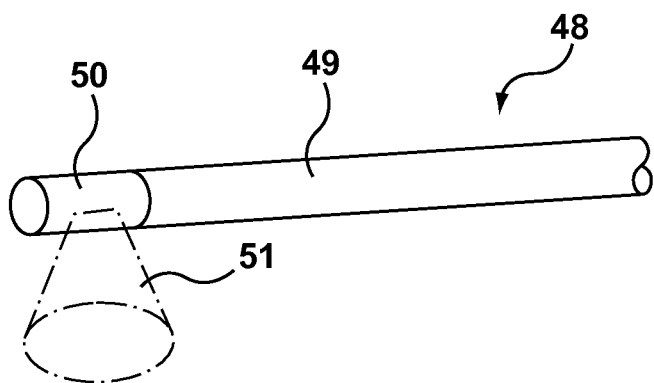
FIG. 6B depicts a distal end of a lateral directed ultrasonic energy ablation device.

FIG. 6A depicts in simplified form an Axial Directed Ultrasonic Energy Ablation (ADUEA) device 44. FIG. 6B depicts a Lateral Directed Ultrasonic Energy Ablation (LDUEA) device 48. These two figures depict in general an axial directed and a lateral directed ultrasonic energy ablation device, which may be configured as an endovascular catheter, which may be steerable or used over a guide wire, for use through a central lumen of an endovascular sheath, or as a percutaneous probe. ADUEA device 44 comprises shaft 45, and axial emitting sonodome 46. Axial emitting sonodome 46 comprises a singular or an array of piezoelectric transducers configured for emitting ultrasonic energy at tissue ablating levels in an axial direction as depicted by ultrasonic energy emission cone 47. LDUEA device 48 comprises shaft 49, and lateral emitting sonodome 50. Lateral emitting sonodome 50 comprises a singular or an array of piezoelectric transducers configured for emitting ultrasonic energy at tissue ablating levels in a lateral direction as depicted by ultrasonic emission cone 51. Exemplary construction techniques that can be used to build ADUEA device 44 and LDUEA device 48 can be found herein, such as in FIG. 29. Distal section of the shaft 49 can be equipped with a deflection or steering mechanism enabling targeting and pointing of the ultrasonic emission beam in the desired direction by manipulating actuators incorporated into the device handle (not shown). Radiopaque markers visible on X-ray can be added to the design to ensure that the ultrasonic emission cone 51 is pointed in the direction of the target that can be the carotid septum wall if the device is placed in the carotid artery or a jugular vein. For example two markers can be placed on two opposite sides of the shaft and alignment of the markers (e.g., so that they are projected as one or as a cross or other distinct superimposed shape on an imaging screen) can assist the operator in pointing the energy emission in the desired direction.

Figure 7:
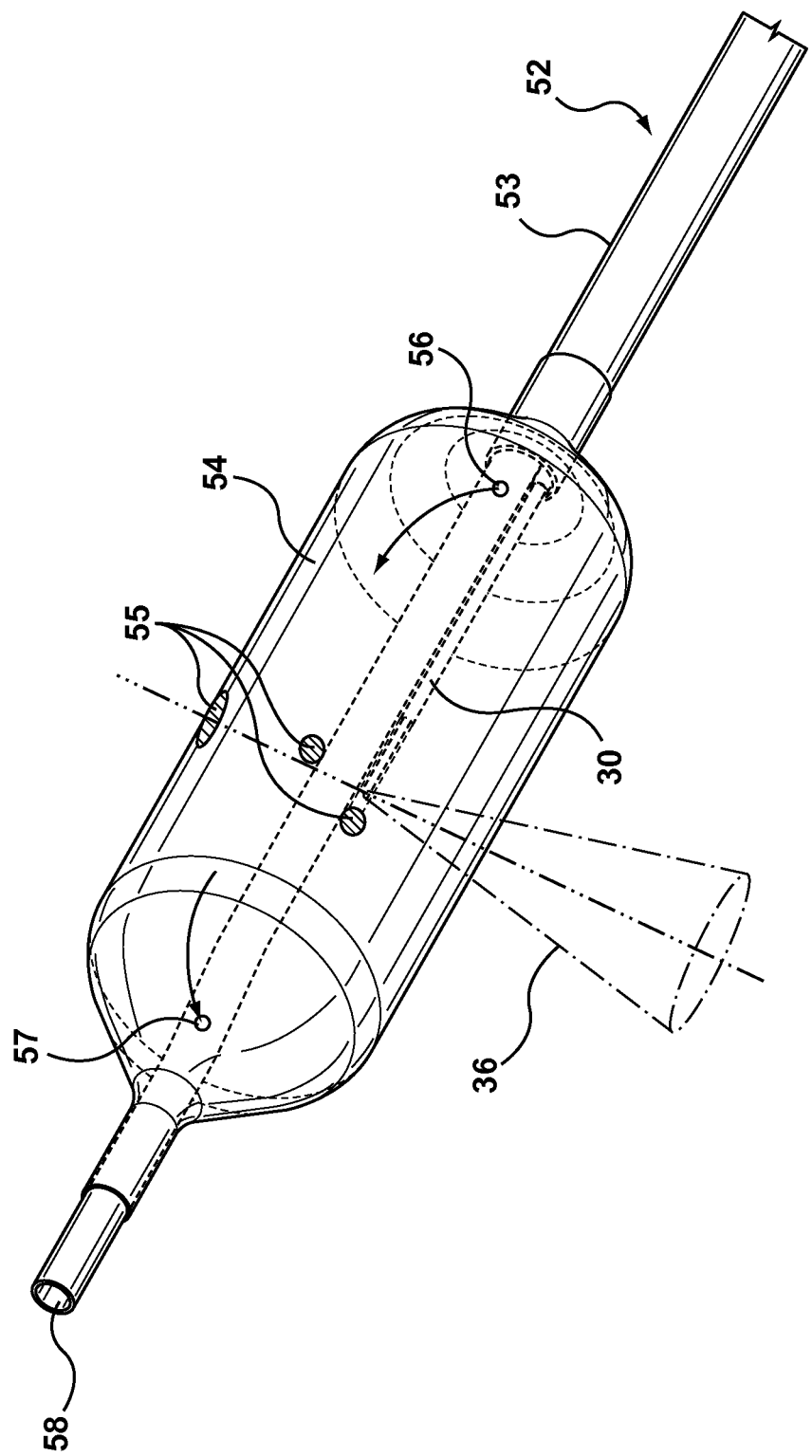
FIG. 7 depicts a distal end of a directed optical energy carotid body ablation balloon catheter.

FIG. 7 depicts a distal portion of a Directed Optical Energy Carotid Body Ablation Balloon (DOECBAB) catheter 52 where the optical energy 36 is directed laterally from inside an optically transparent balloon. DOECBAB catheter 52 comprises lateral optical energy deflecting assembly 30, catheter shaft 53, and balloon 54. Catheter shaft 53 comprises central guide wire lumen 58, a fluid lumen not shown in communication with fluid inlet 56, a fluid lumen not shown in communication with fluid outlet 57, and a lumen not shown housing lateral optical energy deflecting assembly 30. Balloon 54 is mounted over the distal section of catheter shaft 53 and encompasses the distal end of lateral optical energy deflecting assembly 30, fluid inlet 56, and fluid outlet 57. Balloon 54 is made from an optically transparent material such as PET, and is sized based on the intended anatomical positional use. Balloon 54 comprises radiopaque markers 55 on the balloon that provide the user with a substantially unambiguous fluoroscopic indication of the direction of the optical energy 36. During use fluid is circulated under pressure from fluid inlet 56 to fluid outlet 57 by fluid circulation means not shown. The circulation inflates the balloon to displace the blood from optical energy pathway 36, fix and stabilize the position of optical energy pathway 36, and cool the wall of the vessel to prevent overheating and injury of the vessel wall, which could disrupt optical energy transmission through the vessel wall. Those skilled in the art of balloon catheters are familiar with the construction techniques required to build a DOECBAB catheter as disclosed.

Figure 8:
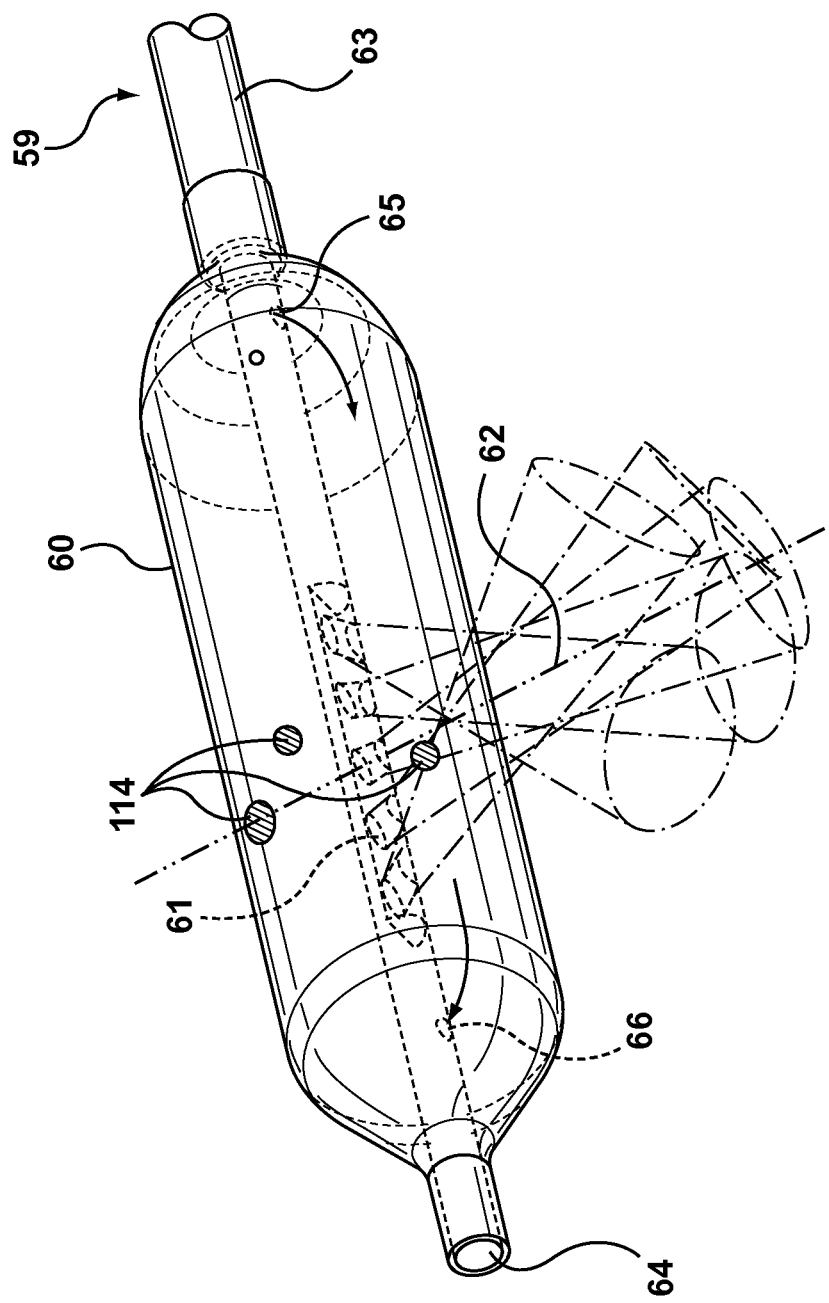
FIG. 8 depicts a distal end of a directed ultrasonic energy carotid body ablation balloon catheter.

FIG. 8 depicts a Directed Ultrasonic Energy Carotid Body Ablation Balloon (DUECBAB) catheter 59 where the ultrasonic energy is directed laterally from inside an ultrasonically transparent balloon. DOECBAB catheter 59 comprises lateral emitting ultrasonic transducer array assembly 61, catheter shaft 63, and balloon 60. Catheter shaft 63 comprises central guide wire lumen 64, a fluid lumen not shown in communication with fluid inlet 65, a fluid lumen not shown in communication with fluid outlet 66, and a lumen not shown comprising lateral emitting ultrasonic transducer array assembly 61 and associated wires connecting lateral emitting ultrasonic transducer array assembly 61 to a source of ultrasonic energy, not shown. Balloon 60 is mounted over the distal section of catheter shaft 63 and encompasses the lateral emitting ultrasonic transducer array assembly 61 that can include one or several emitters of high energy directed ultrasound, fluid inlet 65, and fluid outlet 66. Balloon 60 is made from an ultrasonically transparent material such as polyethylene, and can be sized based on the intended anatomical positional use. Balloon 60 comprises radiopaque markers 114 on the of the balloon surface that provide the user with a substantially unambiguous fluoroscopic indication of the direction of the ultrasonic energy 62. Alignment of such markers with the anatomic landmarks, or each other, for example using biplane angiography enables the operator to direct the emitted ultrasonic energy beam towards the target such as a carotid septum or carotid artery bifurcation.

During use and particularly during ablation, fluid can be circulated under pressure from fluid inlet 65 to fluid outlet 66 by fluid circulation means such as an external fluid pump (not shown). The circulation inflates the balloon defining a focus of ultrasonic energy 62 at a predetermined distance beyond the surface of the balloon as shown, allows fixation and stabilization of the position of ultrasonic energy pathway within the vessel, and to cool the one or more ultrasonic emitters that can get heated during operation and cooling of balloon at the wall of the vessel to prevent overheating and damage of the vessel wall, which could cause trauma and disrupt ultrasonic energy transmission through the vessel wall due to excessive tissue desiccation. Fluid infused into the balloon can be sterile saline and can be recirculated or leaked into a blood vessel through perforations in the wall of the balloon. Such perforations can be specifically located at the wall of the balloon that corresponds to the area where the ultrasonic beam exits the balloon to further cool the surface of the blood vessel thus enabling heating of deep tissues inside the carotid septum (for example, 2 to 8 mm deep) while protecting layers of the vessel wall such as media of the vessel.

Figure 9:
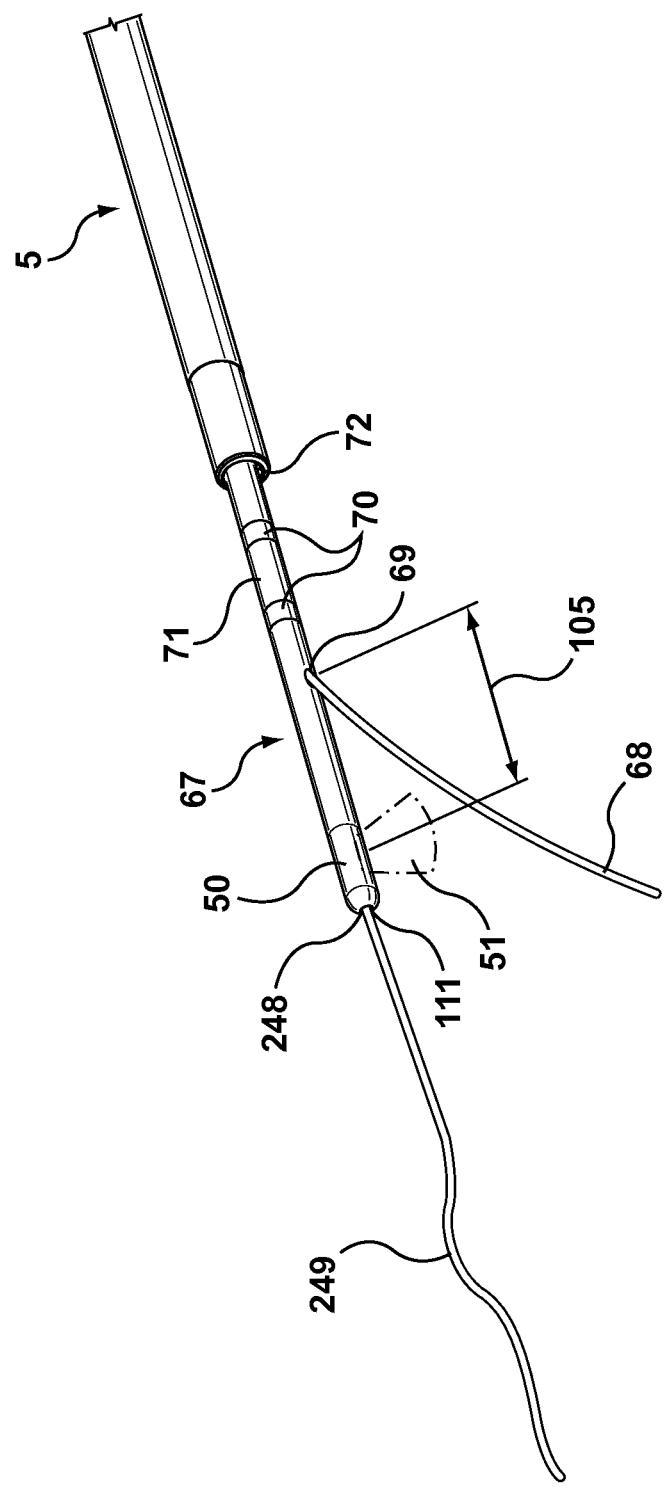
FIG. 9 depicts a distal end of a ultrasonic ablation catheter with a side-port guide wire.

FIG. 9 depicts the distal portion of a carotid access sheath 5 with an endovascular directed ultrasonic energy ablation catheter 67 comprising a single side exiting guide wire port 69, which will be referred to as a Side-Wire DUECBA catheter, extending from the central lumen 72 of carotid access sheath 5. Side-Wire DUECBA catheter 67 comprises a lateral emitting sonodome 50 mounted in the vicinity of the distal end, and a side exiting guide wire port 69 in the vicinity of the distal end, catheter shaft 71 comprising one or more guide wire lumens, not shown, at least one of them in communication with guide wire port 69, a means to connect lateral emitting sonodome to an ultrasonic ablation energy source in the vicinity of the proximal end, not shown, and a means for inserting a guide wire or similar device into the guide wire lumen at the proximal end that may consist of a female luer fitting or Tuohy Borst fitting, not shown. Optionally, a Side-Wire DUECBA catheter may further comprise a guide wire lumen with an exit port 248 in the distal tip 111 of the catheter 67. This lumen may be used to slide the catheter over a guide wire 249 to facilitate delivery of the catheter to, for example, an external carotid artery. The basic elements known to construct an over-the-wire endovascular catheter system are known in the art of tools for cardiac catheterization and stenting. Side-Wire DUECBA catheter 67 is depicted here with guide wire 68 exiting guide wire port 69. Guide wire port 69 may be configured in such a way that guide wire 68 exits guide wire port 69 at an angle of for example 30 to 50 degrees as depicted, or may be configured for a guide wire exit angle that is greater than or less than that depicted. Guide wire port 69 and corresponding lumen may be configured for use with a guide wire between 0.014" and 0.018" diameter. The distance 105 of the guide wire port 69 from the sonodome 50 may be fixed as depicted, or may be user selectable by a distance selection means, not shown. It is anticipated that the distance 105 from the port 69 to sonodome 50 and energy emission beam 51 is approximately 4 to 15 mm in order to use the anatomy of a carotid bifurcation to orient and direct the beam oriented in the direction of a carotid septum or carotid body. For example, in some embodiments distance 105 is about 5 mm to about 10 mm. A carotid body to be ablated is anticipated to be, in most cases, within a zone approximately 6 to 8 mm above the saddle of the carotid bifurcation. With the configuration shown, port 69 is at a distance from sonodome 50 and energy emission beam 51 such that when the guide wire is positioned in an internal carotid artery and coupled with, or engaged with, a carotid bifurcation, the sonodome will be disposed in the external carotid artery at a desired distance from the bifurcation. Distance 105 can thus be selected to be about 4 mm to about 15 mm so that sonodome 50, or other emitter, is disposed in the external carotid artery within about 4 mm to about 15 mm from the bifurcation.

Figure 13:
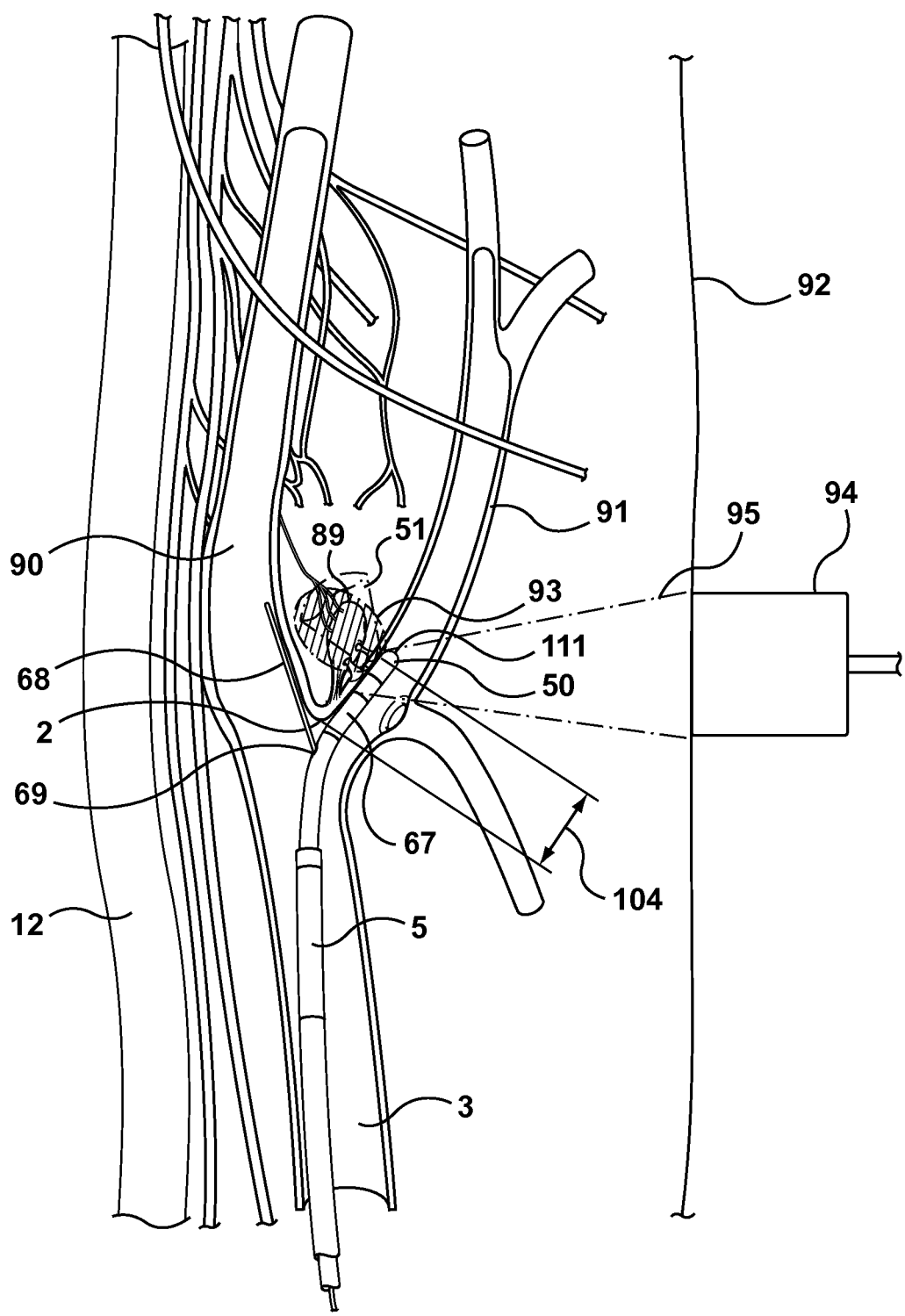
FIG. 13 depicts a directed ultrasonic energy ablation catheter with a side-port guide wire in position for carotid body ablation from within an external carotid artery.

In this embodiment ultrasonic emission beam 51 is laterally aligned with guide wire port 69, a benefit of which is illustrated in FIG. 13. Catheter shaft 71 may comprise at least one catheter shaft electrode 70 configured for electrical neurostimulation. Lateral emitting sonodome 50 may be configured for electrical neurostimulation independently or in conjunction with catheter shaft electrode(s) 70. Side-Wire DUECBA catheter 67 may be configured for use with a carotid access sheath 5 having a working length between 100 cm and 140 cm, and a diameter of 5 French to 8 French. The lateral emitting ultrasonic sonodomes can be used for emission of high energy (i.e., ablative) ultrasound or for emitting low energy ultrasound that can be used for imaging or Doppler signal measurement. Imaging or Doppler signals can be used to identify and confirm the location of a bifurcation and particularly the internal carotid artery, which is characterized by high blood flow velocity and high blood flow pulsations. As illustrated in FIG. 13, when in the correct position, the emitted beam would face the internal carotid artery and detect high pulsation blood flow at a distance of approximately 8 mm.

It is appreciated that the sonodome may get hot during ablation because of the energy inefficiency of the emitter that can heat up, and irrigation by fluid may be desired to keep it cool, especially in an area of contact with a vessel. Alternatively or in addition the sonodome may be offset from the vessel wall to enable flow of blood between the sonodome and the wall of the carotid artery.

FIG. 10 depicts an Axial Directed Energy (ADE) device 77 that directs energy in an axial direction from within a forceps catheter 73 configured for grasping or saddling upon an intercarotid septum. ADE device 77 may be an Axial Directed Optical Energy (ADOE) device 22, and depicted in FIGS. 4A and 4B, or may be an Axial Directed Ultrasonic Energy (ADUE) device 44 as depicted in FIG. 6A. ADE device 77 resides in a central lumen of forceps catheter 73 as shown. Forceps arms 96 are in a slidable relationship with forceps sheath 74. When forceps sheath 74 is pulled in the proximal direction relative to forceps arms 96 the forceps arms expand radially as shown due to preformed bias in the arms towards radial expansion. When forceps sheath 74 is advanced in the distal direction relative to forceps arms 96, forceps arms are forced towards each other by radial constrain applied by forceps sheath tip 112. Other ways of positioning forceps arms can be envisioned such as use of resilient materials that apply tension to the arms and urge them gently to coopt towards the septum. ADE device is configured to deliver directed energy 78 between forceps arms 96. Forceps pads 75 provide an atraumatic bifurcation wall contact with a secure grasping force.

Figure 11:
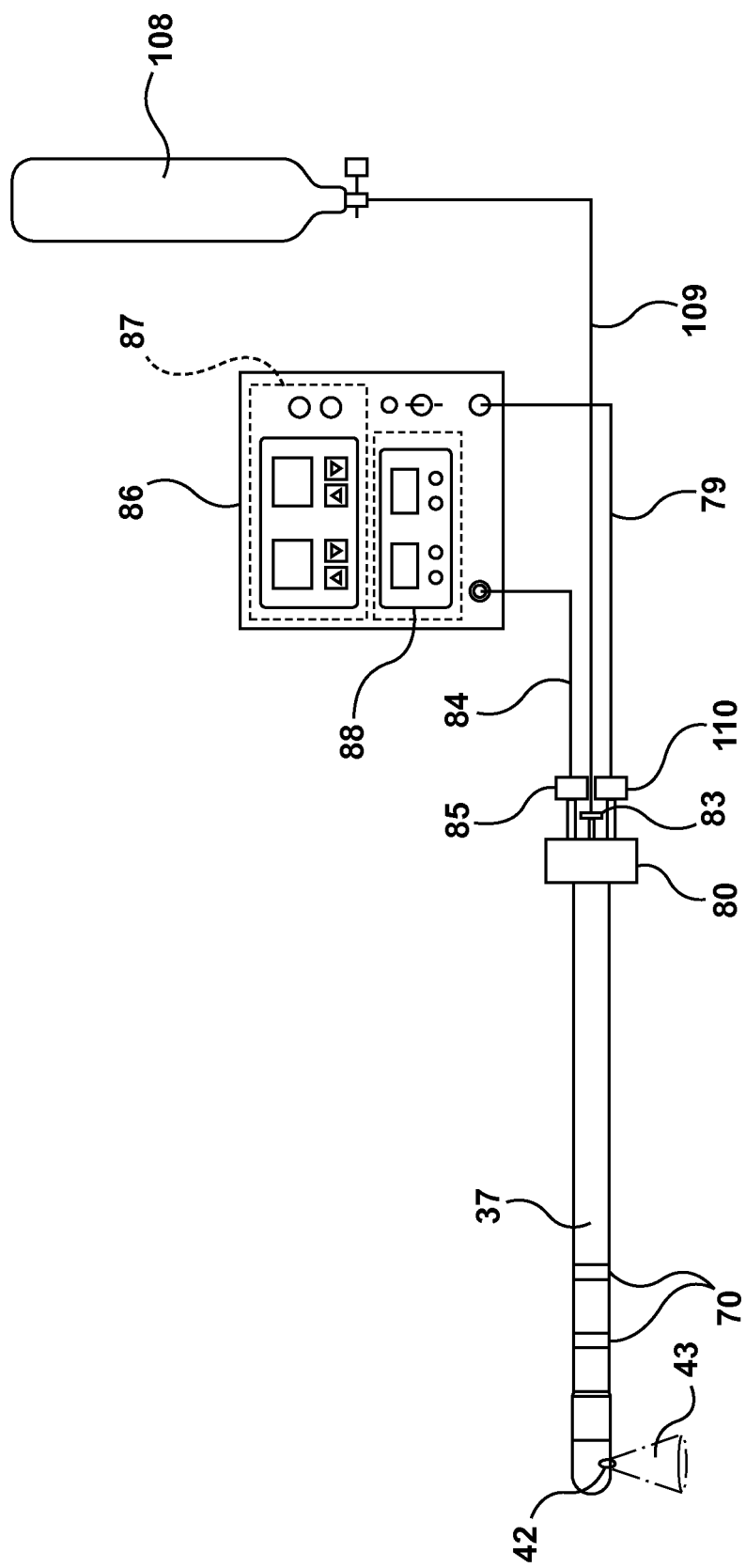
FIG. 11 depicts in simplified schematic form a directed energy carotid body ablation system.

FIG. 11 depicts in simplified schematic form a Directed Energy Carotid Body Ablation (DECBA) system. This illustration depicts a lateral emitting directed optical energy ablation device as an example, but it should understood that a system may be configured in similar manner using axial energy emitting device and lateral and axial ultrasonic energy emitting devices. The device depicted on FIG. 11 can be a Lateral Directed Ultrasonic Energy Ablation (LDUEA) device described in this application. The DECBA system as depicted comprises Lateral Directed Optical Energy Ablation (LDOEA) catheter 37, control console 86, electrical umbilical 84, and optical fiber umbilical 79. Cooling fluid tubes can be included in the connections between the catheter 37 and console 86. Control console 86 has a user interface 87 that provides the user with a means to select directed optical energy ablation parameters, activate and deactivate a directed optical energy ablation, and to monitor the progress of a directed optical energy ablation. Control console 86 may also include a fluid pump for high pressure pumping of cooling fluid from a reservoir such as the exemplified saline bag 108. In addition, control console 86 may have a second user interface 88 that allows the user to select electrical neurostimulation parameters, activate stimulation, deactivate stimulation, and to monitor stimulation applied by neurostimulation electrodes 70. Control console 86 user interface may include other features such as a graphic LCD screen, sound emitters or light displays to show the anatomic sonography and Doppler flow information where emitters and receivers of ultrasonic energy are part of the design of the system. Doppler flow velocity information can be useful in assisting the operator in orienting the high energy emitter that performs the ablation towards the septum.

Figure 12:
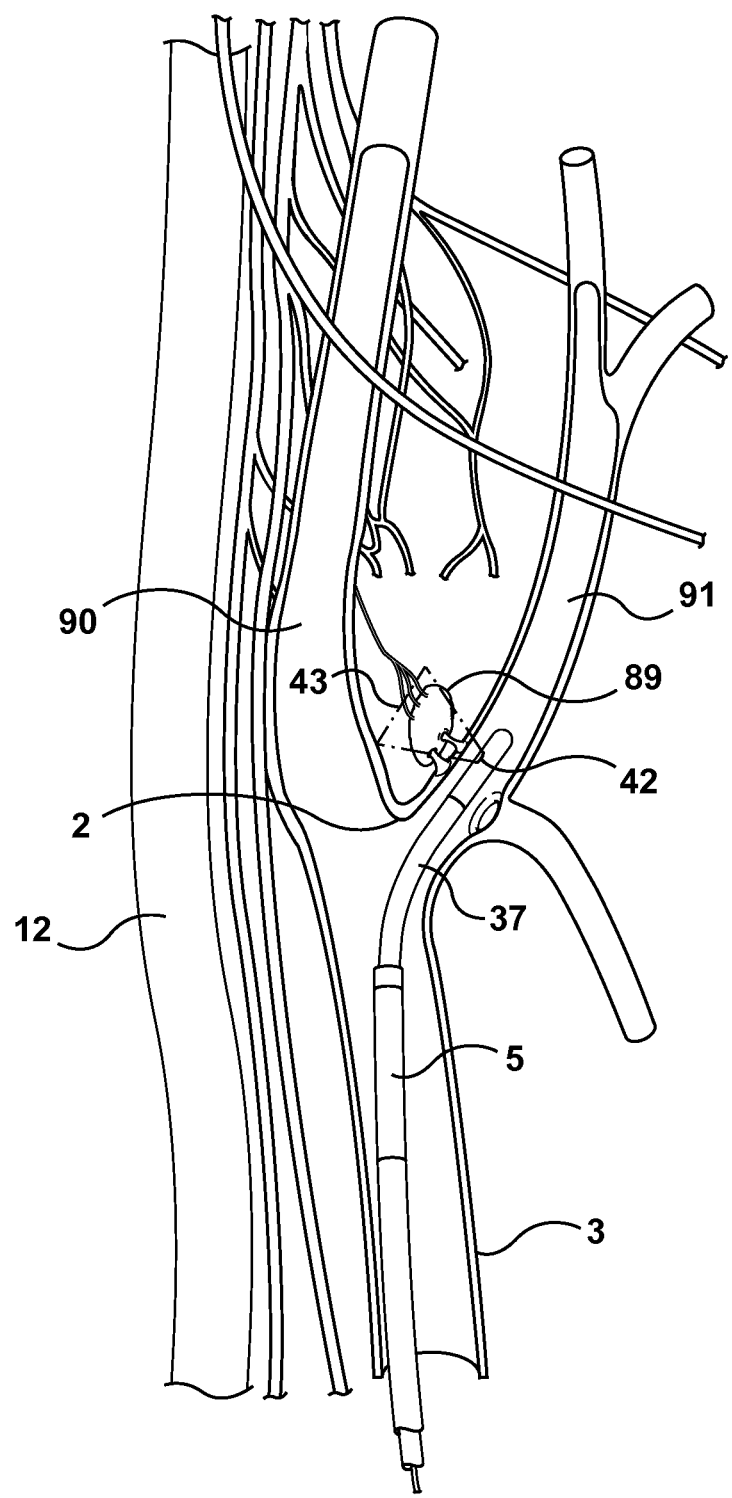
FIG. 12 depicts a lateral directed optical energy ablation device in position for ablation of a carotid body from within an external carotid artery.

Control console 86 may comprise a means to infuse saline through the central lumen and out aperture 42 to displace blood from the optical pathway, and to cool the surface of a vessel wall to prevent heat damage to the vessel and charring of the vessel wall. Irrigation fluid, in the illustrated embodiment, is supplied by a saline bag, which is either gravity feed as shown, or pressurized by a pressure cuff, not shown or by a motorized pump, not shown. Fluid line 109 connects saline bag 108 to the fluid port 83 of proximal terminal 80 of LDOEA catheter 37. Proximal terminal 80 also may comprise electrical connector 85 and optical fiber port 110. Electrical connection can include wire connections for temperature monitoring devices, ultrasonic emitter excitation current and electric stimulation current. Proximal terminal may be configured with a handle and an actuator for use with deflectable tipped catheter configuration, not shown. Console 86 may be configured to supply LDOEA catheter 37 with optical energy in the green spectrum between 500 nm and 550 nm for selective absorption by hemoglobin, or may supply optical energy in the red spectrum and/or infrared spectrum 700 nm to 1100 nm, for selective absorption by neurological tissue. Console 86 may be configured to deliver between 1 and 10 watts of optical power, which may be regulated and selectable by the user. Alternatively console 86 may supply 4 to 20 W of electric power for the excitation of an ultrasonic energy emitter that may deliver 2 to 15 W of ultrasonic (mechanical) energy to the carotid septum. In some embodiments the console supplies electrical power to the ultrasonic emitter so that it delivers between about 10 W and about 30 W of ultrasonic (mechanical) energy to the carotid septum FIG. 12 depicts a Lateral Directed Optical Energy Ablation LDOEA device 37 in position for ablation of a carotid body from within an external carotid artery 91. This illustration depicts a LDOEA device as an example, but it should be understood that a system may be configured in a similar manner using lateral ultrasonic energy emitting devices. The device depicted on FIG. 12 can be a Lateral Directed Ultrasonic Energy Ablation (LDUEA) device described in this application.

Figure 27A:
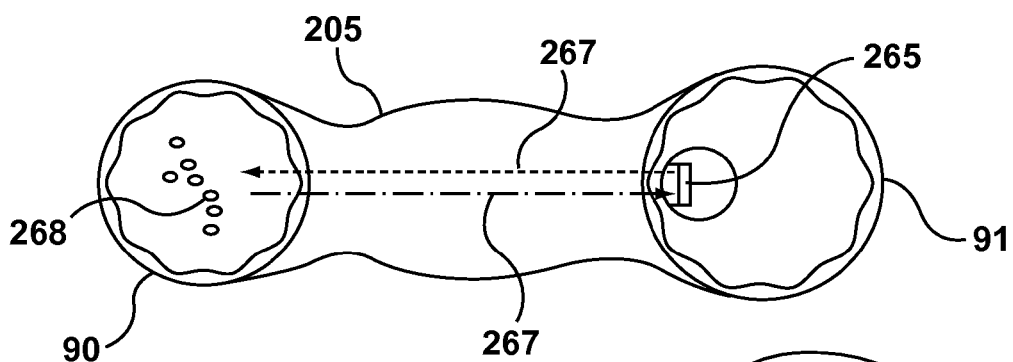
FIGS. 27A and 27B are schematic illustrations of an ultrasound catheter placed in an external carotid artery for carotid body ablation.
Figure 27B:
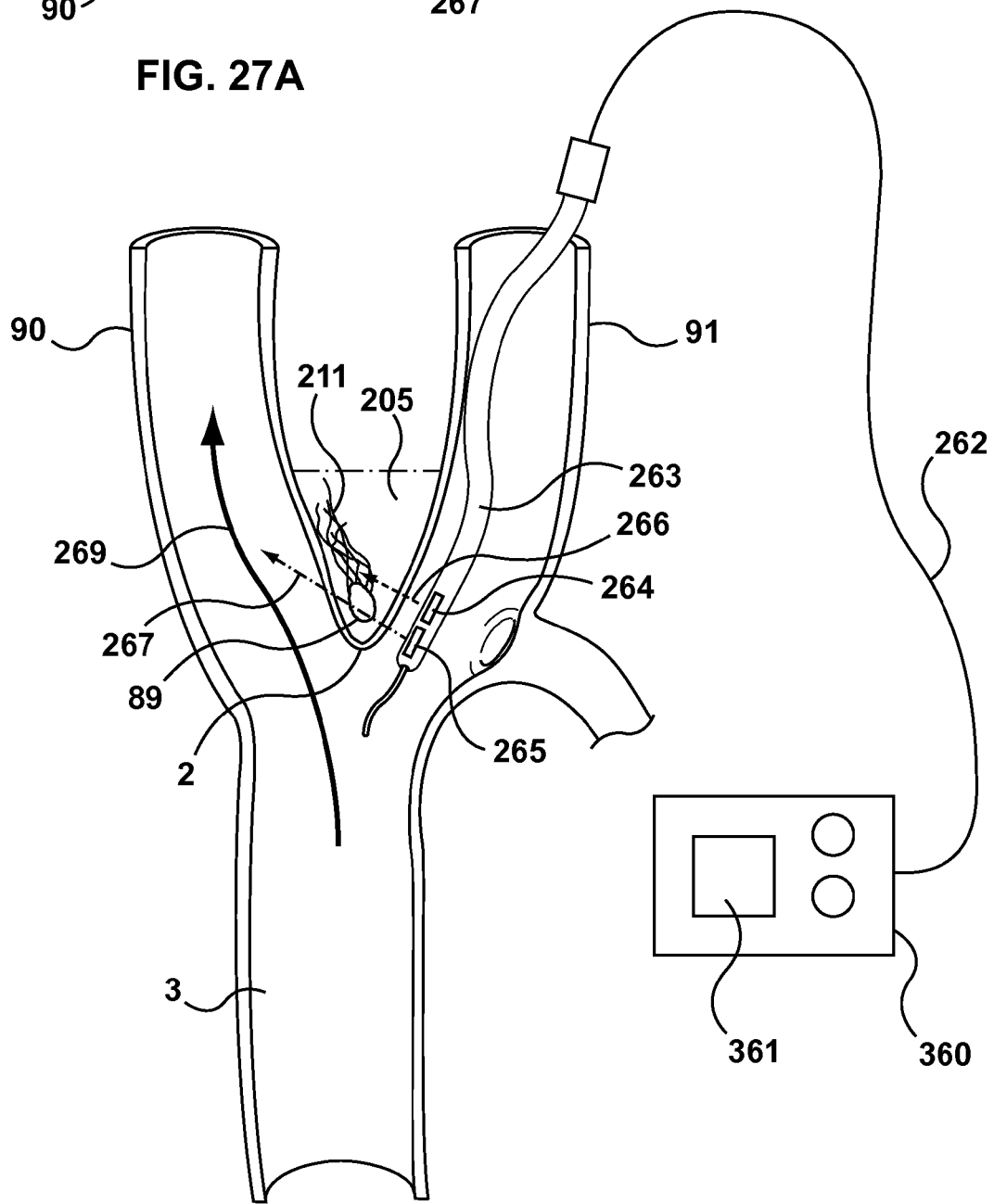

As depicted LDOEA or LDEUA device 37 is placed into external carotid artery 91 through carotid access sheath 5. LDOEA device is aimed in the direction of carotid body 89 by injecting radiopaque contrast agent through aperture 42 while fluoroscopically imaging the region, which provides the user with a fluoroscopic indication of the position of aperture 42, and therefore the orientation of directed optical energy. Doppler signal can be used to find or confirm the right orientation by finding the direction towards the internal carotid artery 90 where the high pulsating blood velocity is present. Any of the emitters herein that are positioned in an external carotid artery can be oriented towards the carotid septum by using a Doppler signal to detect high blood velocity in the internal carotid artery and then orienting the emitter in the direction of the high blood velocity, which will also orient the emitter in the direction of the carotid septum. FIGS. 27A and 27B below illustrate an exemplary embodiment configured with velocity sensing with Doppler.

Once positioned, saline may be flushed through aperture 42 at flow rate to substantially displace blood from optical pathway 43 or to cool the device and the device to blood vessel interface. Then optical energy or directed high power ultrasonic energy is activated at a level and duration sufficient to effect ablation of the function of carotid body 89.

FIG. 13 depicts in simplified schematic form Side-Wire Directed Ultrasonic Energy Carotid Body Ablation DUECBA/LDUEA catheter 67 in position for ablation of a carotid body 89 and immediately following a directed ultrasonic energy ablation. As depicted, lateral emitting sonodome 50 is positioned against the wall of external carotid artery 91 at a position distal to the carotid bifurcation 2, which distance 104 as shown was predetermined prior to the placement of the Side-Wire DUECBA catheter 67. Guide wire 68 is shown exiting side guide wire port 69 into the internal carotid artery 90. The guide wire 68 in conjunction with guide wire port 69 provide a means for positioning lateral emitting sonodome 50 in the external carotid artery, in this case against the wall of the external carotid artery 91. at a predetermined distance 104 based on the distance between the distal tip 111 and the guide wire port 69, and to have lateral ultrasonic emission beam 51 oriented in the direction of carotid body 89. Based on average human anatomy, distance 104 is generally between 4 and 15 mm (e.g., 5 to 10 mm). In the position shown, guide wire port 69 is at a distance from sonodome 50 and energy emission beam 51 such that when guide wire 68 is positioned in the internal carotid artery and coupled with, or engaged with, a carotid bifurcation, the sonodome will be disposed in the external carotid artery at a desired distance from the bifurcation. Distance 104 can thus be selected to be about 4 mm to about 15 mm so that sonodome 50, or other emitter, is disposed in the external carotid artery within about 4 mm to about 15 mm from the bifurcation.

The ultrasonic ablation zone 93 is depicted encompassing the periarterial space comprising the carotid body 89. Also depicted is the carotid access sheath 5 used for placement of Side-Wire DUECBA catheter 67 into the common carotid artery 3. Also depicted is an extracorporeal ultrasonic imaging probe 94 configured for imaging the region containing carotid body 89 from the surface of the patient's neck 92 with ultrasonic imaging beam 95. In addition to imaging the region, ultrasonic imaging transducer may be used to detect the arrival of ultrasonic contrast medium in the capillary bed surrounding carotid body 89, which indicates an optimal time to apply ultrasonic ablation energy to region 93 to effect Directed ultrasonic energy ablation of the carotid body 89 due to the high ultrasonic energy absorption coefficient of the contrast agent. In some embodiments the imaging ultrasound probe can also be positioned within the patient's esophagus, which is closer to the carotid septum than the skin surface, as is described in more detail herein. Ultrasonic contrast agents with high absorption coefficients and high persistence that are suitable for this application are commercially available under the trade names Optison, SonoVue, and Echogen. These commercially available ultrasonic contrast agents comprise micro-bubbles between 2 and 4 microns in diameter, which are smaller than red blood cells, and are suited for perfusion through the capillary bed surrounding a carotid body.

Figure 14:
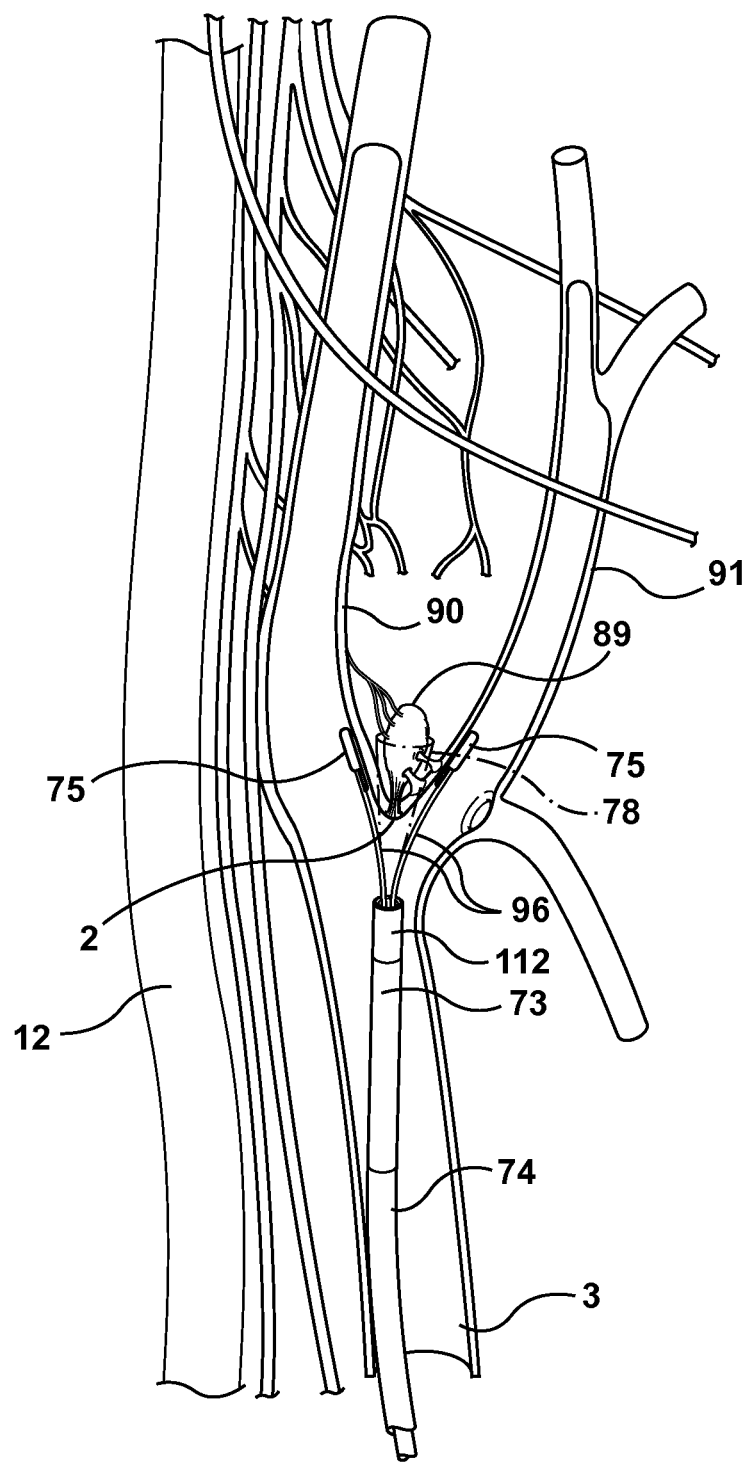
FIG. 14 depicts an axial directed optical energy device used within a bifurcation forceps catheter in position for carotid body ablation from within the common carotid artery.

FIG. 14 depicts an axial directed optical energy ablation device comprising a forceps configured for grasping an intercarotid septum during directed energy carotid body ablation, which will be referred to as Directed Optical Energy Carotid Body Ablation Forceps (DOECBAF) catheter. It can also be a Directed Ultrasonic Energy Carotid Body Ablation DUECBA catheter since ultrasound can be beamed forward and generally behaves in a manner similar to optical energy. Depicted is a DOECBAF catheter 73 in position for ablation of a carotid body 89 immediately following an ablation. The DOECBAF catheter 73 is positioned in the vicinity of the carotid bifurcation 2 with the distal sheath tip 112 just proximal to the carotid bifurcation 2, with one forceps pad 75 positioned against the wall of the external carotid artery 91, and second forceps pad 75 positioned against the wall of the internal carotid artery 90. DOECBAF catheter sheath 74 has been advanced over forceps assembly 96 to apply a squeezing force on the intercarotid septum within which lies the carotid body 89. An axial directed energy ablation probe, not shown, but is similar to the device depicted in FIG. 4 resides within the central lumen of DOECBAF catheter 73 and emits optical energy 78 between the arms of forceps assembly 96, as well as irrigates the optical field with saline to clear the optical energy path of blood or to cool the area to avoid damage to a blood vessel or coagulation of blood. It is appreciated that the pad 75 located in the external carotid artery can serve also as an emitter of ablative or imaging ultrasound energy. In alternative methods of use the distal sheath tip 112 is positioned at bifurcation 2 such that the crotch of the forceps is advanced into contact with the carotid bifurcation. In use the ablation zone of the directed energy is within about 10 to about 15 mm since the distal sheath tip 112 is positioned at the bifurcation.

In addition, a carotid body 89 may be located by squeezing the intercarotid septum. Since the carotid body is a chemoreceptor whose function is to signal hypoxia, squeezing can result in ischemic hypoxia within the intercarotid septum 2, which can cause the carotid body to signal a user detectable physiological response to the forceps induced ischemia. In an alternative embodiment, an axial directed ultrasonic energy ablation device may also be configured with forceps and used in a similar manner as depicted here.

Figure 15:
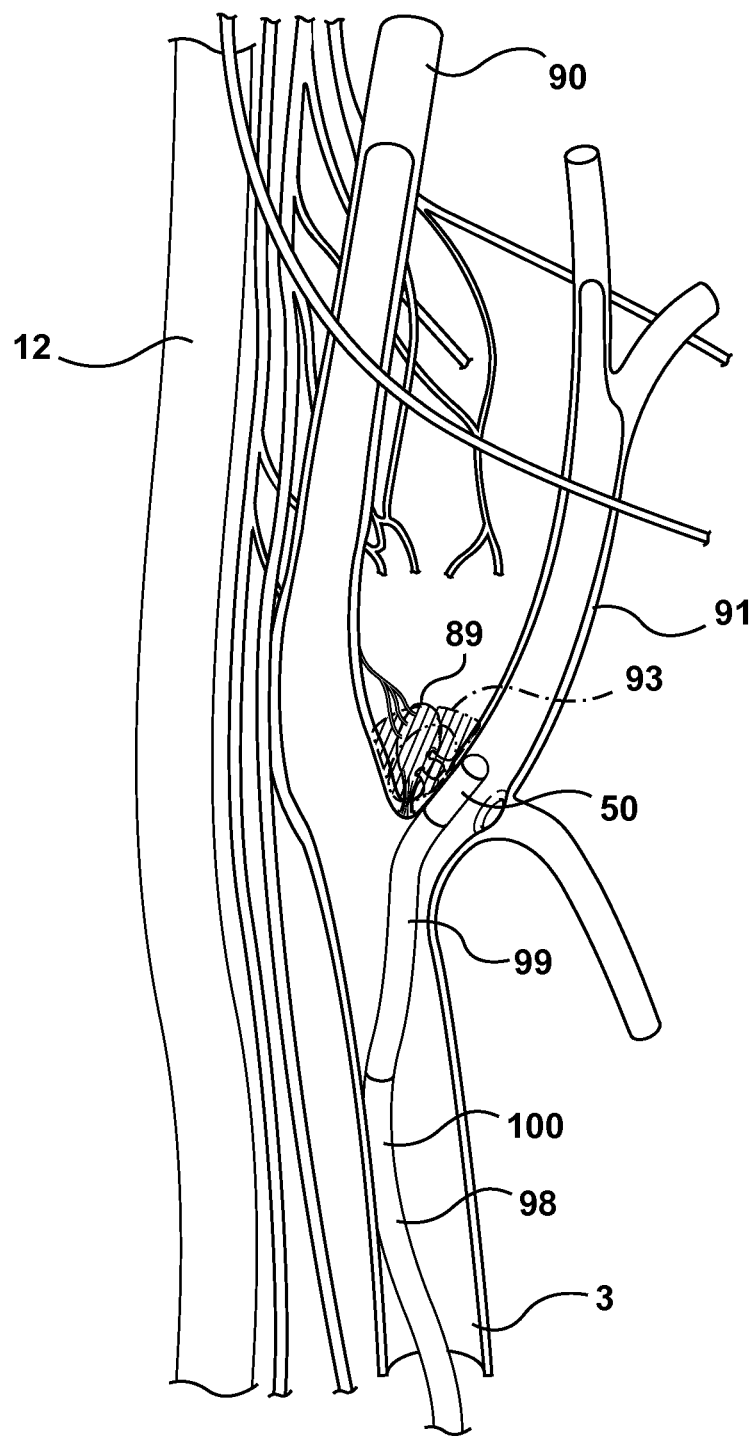
FIG. 15 depicts a steerable lateral directed ultrasonic energy ablation catheter positioned for carotid body ablation from within an external carotid artery.

FIG. 15 depicts a steerable configuration of Lateral Directed Ultrasonic Energy Carotid Body Ablation (LDUECBA) catheter 98 with deflectable tip 99 in position for ablation of carotid body 89 immediate following an ablation with a zone of ablated tissue 93 depicted. As depicted lateral emitting sonodome 50 has been positioned against the wall of external carotid artery 91 immediately adjacent to carotid body 89 by the user using fluoroscopic guidance and the steering capability of LDUECBA catheter 98 comprising deflectable distal segment 99, and non-deflectable segment 100. It is appreciated that the ablation device 50 positioned as depicted may require cooling of the sonodome with irrigating fluid in order to protect the arterial wall from thermal damage or blood from coagulating. It is also appreciated that while the depicted catheter 98 is shown in the femoral access approach configuration it can be also introduced "from above" using temporal artery access. The temporal artery is a tributary of the external carotid artery 91. LDUECBA catheter 98 may also be positioned within the internal carotid artery 90, and alternately the internal jugular vein 12 for directed energy ablation of carotid body 89. Those skilled in the art of catheter construction are familiar with deflectable tipped catheter construction techniques, and therefore will not be further described. It is appreciated though that typically deflectable catheters are made for larger cavities and that a shorter deflected section is expected in the case of carotid body ablation.

It is appreciated that in this and some other previous figures the jugular vein 12 is shown retracted in order to expose the carotid artery bifurcation. FIG. 17A illustrates a more representative configuration of an internal jugular vein with respect to carotid vasculature in which the jugular vein is lateral (i.e. closer to the skin) than the carotid artery and often next to a carotid bifurcation.

Figure 16:
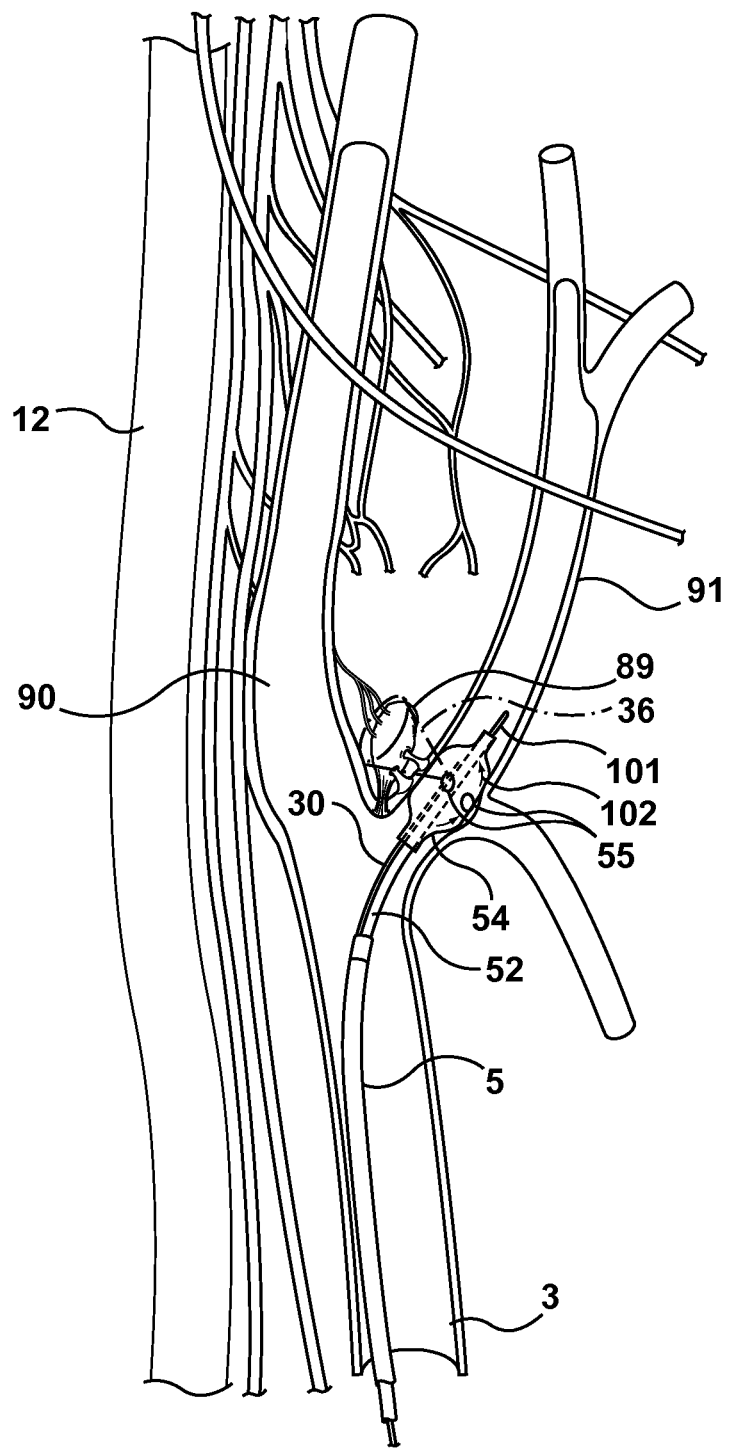
FIG. 16 depicts a directed optical energy carotid body ablation balloon catheter in position for carotid body ablation from within an external carotid artery.

FIG. 16 depicts a Directed Optical Energy Carotid Body Ablation Balloon (DOECBAB) catheter 52 residing in an external carotid artery 91 with the balloon 54 inflated with circulating fluid 102, and optical energy 36 being directed in the direction of carotid body 89 using radiopaque balloon markers 55 and fluoroscopic imaging. It is appreciated that an ultrasonic energy emitter can be positioned inside the balloon 54. If the balloon is filled with media, such as liquid, that conducts ultrasound well, it is practically transparent from the ablation or imaging energy delivery standpoint.

DOECBAB catheter 52 is positioned using carotid access sheath 5, and guide wire 101 by generally known fluoroscopically guided endovascular technique. DOECBAB catheter 52 may be configured to deliver green optical energy between 500 nm and 550 nm for selective absorption by the hemoglobin component of blood within the capillary bed surrounding carotid body 89, or may be configured to deliver red, infrared energy between 700 nm and 1100 nm for selective absorption of neurological tissue associated with carotid body 89. Alternatively, DOECBAB catheter 52 may be located in an internal carotid artery 90 with the lateral directed optical energy assembly 30 aimed at carotid body 89, or located within internal jugular vein 12 with the lateral directed optical energy assembly 30 aimed at carotid body 89. In addition to inflating balloon 54, recirculating fluid 102 provides cooling to the vessel wall, which prevents charring of the vessel wall and disruption of transmission of optical energy through the vessel wall. The DUECBAB catheter 59 depicted in FIG. 8 may also be used in a similar manner as the DOECBAB catheter 52 depicted here. If directed ultrasound energy is used it can be combined with imaging and Doppler sensing using a same or similar emitter hardware and associated electronics. For example, the devices shown in FIGS. 8 and 16 can be oriented in the direction of a carotid body by detecting high blood velocity in the internal carotid artery and then orienting the emitter in the direction of the high blood flow. This will orient the emitter, and thus the delivered energy, in the direction of the septum. This allows for controlled and directed ablation of the septum.

One aspect of this disclosure is a method of ablating a carotid septum. The method can be performed with the devices shown in FIGS. 8 and 16, which can be positioned as generally shown in FIG. 16. The method includes endovascularly positioning one or more directed energy emitters that are configured to emit directed high energy ultrasound within an external carotid artery and proximate to a carotid septum. In some embodiments the one or more directed energy emitters are disposed on a distal region of the catheter or other elongate device.

The method can also include orienting the one or more directed energy emitters towards, or aligning them with, the carotid septum so that the directed energy is delivered into the septum. Orienting the emitter towards the septum from within the external carotid artery allows the directed energy to be delivered towards the target septal tissue rather than towards non-target tissue. Proper orientation of the emitter can be performed with, for example, a side guide wire or similar device, as described herein, or using Doppler to detect blood flow in the internal carotid artery. In some uses of Doppler, the emitter is positioned in the external carotid artery and rotated within the external carotid artery until a sensed Doppler signal is indicative that the emitter is positioned towards the internal carotid artery and thus also the carotid septum. For example, a sensor on the catheter can be used to sense a maximum velocity of the blood flow in the internal carotid artery, at which time the emitter is directed towards the internal carotid artery and thus the septum. Rotating is then stopped and the emitter is determined to be properly oriented towards the septum. Ablation energy can then be delivered into the septum.

In embodiments in which Doppler sensing is used, the catheter can be configured with a Doppler sensor disposed on the catheter and in substantial lateral alignment with the emitter. In this configuration, when the sensor is oriented in the direction of high blood velocity from within the external carotid artery, the emitter is also oriented, or aligned, in the same general direction. The carotid septum is in between the external and internal carotid arteries, and thus when the sensor senses high flow in a cranial direction, the sensor is directed towards the septum. When the sensor and emitter are in lateral alignment, the emitter is also oriented towards the septum. This configuration allows for a sensed velocity to determine that the emitter is properly orientation towards the septum. The directed energy ablation as described herein is in contrast to ablation procedures that create circumferential ablations.

FIG. 17A depicts the use of a steerable Axial Directed Ultrasonic Energy Carotid Body Ablation (ADUECBA) catheter 103 in the internal jugular vein 12 for ablation of carotid body 89. ADUECBA catheter 103 is inserted into a peripheral vein such as the clavicle vein or femoral vein, not shown, and then navigated into the internal jugular vein 12 with axial emitting sonodome 46 positioned at the level of carotid body 89 as shown using standard fluoroscopic guidance. FIG. 17B depicts the manipulation of a wall of an internal jugular vein with the steering function of ADUECBA catheter 103 to position axial emitting sonodome 46 in close proximity to carotid body 89. It is noted here that the internal jugular vein 12 is a mobile and elastic structure and may be manipulated by ADUECBA catheter 103 to position axial emitting sonodome 46 in close proximity to carotid body 89. FIG. 17C depicts a directed ultrasonic energy ablation of carotid body 89 with ablation zone 47 encompassing carotid body 89. The ADUECBA catheter 103 depicted here can include features necessary to prevent overheating of the wall of the jugular vein such as irrigation with fluid and fluid filled balloons that conduct ultrasonic energy from the emitter to the blood vessel wall. Alternatively a steerable Axial Directed Optical Energy Carotid Body Ablation catheter, similar to the device depicted in FIG. 4 may also be used in a similar manner as depicted here.

Figure 18:
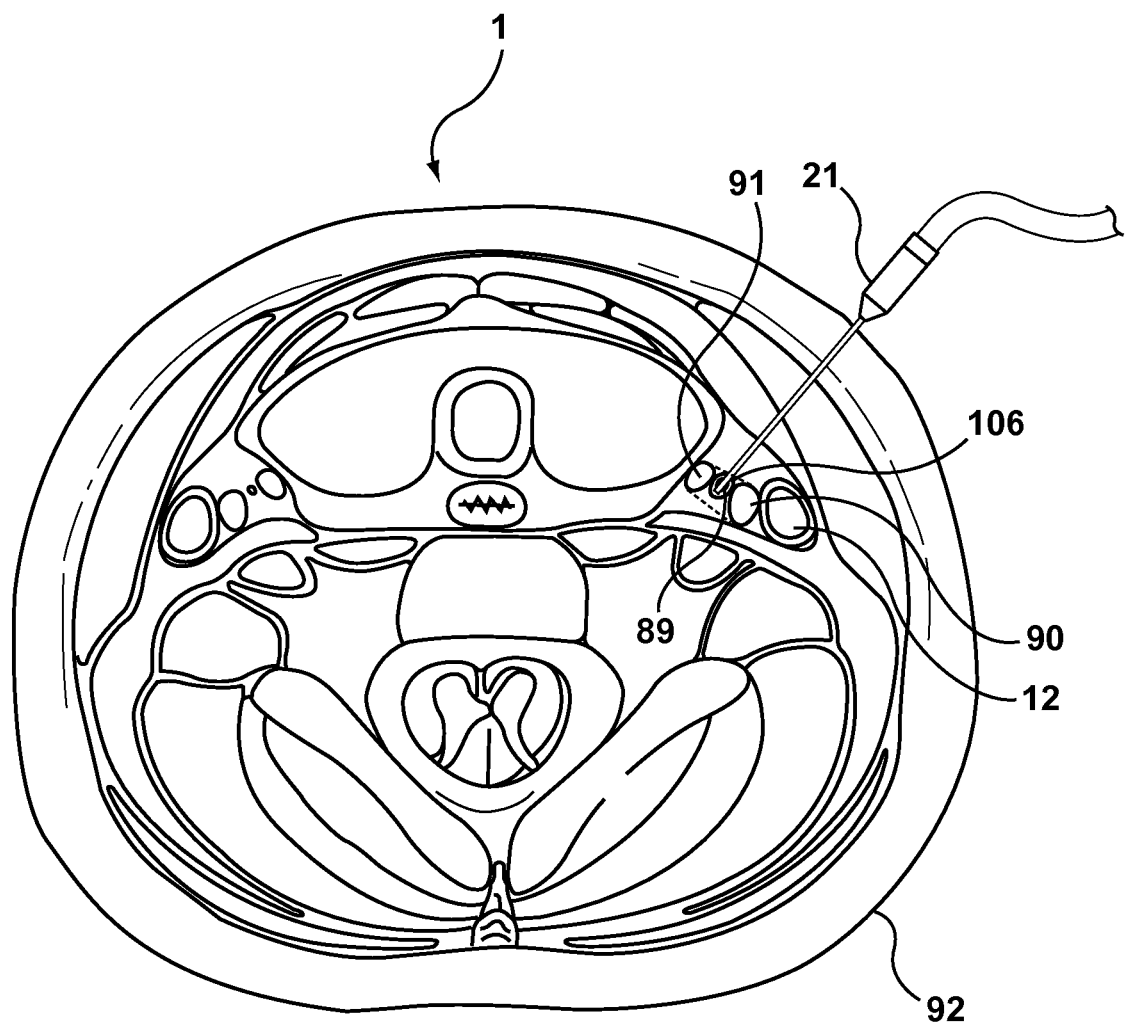
FIG. 18 is a cross sectional view of a patient's neck depicting percutaneous directed energy carotid body ablation.

FIG. 18 is a cross sectional illustration of the neck 92 of a patient 1 depicting a percutaneous Directed Energy Carotid Body Ablation (DECBA) probe 21 ablating a carotid body 89 within the target carotid body ablation zone 106, showing a zone of ablated tissue 106 between external carotid artery 91 and internal carotid artery 90. This figure depicts a percutaneous carotid body access approach for directed energy carotid body ablation. It should be understood, that a percutaneous approach as depicted is compatible with both optical and ultrasonic directed energy modalities, as well as probes with axial or lateral emission.

Figure 19:
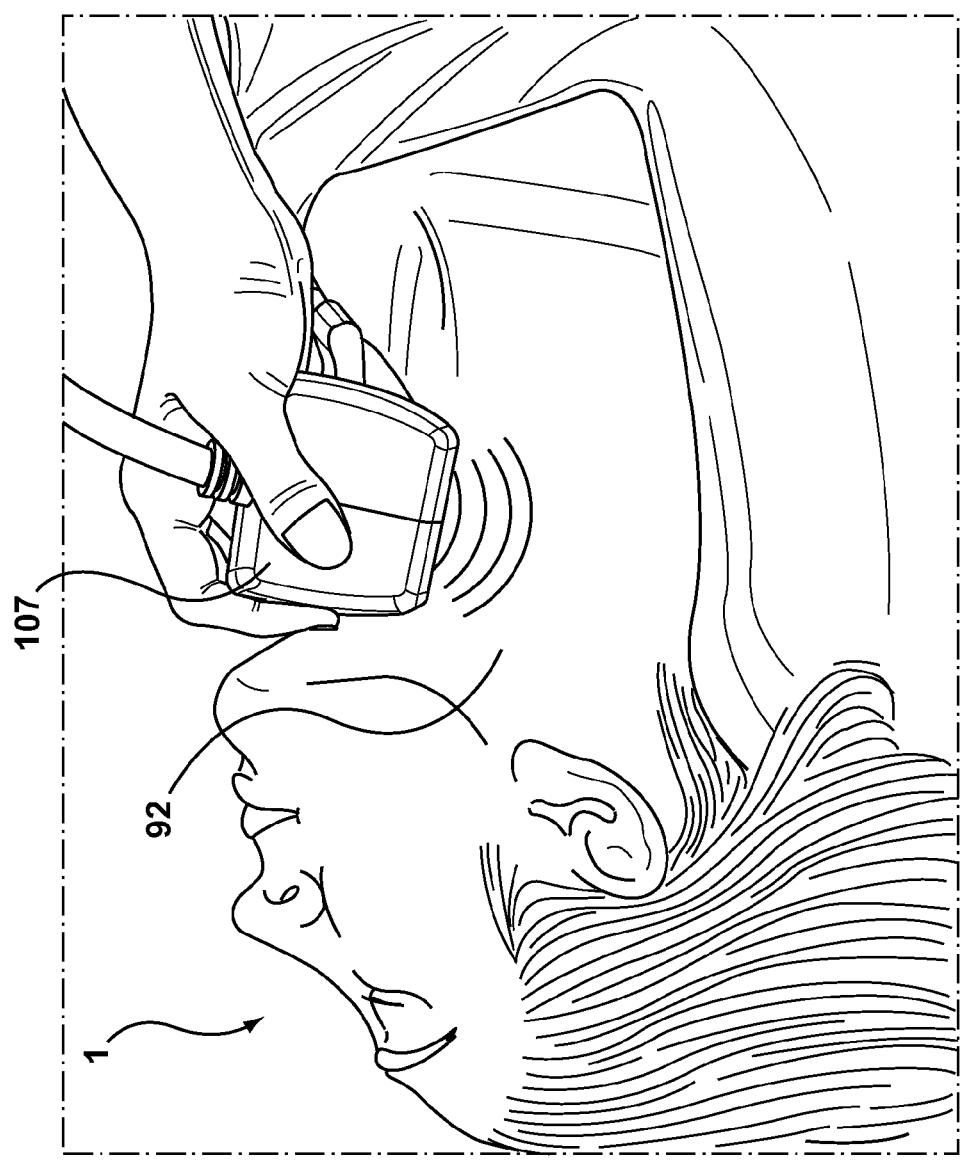
FIG. 19 is a depiction of a contrast enhanced directed ultrasonic energy carotid body ablation using a multifunctional extracorporeal probe.

FIG. 19 is a depiction of a contrast enhanced directed ultrasonic energy carotid body ablation using multifunctional extracorporeal ultrasound probe 107 placed on the neck 92 of a patient 1. Probe 107 comprises a means for ultrasonic imaging of the region of a carotid bifurcation, a means for measuring Doppler flow velocities within the carotid arteries, and a means to direct focused ultrasonic energy at the region of the carotid bifurcation, including a carotid body at an intensity sufficient to interact with micro-bubbles residing within the capillary bed surrounding the carotid body causing an elevation of temperature of the capillary bed sufficient to ablate the function of the carotid body without substantial thermal interaction with surrounding tissue. The imaging and Doppler functions are used to identify target landmarks for aiming the ablative ultrasonic energy. Ultrasonic contrast comprising fluorocarbon micro-bubbles between 2 and 6 microns are injected into a blood vessel of the patient. Upon arrival of the micro-bubbles within the capillary bed surrounding the carotid body, as detected by the imaging function of probe 107, the ablating ultrasonic energy emission is activated for a preset duration, or until, the micro-bubbles clear the capillary bed. Since the ultrasonic interaction of the micro-bubbles within the capillary bed results in ablative temperatures the capillary bed will be rendered incapable of blood perfusion, therefore, the effectiveness of the ablation can be confirmed with a second injection of ultrasonic contrast medium. A lack of presence of micro-bubbles within the carotid body following the second injection of ultrasonic contrast agent will confirm a complete ablation of carotid body function. A reduction in presence of micro-bubbles will indicate a partial reduction in carotid body function, and no change in presence of micro-bubbles between the first and second injection of micro-bubbles indicate a minimal ablation of carotid body function, or no effect on carotid body function. The imaging and Doppler functions provided by the device shown in FIG. 19 can be used with any of the endovascularly delivered devices herein. That is, one device can be endovascularly positioned proximate a carotid septum, while an external device is used for imaging the region and/or Doppler functions.

Figure 20A:
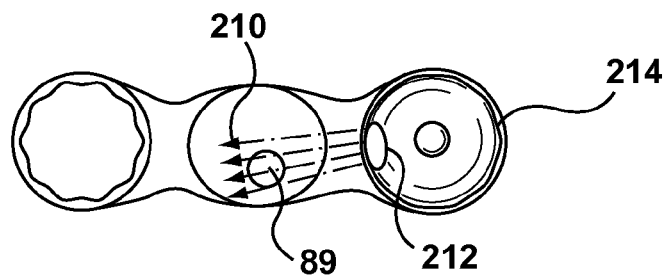
FIGS. 20A and 20B are schematic illustrations of an ultrasound ablation catheter configured to position an emitter in an external carotid artery.
Figure 20B:
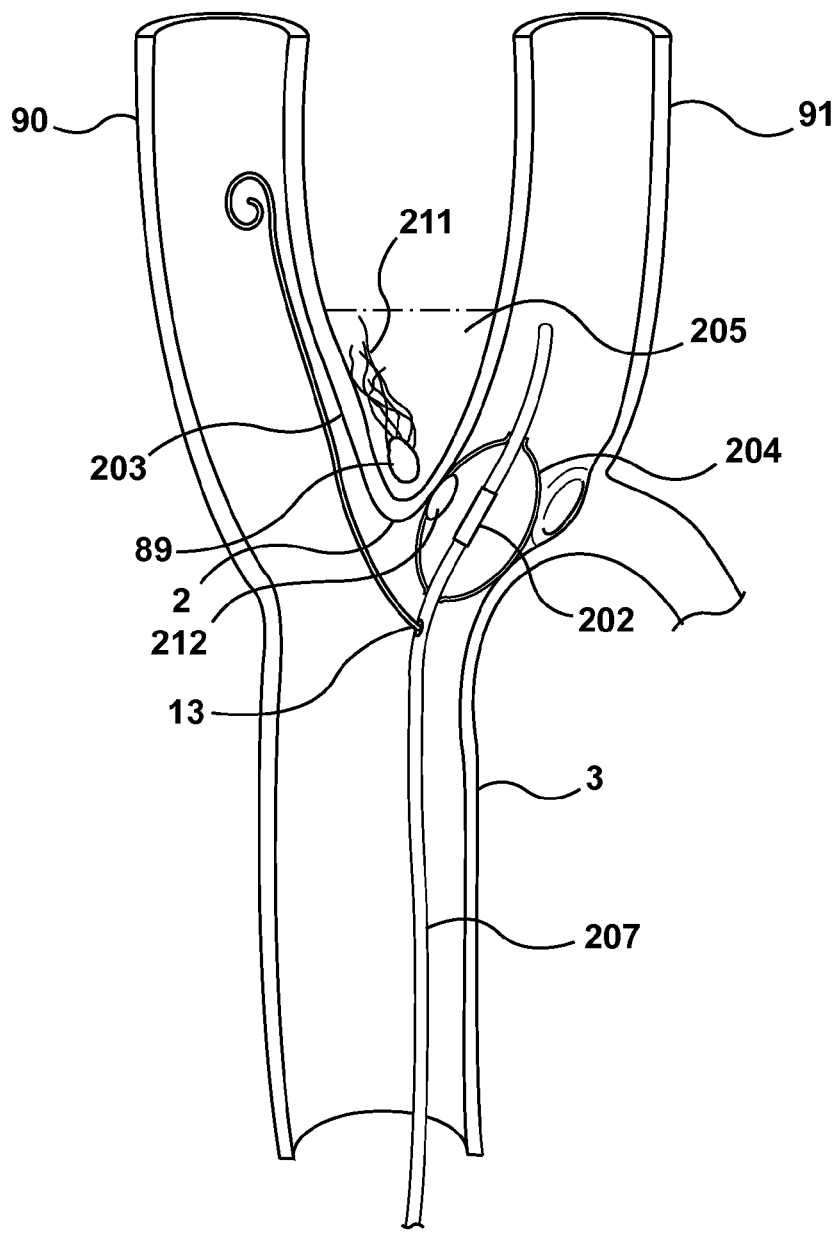

FIGS. 20A and 20B illustrate ablation of carotid body 89 or carotid body afferent nerves 211 with the purpose of substantially reducing afferent nerve signals from the carotid body (carotid body ablation) with thermal heating of tissue by ultrasonic energy. FIG. 20A is a transverse cross-sectional view showing ultrasound waves 210 directed in a radial direction through aperture 212 toward target tissue (e.g., carotid body 89). FIG. 20B is a sagittal cross-sectional view. The purpose of the embodiment is to substantially ablate the contents of the carotid septum 205 while protecting important non-target structures outside of the septum from damage by heat. These important structures may include nerves, other than afferent carotid body nerves, and blood vessels other than blood vessels feeding the carotid body chemosensitive cells.

There are advantages to the use of ultrasound to ablate soft tissue. For example, ultrasound may have capacity to penetrate sufficiently deep into targeted tissue. In some instances this can be a particular advantage for carotid body ablation, such as for patients who have a wider than average carotid body septum. A width of a carotid septum is generally determined as the distance between internal and external carotid arteries at a height of about 10 mm cranial from a carotid saddle. The average carotid body septum width is about 5.5 mm. Ultrasound could therefore provide advantages for patients with a carotid body septal width greater than about 5.5 mm. Research by the authors shows that some humans have a carotid septum as wide as 8-12 mm. Thus ablative energy may need to travel longer to reach the targeted tissue while avoiding lateral spread of convective heating to the areas outside of the carotid septum and collateral damage. Another exemplary advantage is that the nature of healing and recovery from ablation induced by ultrasonic energy may be different from other forms of thermal ablation, such as from RF energy. There is some evidence that ultrasound generates less scaring and fibrosis and allows for some regeneration of nerves. There is some evidence that only efferent nerves regenerate while afferent nerves remain disabled after healing of tissue ablated by ultrasound. In the case of carotid body ablation the afferent or sensory neurons (i.e., the nerves that receive information from the chemoreceptors and send them to the central nervous system) are the target. It is known that the carotid septum is surrounded by some efferent nerves that are not related to chemosensitivity and sympathetic activation. Some efferent neurons or motor neurons receive information from other neurons and send that information to effectors (muscles, glands), which produce a response. In the case of carotid body ablation nearby non-target efferent nerves may conduct signals to muscles of the face, throat, tongue and larynges. Unintended damage to those non-target nerves may result in facial tics, impeded speech or incorrect motion of airway muscles during sleep. In all cases, if such unintended damage occurs, it is very desirable for the patient to achieve fast recovery of those muscle functions. There is some evidence that thermal ablation with ultrasound may allow regeneration of non-target efferent nerves in the case of collateral iatrogenic damage during a carotid body ablation procedure.

The tissue that is ablated during a high intensity ultrasound ablation depends on the configuration of the emitter. Mechanical energy of the emitted sound waves attenuates with distance (i.e., decays). In this regard the emitter can be thought of as being configured to loose ablation power after penetrating a certain depth into tissue. For example, ablation depth can be controlled by varying the frequency at which the ultrasound is emitted. Additionally, the properties of the piezoelectric material used in the transducer effect the depth of ablation. In the embodiments herein, the transmitters are configured to emit high intensity ultrasound energy that loses ablation power after penetrating about 5 mm to about 10 mm into soft tissue. One advantage of this depth range of penetration is that is adequately ablates the carotid body but can avoid the ablation of sensitive non-target tissue, such as non-target nerves in the region. Additionally, the amount of tissue heating that occurs in the carotid septal region by ultrasound is influenced by the cooling effects provided by the blood flow in the internal and external carotid arteries. This cooling effect opposes the heating of tissue. These factors influence the volume of ablated tissue in the septal region in response to the delivery of high intensity ablation ultrasound.

A device for ultrasonic carotid body ablation in the embodiment shown in FIG. 20 comprises an endovascular catheter 207 introduced in to the common carotid artery 3 just below the bifurcation 2 of internal 90 and external 91 carotid arteries that form and define boundaries of the septum 205. Catheter 207 can be introduced into a desired position through a femoral artery and an aorta of a patient using techniques and instruments well known in the field of arterial imaging under fluoroscopic guidance aided by injections of contrast agent. Alternative access can be accomplished via the radial artery in the arm or temporal artery in the head of the patient. Catheter 207 can be equipped with a balloon 204 that is inflatable and can be filled with liquid that conducts ultrasound waves from an emitter that can be a piezoelectric crystal 202 that is the source of the ultrasonic waves and mechanical energy of ultrasound. The crystal is excited by electric current that is applied by a generator positioned external to the patient's body, and when excited, it vibrates at a desired ultrasound frequency. The catheter 207 contains wires that conduct the excitation electric current to the emitter. Other wires can conduct sensor signals such as temperature of the emitter or fluid in the balloon. Ultrasonic waves emanate from the crystal and travel freely through media that is conductive to ultrasound such as water or blood. They get gradually absorbed and attenuated in human soft tissue as they penetrate deeper into it. In the process tissue exposed to high-energy ultrasound is heated. To improve safety and prevent overheating of fluid inside the balloon the catheter can be equipped with a temperature sensor and the system can include temperature control circuits to prevent overheating of tissue and of the device itself. The system can be further equipped with cooling fluid irrigation or recirculation using an external pump in order to cool down the balloon and the blood vessel while delivering acoustic energy to the targeted tissues.

In contrast with previous endovascular systems for ultrasonic ablation of nerves, this embodiment and others described herein are specifically adapted to the positioning, securement and targeting of the carotid septum while protecting the extra-septal tissues, such as non-target nerves and organs, from unintended (collateral) damage. In general, if not guided, focused or directed in some way, ultrasonic energy may propagate from the source in all directions or often predominantly circumferentially. In the case of endovascular catheter ablation this could result in a creation of a circumferential lesion, which is generally not desired in the case of carotid body ablation.

The range of ultrasonic energy delivered may be varied with the properties of tissue and design of the energy delivery device. In general, ultrasound in the range of 10-30 MHz and 10-100 Watts/cm$^2$ is considered high intensity and suitable for ablation of tissue. For the depth of ablation desired in the case of carotid septum ablation frequencies of 10-15 MHz may be most advantageous since penetration of ablative power level of ultrasound deeper than 5 to 8 mm into the tissue may not be desired. For example, depth of ablative penetration less than about 5 mm to about 8 mm from the emitter can target and ablate septal tissue while minimizing damage to non-target non-septal tissue.

FIGS. 20A and 20B illustrate one embodiment in which the ultrasound energy is directed towards the carotid septum and reflected away from the circumference of the carotid artery that is not proximal to the carotid body and carotid body nerves. Balloon 204 may be a low-pressure balloon made of compliant or non-complaint material that is selected to substantially reflect or absorb ultrasound waves. Aperture 212 in the balloon is designed to allow ultrasound energy 210 to escape from the balloon and direct thermal ablation at the contents of the carotid septum 205 and specifically carotid body 89 and afferent nerves of carotid body 211.

The material that reflects or absorbs ultrasound may be a coating on the surface of the balloon. The opposing hemisphere is equipped with an aperture opening that is conductive to sound and pressed against the arterial wall or placed close to the arterial wall in the selected location suitable for ablation of a carotid septum. The material that reflects or absorbs ultrasound can be a layer of gas between two layers of polymer material or a multilayer material where the interface between two polymers reflects sound waves in the desired frequency range. An aperture 212 may be made of a material that transmits ultrasound relatively well compared to the material that the rest of balloon surface is made of. The aperture 212 may further comprise an ultrasonic lens that may be a fluid-filled bubble or a blister made of polymer or hydrogel that has the ability to focus ultrasound. Balloon 204 does not have to tightly conform to, or distend the walls of the carotid artery since ultrasound travels well through blood and a small gap 214 will not severely degrade the performance of ablation. This may be particularly important in anatomy of older patients with hypertension and where deposits of atherosclerotic plaque are encountered.

One of the objectives of the invention is to minimize risk of endothelial damage. Scraping, excessive heating, or any other kind of damage to the inner linings of a blood vessel could facilitate formation of a thrombus. In the illustrated embodiments endothelium is protected due to cooling with a low-pressure or high pressure balloon that is filled with fluid such as saline or water that can absorb thermal energy. If the thermal capacity of the fluid inside the balloon is not sufficient to maintain the surface of the balloon that is contacting the endothelium at a temperature low enough to be safe, forced cooling of the balloon can be employed such as by irrigation of by fluid circulation. In embodiments configured for cooling by irrigation a balloon may comprise pores or escape holes through which fluid may be released into the blood stream during delivery of energy. In embodiments configured for fluid circulation, fluid may be evacuated from a balloon while fresh cold fluid is added to replace it.

Another desirable feature of the embodiment illustrated in FIGS. 20A and 20B is the orientation and positioning of an aperture 212 in relation to the carotid septum. While it is possible for an operator to rotate the balloon in the artery (e.g., by torqueing the shaft) in order to align the aperture with the septum, it is preferred to have a self-aligning system. It is also important to have a self-retaining system that will not easily change position, in particular when carotid arteries or septum move as a result of the patient moving, coughing or breathing. With high-pressure balloons, such retention may be achieved by distending an artery and relying on friction to keep the balloon in place. The proposed embodiment illustrated by FIGS. 20A and 20B uses a low-pressure balloon in order to minimize chance of damage to endothelium. Alignment and retention in this example is achieved by a side port wire 203 that emerges from the shaft of the catheter 207 from a side opening 213 that is proximal to the balloon 204 and aligned with the aperture 212.

FIGS. 20A and 20B illustrates an exemplary ultrasound ablation catheter that supports an ultrasound ablation transducer, wherein the catheter is configured to directionally emit ultrasound ablation energy, a stabilizing device configured to stabilize the position of the ultrasound ablation transducer in an external carotid artery, and an orienting element configured to orient the directionally emitted ultrasound ablation energy primarily towards the carotid septum to ablate carotid septal tissue. In this exemplary embodiment the stabilizing device is inflatable balloon 204 and the orienting element comprises wire 203 and wire port. In alternative embodiments of FIGS. 20A and 20B, emitter 202 can be replaced with any other emitter described herein, such as an emitter configured to direct the high energy ultrasound energy, such as the flat plate emitter shown in FIGS. 29 and 36 below.

Figure 21:
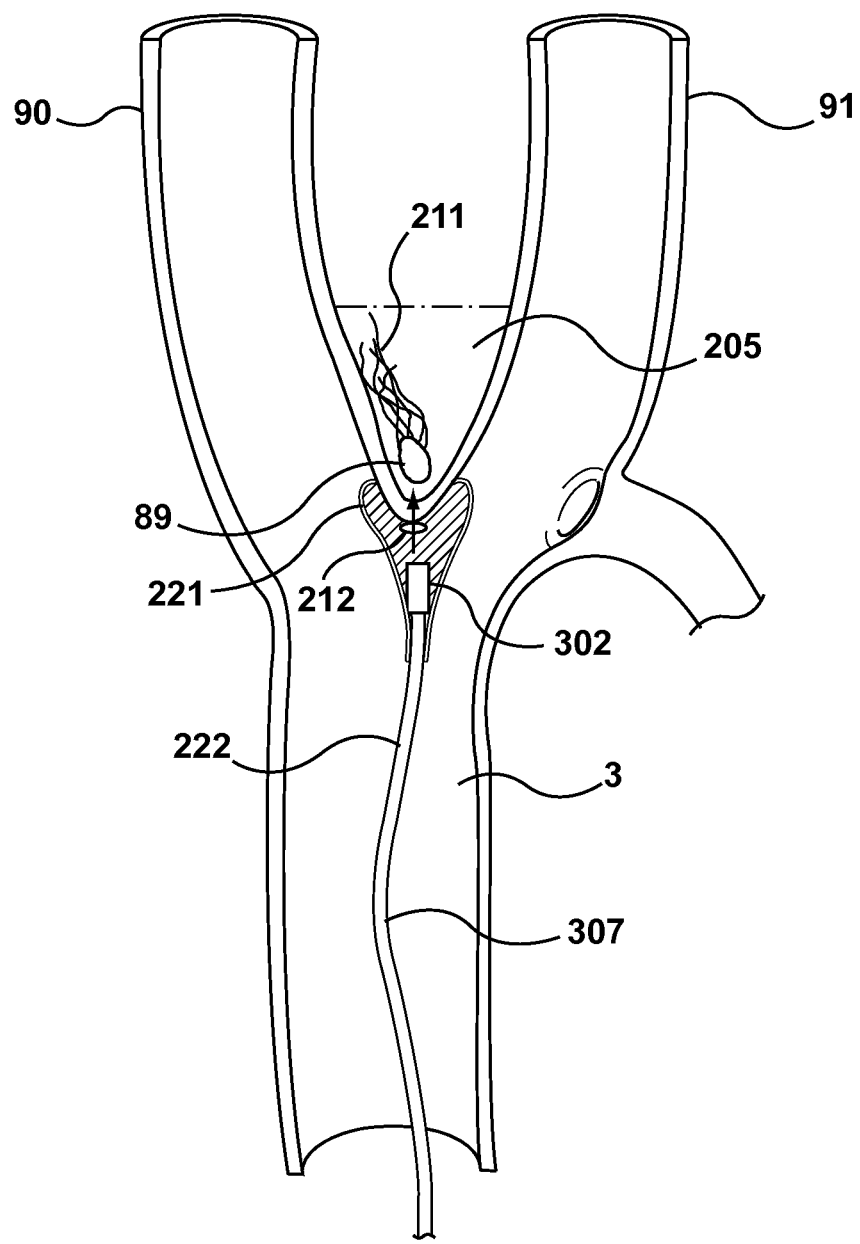
FIG. 21 is a schematic illustration of an ultrasound ablation catheter configured to position an emitter at a carotid bifurcation.

FIG. 21 shows an alternative embodiment comprising a highly compliant balloon 221 designed to conform to a carotid bifurcation. The aperture 212 directs the ultrasonic energy towards the carotid septum 205 and carotid body 89. In order to facilitate placement of the balloon on the carotid bifurcation the distal section 222 of the catheter 307 is deflectable and can be operated with a lever on the catheter handle outside of the body (not shown) with a help of a pull wire incorporated into the catheter shaft. The embodiment in FIG. 21 illustrates a catheter that supports a laser or an ultrasound ablation transducer configured to emit axial directed ablation ultrasound energy relative to the catheter, and a stabilizing device configured to engage tissue proximate a carotid artery bifurcation and stabilize the position of the laser light emitter fiber or ultrasound ablation transducer proximal to the carotid artery bifurcation. In this embodiment the stabilizing device is the balloon.

Figure 22:
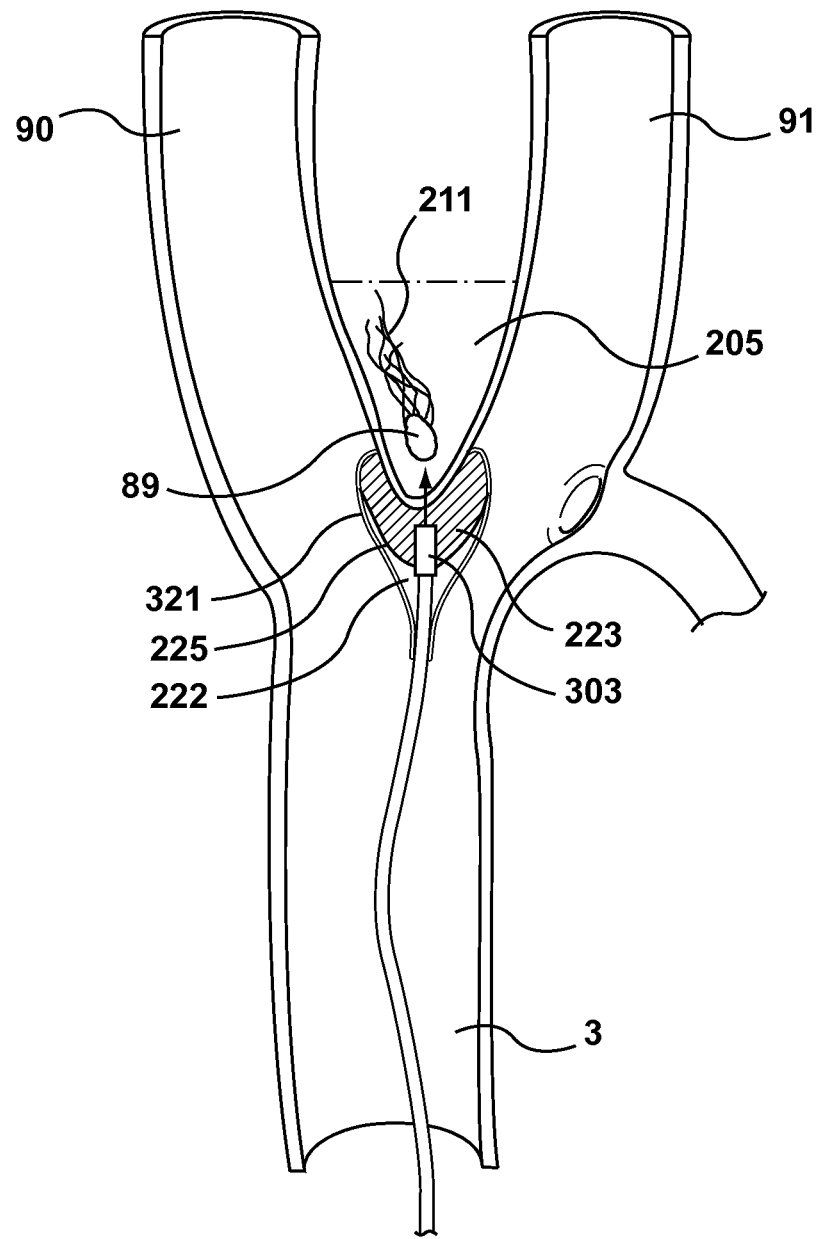
FIG. 22 is a schematic illustration of an ultrasound ablation catheter configured to position an emitter at a carotid bifurcation.

FIG. 22 illustrates an embodiment where at least partially focusing of ultrasound energy is achieved with a parabolic mirror. The mirror is formed by the interface 225 between two different speeds of sound media filled balloon cavities. Both cavities are contained within the balloon 321. Cavity 223 is filled with liquid that conducts ultrasound well, such as water or saline. Cavity 222 is filled with fluid that absorbs ultrasound, such as for example carbon dioxide gas. It is expected that the surface formed by the interface between these two media will reflect ultrasound waves emanating from the source emitter 303 towards the target: carotid septum 205, carotid body 89 and carotid body nerves 211. Furthermore, the effect of focusing and concentrating the energy will allow faster ablation with less electric energy delivered and smaller emitter 303. Furthermore, the focal point of energy delivery, or depth of ablation, where the deposition of energy is maximized can be designed to be several millimeters (e.g., 4 to 12 millimeters away from the balloon and vessel wall interface. In some embodiments the depth of ablation is no greater than about 5 mm to about 8 mm. This may improve targeting of a carotid body and nerves while reducing energy deposition in the vicinity of the vulnerable carotid artery wall layers such as media that can be damaged by excessive heat. It is understood that a perfect mirror may not be required in this application since the target is relatively large and relatively close to the source of energy. Use of non-focused, converging and semi-focused beams is known in the art of endovascular high-energy ultrasound application. A directed energy beam has certain advantages over true high intensity focused ultrasound (HIFU) since the focal point of a true focused beam can be relatively dangerous if through some error it is pointed at a wrong target.

Figure 23:
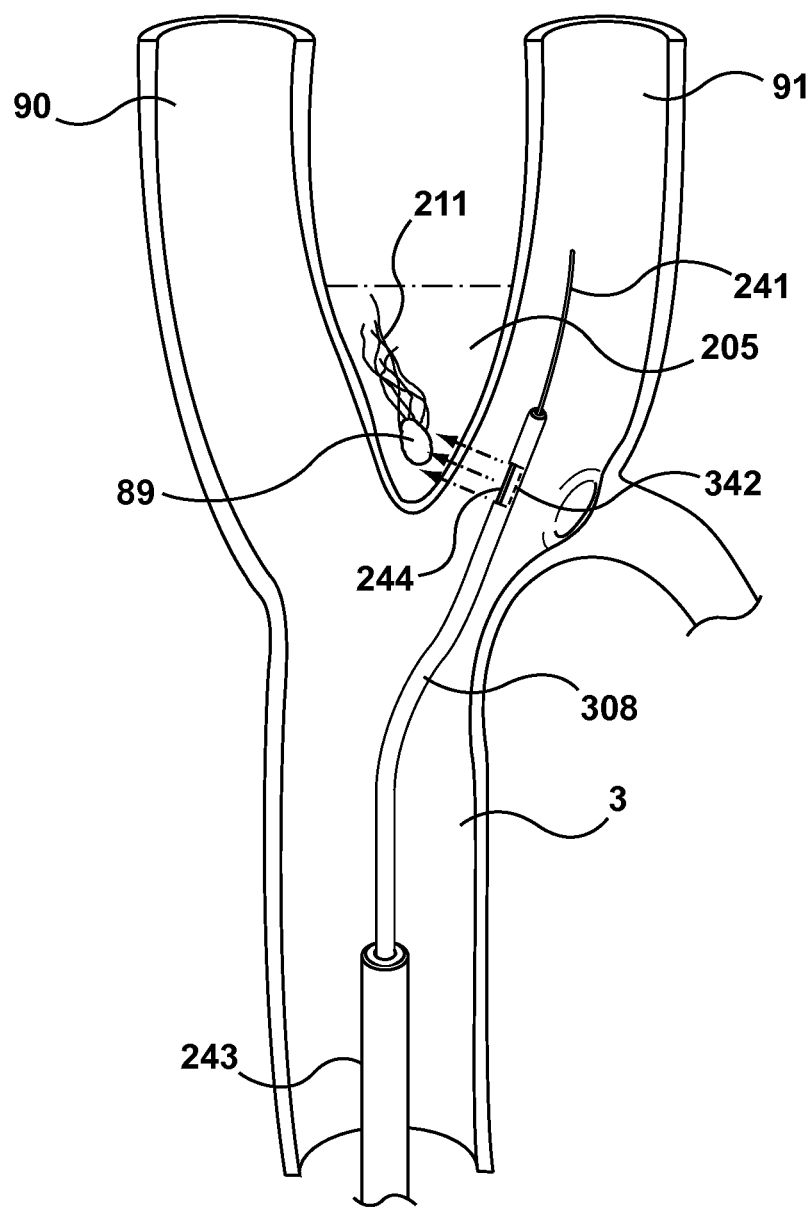
FIG. 23 is a schematic illustration of an ultrasound ablation catheter configured to position an emitter in an external carotid artery.

FIG. 23 illustrates an embodiment of a distal region of a device that does not include a balloon. Balloons may be instrumental but are not specifically needed to deliver ultrasonic energy to the carotid body septum. Blood conducts ultrasound very well and is not expected to heat up dangerously during ablation because of high blood flow in the carotid artery. Catheter 308 is shown deployed from the sheath 243. The sheath can be a steerable sheath to assist positioning of the catheter and ablation element. In the illustrated embodiment a catheter is advanced over a guidewire 241 to assist in fixation of the position of the catheter during the procedure. The guidewire can be advanced deep into branches of the external carotid artery and looped there in order to anchor the system and prevent displacement. A distal end of the catheter may be equipped with an ultrasound-emitting element 244. The element is shielded 242 in the back and prevented from directing energy circumferentially. The emitting element (emitter) can be a micro machined plate or array made out of piezoelectric material. The grooves machined in the array may be adapted to direct the energy in a beam directed substantially orthogonally to the catheter shaft, or laterally. Prior to activating the emission of ultrasound operator may rotate the catheter 308 inside the sheath 243 to achieve the desired position where the emitting surface of the emitter is facing the carotid septum. To facilitate rotation of the catheter a sheath 243 can be advanced into the external carotid artery so that only the distal part of the catheter with the array is protruding. Radiopaque materials and markers can be used to assist an operator in rotating and positioning the emitter.

Figure 24:
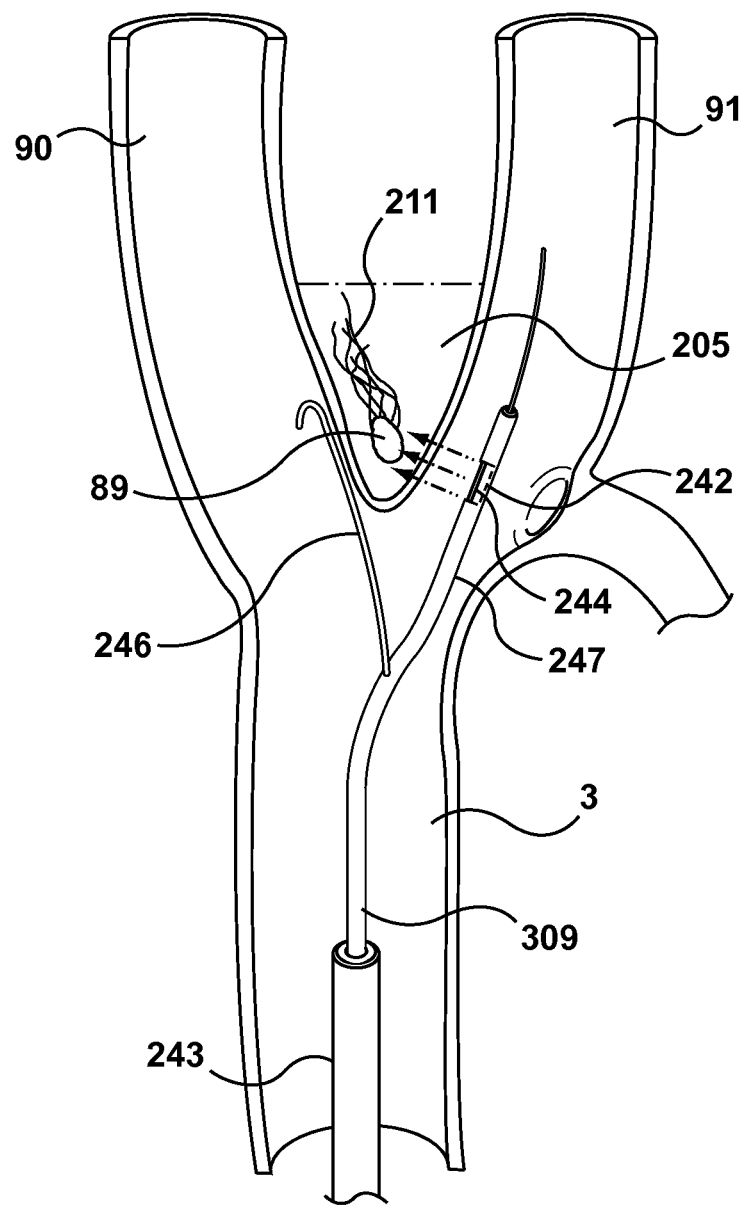
FIG. 24 is a schematic illustration of an ultrasound ablation catheter configured to position an emitter in an external carotid artery.

FIG. 24 illustrates an embodiment configured to facilitate the correct position and retention of the emitter by coupling a bifurcating distal end of the catheter 309 with a carotid bifurcation. Upon emerging from the sheath, distal end of the catheter forms a fork that is positioned over the carotid septum. Two arms of the fork 246 and 247 are placed in the internal and external carotid arteries. Since ultrasound travels well through blood, apposition of either arm to the wall of the septum is not required. This property of the design helps protect endothelium and reduces risk of dislodging plaque. A distal end of the catheter 309 can be equipped with a temperature monitoring device positioned proximate to the emitting element. The temperature monitoring device may be a thermocouple electrically connected to the controller external to the body (not shown). The controller automatically indirectly monitors temperature of blood passing over the surface of the ultrasonic emitter by monitoring temperature of the emitter. If the blood temperature rises above preset safe value, the controller may automatically turn off the delivery of ultrasound or reduce the delivered ultrasonic energy (e.g., by reducing electric excitation power). This feature may be activated in the case of sudden vessel spasm or if the emitter inadvertently contacts the vessel wall (e.g., for a predetermined amount of time). Both conditions can be expected to result in decreased cooling of the emitter and temperature rise.

Figure 25:
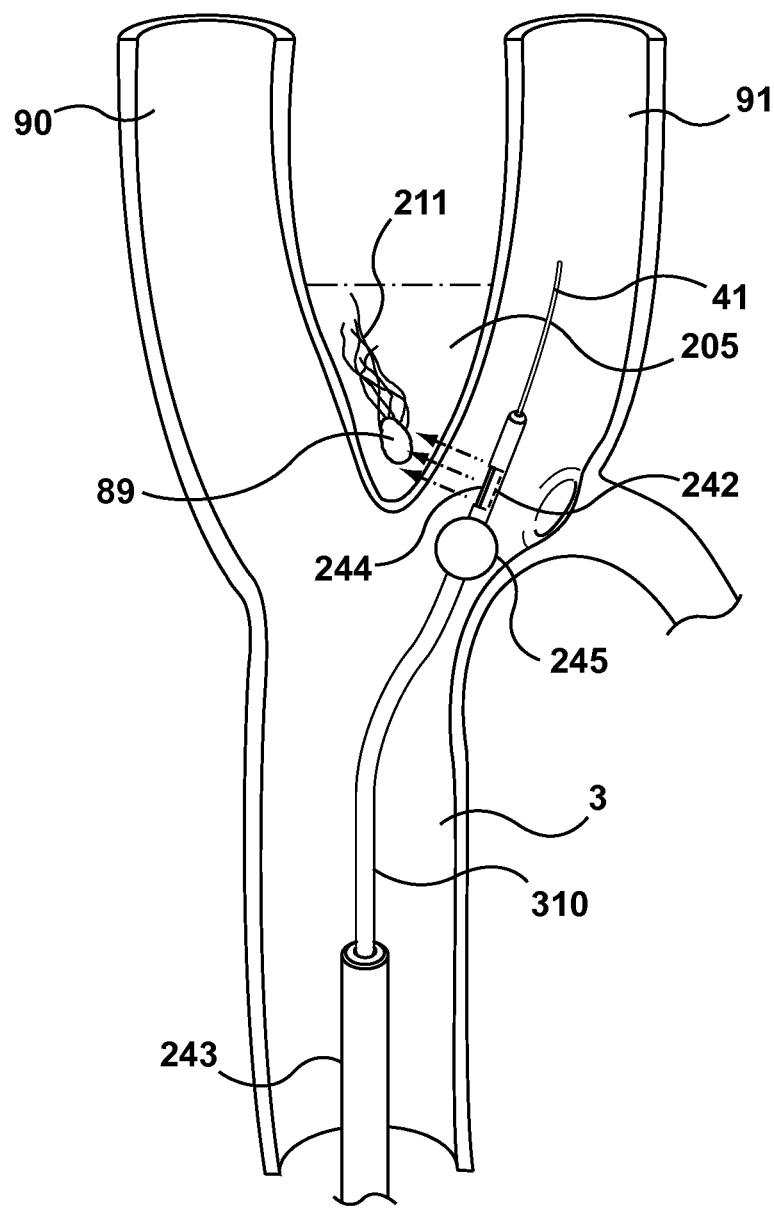
FIG. 25 is a schematic illustration of an ultrasound ablation catheter configured to position an emitter in an external carotid artery.

FIG. 25 illustrates a modification in the embodiment shown on FIG. 23. A small inflatable balloon 245 is shown on the distal tip of the catheter 310 distal or proximal to the emitting element. The purpose of the balloon is to cushion mechanical impacts and to prevent the emitting element from touching the wall of the artery. Mechanical contact can reduce cooling effect of the blood and tissue may get overheated. Alternatively the shaft of catheter 310 can form a coil inside the carotid artery distal to the emitter in order to maintain separation from the arterial wall. Other mechanical features such as multiple balloons, expandable cages and prongs can be used to prevent the hot emitter from contacting on the vessel wall directly. In some embodiments the one or more balloons or expandable devices can be sized and configured to engage with tissue and be stabilized by contact with tissue. This can stabilize the emitter within the vessel as well as prevent the emitter from making tissue contact. In some embodiments balloons are disposed proximally and distally relative to the emitter. If the expandable device is one or more balloons, blood flow around the balloons can be maintained to improve cooling of the emitter, blood and blood vessel. Alternatively, an orienting element such as a side port and side port wire, such as is shown in FIG. 13, can be incorporated into these alternative embodiments to further stabilize and orient the emitter and direct ablation energy.

Figure 26:
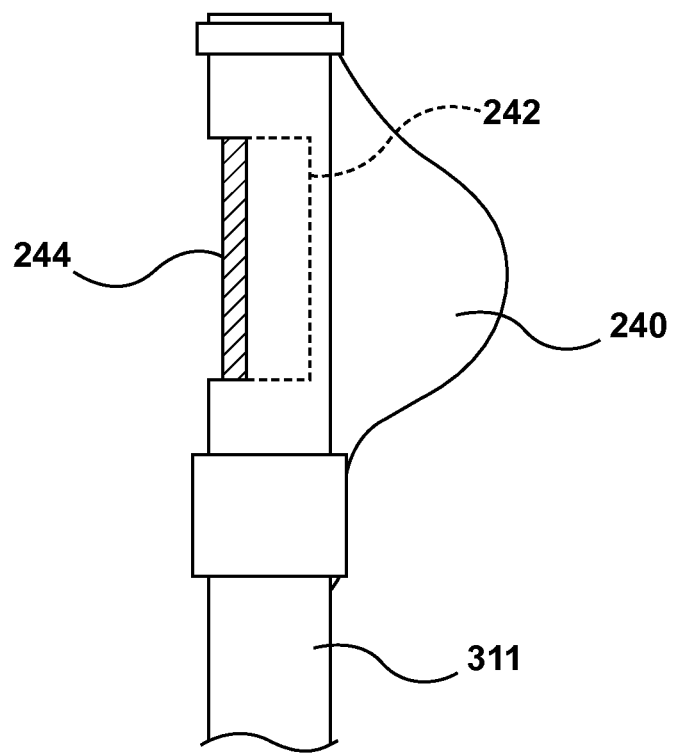
FIG. 26 is a schematic illustration of an ultrasound ablation catheter having shielding.

FIG. 26 shows an exemplary distal end of a catheter 311 with the emitting element 244, shielding 242 and an additional gas-filled balloon 240. The balloon serves to improve reflection and absorption of ultrasonic energy not directed at the target. It can be imagined that many additional elements can be included in order to align the catheter along the carotid septum wall, direct the beam at the septum and prevent migration of the catheter. The exemplary distal end of catheter 311 can be incorporated into any other catheter and features thereof that are described herein.

In the embodiments above ultrasonic energy delivery elements are shown placed generally in the external carotid artery. The external carotid artery may be preferred to the internal carotid artery since manipulation of a device in the external carotid artery is considered generally safer than in the internal carotid artery. The internal carotid artery delivers blood to the brain, while the external carotid artery delivers blood mostly to the face. Inadvertently dislodged plaque or thrombus passed in the blood stream through an internal carotid artery imposes a risk of brain embolism, while the same passed through an external carotid artery does not pose significant amount of such risk. It is understood, however, that in human anatomy there are variations and in some cases placement of an ultrasound-emitting element in an internal carotid artery may be advantageous. Any of the catheters described herein can thus be positioned in an internal carotid artery or an external carotid artery.

As mentioned above, some embodiments herein provide the advantage of positioning the emitter and aiming an ablating beam of high power ultrasound in a desired direction of a carotid septum and preventing accidental or unintended ablation of adjacent structures outside of the septum In some embodiments, a high power ultrasound emitter is oriented inside an external carotid artery and aimed in the direction of the internal carotid artery across the septum using the Doppler detection of the direction towards the internal carotid artery where blood flow velocity is high. Doppler Effect may be used to identify the high blood flow velocity, which may indicate the location of the internal carotid artery. Pulsed wave Doppler Effect can be used to determine blood velocity at the known distance (e.g., 3 to 10 mm) from the Doppler emitter—receiver positioned in the external carotid artery, where the internal carotid artery is expected be, while aiming to avoid interference from other blood flow sources and blood flow in the external carotid artery itself.

Use of a high power emitter is proposed that is at least partially naturally cooled by blood flow. The emitter may be positioned in an external carotid artery so it is spaced from the vessel wall and backed by a reflecting layer (e.g., high density material, layer of gas or foam) in order to direct an ablating beam and increase the efficiency of energy transmission to the septum.

Measuring Blood Flow in Vessels Using Ultrasound

One common way to measure velocities of the circulating blood within arteries of the neck, which is used in externally applied probes of ultrasound machines and in Intravascular Ultrasound (IVUS) catheters, uses the "Doppler principle" or "Doppler Effect", named after Christian Doppler (1803-1853), the Austrian physicist who developed the famous principle. The design of Doppler devices is based on the principle that sound waves from a moving source are compressed or expanded, or that the frequency changes depending on whether the source is moving towards (compressed) or away (expanded) from the observer.

The Doppler principal, as we know it in physics, is a wave theory that describes the relationship between velocity of objects and transmitted or received wave frequencies. This theory was first described in 1842 by Christian Doppler at the Royal Bohemian Society of Science in Prague. H is theory can be applied to measure velocity of moving objects. In medical applications ultrasound utilizes frequencies between 1 and 20 MHz, and in case of soft tissues frequencies in the 4-9 MHz range, which are transmitted from an imaging transducer. The reflected frequency-shifted waves are received by the same transducer.

Importantly, Doppler technology today allows detection of the direction (towards and away from sensor) and magnitude of blood flow in vessels.

To facilitate interpretation of ultrasound, images of flow depicted with color flow or spectral Doppler are essentially obtained from measurements of movement. In ultrasound scanners, a series of pulses is transmitted to detect movement of blood. Echoes from stationary tissue are the same from pulse to pulse. Echoes from moving objects, such as red blood cells, exhibit slight differences in the time for the signal to be returned to the receiver. These differences can be measured as a direct time difference or in terms of a phase shift from which the 'Doppler frequency' is obtained. They are then processed to produce either a color flow display, a Doppler sonogram, an acoustic signal, a wave form, or an electrical signal. For example, blue and red can be used to differentiate blood flowing towards and away from the sensor. In the case of the embodiments disclosed herein it may be important to differentiate blood flow in jugular veins and in carotid arteries that is in an opposite direction and have different velocity and amplitude of velocity pulsations.

An additional modification can be the use of pulsed wave rather than continuous wave ultrasound signals. Pulsed Doppler systems provide depth information and the ability to select depth from which Doppler information is received. It can be instrumental in isolation signals from a targeted blood vessel that is known to be a predicted range of distances from the transducer.

In conventional ultrasound Doppler systems, the velocity component along the beam axis is derived from the observed frequency shift. It is expected that such signal can be almost always obtained in the carotid arteries that converge at an angle. There is some interest in obtaining Doppler information from a transverse orientation of the beam. Recently, it was proposed that by using a pulsed-Doppler system with the beam transversely oriented with respect to the flow, the velocity component transverse to the beam can be derived from the edges of the spectrum. The general principles are outlined below.

These results are generalized to take into account arbitrary angles of incidence, effects of velocity gradients, arbitrary apertures, and arbitrary source pulses. For uniform apertures and transverse flow, it has been previously shown that the Doppler output spectrum is symmetrical about zero frequency, with its width depending on the Doppler effect due to the transverse velocity and the geometry of the problem. For a beam direction oblique to the velocity, it is shown that the spectrum is now shifted, and is centered about the classical Doppler frequency. For velocity gradients and transverse flows the spectrum remains symmetrical, with the edges corresponding to the maximal velocity; however, the profile becomes peaked at the center. For oblique incidence, an asymmetrical spectrum is obtained and its edges are related to the maximal and minimal velocities within the sampling volume.

In addition to the access routes described herein, access to an external carotid artery can also be gained from a temporal artery and can be guided by fluoroscopy and aided by a radiographic contrast solution, guided by external ultrasound, or combination of both. A carotid bifurcation can be detected by external ultrasound. An entry point into a temporal artery near an ear can also be determined using ultrasound or palpated. Using this information, the distance from the temporal artery entry point to the bifurcation can be measured. A catheter may be delivered through said entry point and an ultrasound emitter may be advanced said distance into the arterial system in order to place the emitter proximate the carotid artery bifurcation. Position of the emitter may be confirmed to be in an external carotid artery just above a bifurcation (e.g., within about 10 mm or within about 15 mm) with external (through the skin) ultrasound, esophageal ultrasound or endovascular ultrasound for example in jugular vein. For example, visualization of an emitter or catheter tip can be facilitated by making the emitter or the catheter tip echogenic, that is, reflective of sound waves by incorporation of micro bubbles or gas. Alternatively, the emitter backing material, designed to reflect and direct ablation, can be used for detection via external ultrasound visualization. Moreover, vibrating ultrasonic transducer emitter in the catheter tip may be used to emit low power waves detectable externally using an ultrasound probe.

Minimum X-ray and radio contrast exposure is beneficial for patients and physicians. Catheter and emitter position can be quickly confirmed by X-ray while the introduction and positioning is done under sonography guidance.

Ultrasound-guided percutaneous arterial access is a relatively simple procedure. A technique for temporal artery access may be similar to that used in other small vessels, such as the radial or tibial artery. The temporal artery, with a diameter of about 2.5 to about 3.0 mm is comparable to that of the radial artery and is usually superficial and easy to visualize on ultrasound. A transverse or cross-sectional view of the artery can be helpful in placing a 20 to 22 gauge introducer needle. Then, a guidewire may be smoothly advanced endoluminally into a carotid artery. The clinical justification for the safety of the temporal approach is that this vessel is often sacrificed intentionally without harmful sequelae during biopsy to evaluate possible temporal arteritis. In addition, it is relatively easy to obtain hemostasis in the temporal artery because it directly overlies the bone. Even if a hematoma occurred, it would be relatively easy to control.

As in other embodiments herein, FIGS. 27A and 27B illustrate an exemplary device and method of ablation, via thermal heating and other effects of ultrasonic energy, of a carotid body 89 and carotid body afferent nerves 211 with an objective of substantially reducing afferent nerve signals from the carotid body. FIGS. 27A and 27B also illustrate an embodiment of a method of positioning via temporal artery access (which is located behind the ear but not shown), which may further reduce or eliminate risks of embolization, which could be caused by manipulating devices in an aortic arch. It is understood that the devices in FIGS. 27A and 27B could be positioned using any of the access routes described herein. FIG. 27A illustrates a transverse cross-sectional view of an internal carotid artery 90 and external carotid artery 91 with an ultrasound emitter 265 directing an ultrasound beam 267 through a carotid septum 205 to an internal carotid artery 90. FIG. 27B is a sagittal cross-sectional view of the same. This embodiment illustrates an exemplary method of substantially ablating carotid septum 205 while protecting important non-target structures outside of the septum from damage by heat to avoid iatrogenic injury. Exemplary non-target structures include nerves, other than afferent carotid body nerves and blood vessels other than blood vessels supplying blood to the carotid body chemosensitive cells. In this embodiment an ablation device is placed in an external carotid artery 91, thus potentially reducing risk of brain embolization that may occur if the device were positioned in the internal carotid artery. This embodiment addresses the need to direct the energy beam 266 towards the carotid septum 205 by orienting the ablation energy emitter 264 towards the septum and the internal carotid artery blood flow using blood velocity detection methods and devices such as an endovascular Doppler method and device. The device for ultrasonic carotid body ablation shown in in this embodiment is an endovascular catheter 263 introduced into an external carotid artery 91 just above (cranial to) a carotid bifurcation 2. The device shown in FIGS. 27A and 27B can be introduced via a puncture of the temporal artery (not shown) that is a facial branch of the external carotid artery. Catheter 263 may be introduced into the desired position also through the femoral artery, the aorta, and the common carotid artery of a patient using techniques and instruments known in the field of arterial catheterization and imaging under fluoroscopic guidance aided by injections of contrast agent. As shown in FIG. 27B, catheter 263 is shown introduced into the external carotid artery 91 from a cranial direction using access via a temporal artery (not shown).

A distal section of the catheter 263 is equipped with two energy emitting and at least one energy receiving ultrasonic elements 264 and 265. Alternatively the same transducer can be used to emit high energy ultrasound for ablation and emit and receive low energy ultrasound for Doppler flow sensing. For example, Doppler sensing can be performed in the pulsed mode. It is also understood that modern technology allows to combine ultrasonic elements and to create ultrasonic emitter and receiver arrays. In the illustrated embodiment the emitting element 265 is also a receiving element and is a low energy element used for Doppler-based blood velocity measurement. The low energy beam 267 is emitted at an angle that is not orthogonal to the blood flow stream 269 in the internal carotid artery. Emitted energy beam 267 bounces off the moving reflective elements 268 that can be red blood cells in the blood stream flowing in the internal carotid artery 90. The Doppler frequency shift between the emitted 267 and reflected beams is maximized as the distal section of catheter 263 becomes substantially coplanar with the internal carotid artery 90. Catheter 263 is connected by cable 262 to a controller 360. The controller 360 is equipped with software logic and a user interface 361. The user interface 361 can display information, including numeric, graphic or acoustic representation of the Doppler signal, and advise a user on the relative orientation of the catheter's energy emitting element 264 or 265 and the blood flow 269 in the internal carotid artery 90 in order to align, or orient, the ablating energy beam 266 with the septum 205 and prevent collateral damage of non-target structures. For example, the distal end can be moved until Doppler frequency shift is maximized, which indicates that the emitters are oriented towards the carotid septum. Ablation can then be initiated to direct the ultrasound energy towards the septum. The distal end of the catheter 263 may also be equipped with a temperature monitoring device positioned proximate to the emitting element 264. Temperature monitoring device may be a thermocouple (not shown) electrically connected to the controller 360 external to the patient's body. The controller 360 automatically monitors temperature of the emitter and temperature of blood passing over the surface of the ultrasonic emitter 264.

The embodiment in FIGS. 27A-27B can be modified to include any of the features of any other embodiment herein. For example, the one or more emitters can be disposed within an inflatable balloon, such as is described above with respect to FIG. 16. For example, a balloon can assist in stabilizing, orienting, and cooling the one or more emitters.

Figure 28A:
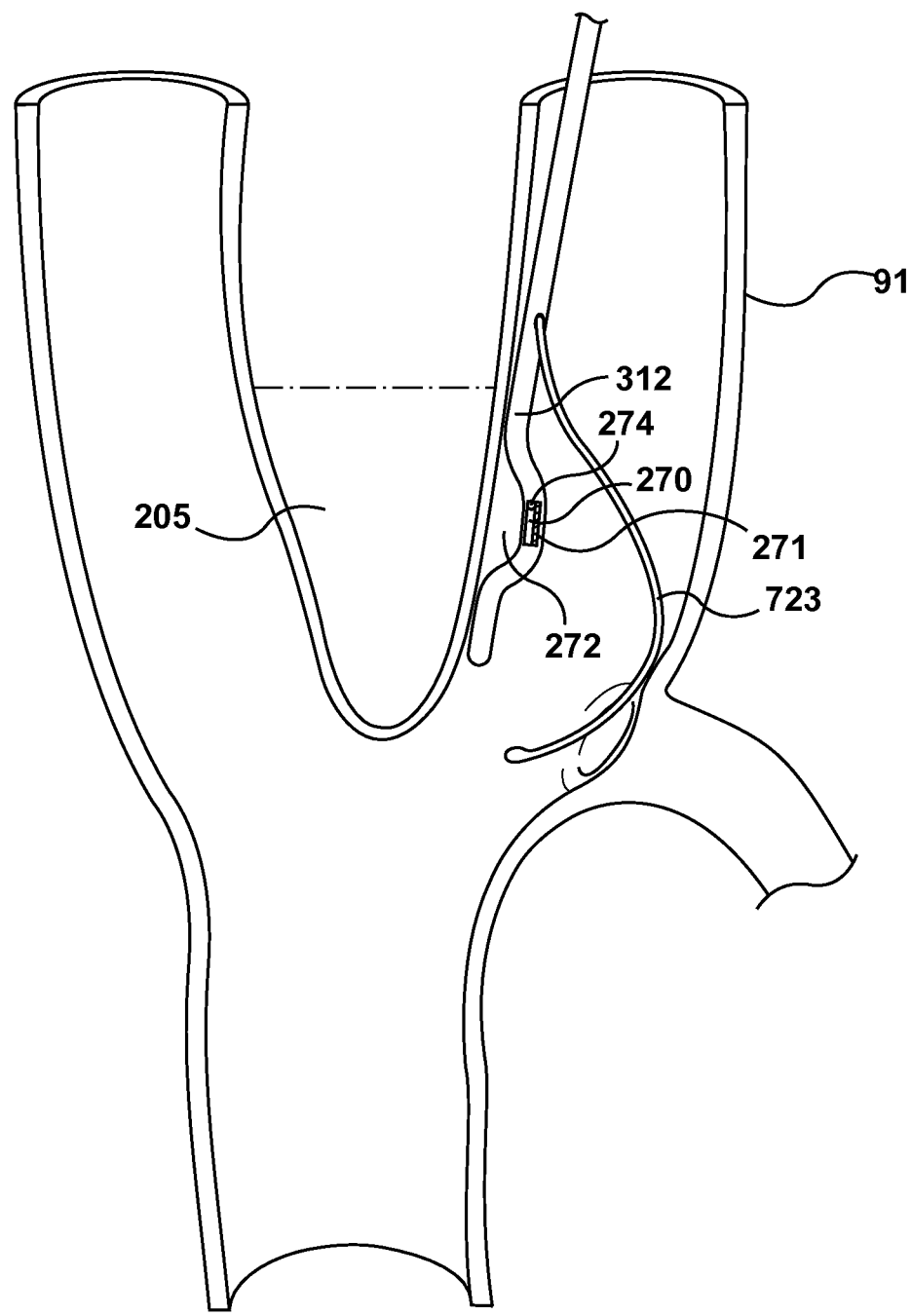

FIG. 28A shows a distal region of an exemplary catheter 312 shaped to prevent the energy emitter 270 from contacting the vessel wall of external carotid artery 91. A gap 272 between the emitter and the vessel wall ensures that the emitter and the wall are cooled by blood. The shaft of the catheter may comprise a preformed shape that curves the section of the shaft containing the emitter away from the axis of the catheter shaft in the opposite direction than the directed energy beam. Thermocouple 274 may ensure that excitation energy is turned off or reduced if the emitter and adjacent areas become too hot for safety, for example above 40 to 60 Deg. C. Catheter 312 also illustrates a reflective backing element 271 that may be a thin layer of gas such as air or carbon dioxide or a metal layer such as brass or a material structure that contains bubbles of gas. It is generally accepted that the layer of gas thicker than 1 mm is an acoustic insulator. The reflective element serves to reduce acoustic losses and direct the ultrasonic beam towards the septum 205. Catheter 312 incorporates an exit port for a guidewire 273 that can be used to offset and bias the catheter assembly towards the septum 205 and the ablation target. Improved acoustic attenuation materials and applications can be used in the construction of the catheter.

FIG. 28B illustrates an embodiment where the separation and cooling of the emitter 264 is achieved by two helical segments of the catheter 374 and 375 proximal and distal of the emitter. A catheter may be straight when introduced over a guide wire and form helical coils when the wire is withdrawn or pulled back. FIG. 28C shows an embodiment where the directional energy application emitter 264 is assisted in positioning away from the vessel wall and cooled by blood flow by collapsible struts 276. FIG. 28D discloses a catheter with an at least partially focused array of emitters 275. The distal regions of the catheters shown in the embodiments of FIGS. 28B-28D can be incorporated into any of the catheter designs herein.

Embodiments of ultrasonic transducers for placement in a patient's body for ultrasonic ablation of a carotid body are described herein. Such ultrasound transducers may be employed in any carotid body ultrasound ablation device described herein. For example, any of the ultrasonic transducers herein may be incorporated in a carotid body ablation catheter having a deployable or expandable structure (e.g., a balloon, cage, basket, mesh, or coil) to position, align, and maintain stable position of the transducer in a vessel such as an external carotid artery or internal jugular vein.

Figure 29A:
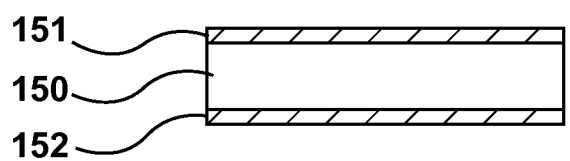
FIGS. 29A, 29B, 29C, 29D, and 29E are schematic illustrations of embodiments of an ultrasound transducer.

FIG. 29A illustrates an exemplary embodiment of an ultrasound transducer. As shown in FIG. 29A, an ultrasound transducer may be a non-focused, flat single element transducer, with two major surfaces approximately parallel to each other. The transducer aperture shape may be rectangular, or alternatively it may be round, oval or any other shape designed to fit an ablation device (e.g., catheter or probe). The width of the transducer aperture may be limited by the size (e.g., diameter) of the ablation device, for instance, to 2F, 3F, 4F, 5F, 6F, 7F, 8F, 9F, 10F, 11F. The length of the transducer aperture may be made larger than its width by increasing the length of the device distal assembly. The lengths of 4 to 6 mm have been proposed as a reasonable compromise between desired surface area and the ability of catheter to bend and navigate through anatomy. The surface of the rectangular essentially flat plate transducer can be made slightly convex in order to ensure convergence of the emitted ultrasonic energy beam.

It is generally desired to position the transducer with the emitter face surface pointing towards the target. The distal assembly containing the ultrasound transducer element of the ablation device may be guided in to place, for example in an external carotid artery, for instance, by using low intensity ultrasound Doppler guidance by the means of sensing blood flow in the internal carotid artery. The sample volume of the pulse wave Doppler along the ultrasound beam axis is adjustable in length and location. The location of the sample volume along the beam axis is preferably set to cover a range of about 5 to 15 mm from the transducer face. The ultrasound beam may be aligned with the aid of Doppler to cover a carotid body for ablation. Once the transducer is determined to be properly aligned, the carotid body and other desired target structures may be ablated using high intensity continuous wave, or high duty cycle (preferably greater than 30%) pulsed wave ultrasound. Pulsed ultrasound has advantage of cooling of the transducer and blood vessel by blood flow while the carotid septum more remote from the carotid blood flow continues to be heated. Ultrasound Doppler guidance and ultrasound ablation may be performed with the same transducer element, or alternatively with a separate transducer elements. Alternatively, the ultrasound transducer may consist of an annular array, for instance, a two-element array with a center disc for high intensity ablation and an outer ring for low intensity Doppler use.

The transducers herein can be configured to achieve thermal ablation with a maximum heating zone centered in tissue about 3 to about 10 mm from the transducer face along the ultrasound beam axis. In some embodiments the transducer is configured to achieve thermal ablation with a maximum heating zone centered in tissue about 5 mm to about 8 mm from the transducer face. As set forth elsewhere herein, ablating in tissue this far from the transducer can allow for selective carotid body ablation while minimizing the risks associated with ablating other non-target tissue. Heating of tissue by endovascular ultrasound is affected by cooling by blood and by dissipation of mechanical energy of an ultrasonic beam in the tissue. The location of the maximum heating zone depends on the transducer design, specifically, the aperture size and frequency of operation, which defines the attenuation with distance and the shape of the ultrasound beam. In general, a higher frequency ultrasonic wave attenuates in a shorter distance as it travels though tissue and is absorbed. The maximum heating zone location may be fixed with a single element transducer. Alternatively, an ultrasound beam may be steered to a desired maximum heating zone location using phased array technology, acoustic lenses or geometrically focused transducers. The device may be designed to achieve a volume of ablated tissue of about 8 to 300 mm$^3$ (e.g., about 154+/−146 mm$^3$). The combination of delivered energy, shape, direction of the ultrasound beam, and application time sequence may determine the volume of ablated tissue. Energy delivery, e.g., power settings and mode of operation (e.g., pulsed wave vs. continuous application time sequence), may be used to enhance heating in a target location or zone and achieve repeatable target tissue temperature over time. In an example embodiment, for a transducer having a width of about 2 mm and length of about 4 mm, an ultrasound frequency of operation may be chosen to be about 10 to about 30 MHz, (e.g., 15 to 25 MHz). In some embodiments the ultrasound is delivered at a frequency of between about 10-25 MHz. In some embodiments the ultrasound is delivered at a frequency of between about 10-20 MHz. In some embodiments the ultrasound is delivered at a frequency of between about 10-15 MHz. In some embodiments the ultrasound is delivered at a frequency of between about 15-30 MHz. In some embodiments the ultrasound is delivered at a frequency of between about 15-25 MHz. In some embodiments the ultrasound is delivered at a frequency of between about 15-20 MHz. In some embodiments the ultrasound is delivered at a frequency of between about 20-30 MHz. In some embodiments the ultrasound is delivered at a frequency of between about 20-25 MHz. In some embodiments the ultrasound is delivered at a frequency of between about 25-30 MHz.

The ultrasound transducer may be operated in the thickness resonance mode, i.e., the frequency of operation is substantially determined by the half wavelength thickness of the piezoelectric transducer element. The transducer element may be made of PZT-4 (Navy I) or PZT-8 (Navy III) type piezoceramic material or equivalent that exhibits low losses under high power driving conditions and may be incorporated in a piezocomposite structure. High intensity, high duty cycle, mode of operation may result in self-heating of the transducer element and surrounding structural elements. Therefore, the temperature of transducer or adjacent elements may be monitored with a temperature sensor (e.g., a thermocouple). If temperature is deemed to be too high, the transducer may be cooled down during use by a means of reducing duty cycle, or electrical power output into the transducer, or irrigation or circulating fluid cooling. Alternatively, transducer efficiency may be enhanced to reduce transducer self-heating by a means of electrical and acoustic impedance matching. For instance, the capacitive reactance of electrical transducer impedance may be cancelled or reduced by a means of inductive tuning. If the transducers perform imaging or Doppler sensing function the acoustic impedance, defined as a product of speed of sound and density, of commonly used piezoelectric materials is much higher than acoustic impedance of soft tissue (e.g., about 20×). Therefore, coupling of acoustic energy from the transducer element to soft tissue is poor. A means of improving coupling of acoustic energy may be to use a matching layer, or multiple matching layers, of about quarter wavelength thickness at the frequency of operation, on the transducer face between the transducer element and tissue. Theoretically, the acoustic impedance of a matching layer should be close to the geometric mean of that of the source, piezoelectric transducer element (about 30 MRayl), and load, soft tissue (about 1.5 MRayl). It is understood that some methods of improving acoustic efficiency may be relevant more to high energy delivery and some more to imaging and Doppler sensing.

In some embodiments the effectiveness of a therapeutic high energy mode transducer operating in continuous mode at or near resonance frequency can be optimized by including a matching layer made of material with acoustical impedance lower than the acoustical impedance of soft tissue or water (about 1.5 MRyal) divided by a transducer mechanical quality factor (between 0 and 100 measured in water). A common means of improving power transfer between water and acoustically hard ceramic by insertion of a quarter wavelength matching layer is not applicable in the case of a planar transducer undergoing large displacement at resonance. A thin therapeutic matching layer can be constructed, for example, by bonding a thin layer of polyester, polyurethane, or polyimide polymer directly to an emitting surface of the ceramic transducer. Alternatively, a therapeutic matching layer can be constructed of polyvinylidene fluoride (PVDF), which may be used as an imaging element or multi-element imaging array directly attached to the surface of a therapeutic transducer. PVDF is a piezoelectric polymer with low acoustic impedance well suited for ultrasound imaging. Deposition of PVDF on the emitting surface of a high impedance, hard, therapeutic ceramic may help to miniaturize the design and optimize power transmission in therapeutic mode and obtain an ultrasound imaging function in the same stack of transducer.

FIG. 29A shows an exemplary piezoelectric transducer element 150 with a top (or front) electrode 151 and bottom (or back) electrode 152. The transducer element 150 may be made of PZT-4 (Navy I) or PZT-8 (Navy III) type piezoceramic material. PZT-4 and PZT-8 type materials are known as "hard PZT", which have a relative high mechanical quality factor (e.g., about 500 to about 1000) and high Curie temperature (e.g., greater than 300° C.), and are therefore well suited for high intensity and high duty cycle use. The top 151 and bottom 152 electrode of the transducer element may be solderable to provide reliable electrical connections to transducer surfaces. The electrode with negative polarity is preferably on the outer radiation surface of the transducer, facing the tissue target. In this embodiment that is the top electrode 151.

Figure 29B:
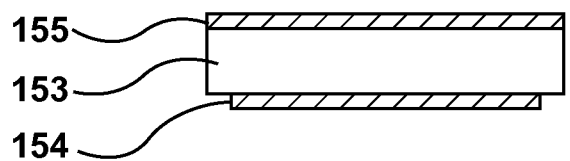

FIG. 29B shows an exemplary piezoelectric transducer element 153 with an undersized electrode 154 on the back side of the element. The purpose of the undersized electrode is to avoid the possibility of unwanted electrical connections (i.e., short circuit) to the transducer housing assembly. The top (or front) electrode 155 may cover approximately the full face of the transducer element 153.

Figure 29C:
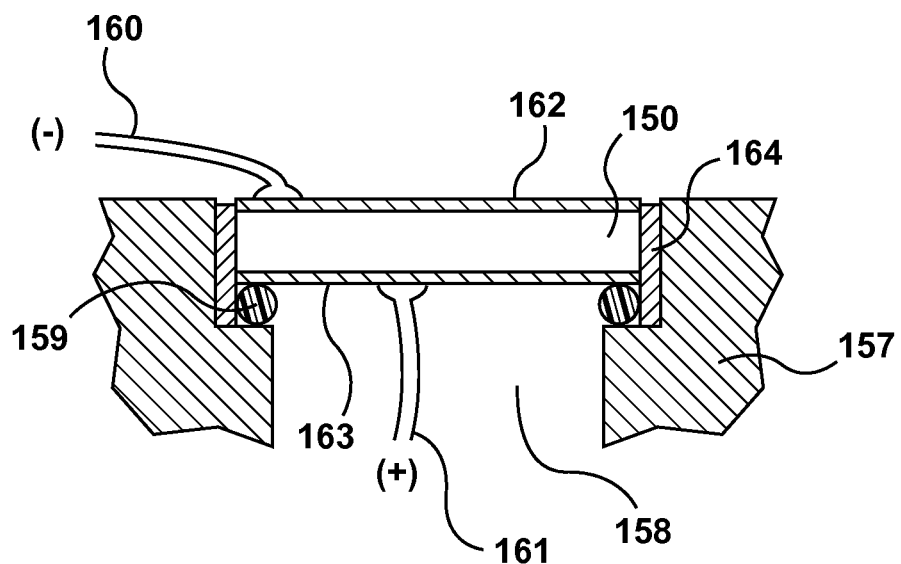

FIG. 29C shows an example of mounting of a transducer element 150 into a housing assembly 157 of which only a partial view is shown for illustration purposes. The transducer element 150 may be located approximately at or close to the axis of a shaft of an ablation device (e.g., catheter or probe) to allow a maximum transducer width. The transducer element 150 rests over a backing cavity 158 on an acoustic insulator 159, for instance an O-ring or frame made of soft compliant material. The purpose of the insulator is to isolate the acoustic vibration of the transducer element from the housing assembly. The sides of the transducer element 150 may be sealed with filler 164 that provides hermetic sealing. At the backside of the transducer element a backing cavity 158 may be filled with gaseous or foamy material of low acoustic impedance. Low acoustic impedance may be defined as a product speed of sound and density of material. The backing cavity is hermitically sealed from the environment (not shown) to prevent any liquid from coming in contact with the backside of the transducer element 150. Electrical connections may comprise negative polarity 160 connected to the front transducer electrode 162, and positive polarity 161 connected to the back transducer electrode 163. Electrical connections may be soldered or welded for example.

Alternatively a material with high acoustic impedance can be used to prevent spreading of energy in the direction other than target. Backing can be made of dense and high sound speed materials such as metals, for example bronze, that reflect acoustic energy. Generally transition or interface between materials with significantly different acoustic properties (e.g., speed of sound) will reflect acoustic energy.

Figure 29D:
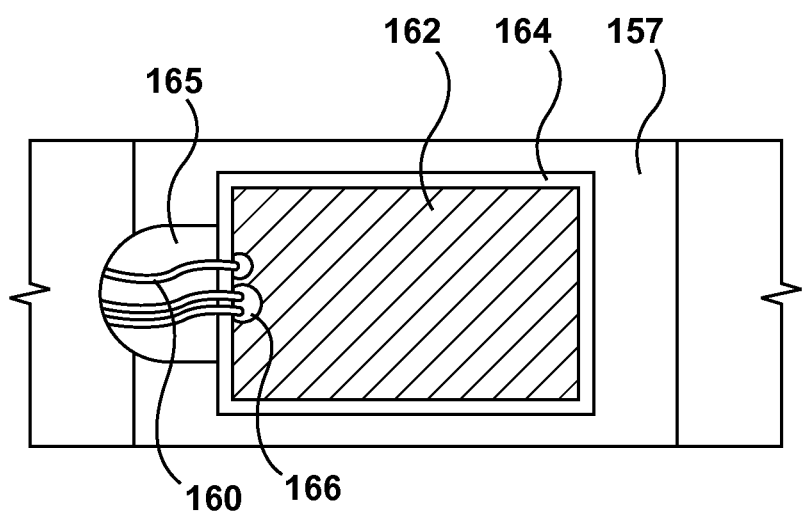

FIG. 29D shows a top view, or front face, of a transducer distal assembly. A wire lumen 165 may provide a path for electrical wiring to the transducer that at the proximal end of the device is connected to a controller that may contain a pulse wave Doppler circuitry and a RF signal source for ablation. The same wire lumen 165 may be used for thermocouple wires connected to a thermocouple 166 positioned on the transducer element and/or distal assembly of the device.

Figure 29E:
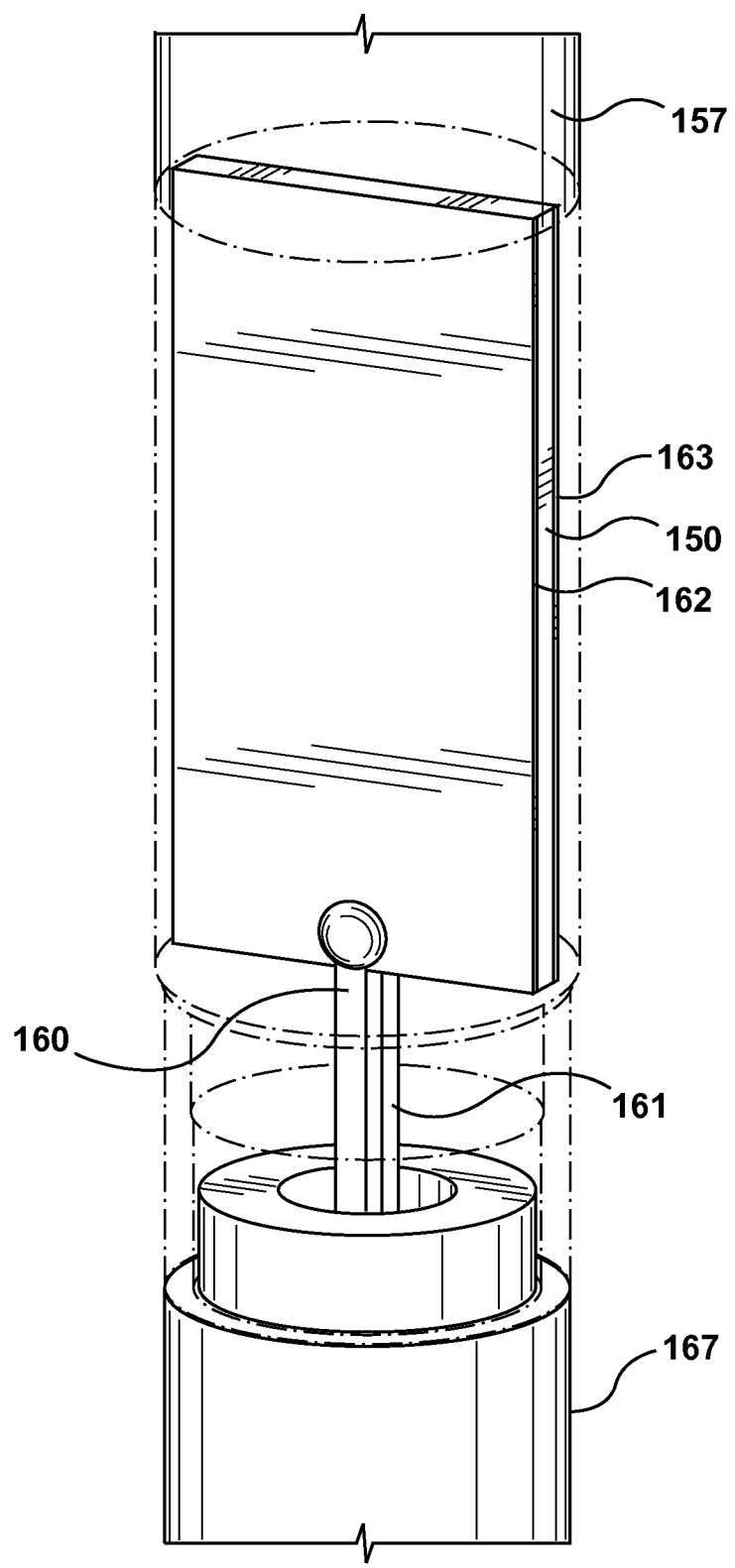

FIG. 29E shows an embodiment of a distal portion of an ultrasound ablation catheter comprising a rectangular ultrasound transducer 150 (as shown in FIGS. 29A, 29C, and 29D) positioned at or near an axis of the catheter shaft 167. The catheter may be configured to be controllably deflectable by applying tension to pull wires with an actuator in a handle. The pull wires may run through the shaft and be anchored near the distal portion of the catheter.

Ultrasound Carotid Body Ablation from an Endovascular Catheter Positioned in a Jugular Vein The disclosure herein includes embodiments in which an endovascular ultrasound ablation catheter is delivered to an internal jugular vein or one of its tributaries to direct ablative energy to a carotid septum. Trans-venous instruments can have an advantage over trans-arterial ones in that they have a lower risk of brain embolization. Additionally, a larger instrument can be used in trans-venous approaches.

One aspect of the disclosure is a method of carotid body ablation that includes introducing an elongate device such as a catheter into the venous system of the patient, advancing a distal end of the catheter into a jugular vein or one of its tributaries proximate to a carotid septum, wherein the distal region includes a directional emitter of high energy ultrasound capable of delivering ablative acoustic energy, aligning the emitter with the carotid septum, and directing energy into the septum to ablate the carotid body.

Figure 30A:
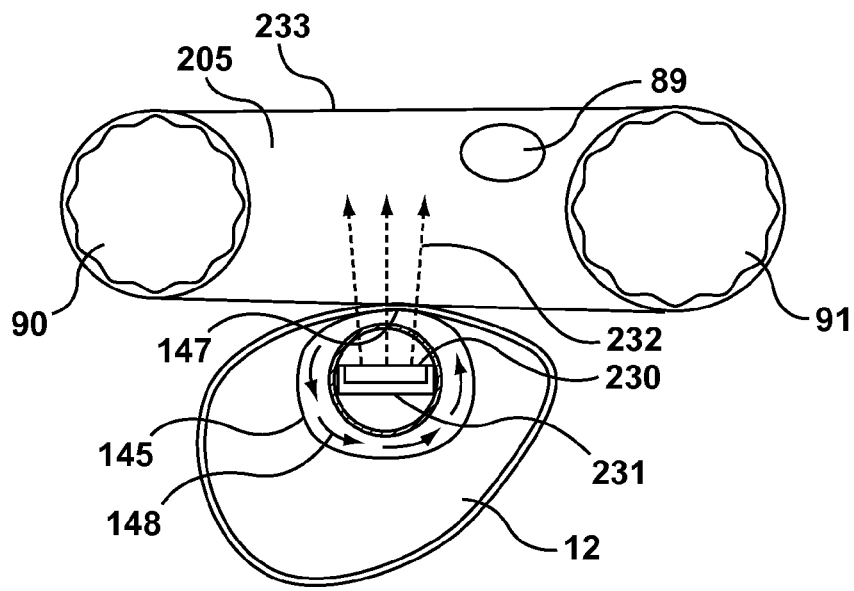
FIGS. 30A and 30B are schematic illustrations of an ultrasound CBA catheter delivered to an internal jugular vein.
Figure 30B:
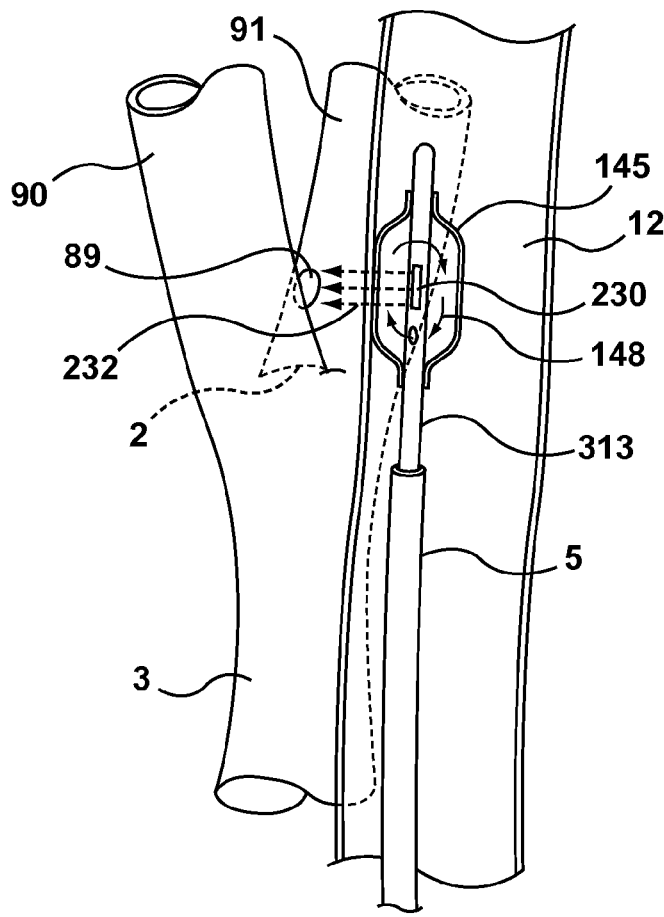

FIGS. 30A and 30B illustrate an exemplary embodiment of a trans jugular ultrasound ablation catheter. As can be seen FIG. 30A, the proximity of a jugular vein to a carotid septum and carotid body provides an opportunity to ablate the carotid body with a device positioned in a jugular vein. Catheter 313, as shown in FIGS. 30A and 30B, includes an ultrasonic emitter 230 and optional receiver. The emitter is capable of delivering high-energy ultrasound in a selected direction (e.g., directed high energy unfocused ultrasound beam). Reflective backing 231 (e.g., an acoustic insulator made from, for example, air, foam, or dense metal) reflects ultrasound waves 232 or ensures they are mostly directed in the desired direction. Frequency, power, duration and aperture are calculated or experimentally determined, considerations of which are described in detail above, to ablate tissue within a carotid septum 205 but to prevent ablative energy from penetrating through and beyond the septum, for example beyond a medial boundary 233 of the carotid septum. For example, the emitter can be configured so that ablation energy delivered may be deposited no more than about 12 mm, 11 mm, 10 mm, 9 mm, 8 mm, 7 mm, 6 mm, 5 mm, 4 mm, or 3 mm into tissue from emitter 230. In some embodiments the emitter is configured such that the high energy ablation ultrasound will lose ablation power after penetrating about 3 mm to about 12 mm into soft tissue, such as about 3 mm into soft tissue, about 4 mm into soft tissue, about 5 mm into soft tissue, about 6 mm into soft tissue, about 7 mm into soft tissue, about 8 mm into soft tissue, about 9 mm into soft tissue, about 10 mm into soft tissue, about 11 mm into soft tissue, or about 12 mm into soft tissue. There may be some patient to patient variability in the size of a septum, and thus it may be beneficial to obtain visualization of the septum prior to ablation, obtain an estimated size of the septum, and use delivery parameters based on the estimated size.

Excitation frequencies in the range of about 10 to about 30 MHz, such as between about 10 MHz to about 20 MHz, can be expected to produce the desired effect, including sufficient depth of penetration of ablative energy and at the same time containment of the desired ablation zone. Cooling from blood flow within internal 90 and external 91 carotid arteries may assist containment of the ablative thermal energy, or ablation zone, in a carotid septum. Thus a heat distribution from an ablative ultrasound beam may be shaped additionally by inhomogeneous heat conduction of the area influenced by cooling blood flow and enhancing ultrasound induced heating related bio-effects in the target space between the internal carotid artery 90 and external carotid artery 91 (i.e. carotid septum 205). Due to high blood flow and consequent effective thermal cooling of blood vessels, ultrasound energy in the selected frequency range travels through the vessel walls and blood without significant biologic effects and therefore only the septum will be selectively heated. One aspect of this disclosure is a method of delivering high intensity ablative ultrasound towards the carotid septum while utilizing the cooling effects of the blood in the internal and external carotid arteries to selectively ablate only septal tissue. Some attenuation through scattering can be expected to reduce the posterior ultrasound effects and protect non-target structures behind the arteries. This principle can be classified as forming of a lesion using thermal heating by an ultrasound beam that is shaped in the tri-vessel space. In some embodiments the emitted ultrasound energy ablates septal tissue by increasing the temperature of the septal tissue to greater than about 45 degrees C., yet tissue outside of the septum remains less than about 45 degrees C. and is thus not ablated. Ablation is a function of temperature and time, and longer exposure to lower energy and temperature can also ablate tissue. This disclosure focuses mainly on temperature and includes treatments that last about 5 to about 60 seconds. The temperatures mentioned herein however shall not be interpreted as strict limitations.

Choice of ultrasound therapeutic parameters such as power, frequency, time and regime (e.g., pulsed or continuous) may ensure that an ultrasound beam does not ablate tissues deeper than about 812 mm from the jugular vein. For the typical attenuation of ultrasound in muscle tissue of 1 dB/cm/MHz, the characteristic depth of unfocused ultrasound penetration in tissue is the inverse of attenuation coefficient divided by frequency. For example, at 10 MHz the characteristic penetration depth is 7.7 mm and at 20 MHz the characteristic penetration depth is 3.8 mm, which roughly corresponds to a one example of a range of target distances in a trans-jugular catheter configuration.

FIG. 30B illustrates catheter 313 introduced from below (e.g., via femoral vein access). An endovascular approach from below may comprise puncture of a femoral vein in the groin of the patient and threading the catheter through vena cava into a desired jugular vein, such as is shown in FIG. 2. Other alternative approaches such as from a jugular veins and branches of jugular vein and other veins of the body such as a subclavian vein are also possible and may have advantages in some clinical situations.

Directing the beam from a jugular vein 12 into the septum between two carotid branches benefits the shaping of the lesion by cooling effects from carotid arteries. As illustrated by FIG. 30A the energy beam 232 is constrained between two carotid artery branches that are protected from thermal damage by high flow of blood. The anatomy in this region therefore provides an intrinsic advantage in that if the beam is slightly misaligned and points at a slightly wrong angle, it will encounter the internal or external carotid artery, which will resist heating of immediately surrounding tissue by its cooling effect. The beam, or portion of the beam directed between the brunches, will be subject to less cooling and will result in ablation of tissue where the target organs, such as carotid body 89 and associated nerves, are expected to reside (i.e., in a carotid septum). As a result, the carotid septum is selectively heated and thermally ablated, which is one of the aspects of this disclosure. As set forth above, this disclosure also includes methods of selectively ablating target tissue by delivering high intensity ultrasound energy into a region of the anatomy so that blood flow will provide a cooling effect and therefore facilitate the containment of the ablated tissue to a desired region. In the case in this embodiment, the ablated tissue is contained in the carotid septum.

Directing and targeting an ultrasound ablation beam 232 at a target site such as a carotid septum 205 from within a jugular vein may be facilitated by detecting vasculature such as the common carotid artery 3, internal carotid artery 90 and external carotid artery 91, and carotid bifurcation 2 using diagnostic ultrasound such as Doppler ultrasound. Such diagnostic ultrasound may provide an indication (e.g., visual images, acoustic, or electrical signals) of the vasculature by detecting blood velocity, direction of flow, pulsations of flow and turbulence while manipulating a catheter (e.g., rotational and translational manipulation) that comprises at least one ultrasound transducer.

In some embodiments translational aiming (in some instances being aligned with) may be achieved by detecting a carotid bifurcation saddle 2 and aiming an ultrasound treatment transducer (also referred to herein as an ultrasound ablation transducer or ultrasound ablation emitter) with a target site relative to the carotid bifurcation saddle. In some embodiments the ultrasound treatment transducer is aimed about 5 to about 15 mm cranial to the bifurcation, saddle in some embodiments about 10 to about 15 mm cranial to the bifurcation saddle, in some embodiments about 10 mm to about 12 mm cranial to the bifurcation saddle, and in some embodiments about 5 to about 10 mm cranial to the bifurcation saddle. A carotid bifurcation saddle can be detected from a position along the length of a jugular vein 12 as a location where one strong blood velocity signal representing a common carotid artery 3 separates abruptly into two arteries, the internal 90 and external 91 carotid arteries. An ultrasound ablation beam may be aimed at a location about 5 to about 15 mm above the level of the bifurcation saddle by advancing or retracting the catheter. Aiming the beam at a location about 5 to about 15 mm caudal to the bifurcation saddle aims the beam into the carotid septum to facilitate ablating the carotid body.

In some embodiments a method of ablation includes detecting one or both of the internal and external carotid arteries. They can be detected by rotating a diagnostic transducer, which can occur with a catheter and/or balloon, or within the catheter and/or balloon. The treatment transducer can then be aimed at a target site relative to the internal and external carotid arteries. In some embodiments the external and internal carotid arteries are detected, and the treatment transducer is rotationally aimed approximately between the internal and external carotid arteries. In this orientation relative the two arteries, the ultrasound treatment transducer is aimed to ablate the septal tissue and thus the carotid body. In other embodiments aiming the beam is aided by other visualization techniques, such as MRI, CTA, or Fluoroscopy.

In some embodiments an ultrasound carotid body ablation catheter comprises at least one diagnostic ultrasound transducers and an ultrasound treatment transducer, wherein the transducers are positioned on the catheter relative to one another such that when the diagnostic ultrasound transducers are aligned with vasculature landmarks, the treatment transducer is aligned with a target ablation site (e.g., carotid septum). Carotid vascular landmark as used herein includes an internal carotid artery, an external carotid artery, a carotid bifurcation, and a common carotid artery. This configuration allows an alignment of a diagnostic transducer and a landmark to indicate an alignment of a treatment transducer and target tissue. In some embodiments when the diagnostic transducer is aligned with the landmark, the treatment transducer will be in a proper position to be activated without additional movement to successfully ablate the target tissue. In FIGS. 31A, 31B, 32A, and 32B diagnostic ultrasound transducer 125 may be positioned a predetermined distance, such as about 5 to about 15 mm, proximal to a treatment ultrasound transducer on a catheter such that when the diagnostic transducer 125 is aligned with a landmark 2, in this case a carotid bifurcation, the treatment transducer 126 is a predetermined distance 127 (e.g., about 5 to about 15 mm) distal to the bifurcation and aligned with an ablation target 128 in a carotid septum. The diagnostic transducer 125 may provide a signal as feedback to material (e.g., tissue, blood flow) reflecting ultrasound waves in the transducer's zone of capture 129. A sweeping motion may be created to search for the landmark, such as a common carotid artery, or carotid bifurcation by rotationally or translationally moving the catheter or by electrically or mechanically manipulating the transducer. Feedback from the diagnostic transducer 125 may be processed as images 130 as shown in FIG. 32B, acoustic sounds, waveforms, or electrical signals.

Figure 33B:
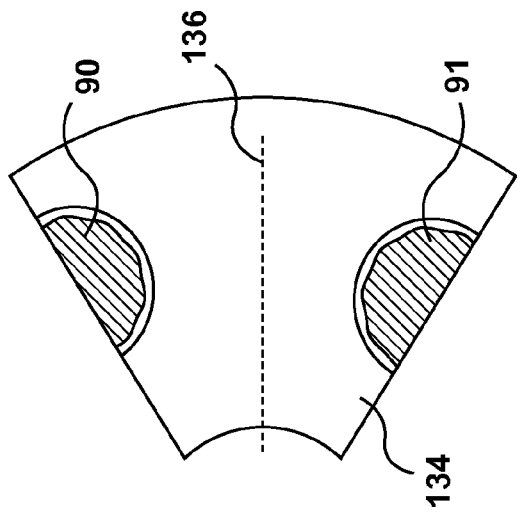
Figure 33C:
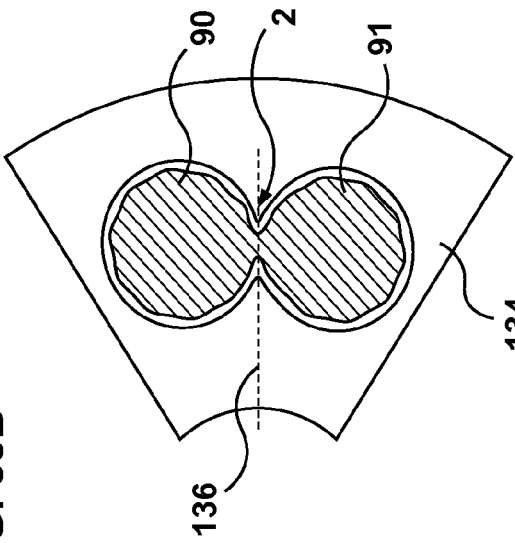
Figure 33A:
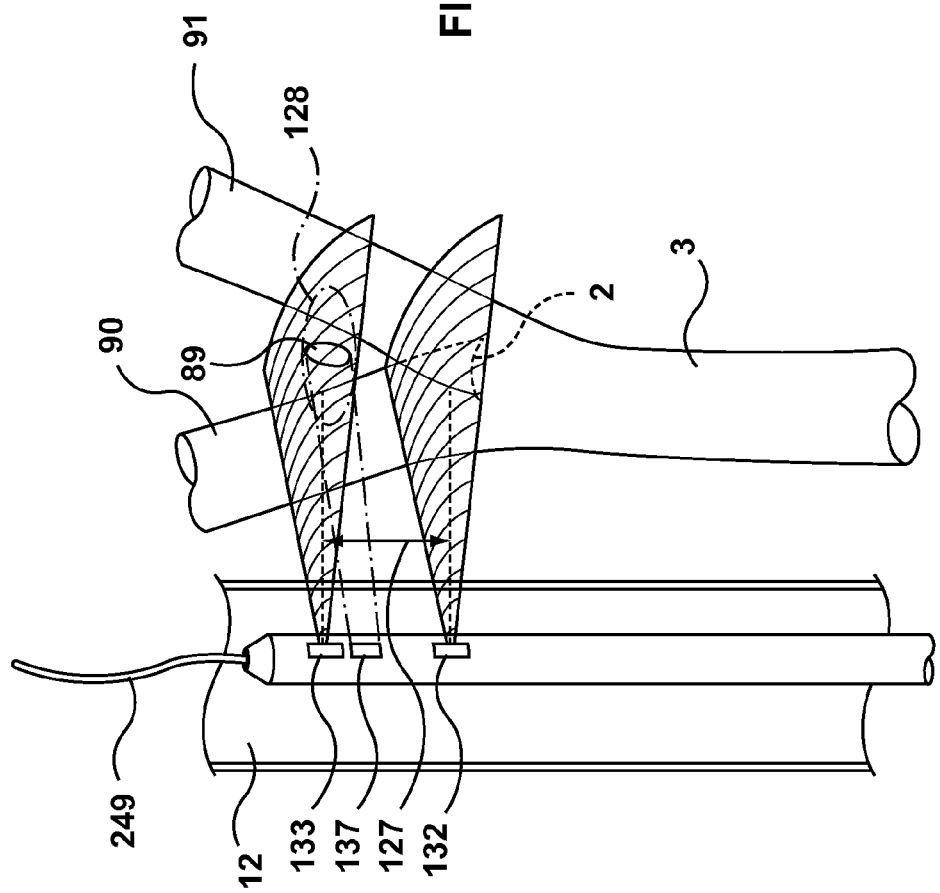

FIGS. 33A-C illustrate an exemplary ablation catheter that includes first and second diagnostic ultrasound transducers. As shown in FIG. 33A, the catheter may further comprise a first diagnostic ultrasound transducer 132 and a second diagnostic ultrasound transducer 133 configured to detect an internal 90 and external 91 carotid artery. The transducers can be configured to capture an image 134, as shown in FIGS. 33B and 33C, an acoustic signal, or an electrical signal. FIGS. 33B and 33C illustrate a trans-section of the two arteries. The second diagnostic ultrasound transducer 133 is positioned on the catheter so it is aiming the same direction as the treatment transducer 137. When the catheter is rotated to a position in which the second diagnostic transducer is centered 136 between the internal and external carotid arteries, as shown in FIG. 33B, and the first diagnostic transducer 132 is aimed at the carotid bifurcation 2, as shown in FIG. 33C, the ultrasound treatment transducer 137 is aligned with a target site 128 in a septum approximately centered between the internal and external carotid arteries and above the bifurcation a predetermined distance, such as between about 5 to about 15 mm, about 5 to about 10 mm, about 8 to about 10 mm, or about 10 mm to about 15 mm.

FIGS. 34A-D illustrate an exemplary ablation catheter with three diagnostic ultrasound transducers and one treatment ultrasound transducer. As shown in FIGS. 34A-D, the catheter includes a first diagnostic transducer 140 disposed on the catheter to align with a carotid bifurcation 2, a second diagnostic transducer 141 disposed on the catheter to align with an internal carotid artery 90, and a third diagnostic transducer 142 to align with an external carotid artery 91. The catheter also includes an ultrasound treatment transducer 143 positioned on the catheter relative to the three diagnostic transducers to aim an ablation beam at a target site between the internal and external carotid arteries and a predetermined distance, such as about 5 to about 15 mm, about 5 to about 10 mm, about 8 to about 10 mm, or about 10 to about 15 mm, cranial of a carotid bifurcation when the diagnostic transducers are aligned. Alternatively, one or more of the diagnostic transducers may be moveable in relation to the catheter shaft. For example, diagnostic transducers 141 and 142 shown in FIG. 34A may mechanically move (e.g., with a gearing mechanism) to adjust the angle between the two transducers while maintaining the treatment transducer 143 centered between the two moving diagnostic transducers. This may allow the alignment to adjust to varying septum widths. In use, all of the catheters and methods shown in FIGS. 30-34 create a lesion that is contained substantially in the carotid septum, and thus avoiding non-target tissue. In addition, a combination of blood flow cooling in the vein and a choice of ultrasound therapeutic regime can help cool the vein and the emitter that may get hot during operation while enhancing the ultrasound heating of the carotid septum.

An ultrasound transducer may optionally also be capable of delivering and receiving low power ultrasound that can be used for imaging of carotid arteries, Doppler imaging, or pulse Doppler imaging. Examples of transducers configured in this regard are described herein. Doppler signal feedback to an operator or computer controlling energy delivery need not be necessarily an image. It can be an indicator such as a curve, a number, an acoustic signal, an LED bar, or an indicator light color or intensity.

Alternatively or additionally, ultrasound imaging may be applied from an external transducer placed on skin of a patient's neck and used to guide therapy. Externally applied ultrasound imaging may incorporate biplane imaging and Doppler flow enhanced imaging. Alternatively, additional ultrasound emitters and receivers can be incorporated in the catheter design.

Alternatively or additionally, single or multiple ultrasound transducers may be positioned on the distal section of a trans jugular catheter such that ultrasound reverberation between the exterior of the neck surface and ultrasound transducers is sensed in electrical impedance or by means of ultrasonic imaging thus allowing alignment of the catheter with respect to the lateral landmarks of the neck effectively pointing the therapeutic transducer in a medial direction toward the inter-carotid septum. The lateral reflections provide acoustic guidance to the catheter ultrasound transducers with the effect maximized when catheter ultrasound imaging transducer becomes substantially coplanar with the exterior neck surface, which may coincide with a desired rotational position relative to the bifurcation of the carotid arteries. Alternatively, similar lateral guidance may be achieved by placing a substantially flat echogenic reflector or active low power ultrasound transducer on the surface of the neck.

In some embodiments herein the ablation catheter may be advanced into an internal jugular vein from the groin, from a subclavian, from a brachial vein, or by direct puncture using methods somewhat similar to ones used for biopsy or central access catheter placement. In some cases a facial vein, or other vein branching from an internal jugular vein, may provide a closer proximity to a carotid septum for placement of an energy delivery element of the catheter. The jugular vein as a venous position for the catheter is therefore merely illustrative.

As described in methods herein, a catheter may be advanced up and down the jugular vein until a bifurcation of a common carotid artery and carotid septum just above it are clearly detected. If external ultrasound is used, the catheter may be made visible with ultrasound by addition of an echogenic coating. This can be confirmed by a Doppler pulsatile velocity signal or ultrasonic imaging. A space, indicating a carotid septum, between two large vessels with high pulsatile blood flow should be easily detectable. Pulsed Doppler at the preselected depth of 3 to 10 mm (e.g., 3 to 5 mm) can be chosen to avoid interference from venous blood flow.

In some embodiments a catheter positioned in a jugular vein may be rotated around its axis until the ablation, or treatment, transducer aperture is facing the carotid septum pointing into the gap between internal and external arteries. Alternatively a transducer with a directional emitter can be rotated inside the catheter. If the Doppler emitter and receiver are located in the distal portion of the catheter placed in a jugular vein, certain advantages may be realized. A low energy Doppler beam can be facing the same direction as the high energy ablation beam. A Doppler signal can then be used for targeting and directing the ablation beam into the septum. The septum can be located as a valley of low velocity area between two peaks or high velocity areas. Alternatively, several Doppler transducers can be incorporated in the distal tip aiming beams silently at an angle to the direction of the face of the aperture of the high energy beam in order to detect both carotid arteries by their high velocity flow. A vein may be distended and a catheter tip maneuvered into position so that a high-energy emitter is aiming into the middle of the gap between two strong Doppler signals representing an internal and external carotid artery. A computer algorithm may assist or automate such aiming.

During ablation the ultrasonic energy emitter may get hot and may require cooling. The catheter may be configured to position the transducer in an internal jugular vein so it does not touch the wall of the jugular vein while delivering high energy for the purpose of ablation. For example, the catheter may comprise a protective membrane such as balloon 145, as shown in FIGS. 30A and 30B. The balloon 145 separates the transducer 146 from the vessel wall 147 while providing a conduit for an energy beam and cooling of the transducer, the blood in the vein 12, and the tissue of the wall of the jugular vein. The balloon 145 may be made of a thin polymer film that can be compliant or not compliant but is capable of sustaining some pressure, providing firm contact with the wall of the vessel and conducting ultrasound in the selected frequency range without significant attenuation, reflection or heating. The balloon may be filled with a circulating fluid 148, such as sterile water or saline, which is biocompatible and conducts ultrasound well without absorbing significant energy. The fluid may be externally chilled, recirculated by an external pump (not shown) through the catheter shaft, or can be just infused and released into the bloodstream in relatively small quantities sufficient to keep the fluid and the emitter submerged in fluid at a desired low temperature.

Figure 35A:
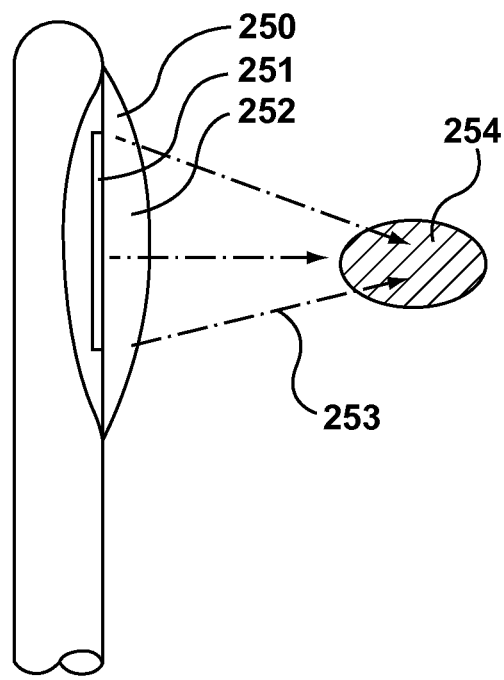
FIGS. 35A and 35B are schematic illustrations of an ultrasound CBA catheter with an adjustable focus distance.
Figure 35B:
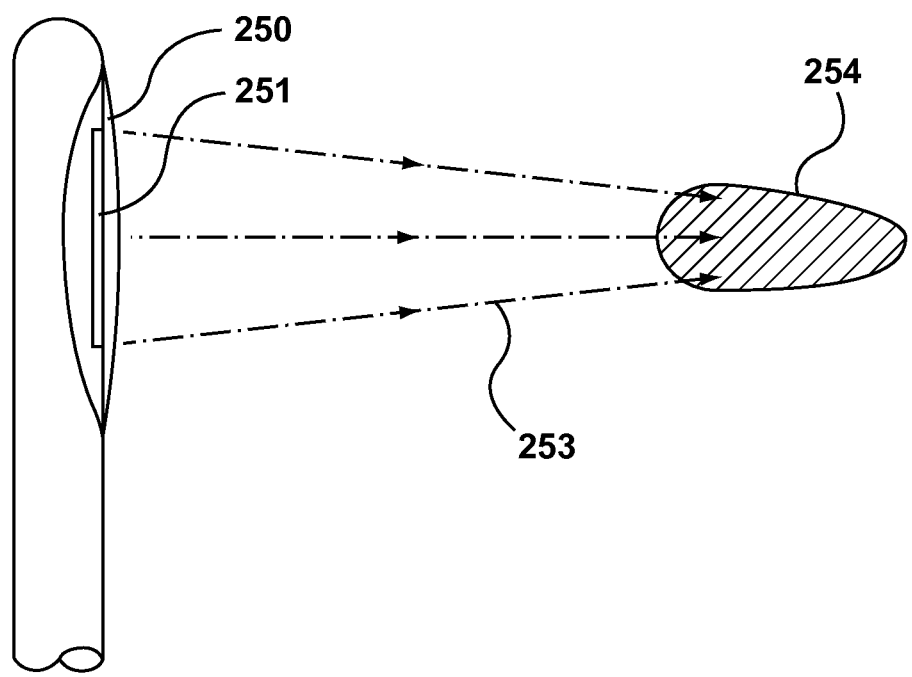

A protective membrane may fully encompass the distal end of the catheter forming a balloon around ultrasound transducers or, as shown in FIGS. 35A and 35B, a protective membrane 250 may partially encompass a selected ultrasound transducer 251. The protective membrane can be formed around a therapeutic transducer in a shape of a convex, concave, or Fresnel acoustic lens and filled with liquid coolant fluid 252 such as Fluorinert with acoustic properties substantially different from that of blood. An ultrasonic beam may be shaped by a protective membrane lens to a predefined focused or defocused pattern in order to obtain selected regional sensitivity in Doppler imaging or a delivered therapeutic dose in the ablation area. Alternatively a transducer with a predefined thin-wall expandable protective membrane may form a directional emitter that can be manipulated to form a directional beam that can be targeted to different depths. The target depth of Doppler emitters and receivers may be configured to enable ultrasound beam shaping and focusing advantages realized when facing substantially different anatomy in the jugular vein and carotid complex.

The ablation depth control may be achieved by placing a catheter in a jugular vein and manipulating the lens internal fluid pressure to expand the protective membrane in a predefined repeatable shape that produces an acoustic convergent or divergent lens effect to the ultrasound beam and preferentially targets the ultrasound beam into a specific target depth in the bifurcation of a carotid artery and a carotid septum. For example, as shown in FIG. 35A a membrane 250 is inflated with coolant 252 creating a lens shape that focuses an ultrasound beam 253 on a target region 254. Comparatively as shown in FIG. 35B the membrane 250 may be inflated with coolant 252 at a different pressure to alter the lens shape to focus the ultrasound beam 253 on a target region at a different distance. The expandable membrane can be formed from a variety of compliant polymer materials such as Kraton (styrene blend), polyethylene, polypropylene, Pebax, or Latex. Alternatively, an expandable membrane may be used to control the positioning of the catheter inside the jugular vein with respect to the distance to the carotid complex.

Figure 36:
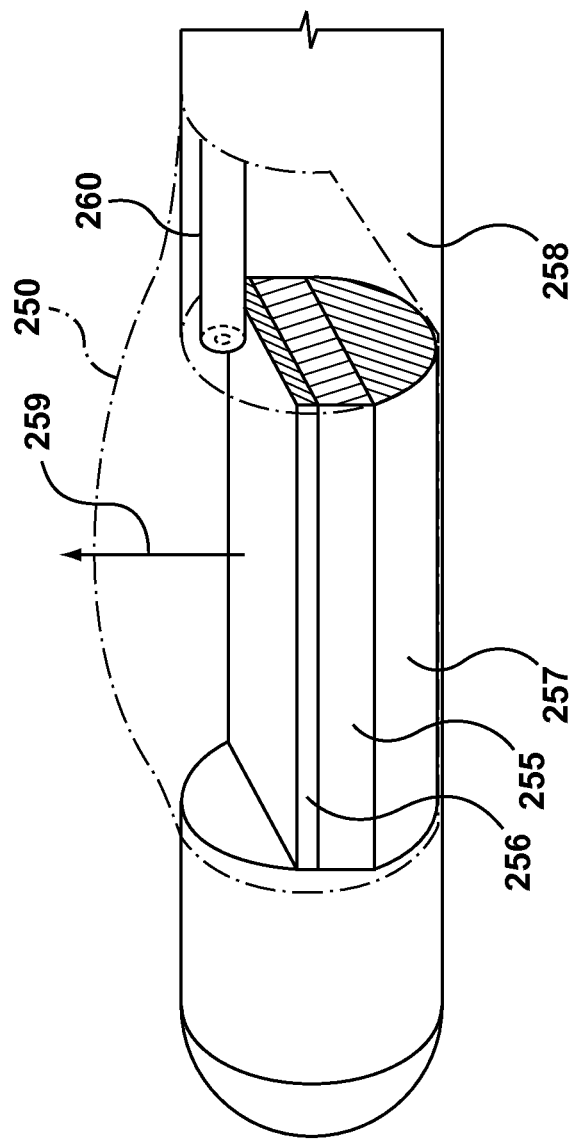
FIG. 36 is a schematic illustration of an ultrasound CBA catheter with an adjustable focus distance.

A distal end of an embodiment of a carotid body ablation catheter, shown in FIG. 36, comprises an ultrasound transducer 255 and a PVDF imaging array 256 positioned near a distal end of a catheter shaft 258. An acoustic insulator 257 such as brass may be positioned on a backside of the transducer 255 to ensure an imaging or ablation beam is directed in a direction 259 orthogonal to the front surface of the transducer 255. An expandable membrane 250 encompasses a cavity in front of the transducer. Liquid, such as a coolant, may be injected into the membrane cavity through an inflation lumen or tube 260 to inflate the membrane 250 to a desired shape, which may focus or direct the ultrasound beam.

In alternative embodiments, any of the catheters comprising an ultrasound ablation transducer and an expandable membrane, such as those in FIG. 16, 35A, 35B, or 36, can also include any of the diagnostic transducers described herein, such as those shown in FIGS. 31A-B, 32A-B, 33A-C mounted to the catheter, which may be used to assist in positioning the ablation transducer and aligning it with respect to one or more vascular landmarks, such as a carotid bifurcation, internal carotid artery, external carotid artery, or combination thereof, to direct an ablation ultrasound beam toward a target tissue volume, such as a carotid septum or position within a carotid septum.

An ablation catheter may comprise an ultrasound ablation transducer and an expandable membrane, such as membrane 250 shown in FIG. 35A, 35B, or 36, wherein the ultrasound ablation transducer may also be used for diagnostic ultrasound such as Doppler. These catheters may be positioned in an external carotid artery and rotated while assessing a diagnostic signal, which may be used to find vessels such as an internal carotid artery or internal jugular vein. The transducer may be placed at a desired distance cranial from a carotid bifurcation in an external carotid artery, for example about 5 to about 15 mm, or about 5 to about 10 mm, with the help of fluoroscopic imaging. For example, the catheter may have a radiopaque marker positioned the desired distance (e.g., about 5 mm to about 15 mm, or about 5 mm to about 10 mm) proximal to the transducer; contrast may be delivered to a common carotid artery (e.g., from a delivery sheath), a radiographic image may be taken of the carotid arteries and the distal portion of the catheter, and the radiopaque marker may be aligned with the carotid bifurcation. When the diagnostic transducer is aimed at an internal carotid artery or approximately the center of an internal carotid artery and the transducer is positioned a desired distance cranial from the carotid bifurcation it may be expected that the transducer is aimed through a carotid septum. An ablation ultrasound beam may be directed into the target tissue in the carotid septum. Optionally, the catheter may further comprise a deflectable section proximal to the transducer (e.g., between about 5 mm and about 30 mm proximal to the transducer) that may be used to direct the angle of the ultrasound beam with respect to the external carotid artery, which may be useful to adjust for a variety of carotid vasculature geometries such as narrow or wide bifurcation angles. Optionally, the catheter may further comprise a deployable structure such as a balloon, cage, mesh or helix positioned on the catheter distal to the transducer, which may be used to engage and stabilize the distal portion of the catheter in an external carotid artery. The deployable structure may deploy to a size suitable to engage in an external carotid artery, for example having a diameter of about 4 to about 6 mm. The deployable structure may retract so it can fit in a delivery sheath, for example having a diameter of less than about 3 mm (e.g., between about 2 mm and about 2.4 mm).

The disclosure herein also includes methods, devices, and systems for ablating a target site by positioning an ablation needle within a lumen of a vein adjacent to the target site, inserting the needle through the vein and into perivascular space containing the target site, delivering an ablation agent into the perivascular space by using the needle, and withdrawing the needle from the perivascular space back into the vein. There may be potential benefits for positioning a device via a trans-venous approach for a carotid body ablation procedure compared to a trans-arterial approach. For example, jugular veins have thinner walls compared to carotid arteries which may be easier to pass an ablation needle through; jugular veins are distensible and flexible and a change in conformation may be achieved by applying force from inside or outside the vessel which may be advantageous for facilitating position of a catheter or accessing a target ablation site; jugular veins have no atherosclerotic or arteriosclerotic disease and blood flows away from the brain eliminating a risk of causing a brain embolism, which may be a concern with a procedure in carotid arteries; a trans jugular approach may access an intercarotid septum from a lateral side; perforation with a needle or catheter through a wall of a vein (e.g., jugular, facial veins) has less risk of complications such as hematoma due to compressibility of the venous vessel compared to carotid arteries; possible reduction of blood flow in a jugular vein has less risk of flow limitation to the brain compared to reduction of flow in an internal carotid artery.

Figure 37:
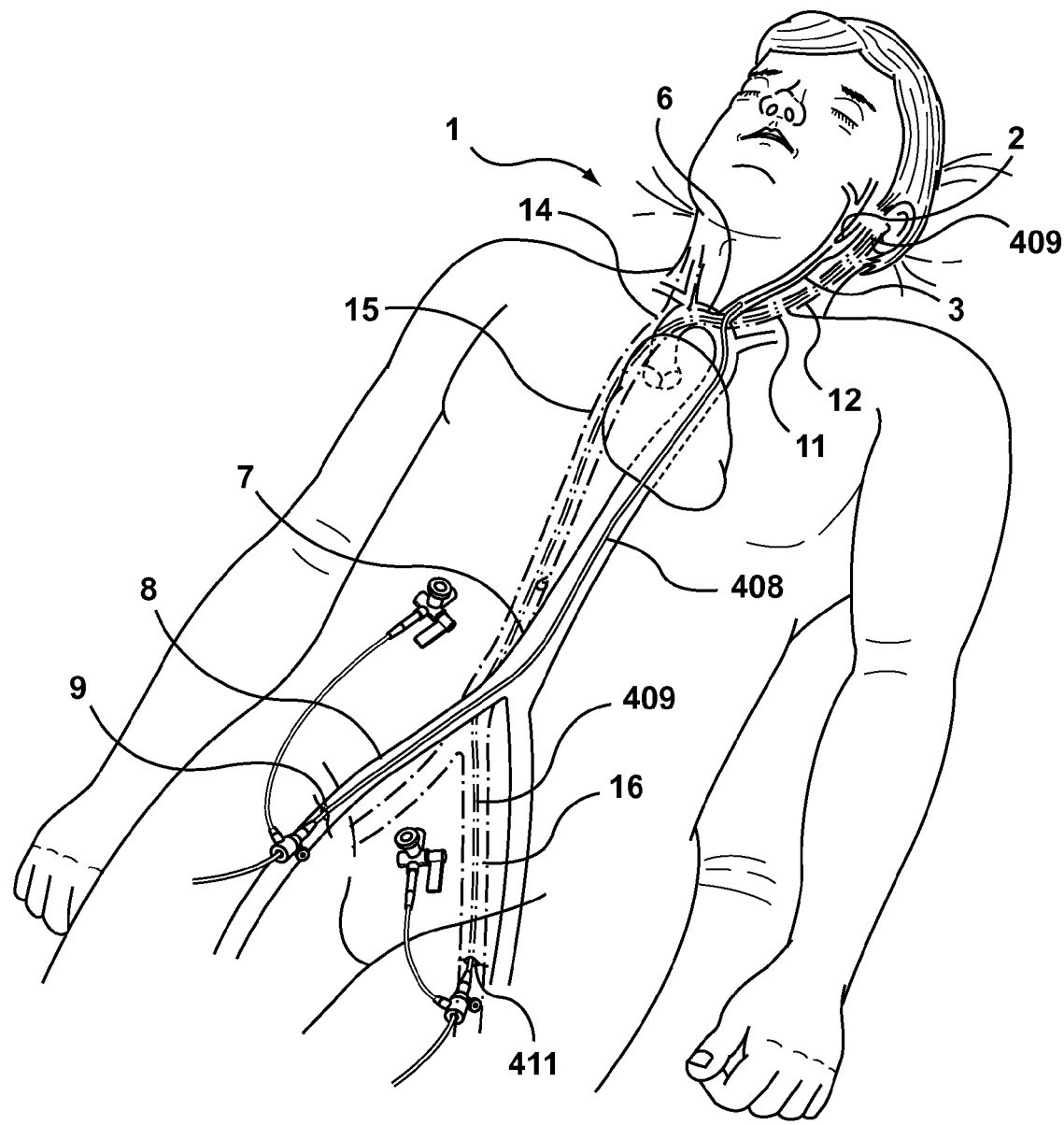
FIG. 37 is a schematic illustration showing a patient lying in supine position with a tip of a small caliber angiography catheter residing in a left common carotid artery, and a Transvenous Interstitial Carotid Body Ablation (TVICBA) catheter in position in a left internal jugular vein.

FIG. 37 depicts in simplified schematic form the placement of a Trans-Venous Interstitial Carotid Body Ablation (TVICBA) catheter 409 into a patient 1 via an endovascular approach with a femoral vein puncture 411. The distal end of the TVICBA catheter 409 is depicted in the left internal jugular vein 12 at the level of the left carotid artery bifurcation 2 positioned for interstitial carotid body ablation. As depicted the TVICBA catheter 409 is inserted into the patient at insertion site 411 in the vicinity of the groin into a femoral vein 16 and advanced through the inferior vena cava 15, superior vena cava 14, left common jugular vein 11 and into the left internal jugular vein 12. Alternatively, the insertion site may be selected to gain venous access through a brachial vein, a subclavian vein, a common jugular vein 11, or any suitable peripheral vein. Furthermore, the distal end of the TVICBA catheter 409 may be positioned for interstitial carotid body ablation in other than the internal jugular vein 12 (e.g., facial vein, not shown) depending on the particular vascular and neural anatomy of the patient 1. Also depicted is an angiographic catheter 408 positioned in the common carotid artery 3 for the purpose creating an arterial angiographic image of the region of the carotid bifurcation 2 for the purpose of guiding trans-venous interstitial ablation of the carotid body. As depicted, angiographic catheter 408 is inserted into a femoral artery 8 through insertion site 9 in the groin, then advanced through the abdominal aorta 7, the aortic arch 6 and into the left common carotid artery 3 using standard angiographic techniques. It would be understood to those skilled in the art of endovascular interventions that means other than carotid artery angiography can be used to guide trans-venous interstitial carotid body ablation. For example, extracorporeal ultrasonic imaging of the neck may be used, as well as intravascular ultrasound, computed tomography angiography, and other known modalities alone or in combination.

Figure 38:
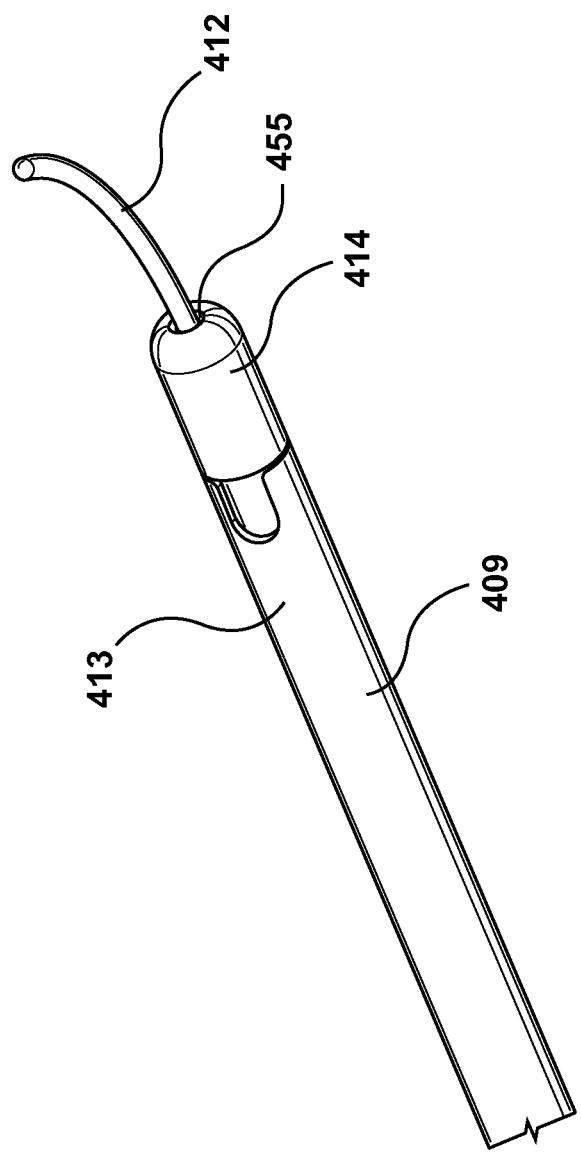
FIG. 38 is a schematic illustration of a distal region of a TVICBA catheter showing an outer sheath, distal tip, and guide wire.
Figure 39:
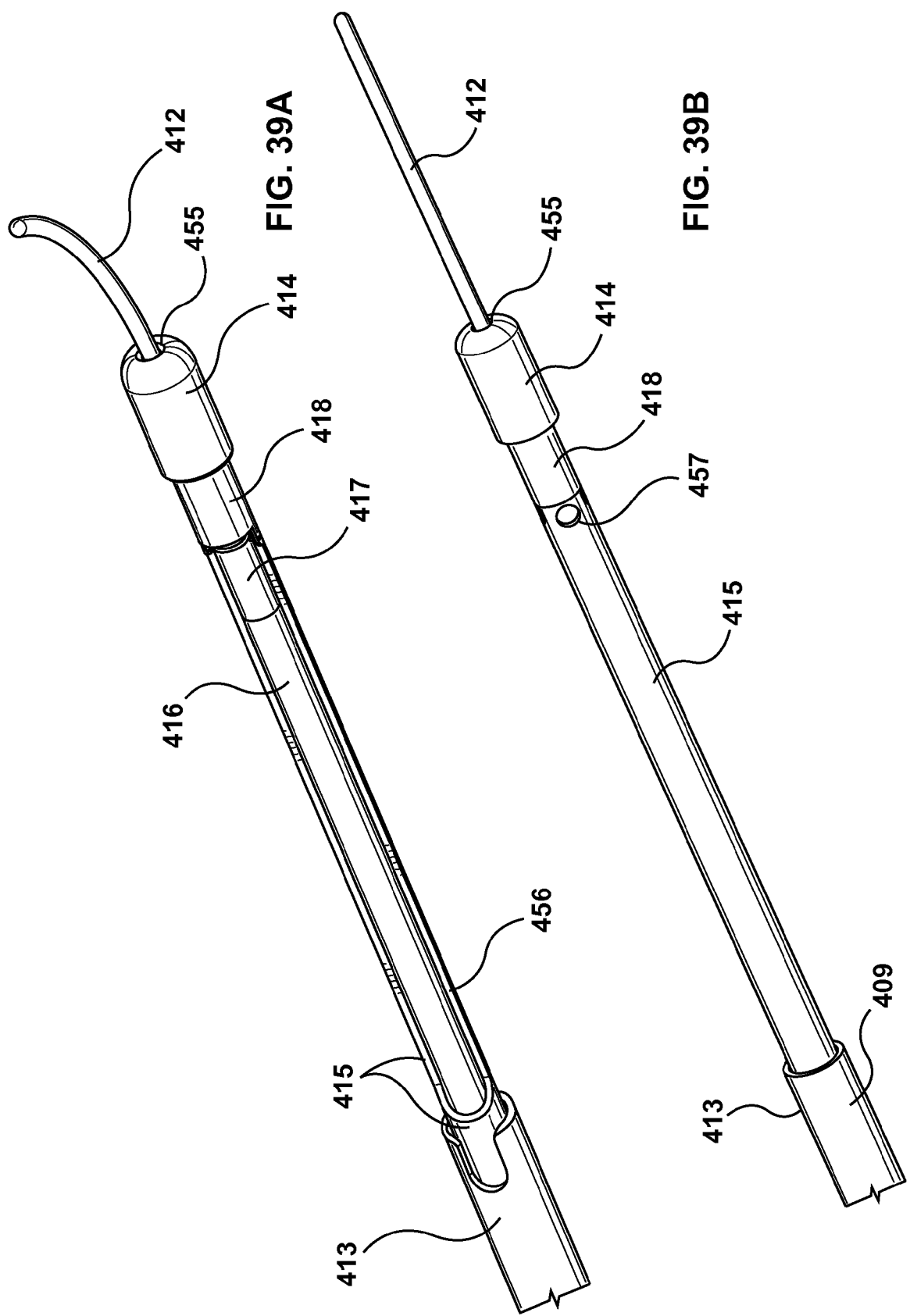
FIGS. 39A and 39B are schematic illustrations of the distal region of a TVICBA catheter showing the outer sheath retracted revealing an inner sheath and a needle sheath.

FIG. 38 is an illustration of the distal region of TVICBA catheter 409 in its venous insertion and navigation configuration depicting atraumatic distal tip 414, central lumen 455, guide wire 412 extending beyond central lumen 455, and retractable outer sheath 413. Note: FIGS. 38 through 42 depict the operational features of the TVICBA catheter, and FIGS. 43 and 44 will depict enabling construction details.

FIG. 39A and FIG. 39B are illustrations of the distal region of TVICBA catheter 409 with outer sheath 413 retracted. The retraction of outer sheath 413 is a first step in configuring TVICBA catheter 409 for trans-venous interstitial carotid body ablation once the distal end of TVICBA catheter 409 has been positioned in a vein proximate to a carotid body. FIG. 39A depicts one side of the TVICBA catheter showing outer sheath 413 retracted exposing inner sheath 415 in a coaxial relationship with outer sheath 413, needle sheath 416 in a coaxial relationship with inner sheath 415 and outer sheath 416, needle sheath tip/hinge ferrule 417, inner sheath tip/hinge ferrule 418, and needle sheath fenestration 456 in wall of inner sheath 415. Also guide wire 142 which traverses the length of TVICBA catheter 409 occupying central lumen 455 of distal tip 414, and central lumen of needle sheath 416 and needle sheath tip/hinge ferrule 417, not shown. FIG. 39B depicts the opposite side of TVICBA catheter 409 shown in FIG. 39A. FIG. 39B depicts outer sheath 413 retracted, inner sheath 415, inner sheath tip/hinge ferrule 418, and needle fenestration 457 in the wall of inner sheath 415. Also depicted is guide wire 142 residing in central lumen 455, of distal tip 414.

Figure 40:
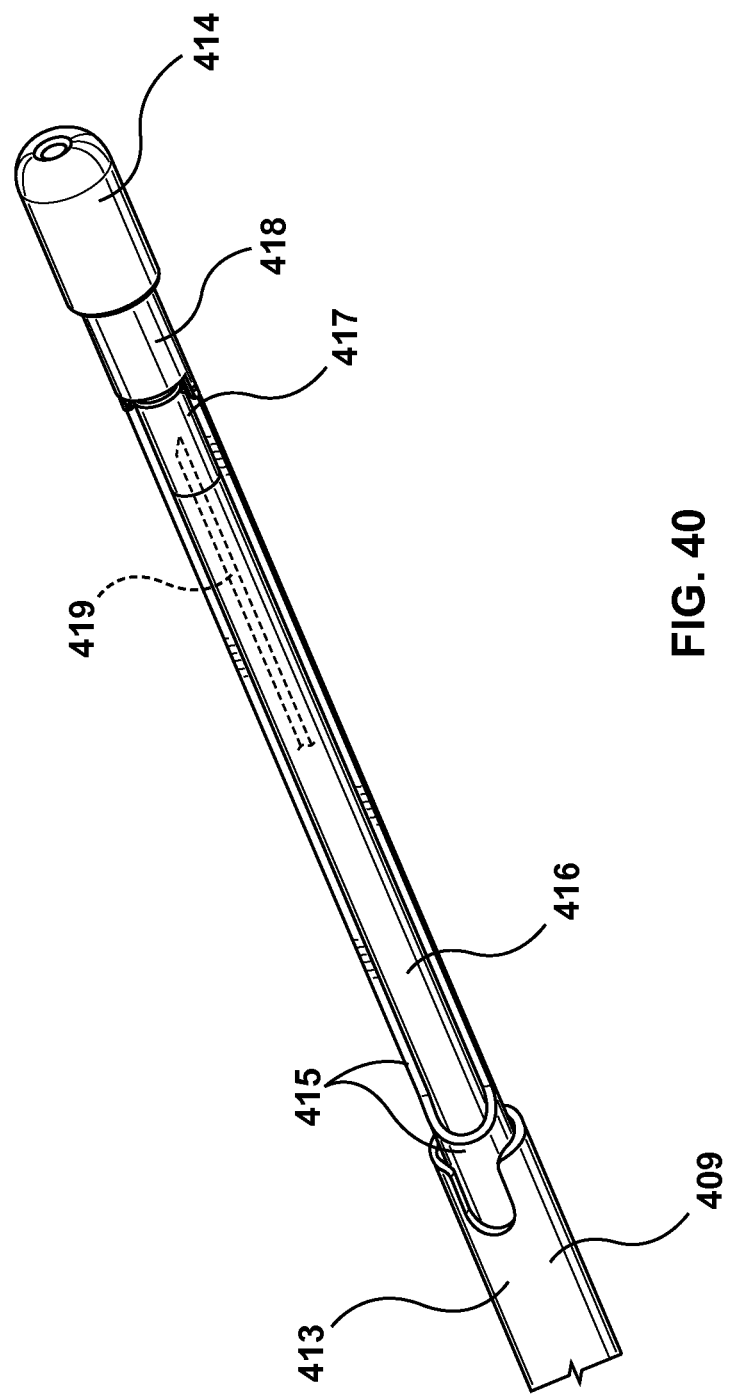
FIG. 40 is a schematic illustration of the distal region of a TVICBA catheter with a guide wire withdrawn from the catheter and replaced with an ablation needle assembly.

FIG. 40 is an illustration of the distal region of TVICBA catheter 409 showing a second step in configuring TVICBA catheter 409 for trans-venous interstitial carotid body ablation, depicting guide wire 142 removed from TVICBA catheter 409 and interstitial ablation needle assembly 419 inserted in the central lumen of needle sheath 416, with the distal tip of ablation needle assembly 419 residing within the central lumen of needle sheath tip/hinge ferrule 417, as shown.

Figure 41:
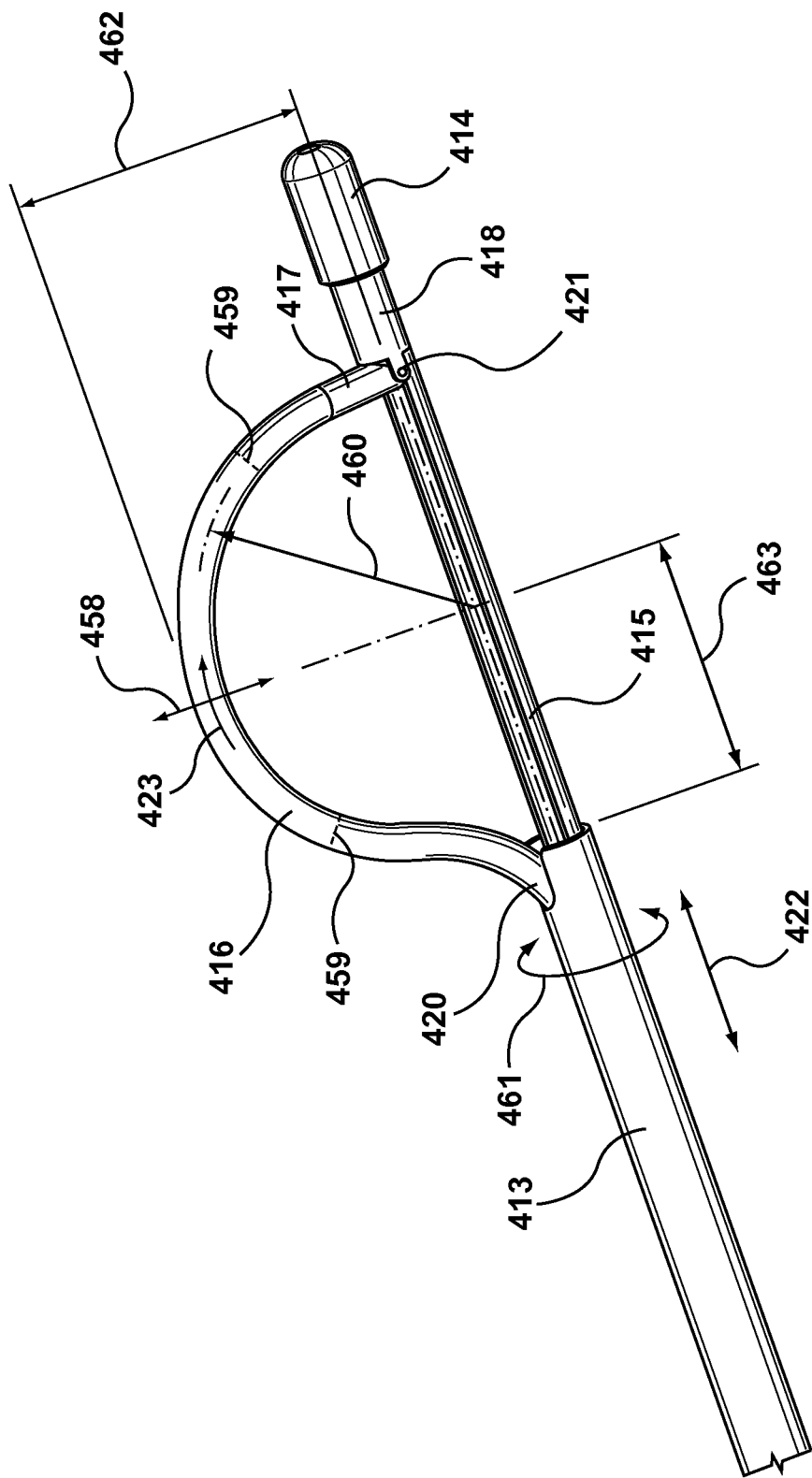
FIG. 41 is a schematic illustration of the distal region of a TVICBA catheter configured for ablation needle deployment.

FIG. 41 is an illustration of the distal region of TVICBA catheter 409 showing a third step in configuring TVICBA catheter 409 for trans-venous interstitial carotid body ablation, depicting needle sheath 416 being axially advanced 423 relative to inner sheath 415 causing needle sheath 416 to buckle in a radial direction 458 through needle sheath fenestration 456 in the wall of inner sheath 415. Needle sheath tip/hinge ferrule 417, and inner sheath tip/hinge ferrule 418 are configured to rotate relative to each other about hinge 421 until needle sheath tip/hinge ferrule 417 is substantially perpendicular to inner sheath tip/hinge ferrule 418 as shown, with needle sheath tip/hinge ferrule 418 defining a direction of insertion of ablation needle assembly 419 into a target ablation site (e.g., an intercarotid septum associated with a carotid body). Needle sheath 416 is advanced in axial direction 423 until needle sheath 416 engages the wall of the vein in region 459 of needle sheath 416 forcing the remainder of TVICBA catheter 409 against the opposing venous wall. Outer sheath 413 is positioned in axial direction 422 at distance 463 to substantially define the radius of curvature 460 of needle sheath 416 in conjunction with axial displacement 423 of needle sheath 416 as shown, resulting in radial displacement 462 of needle sheath 416. Torque key 420 in outer sheath 413 engages needle sheath 416 as shown and provides user applied torque 461 from the proximal end of TVICBA catheter 409 to the distal end, which is depicted in this figure. Applied torque 461 in combination with the radial displacement 462 and the substantially perpendicular relationship between inner sheath tip/hinge 417 and needle sheath tip/hinge 418 provide the user with the ability to manipulate the venous lumen in which TVICBA catheter 409 resides due to the elastic nature of veins, and their mobility within the surrounding anatomy in order to obtain a safe ablation needle 419 insertion pathway.

Figure 42:
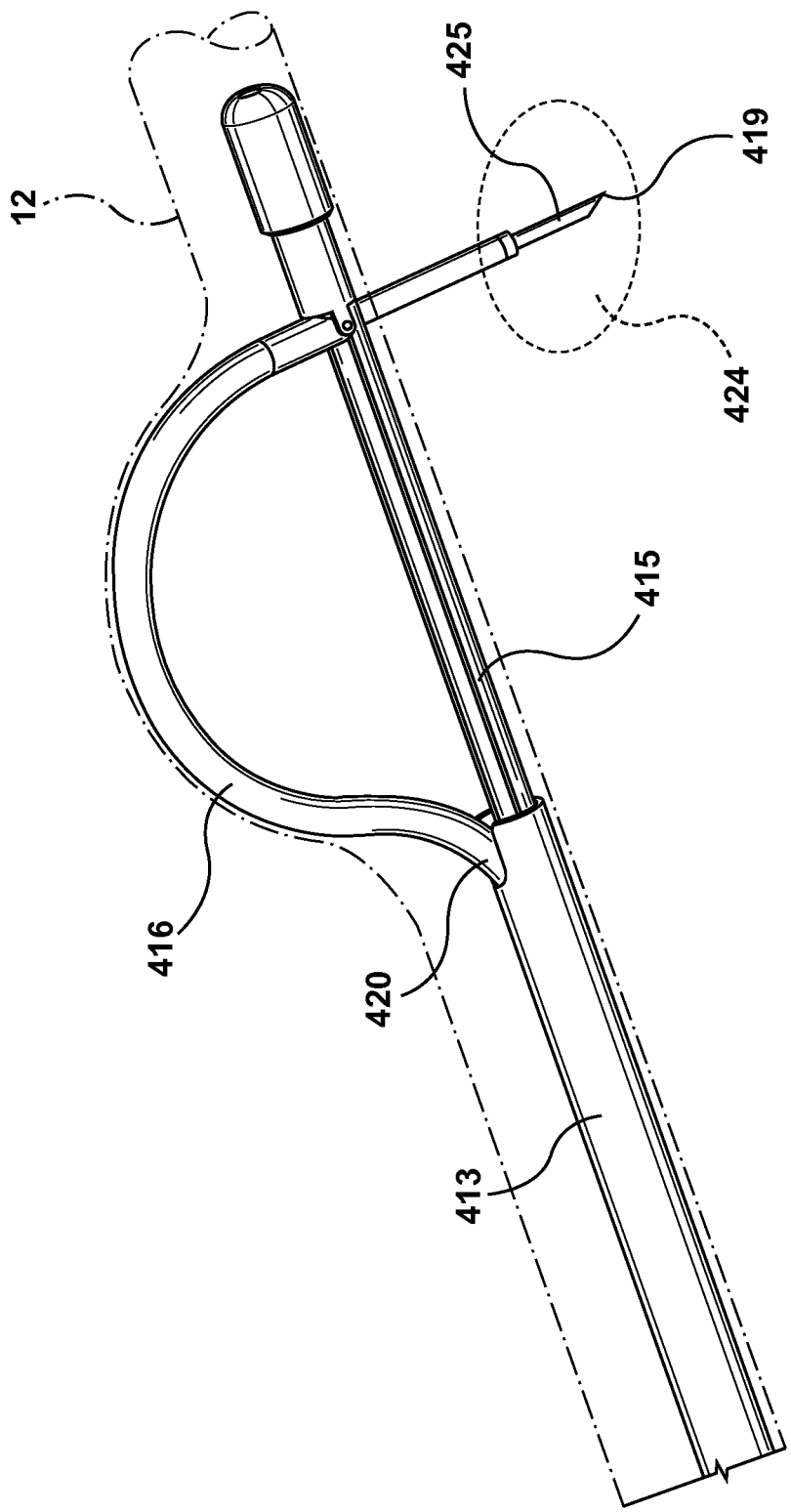
FIG. 42 is a schematic illustration of a TVICBA catheter with the ablation needle deployed in an ablation configuration showing a relationship between a carotid body, and an access vein.

FIG. 42 is an illustration of the distal region of TVICBA catheter 409 showing the final step in configuring TVICBA catheter 409 for trans-venous interstitial carotid body ablation, depicting ablation needle assembly 419 being inserted through the wall of internal jugular vein 12 into immediate vicinity of carotid body 89. As depicted the distal end of ablation needle assembly 419 comprises an RF ablation electrode 425. Ablation needle assembly 419, may be configured for alternative ablation modalities including bi-polar RF ablation, laser ablation, chemo-ablation, ultrasonic thermal ablation and microwave ablation. The alternative needle ablation modality configurations are familiar to those skilled in the art needle ablation and therefore are not further described. Ablation needle assembly 419 may further comprise at least one electrode in the vicinity of its distal end configured to electrically stimulate or blockade nervous function. Needle electrode configurations for electrical neural stimulation and blockade are familiar to those skilled in the art of electrical stimulation and blockade, and are not further described.

Figure 43:
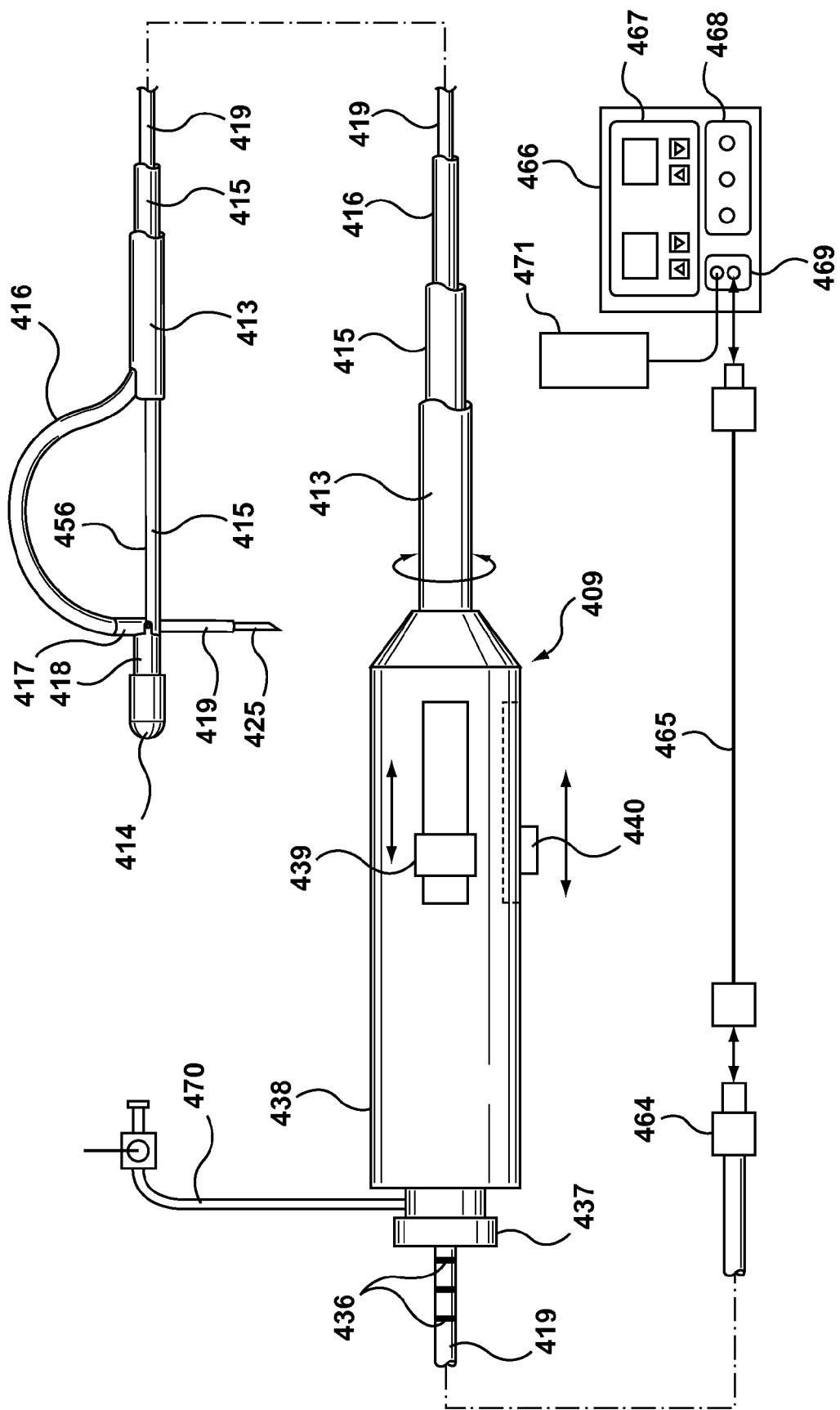
FIG. 43 is a schematic illustration of the TVICBA system.

FIG. 43 is an illustration in schematic form of the TVICBA system. The TVICBA system comprises TVICBA catheter 409, ablation needle assembly 419, control console 466, and umbilical 465. TVICBA catheter comprises outer sheath 413, inner sheath 415, distal tip 414, needle sheath 416, inner sheath tip/hinge ferrule 418, needle sheath tip/hinge ferrule 417, and handle assembly 438. Handle assembly 438 comprises Tuohy Borst fitting 37, which serves as a fluid-tight port for insertion of a guide wire, not shown, or ablation needle assembly 419 into TVICBA central lumen defined by needle sheath 416, needle tip/hinge ferrule 417 and distal tip 414. Fluid port/stopcock 70 provides the user with fluidic access to the central lumen for displacing air prior to use, and infusing or withdrawing liquid into/from the patient's venous system. Outer sheath actuator 39 is configured for user retraction or axial positioning of outer sheath 413. Needle sheath actuator is configured for user adjustment of the axial relationship between inner sheath 415 and needle sheath 416, and is used to create and adjust the radial displacement of needle sheath 416 as previously described. Handle 438 is configured to translate torque applied to handle 438 by the user to outer sheath 413. Outer sheath 413 is constructed from a polymer material such as Pebax or urethane, and may comprise a braided structure within its wall to facilitate the transmission of torque along its length. Outer sheath 413 may have a range of outer diameters between 8 and 14 French, and is configured for inner sheath 415 to reside within its inner diameter. Inner sheath 415 is constructed from a polymer material such as Pebax or urethane, and may comprise a braided structure within its wall to facilitate the transmission of torque along its length. Inner sheath 415 may have a range of outer diameters between 6 and 12 French, and is configured for needle sheath 416 to reside within its inner lumen. Inner sheath tip/hinge ferrule 418 is mounted at the distal end of inner sheath 415 with an adhesive. Inner sheath tip/hinge ferrule 418 may be machined from stainless steel, or formed from a polymeric material. Distal tip 414 is mounted to inner sheath tip/hinge in a coaxial relationship using adhesive. Distal tip 414 may be molded from a polymeric material. Needle sheath 416 is constructed from a polymer material such as Pebax or urethane, and may comprise a coiled structure within its wall to facilitate the curvature of radial displacement (previously described) without kinking. Needle sheath 416 may have a range of outer diameters between 4 and 6 French, and is configured for a guide wire or ablation needle assembly 419 to reside within its inner lumen. Needle sheath tip/hinge ferrule 417 is mounted at the distal end of needle sheath 416 with an adhesive. Needle sheath tip/hinge ferrule 417 may be machined stainless steel, or formed from a polymeric material. The functional length (in vivo length) of TVICBA catheter is between 10 and 110 cm and is dependent on the venous insertion location. Ablation needle assembly is inserted into the central lumen of TVICBA catheter 409 through Tuohy Borst fitting 437 of handle 438. Needle insertion depth markers 436 may be applied near the proximal end of ablation needle assembly as shown. An electrical connector 464 in the vicinity of the proximal end connects the electrode(s) 425 to the TVICBA control console 466 via electrical umbilical 465. Ablation needle assembly is described in detail in FIGS. 44A and 44B. Control console 466 comprises an ablation energy source, in this embodiment RF electricity, a control circuit to control the ablation energy, not shown, ablation user interface 467 provides the user with a selection of ablation parameters, which may include, power, temperature, and duration of ablation. User interface 467 also provides the user with a means to monitor the status of the console, status of the ablation, a means to initiate an ablation and a means to terminate an ablation. Electrical stimulation/blockade user interface 468 provides the user with a selection of stimulation or blockade parameters, a means to initiate a stimulation or blockade, and a means to terminate a stimulation or blockade. Patient indifferent electrode 471 is applied to the skin of the patient and is used complete the RF ablation circuit. The above mentioned means for controlling ablations or stimulation or blockade are known to those skilled in the art of control console design and are not further described herein.

FIG. 44A is an illustration of the distal region of ablation needle assembly 419. FIG. 44B is a sectional view of the distal region of ablation needle assembly 419. Ablation needle assembly 419 comprises needle tip 428, coil 427, insulation sleeve 426, thermistor 430, inner liner 429, proximal electrical connector 464 not shown, and optional depth of insertion markers 436, not shown. Needle tip 428 is fabricated from stainless steel hypo tube and has a caliber of 18 to 24 gauge. The distal tip of needle tip 428 is machined to a point optimal for venous puncture as shown. The length of needle tip 428 is between 5 mm and 10 mm. Needle tip 428 is welded or soldered to coil 427 as shown. Coil 427 is fabricated from a metallic wire with a diameter between 0.001 and 0.006 inches. Coil 428 is covered with insulative sleeve 426, which is configured to electrically isolate coil 428 from neutral return paths. RF ablation electrode 425 is formed by the surface of needle tip 428 not covered by insulative sleeve 426 as shown. Inner liner 429 resides within coil 428 proximal to distance 472. The length of ablation electrode assembly 419 defined by distance 472 is the segment that traverses the buckled segment of needle sheath 416, not shown used for radial displacement as previously described. Inner liner 429 provides axial stiffness in the proximal segment to facilitate needle insertion. The segment distal to inner liner 429 is configured to be sufficiently flexible to traverse the curved segment of needle sheath 416 during ablation needle assembly 419 insertion into the intercarotid septum.

Figure 45:
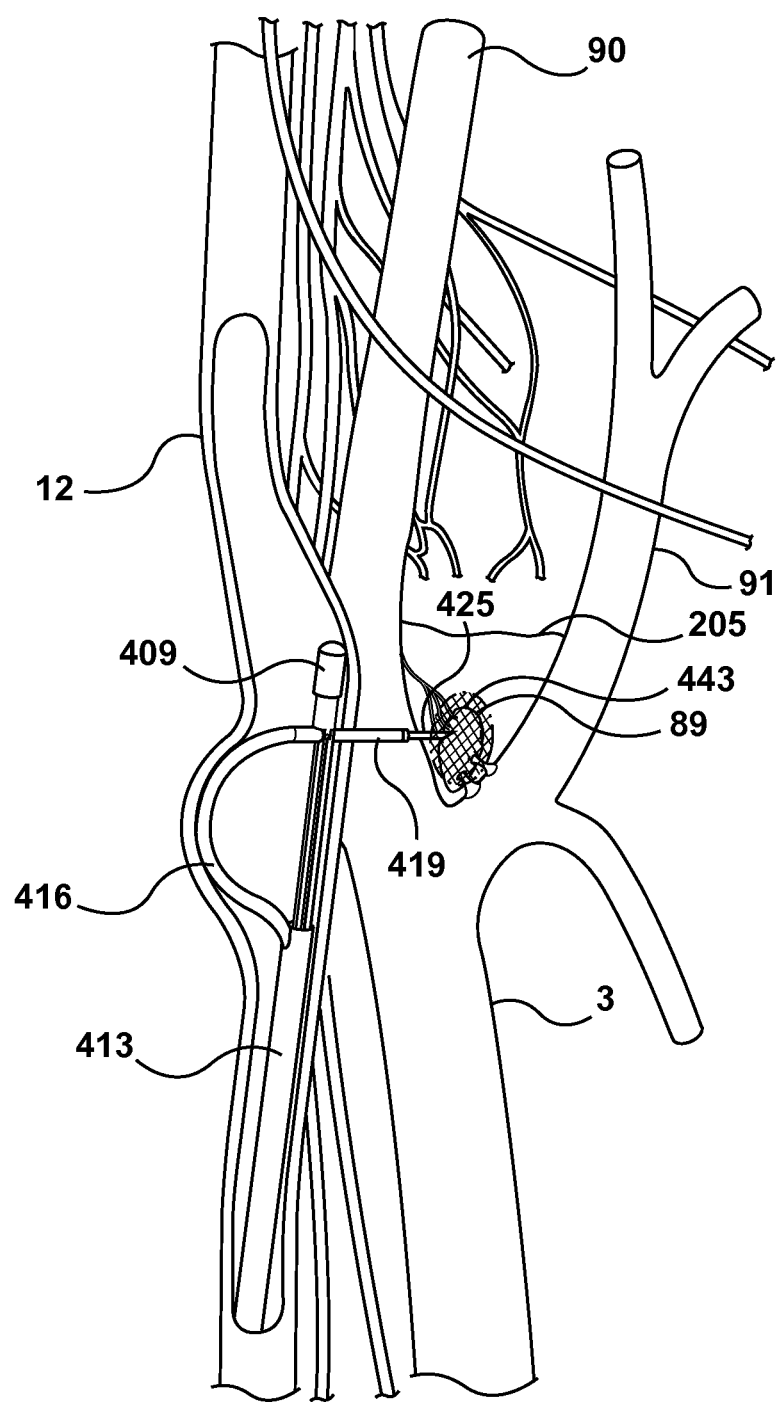
FIG. 45 is a schematic illustration of a sagittal view depicting the TVICBA catheter residing in an internal jugular vein, with a RF ablation needle deployed through a wall of the jugular vein with its distal tip residing in an intercarotid septum.

FIG. 45 is an illustration of a sagittal view showing TVICBA catheter 409 positioned within internal jugular vein 12 with ablation needle assembly 419 traversing the wall of internal jugular vein 12 and RF ablation electrode positioned within the intercarotid septum 205 between internal carotid artery 90 and external carotid artery 91 and in immediate proximity to carotid body 89. RF ablation zone 443 is shown being substantially localized to the vicinity of carotid body 89. Also shown is the effect of radial displacement of needle sheath 416 on the lateral and contralateral wall of internal jugular vein 12.

Figure 46A:
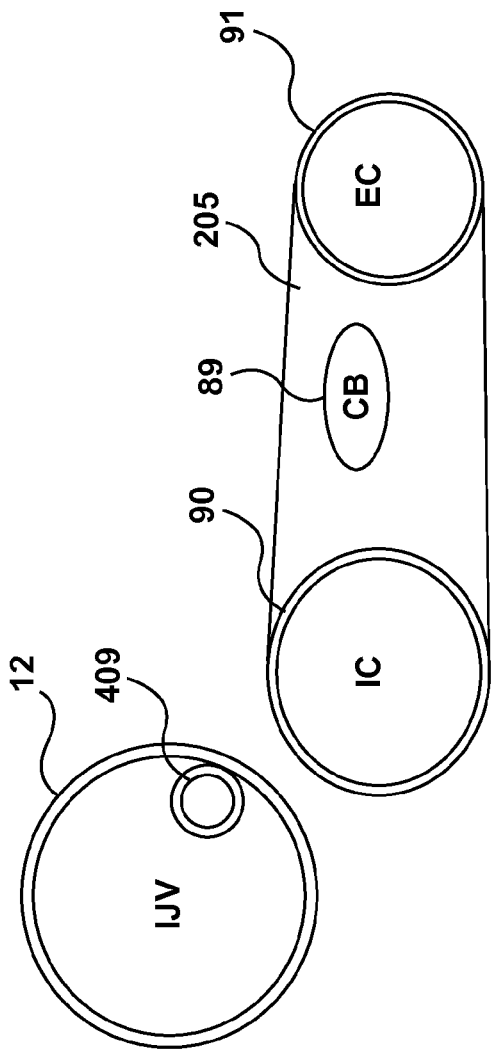
FIGS. 46A and 46B are schematic images depicting in cross section spatial relationships between an internal jugular vein, an internal carotid artery, an external carotid artery and a carotid body.
Figure 46B:
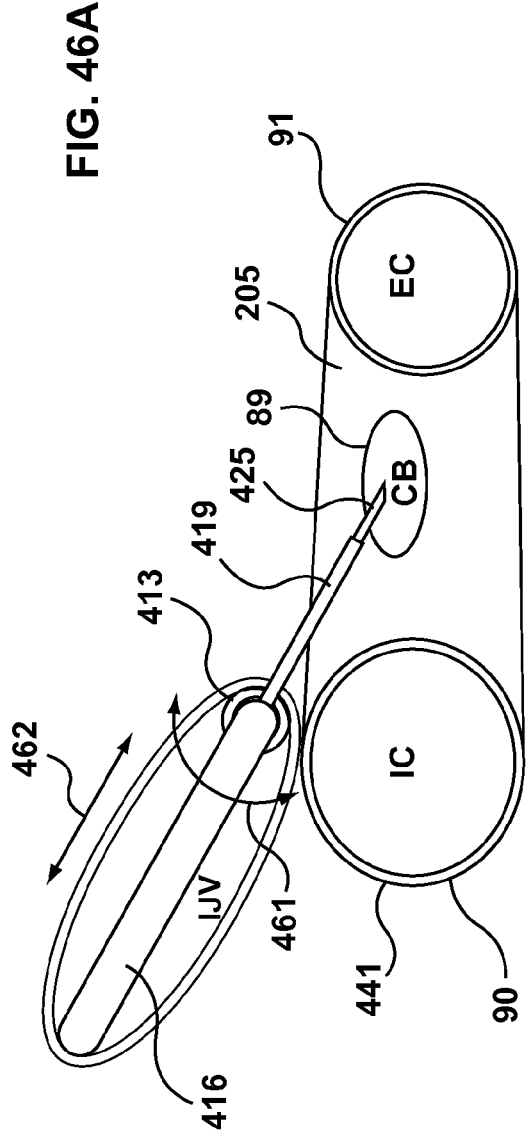

FIG. 46A and FIG. 46B are schematic cross sectional illustrations of the deployment of RF ablation electrode 425 into the intercarotid septum 205 into immediate proximity of carotid body 89 with anatomy that does not normally provide direct safe RF ablation needle access. FIG. 46A depicts a common anatomical arrangement where the internal jugular vein 12 is distant from carotid body 89, and substantially behind internal carotid artery 90. TVICBA catheter 409 is positioned within internal jugular vein 12 at the closest proximity to target carotid body 89. Then as shown in FIG. 46B, TVICBA catheter 409 is configured for needle deployment, using radial displacement 462 of needle sheath 416, and user applied torque 461, thereby manipulating the lumen of internal jugular vein 12 to provide a direct and safe needle insertion pathway.

Figure 47:
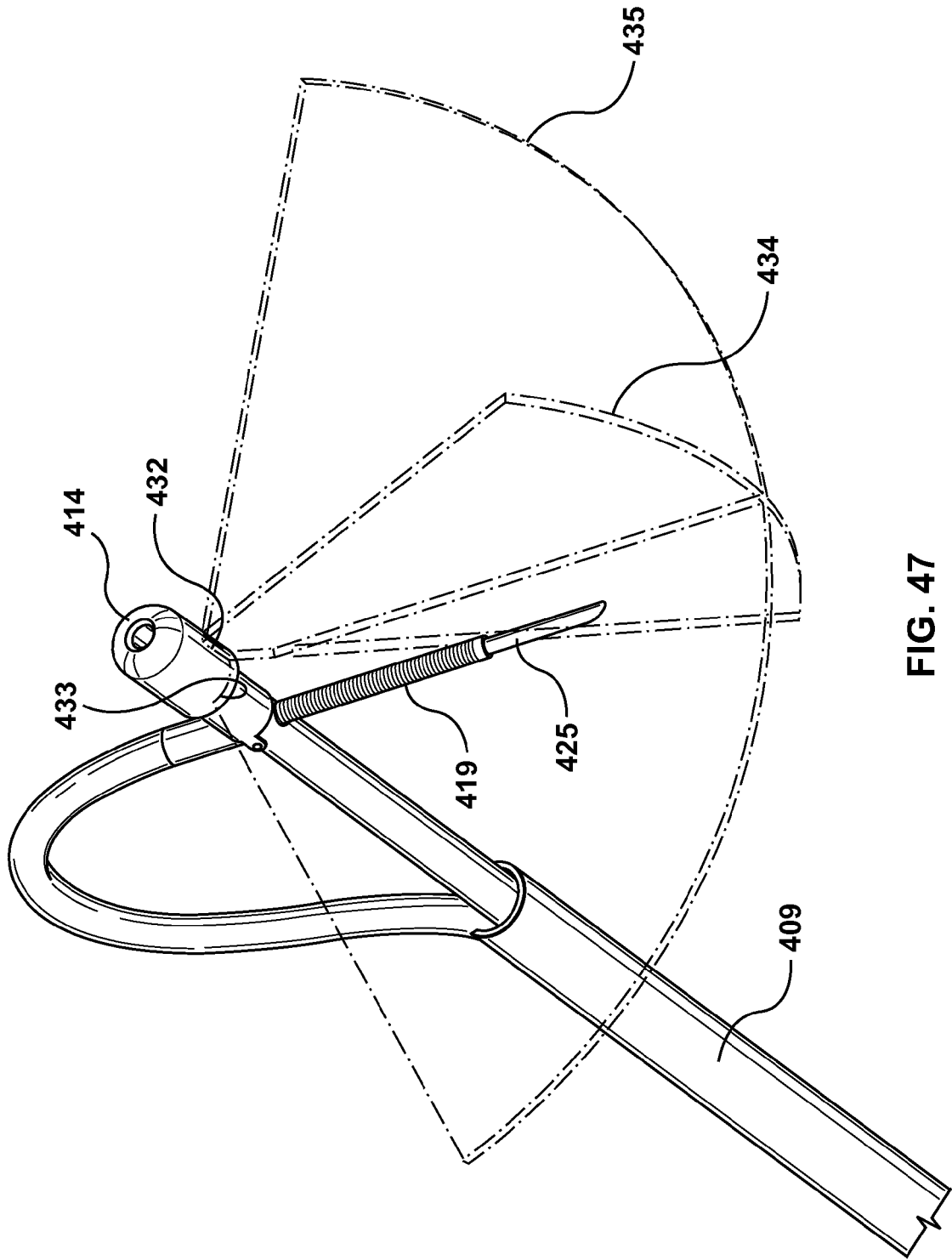
FIG. 47 is a schematic illustration of the distal end of a TVICBA catheter with integrated 2-axis ultrasound imaging capability.

FIG. 47 is an illustration of a TVICBA catheter comprising two integrated ultrasonic imaging transducers. As depicted TVICBA catheter 409 has radial ultrasonic imaging transducer 433, and axial ultrasonic imaging transducer 432 mounted on distal tip 414. Radial ultrasonic imaging transducer 433 is configured to image in a radial planar segment relative to TVICBA catheter 409 in the direction of ablation needle assembly 419 deployment as represented by phantom ultrasonic imaging beam 435. Axial ultrasonic imaging transducer 432 is configured to image in an axial planar segment relative to TVICBA catheter 409 in line with ablation needle assembly 419 deployment as represented by phantom ultrasonic imaging beam 434. Axial ultrasonic imaging transducer 432 is additionally configured to image ablation electrode 425 position during deployment to provide the user with confirmation of the precise location of ablation electrode 425 with the intercarotid septum. Axial ultrasonic imaging transducer 432 or radial ultrasonic imaging transducer 432 may be configured to image a change in tissue echogenicity due to desiccation from RF ablation to provide the user an indication of ablation volume and shape. Axial ultrasonic imaging transducer 432 or radial ultrasonic imaging transducer 433 may be configured for color flow Doppler ultrasonic imaging to enhance positional imaging information by color highlighting of the carotid arterial structure, and to image a cessation of blood flow in the capillary bed associated with a carotid body as an indication of ablation effectiveness, and as an indication clinical technical success. As depicted, axial ultrasonic imaging transducer 432 and radial ultrasonic imaging transducer 433 are solid state phased linear array transducers. Those skilled in the art of ultrasonic imaging transducers are familiar with configuration means of phased linear array transducers for detecting a change in tissue echogenicity due to desiccation, and for color flow Doppler imaging, therefore, construction techniques are not further described. Also, those skilled in the art ultrasonic imaging transducers will recognize that there are alternative ultrasonic imaging transducer arrangements, including linear actuated and rotary actuated transducers.

Figure 48A:
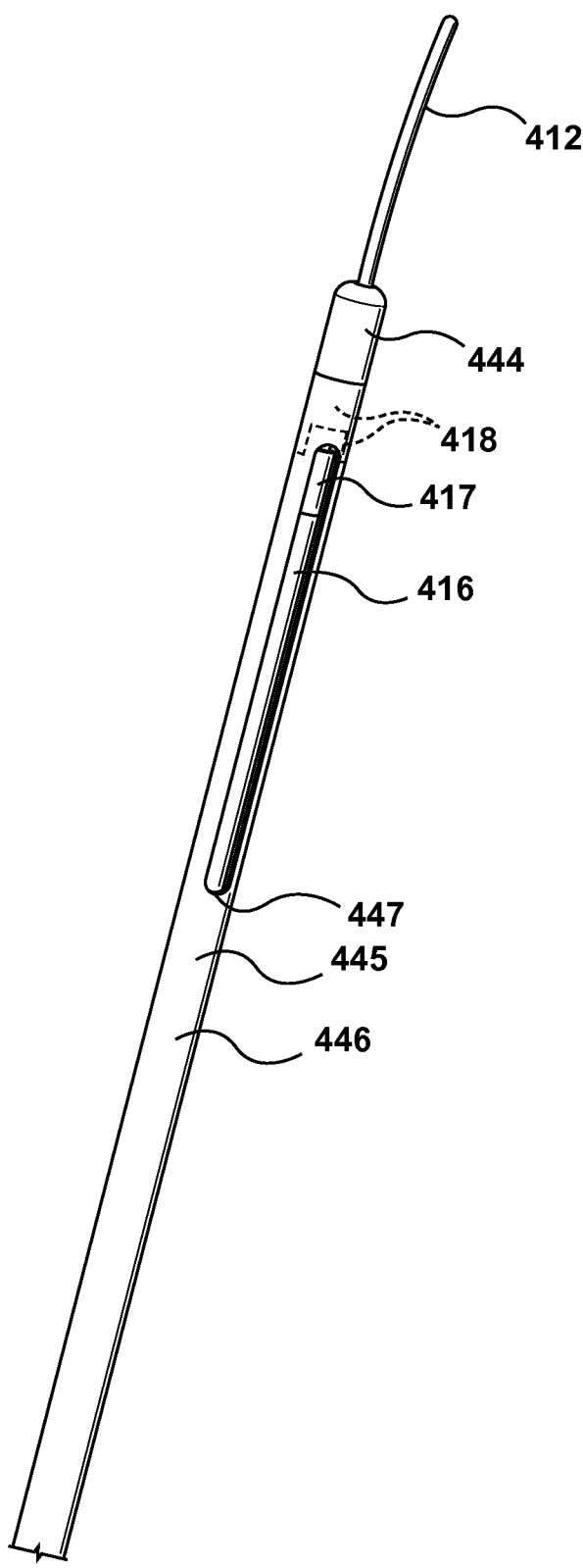
FIGS. 48A and 48B are schematic illustrations of a distal region of an alternative TVICBA catheter design.
Figure 48B:
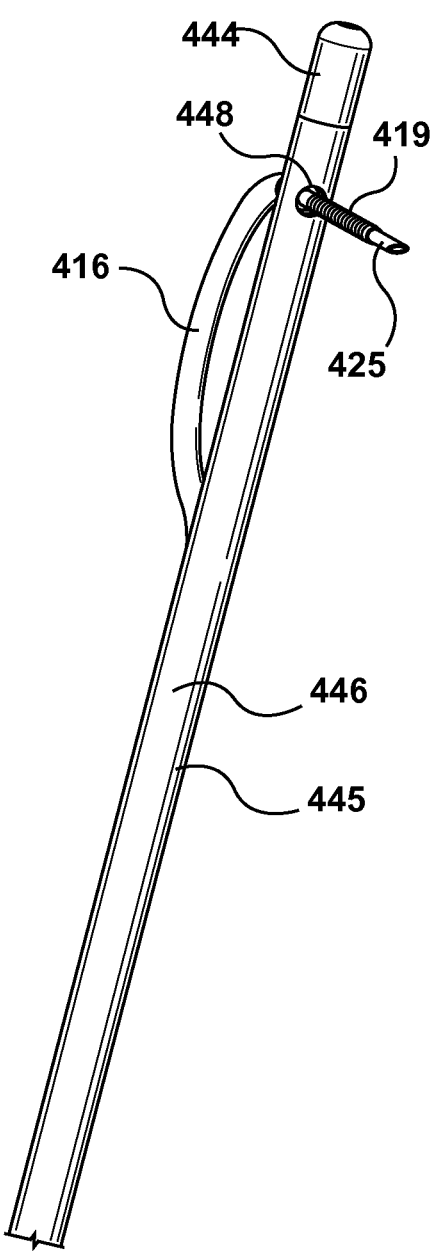

FIGS. 48A and 48B depict the distal end of an alternative TVICBA catheter design. FIG. 48A is an illustration of the distal region of alternative TVICBA catheter 445 showing needle sheath fenestration 447. FIG. 48B is an illustration of the opposing side of distal region of alternative TVICBA catheter 445 showing needle fenestration 448. Alternate TVICBA catheter 446 is similar to TVICBA catheter 409 described above, minus the retractable outer sheath 413. The retractable sheath 413 of TVICBA catheter 409 functionally provides for a variable length needle sheath fenestration; alternative TVICBA catheter 446 has a fixed length needle sheath fenestration 447. Catheter shaft 445 is configured to house needle sheath 416 within, and may comprise a braided structure to facilitate translation of torque along its length. As an alternative to an adjustable length needle sheath fenestration, alternative TVICBA catheter 446 may be provided with multiple sized needle fenestration 447 lengths to accommodate various anatomic situations.

Figure 49:
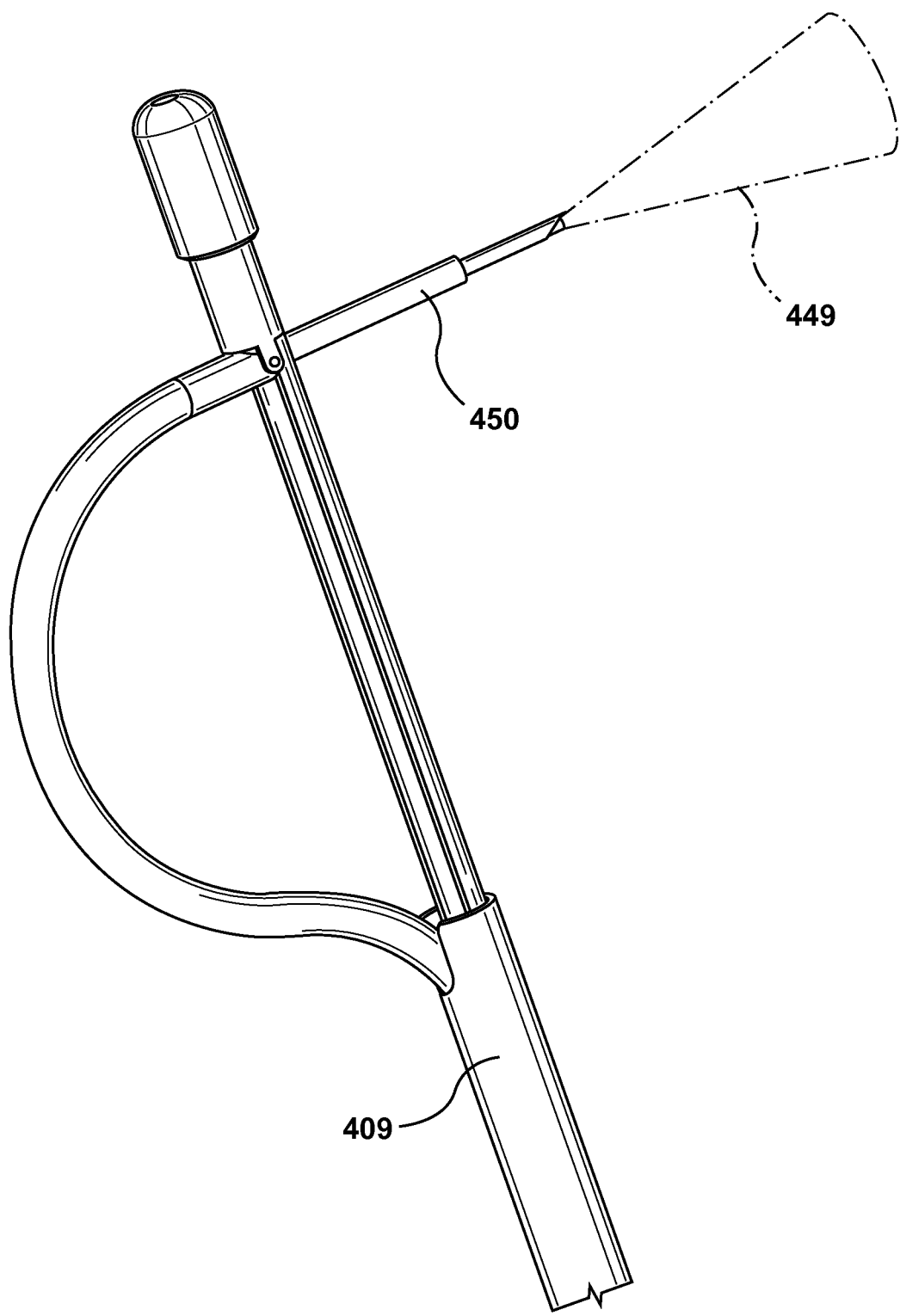
FIG. 49 is a schematic illustration of a distal region of a TVICBA catheter using a selective carotid body ablation modality using green laser energy.

FIG. 49 is an illustration of the distal region of TVICBA catheter 409 using a green laser ablation modality. A carotid body is reported to be the most highly perfused organ in the human body and is surrounded by a dense arterial capillary network. Green laser light in the vicinity of 500 nm to 550 nm (e.g., about 532 nanometers) wavelength is known to be highly absorbed by hemoglobin, and relatively weakly absorbed by neurological tissues. Laser ablation needle assembly 450 may be designed to interchange with RF ablation needle assembly 419 using TVICBA catheter 409 or TVICBA catheter 446. Laser ablation needle assembly 450 is similar in construction to RF ablation needle assembly 419 except an optical fiber traverses the central lumen for the entire length of needle assembly 450 and is terminated at the distal end with a polished surface configured for transmitting light into the intercarotid septum, and is terminated at the proximal end with an optical connector configured to receive laser energy from a laser energy source. Green laser ablation of the carotid body as described provides selective ablation of the carotid body by targeting the hemoglobin component of blood circulating through the carotid body capillary network, while avoiding injury to local vital nervous structures due to the low absorption coefficient of green laser energy by the vital nervous structures. Those skilled in the art of interstitial laser ablation are familiar with techniques for constructing a laser ablation needle for green laser light ablation, therefore construction techniques are not further described.

Figure 50:
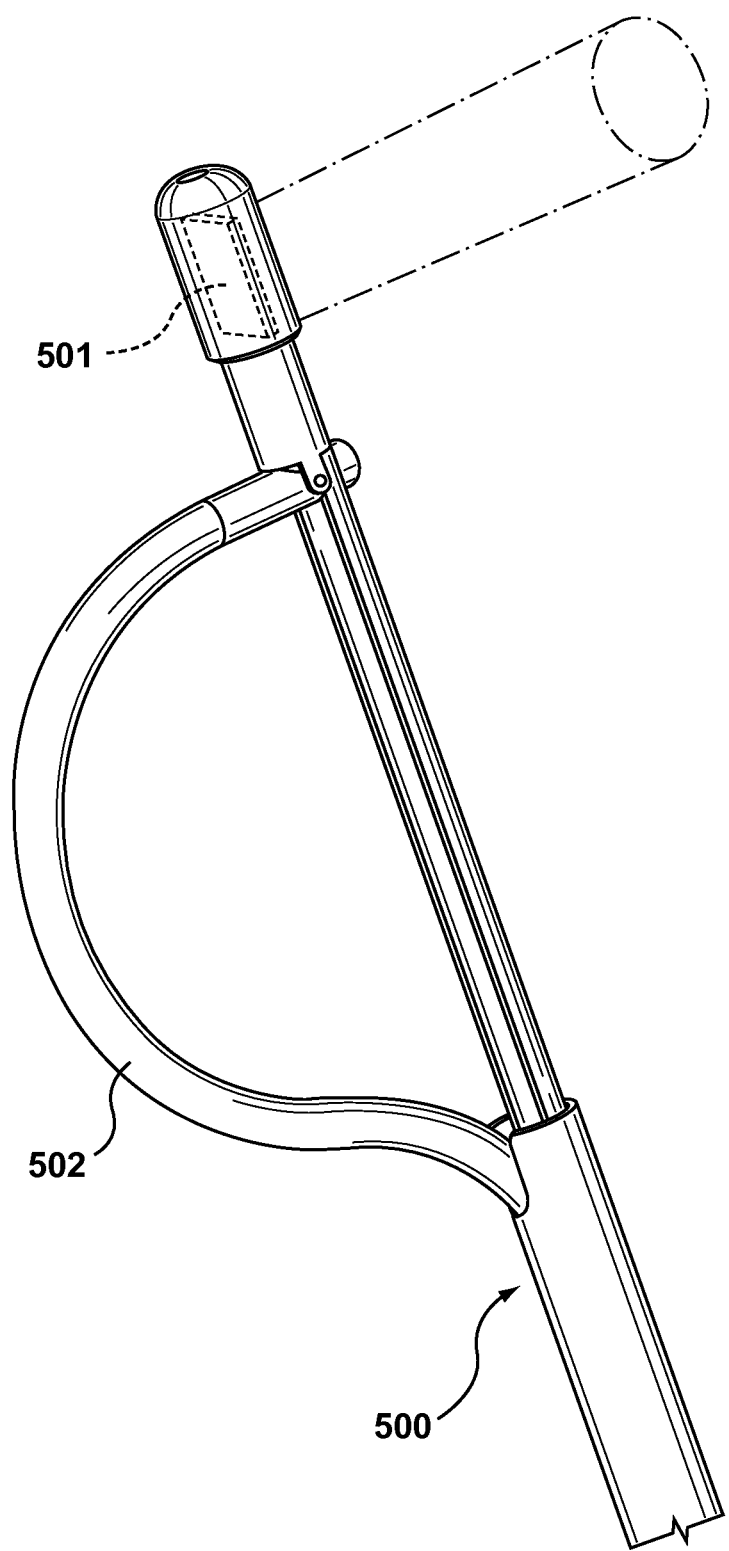
FIG. 50 is a schematic illustration of a distal region of a trans-venous carotid body ultrasound ablation catheter.

FIG. 50 is an illustration of the distal region of an alternative embodiment of a trans-venous carotid body ablation catheter 500 using an ultrasound transducer 501 for emitting ablative energy from a vein (e.g., an internal jugular vein) to a target ablation zone (e.g., carotid body). The catheter is constructed and functions similar to catheter 409 shown in FIG. 49. However, catheter 500 is not intended to puncture the wall of the vein. Deployable wire 502 may be deployed from a substantially straight retracted configuration to a deployed arch as shown. The arch may facilitate manipulation of a vein (e.g., internal jugular vein) to gain a suitable position relative to an ablation target, such as a carotid septum. In some embodiments catheter 500 can ablate a carotid body from within an external carotid artery.

Additional embodiments of TVICBA catheter are anticipated. A deflectable tip using an internal pull wire may be incorporated to further facilitate manipulation of the venous wall. Also, a blunt tip needle may be used instead of a pointed tip needle as depicted above, where RF or laser energy is used to facilitate insertion of the needle into the intercarotid septum. A blunt tip needle may reduce incidence of unintentional needle induced trauma.

Methods of Therapy:

An ablation energy source (e.g., energy field generator) may be located external to the patient. Various types of ablation energy generators or supplies, such as electrical frequency generators, ultrasonic generators, microwave generators, laser consoles, and heating or cryogenic fluid supplies, may be used to provide energy to the ablation element at the distal tip of the catheter. An electrode or other energy applicator at the distal tip of the catheter should conform to the type of energy generator coupled to the catheter. The generator may include computer controls to automatically or manually adjust frequency and strength of the energy applied to the catheter, timing and period during which energy is applied, and safety limits to the application of energy. It should be understood that embodiments of energy delivery electrodes described hereinafter may be electrically connected to the generator even though the generator is not explicitly shown or described with each embodiment.

An endovascular ultrasonic ablation catheter configured to aim ultrasonic energy at a carotid septum may comprise ultrasound visualization capabilities. The ultrasound visualization may comprise Doppler to image blood flow. A catheter may be rotated within an external carotid artery using Doppler to identify when it is aimed through a carotid septum at an internal carotid artery. An ultrasound ablation may be aimed toward the direction of the internal carotid artery and be deposited in a targeted carotid septum.

An ablated tissue lesion at or near the carotid body may be created by the application of ablation energy from an ablation element in a vicinity of a distal end of the carotid body ablation device. The ablated tissue lesion may disable the carotid body or may suppress the activity of the carotid body or interrupt conduction of afferent nerve signals from a carotid body to sympathetic nervous system. The disabling or suppression of the carotid body reduces the responsiveness of the glomus cells to changes of blood gas composition and effectively reduces activity of afferent carotid body nerves or the chemoreflex gain of the patient.

A method in accordance with a particular embodiment includes ablating at least one of a patient's carotid bodies based at least in part on identifying the patient as having a sympathetically mediated disease such as cardiac, metabolic, or pulmonary disease such as hypertension, insulin resistance, diabetes, pulmonary hypertension, drug resistant hypertension (e.g., refractory hypertension), congestive heart failure (CHF), or dyspnea from heart failure or pulmonary disease causes.

A procedure may include diagnosis, selection based on diagnosis, further screening (e.g., baseline assessment of chemosensitivity), treating a patient based at least in part on diagnosis or further screening via a chemoreceptor (e.g., carotid body) ablation procedure such as one of the embodiments disclosed. Additionally, following ablation a method of therapy may involve conducting a post-ablation assessment to compare with the baseline assessment and making decisions based on the assessment (e.g., adjustment of drug therapy, re-treat in new position or with different parameters, or ablate a second chemoreceptor if only one was previously ablated).

A carotid body ablation procedure may comprise the following steps or a combination thereof: patient sedation, locating a target peripheral chemoreceptor, visualizing a target peripheral chemoreceptor (e.g., carotid body), confirming a target ablation site is or is proximate a peripheral chemoreceptor, confirming a target ablation site is safely distant from vital structures that are preferably protected (e.g., hypoglossal, sympathetic and vagus nerves), providing stimulation (e.g., electrical, mechanical, chemical) to a target site or target peripheral chemoreceptor prior to, during or following an ablation step, monitoring physiological responses to said stimulation, providing temporary nerve block to a target site prior to an ablation step, monitoring physiological responses to said temporary nerve block, anesthetizing a target site, protecting the brain from potential embolism, thermally protecting an arterial or venous wall (e.g., carotid artery, jugular vein) or a medial aspect of an intercarotid septum or vital nerve structures, ablating a target site or peripheral chemoreceptor, monitoring ablation parameters (e.g., temperature, pressure, duration, blood flow in a carotid artery), monitoring physiological responses during ablation and arresting ablation if unsafe or unwanted physiological responses occur before collateral nerve injury becomes permanent, confirming a reduction of chemoreceptor activity (e.g., chemosensitivity, HR, blood pressure, ventilation, sympathetic nerve activity) during or following an ablation step, removing a ablation device, conducting a post-ablation assessment, repeating any steps of the chemoreceptor ablation procedure on another peripheral chemoreceptor in the patient.

Patient screening, as well as post-ablation assessment may include physiological tests or gathering of information, for example, chemoreflex sensitivity, central sympathetic nerve activity, heart rate, heart rate variability, blood pressure, ventilation, production of hormones, peripheral vascular resistance, blood pH, blood PCO2, degree of hyperventilation, peak VO2, VE/VCO2 slope. Directly measured maximum oxygen uptake (more correctly pVO2 in heart failure patients) and index of respiratory efficiency VE/VCO2 slope has been shown to be a reproducible marker of exercise tolerance in heart failure and provide objective and additional information regarding a patient's clinical status and prognosis.

A method of therapy may include electrical stimulation of a target region, using a stimulation electrode, to confirm proximity to a carotid body. For example, a stimulation signal having a 1-10 milliamps (mA) pulse train at about 20 to 40 Hz with a pulse duration of 50 to 500 microseconds (μs) that produces a positive carotid body stimulation effect may indicate that the stimulation electrode is within sufficient proximity to the carotid body or nerves of the carotid body to effectively ablate it. A positive carotid body stimulation effect could be increased blood pressure, heart rate, or ventilation concomitant with application of the stimulation. These variables could be monitored, recorded, or displayed to help assess confirmation of proximity to a carotid body. A catheter-based technique, for example, may have a stimulation electrode proximal to the ablation element used for ablation. Alternatively, the ablation element itself may also be used as a stimulation electrode. Alternatively, an energy delivery element that delivers a form of ablative energy that is not electrical, such as a cryogenic ablation applicator, may be configured to also deliver an electrical stimulation signal as described earlier. Yet another alternative embodiment comprises a stimulation electrode that is distinct from an ablation element. For example, during a surgical procedure a stimulation probe can be touched to a suspected carotid body that is surgically exposed. A positive carotid body stimulation effect could confirm that the suspected structure is a carotid body and ablation can commence. Physiological monitors (e.g., heart rate monitor, blood pressure monitor, blood flow monitor, MSNA monitor) may communicate with a computerized stimulation generator, which may also be an ablation generator, to provide feedback information in response to stimulation. If a physiological response correlates to a given stimulation the computerized generator may provide an indication of a positive confirmation.

Alternatively or in addition a drug known to excite the chemo sensitive cells of the carotid body can be injected directly into the carotid artery or given systemically into patients vein or artery in order to elicit hemodynamic or respiratory response. Examples of drugs that may excite a chemoreceptor include nicotine, atropine, Doxapram, Almitrine, hyperkalemia, Theophylline, adenosine, sulfides, Lobeline, Acetylcholine, ammonium chloride, methylamine, potassium chloride, anabasine, coniine, cytosine, acetaldehyde, acetyl ester and the ethyl ether of i-methylcholine, Succinylcholine, Piperidine, monophenol ester of homo-isomuscarine and acetylsalicylamides, alkaloids of veratrum, sodium citrate, adenosinetriphosphate, dinitrophenol, caffeine, theobromine, ethyl alcohol, ether, chloroform, phenyldiguanide, sparteine, coramine (nikethamide), metrazol (pentylenetetrazol), iodomethylate of dimethylaminomethylenedioxypropane, ethyltrimethylammoniumpropane, trimethylammonium, hydroxytryptamine, papaverine, neostigmine, acidity.

Described methods may include ultrasound activated drug delivery to carotid complex. Drugs can be incorporated into particles capable of ultrasound activation. Intravenous or direct intratumoral injection of such drug compositions comprising microbubbles, nanoparticles, liposomes and biologically active agents encapsulated in polymers undergo a physical change when subjected to ultrasound beam. The compositions include microemulsions which may create microbubbles as cavitation nuclei in the process of injection and enhance intracellular drug delivery in the carotid complex. The administration of the ultrasound beam to a carotid complex perfused with encapsulated drugs may stimulate a release of the therapeutic agent to a selected volume affected by the application of ultrasound. In addition to a release of a therapeutic agent the microbubbles generated in situ during an ultrasound irradiation procedure may produce additional guidance to ultrasound imaging.

A method of therapy may further comprise applying electrical or chemical stimulation to the target area or systemically following ablation to confirm a successful ablation. Heart rate, blood pressure or ventilation may be monitored for change or compared to the reaction to stimulation prior to ablation to assess if the targeted carotid body was ablated. Post-ablation stimulation may be done with the same apparatus used to conduct the pre-ablation stimulation. Physiological monitors (e.g., heart rate monitor, blood pressure monitor, blood flow monitor, MSNA monitor) may communicate with a computerized stimulation generator, which may also be an ablation generator, to provide feedback information in response to stimulation. If a physiological response correlated to a given stimulation is reduced following an ablation compared to a physiological response prior to the ablation, the computerized generator may provide an indication ablation efficacy or possible procedural suggestions such as repeating an ablation, adjusting ablation parameters, changing position, ablating another carotid body or chemosensor, or concluding the procedure.

The devices described herein may also be used to temporarily stun or block nerve conduction via electrical neural blockade. A temporary nerve block may be used to confirm position of an ablation element prior to ablation. For example, a temporary nerve block may block nerves associated with a carotid body, which may result in a physiological effect to confirm the position may be effective for ablation. Furthermore, a temporary nerve block may block vital nerves such as vagal, hypoglossal or sympathetic nerves that are preferably avoided, resulting in a physiological effect (e.g., physiological effects may be noted by observing the patient's eyes, tongue, throat or facial muscles or by monitoring patient's heart rate and respiration). This may alert a user that the position is not in a safe location. Likewise absence of a physiological effect indicating a temporary nerve block of such vital nerves in combination with a physiological effect indicating a temporary nerve block of carotid body nerves may indicate that the position is in a safe and effective location for carotid body ablation.

Important nerves may be located in proximity of the target site and may be inadvertently and unintentionally injured. Neural stimulation or blockade can help identify that these nerves are in the ablation zone before the irreversible ablation occurs. These nerves may include the following:

Vagus Nerve Bundle—The vagus is a bundle of nerves that carry separate functions, for example a) branchial motor neurons (efferent special visceral) which are responsible for swallowing and phonation and are distributed to pharyngeal branches, superior and inferior laryngeal nerves; b) visceral motor (efferent general visceral) which are responsible for involuntary muscle and gland control and are distributed to cardiac, pulmonary, esophageal, gastric, celiac plexuses, and muscles, and glands of the digestive tract; c) visceral sensory (afferent general visceral) which are responsible for visceral sensibility and are distributed to cervical, thoracic, abdominal fibers, and carotid and aortic bodies; d) visceral sensory (afferent special visceral) which are responsible for taste and are distributed to epiglottis and taste buds; e) general sensory (afferent general somatic) which are responsible for cutaneous sensibility and are distributed to auricular branch to external ear, meatus, and tympanic membrane. Dysfunction of the vagus may be detected by a) vocal changes caused by nerve damage (damage to the vagus nerve can result in trouble with moving the tongue while speaking, or hoarseness of the voice if the branch leading to the larynx is damaged); b) dysphagia due to nerve damage (the vagus nerve controls many muscles in the palate and tongue which, if damaged, can cause difficulty with swallowing); c) changes in gag reflex (the gag reflex is controlled by the vagus nerve and damage may cause this reflex to be lost, which can increase the risk of choking on saliva or food); d) hearing loss due to nerve damage (hearing loss may result from damage to the branch of the vagus nerve that innervates the concha of the ear): e) cardiovascular problems due to nerve damage (damage to the vagus nerve can cause cardiovascular side effects including irregular heartbeat and arrhythmia); or f) digestive problems due to nerve damage (damage to the vagus nerve may cause problems with contractions of the stomach and intestines, which can lead to constipation).

Superior Laryngeal Nerve—the superior laryngeal nerve is a branch of the vagus nerve bundle. Functionally, the superior laryngeal nerve function can be divided into sensory and motor components. The sensory function provides a variety of afferent signals from the supraglottic larynx. Motor function involves motor supply to the ipsilateral cricothyroid muscle. Contraction of the cricothyroid muscle tilts the cricoid lamina backward at the cricothyroid joint causing lengthening, tensing and adduction of vocal folds causing an increase in the pitch of the voice generated. Dysfunction of the superior laryngeal nerve may change the pitch of the voice and causes an inability to make explosive sounds. A bilateral palsy presents as a tiring and hoarse voice.

Cervical Sympathetic Nerve—The cervical sympathetic nerve provides efferent fibers to the internal carotid nerve, external carotid nerve, and superior cervical cardiac nerve. It provides sympathetic innervation of the head, neck and heart. Organs that are innervated by the sympathetic nerves include eyes, lacrimal gland and salivary glands. Dysfunction of the cervical sympathetic nerve includes Homer's syndrome, which is very identifiable and may include the following reactions: a) partial ptosis (drooping of the upper eyelid from loss of sympathetic innervation to the superior tarsal muscle, also known as Müller's muscle); b) upside-down ptosis (slight elevation of the lower lid); c) anhidrosis (decreased sweating on the affected side of the face); d) miosis (small pupils, for example small relative to what would be expected by the amount of light the pupil receives or constriction of the pupil to a diameter of less than two millimeters, or asymmetric, one-sided constriction of pupils); e) enophthalmos (an impression that an eye is sunken in); f) loss of ciliospinal reflex (the ciliospinal reflex, or pupillary-skin reflex, consists of dilation of the ipsilateral pupil in response to pain applied to the neck, face, and upper trunk. If the right side of the neck is subjected to a painful stimulus, the right pupil dilates about 1-2 mm from baseline. This reflex is absent in Homer's syndrome and lesions involving the cervical sympathetic fibers.)
Visualization:

An optional step of visualizing internal structures (e.g., carotid body or surrounding structures) may be accomplished using one or more non-invasive imaging modalities, for example fluoroscopy, radiography, arteriography, computer tomography (CT), computer tomography angiography with contrast (CTA), magnetic resonance imaging (MRI), or sonography, or minimally invasive techniques (e.g., IVUS, endoscopy, optical coherence tomography, ICE). A visualization step may be performed as part of a patient assessment, prior to an ablation procedure to assess risks and location of anatomical structures, during an ablation procedure to help guide an ablation device, or following an ablation procedure to assess outcome (e.g., efficacy of the ablation). Visualization may be used to: (a) locate a carotid body, (b) locate vital structures that may be adversely affected, or (c) locate, identify and measure arterial plaque.

Endovascular (for example transfemoral) arteriography of the common carotid and then selective arteriography of the internal and external carotids may be used to determine a position of a catheter tip at a carotid bifurcation. Additionally, ostia of glomic arteries (these arteries may be up to 4 mm long and arise directly from the main parent artery) can be identified by dragging the dye injection catheter and releasing small amounts ("puffs") of dye. If a glomic artery is identified it can be cannulated by a guide wire and possibly further cannulated by small caliber catheter. Direct injection of dye into glomic arteries can further assist the interventionalist in the ablation procedure. It is appreciated that the feeding glomic arteries are small and microcatheters may be needed to cannulate them.

Alternatively, ultrasound visualization may allow a physician to see the carotid arteries and even the carotid body. Another method for visualization may consist of inserting a small needle (e.g., 22 Gauge) with sonography or computer tomography (CT) guidance into or toward the carotid body. A wire or needle can be left in place as a fiducial guide, or contrast can be injected into the carotid body. Runoff of contrast to the jugular vein may confirm that the target is achieved.

Computer Tomography (CT) and computer tomography angiography (CTA) may also be used to aid in identifying a carotid body. Such imaging could be used to help guide an ablation device to a carotid body.

Ultrasound visualization (e.g., sonography) is an ultrasound-based imaging technique used for visualizing subcutaneous body structures including blood vessels and surrounding tissues. Doppler ultrasound uses reflected ultrasound waves to identify and display blood flow through a vessel. Operators typically use a hand-held transducer/transceiver placed directly on a patient's skin and aimed inward directing ultrasound waves through the patient's tissue. Ultrasound may be used to visualize a patient's carotid body to help guide an ablation device. Ultrasound can be also used to identify atherosclerotic plaque in the carotid arteries and avoid disturbing and dislodging such plaque.

Visualization and navigation steps may comprise multiple imaging modalities (e.g., CT, fluoroscopy, ultrasound) superimposed digitally to use as a map for instrument positioning. Superimposing borders of great vessels such as carotid arteries can be done to combine images.

Responses to stimulation at different coordinate points can be stored digitally as a 3-dimensional or 2-dimensional orthogonal plane map. Such an electric map of the carotid bifurcation showing points, or point coordinates that are electrically excitable such as baroreceptors, baroreceptor nerves, chemoreceptors and chemoreceptor nerves can be superimposed with an image (e.g., CT, fluoroscopy, ultrasound) of vessels. This can be used to guide the procedure, and identify target areas and areas to avoid.

In addition, as noted above, it should be understood that a device providing therapy can also be used to locate a carotid body as well as to provide various stimuli (electrical, chemical, other) to test a baseline response of the carotid body chemoreflex (CBC) or carotid sinus baroreflex (CSB) and measure changes in these responses after therapy or a need for additional therapy to achieve the desired physiological and clinical effects.

Patient Selection and Assessment:

In an embodiment, a procedure may comprise assessing a patient to be a plausible candidate for carotid body ablation. Such assessment may involve diagnosing a patient with a sympathetically mediated disease (e.g., MSNA microneurography, measure of cataclomines in blood or urine, heart rate, or low/high frequency analysis of heart rate variability may be used to assess sympathetic tone). Patient assessment may further comprise other patient selection criteria, for example indices of high carotid body activity (i.e. carotid body hypersensitivity or hyperactivity) such as a combination of hyperventilation and hypocarbia at rest, high carotid body nerve activity (e.g., measured directly), incidence of periodic breathing, dyspnea, central sleep apnea elevated brain natriuretic peptide, low exercise capacity, having cardiac resynchronization therapy, atrial fibrillation, ejection fraction of the left ventricle, using beta blockers or ACE inhibitors.

Patient assessment may further involve selecting patients with high peripheral chemosensitivity (e.g., a respiratory response to hypoxia normalized to the desaturation of oxygen greater than or equal to about 0.7 l/min/min $SpO_2$), which may involve characterizing a patient's chemoreceptor sensitivity, reaction to temporarily blocking carotid body chemoreflex, or a combination thereof.

Although there are many ways to measure chemosensitivity they can be divided into (a) active provoked response and (b) passive monitoring. Active tests can be done by inducing intermittent hypoxia (such as by taking breaths of nitrogen or $CO_2$ or combination of gases) or by rebreathing air into and from a 4 to 10 liter bag. For example: a hypersensitive response to a short period of hypoxia measured by increase of respiration or heart rate may provide an indication for therapy. Ablation or significant reduction of such response could be indicative of a successful procedure. Also, electrical stimulation, drugs and chemicals (e.g., dopamine, lidocane) exist that can block or excite a carotid body when applied locally or intravenously.

The location and baseline function of the desired area of therapy (including the carotid and aortic chemoreceptors and baroreceptors and corresponding nerves) may be determined prior to therapy by application of stimuli to the carotid body or other organs that would result in an expected change in a physiological or clinical event such as an increase or decrease in SNS activity, heart rate or blood pressure. These stimuli may also be applied after the therapy to determine the effect of the therapy or to indicate the need for repeated application of therapy to achieve the desired physiological or clinical effect(s). The stimuli can be either electrical or chemical in nature and can be delivered via the same or another catheter or can be delivered separately (such as injection of a substance through a peripheral IV to affect the CBC that would be expected to cause a predicted physiological or clinical effect).

A baseline stimulation test may be performed to select patients that may benefit from a carotid body ablation procedure. For example, patients with a high peripheral chemosensitivity gain (e.g., greater than or equal to about two standard deviations above an age matched general population chemosensitivity, or alternatively above a threshold peripheral chemosensitivity to hypoxia of 0.5 or 0.7 ml/min/%O2) may be selected for a carotid body ablation procedure. A prospective patient suffering from a cardiac, metabolic, or pulmonary disease (e.g., hypertension, CHF, diabetes) may be selected. The patient may then be tested to assess a baseline peripheral chemoreceptor sensitivity (e.g., minute ventilation, tidal volume, ventilator rate, heart rate, or other response to hypoxic or hypercapnic stimulus). Baseline peripheral chemosensitivity may be assessed using tests known in the art which involve inhalation of a gas mixture having reduced $O_2$ content (e.g., pure nitrogen, $CO_2$, helium, or breathable gas mixture with reduced amounts of $O_2$ and increased amounts of $CO_2$) or rebreathing of gas into a bag. Concurrently, the patient's minute ventilation or initial sympathetically mediated physiologic parameter such as minute ventilation or HR may be measured and compared to the $O_2$ level in the gas mixture. Tests like this may elucidate indices called chemoreceptor set point and gain. These indices are indicative of chemoreceptor sensitivity. If the patient's chemosensitivity is not assessed to be high (e.g., less than about two standard deviations of an age matched general population chemosensitivity, or other relevant numeric threshold) then the patient may not be a suitable candidate for a carotid body ablation procedure. Conversely, a patient with chemoreceptor hypersensitivity (e.g., greater than or equal to about two standard deviations above normal) may proceed to have a carotid body ablation procedure. Following a carotid body ablation procedure the patient's chemosensitivity may optionally be tested again and compared to the results of the baseline test. The second test or the comparison of the second test to the baseline test may provide an indication of treatment success or suggest further intervention such as possible adjustment of drug therapy, repeating the carotid body ablation procedure with adjusted parameters or location, or performing another carotid body ablation procedure on a second carotid body if the first procedure only targeted one carotid body. It may be expected that a patient having chemoreceptor hypersensitivity or hyperactivity may return to about a normal sensitivity or activity following a successful carotid body ablation procedure.

In an alternative protocol for selecting a patient for a carotid body ablation, patients with high peripheral chemosensitivity or carotid body activity (e.g., ≥about 2 standard deviations above normal) alone or in combination with other clinical and physiologic parameters may be particularly good candidates for carotid body ablation therapy if they further respond positively to temporary blocking of carotid body activity. A prospective patient suffering from a cardiac, metabolic, or pulmonary disease may be selected to be tested to assess the baseline peripheral chemoreceptor sensitivity. A patient without high chemosensitivity may not be a plausible candidate for a carotid body ablation procedure. A patient with a high chemosensitivity may be given a further assessment that temporarily blocks a carotid body chemoreflex. For example a temporary block may be done chemically, for example using a chemical such as intravascular dopamine or dopamine-like substances, intravascular alpha-2 adrenergic agonists, oxygen, in general alkalinity, or local or topical application of atropine externally to the carotid body. A patient having a negative response to the temporary carotid body block test (e.g., sympathetic activity index such as respiration, HR, heart rate variability, MSNA, vasculature resistance, etc. is not significantly altered) may be a less plausible candidate for a carotid body ablation procedure. Conversely, a patient with a positive response to the temporary carotid body block test (e.g., respiration or index of sympathetic activity is altered significantly) may be a more plausible candidate for a carotid body ablation procedure.

There are a number of potential ways to conduct a temporary carotid body block test. Hyperoxia (e.g., higher than normal levels of $PO_2$) for example, is known to partially block (about a 50%) or reduce afferent sympathetic response of the carotid body. Thus, if a patient's sympathetic activity indices (e.g., respiration, HR, HRV, MSNA) are reduced by hyperoxia (e.g., inhalation of higher than normal levels of $O_2$) for 3-5 minutes, the patient may be a particularly plausible candidate for carotid body ablation therapy. A sympathetic response to hyperoxia may be achieved by monitoring minute ventilation (e.g., reduction of more than 20-30% may indicate that a patient has carotid body hyperactivity). To evoke a carotid body response, or compare it to carotid body response in normoxic conditions, $CO_2$ above 3-4% may be mixed into the gas inspired by the patient (nitrogen content will be reduced) or another pharmacological agent can be used to invoke a carotid body response to a change of $CO_2$, pH or glucose concentration. Alternatively, "withdrawal of hypoxic drive" to rest state respiration in response to breathing a high concentration $O_2$ gas mix may be used for a simpler test.

An alternative temporary carotid body block test involves administering a sub-anesthetic amount of anesthetic gas halothane, which is known to temporarily suppress carotid body activity. Furthermore, there are injectable substances such as dopamine that are known to reversibly inhibit the carotid body. However, any substance, whether inhaled, injected or delivered by another manner to the carotid body that affects carotid body function in the desired fashion may be used.

Another alternative temporary carotid body block test involves application of cryogenic energy to a carotid body (i.e. removal of heat). For example, a carotid body or its nerves may be cooled to a temperature range between about −15° C. to 0° C. to temporarily reduce nerve activity or blood flow to and from a carotid body thus reducing or inhibiting carotid body activity.

An alternative method of assessing a temporary carotid body block test may involve measuring pulse pressure. Non-invasive pulse pressure devices such as Nexfin (made by BMEYE, based in Amsterdam, The Netherlands) can be used to track beat-to-beat changes in peripheral vascular resistance. Patients with hypertension or CHF may be sensitive to temporary carotid body blocking with oxygen or injection of a blocking drug. The peripheral vascular resistance of such patients may be expected to reduce substantially in response to carotid body blocking. Such patients may be good candidates for carotid body ablation therapy.

Yet another index that may be used to assess if a patient may be a good candidate for carotid body ablation therapy is increase of baroreflex, or baroreceptor sensitivity, in response to carotid body blocking. It is known that hyperactive chemosensitivity suppresses baroreflex. If carotid body activity is temporarily reduced the carotid sinus baroreflex (baroreflex sensitivity (BRS) or baroreflex gain) may be expected to increase. Baroreflex contributes a beneficial parasympathetic component to autonomic drive. Depressed BRS is often associated with an increased incidence of death and malignant ventricular arrhythmias. Baroreflex is measurable using standard non-invasive methods. One example is spectral analysis of RR interval of ECG and systolic blood pressure variability in both the high- and low-frequency bands. An increase of baroreflex gain in response to temporary blockade of carotid body can be a good indication for permanent therapy. Baroreflex sensitivity can also be measured by heart rate response to a transient rise in blood pressure induced by injection of phenylephrine.

An alternative method involves using an index of glucose tolerance to select patients and determine the results of carotid body blocking or removal in diabetic patients. There is evidence that carotid body hyperactivity contributes to progression and severity of metabolic disease.

In general, a beneficial response can be seen as an increase of parasympathetic or decrease of sympathetic tone in the overall autonomic balance. For example, Power Spectral Density (PSD) curves of respiration or HR can be calculated using nonparametric Fast Fourier Transform algorithm (FFT). FFT parameters can be set to 256-64 k buffer size, Hamming window, 50% overlap, 0 to 0.5 or 0.1 to 1.0 Hz range. HR and respiratory signals can be analyzed for the same periods of time corresponding to (1) normal unblocked carotid body breathing and (2) breathing with blocked carotid body.

Power can be calculated for three bands: the very low frequency (VLF) between 0 and 0.04 Hz, the low frequency band (LF) between 0.04-0.15 Hz and the high frequency band (HF) between 0.15-0.4 Hz. Cumulative spectral power in LF and HF bands may also be calculated; normalized to total power between 0.04 and 0.4 Hz (TF=HF+LF) and expressed as % of total. Natural breathing rate of CHF patient, for example, can be rather high, in the 0.3-0.4 Hz range.

The VLF band may be assumed to reflect periodic breathing frequency (typically 0.016 Hz) that can be present in CHF patients. It can be excluded from the HF/LF power ratio calculations.

The powers of the LF and HF oscillations characterizing heart rate variability (HRV) appear to reflect, in their reciprocal relationship, changes in the state of the sympathovagal (sympathetic to parasympathetic) balance occurring during numerous physiological and pathophysiological conditions. Thus, increase of HF contribution in particular can be considered a positive response to carotid body blocking.

Another alternative method of assessing carotid body activity comprises nuclear medicine scanning, for example with ocretide, somatostatin analogues, or other substances produced or bound by the carotid body.

Furthermore, artificially increasing blood flow may reduce carotid body activation. Conversely artificially reducing blood flow may stimulate carotid body activation. This may be achieved with drugs known in the art to alter blood flow.

There is a considerable amount of scientific evidence to demonstrate that hypertrophy of a carotid body often accompanies disease. A hypertrophied (i.e. enlarged) carotid body may further contribute to the disease. Thus identification of patients with enlarged carotid bodies may be instrumental in determining candidates for therapy. Imaging of a carotid body may be accomplished by angiography performed with radiographic, computer tomography, or magnetic resonance imaging.

It should be understood that the available measurements are not limited to those described above. It may be possible to use any single or a combination of measurements that reflect any clinical or physiological parameter effected or changed by either increases or decreases in carotid body function to evaluate the baseline state, or change in state, of a patient's chemosensitivity.

There is a considerable amount of scientific evidence to demonstrate that hypertrophy of a carotid body often accompanies disease. A hypertrophied or enlarged carotid body may further contribute to the disease. Thus identification of patients with enlarged carotid bodies may be instrumental in determining candidates for therapy.

Further, it is possible that although patients do not meet a preselected clinical or physiological definition of high peripheral chemosensitivity (e.g., greater than or equal to about two standard deviations above normal), administration of a substance that suppresses peripheral chemosensitivity may be an alternative method of identifying a patient who is a candidate for the proposed therapy. These patients may have a different physiology or co-morbid disease state that, in concert with a higher than normal peripheral chemosensitivity (e.g., greater than or equal to normal and less than or equal to about 2 standard deviations above normal), may still allow the patient to benefit from carotid body ablation. The proposed therapy may be at least in part based on an objective that carotid body ablation will result in a clinically significant or clinically beneficial change in the patient's physiological or clinical course. It is reasonable to believe that if the desired clinical or physiological changes occur even in the absence of meeting the predefined screening criteria, then therapy could be performed.

A patient may be assessed for suitability for a trans-venous carotid body ablation procedure. For example, a patient having a high risk of brain embolism due to abundance of plaque in their carotid arteries may be poorly suited for a carotid body ablation procedure involving a trans-arterial approach and thus may be more suited for a trans-venous approach. Presence of plaque may be assessed using an imaging technology such as sonography. A patient having an internal jugular vein in a position relative to carotid arteries such that a target ablation site may be accessed with a trans-venous carotid body ablation catheter, or such that the jugular vein may be manipulated to access a target ablation site may be selected for a trans-venous carotid body ablation procedure. Relative position of an internal jugular vein, carotid arteries, and a target ablation site may be determined using an imaging modality such as CTA or sonography.

While the invention has been described in connection with what is presently considered to be the best mode, it is to be understood that the invention is not to be limited to the disclosed embodiment(s). The invention covers various modifications and equivalent arrangements included within the spirit and scope of the appended claims.

Overview:

Ablation of a target ablation site (e.g., peripheral chemoreceptor, carotid body) via directed energy in patients having sympathetically mediated disease and augmented chemoreflex (e.g., high afferent nerve signaling from a carotid body to the central nervous system as in some cases indicated by high peripheral chemosensitivity) has been conceived to reduce peripheral chemosensitivity and reduce afferent signaling from peripheral chemoreceptors to the central nervous system. Additionally, ablation of a target ablation site (e.g., peripheral chemoreceptor, carotid body) via a transvenous endovascular approach in patients having sympathetically mediated disease and augmented chemoreflex (e.g., high afferent nerve signaling from a carotid body to the central nervous system as in some cases indicated by high peripheral chemosensitivity) has been conceived to reduce peripheral chemosensitivity and reduce afferent signaling from peripheral chemoreceptors to the central nervous system. The expected reduction of chemoreflex activity and sensitivity to hypoxia and other stimuli such as blood flow, blood $CO_2$, glucose concentration or blood pH can directly reduce afferent signals from chemoreceptors and produce at least one beneficial effect such as the reduction of central sympathetic activation, reduction of the sensation of breathlessness (dyspnea), vasodilation, increase of exercise capacity, reduction of blood pressure, reduction of sodium and water retention, redistribution of blood volume to skeletal muscle, reduction of insulin resistance, reduction of hyperventilation, reduction of tachypnea, reduction of hypocapnia, increase of baroreflex and barosensitivity of baroreceptors, increase of vagal tone, or improve symptoms of a sympathetically mediated disease and may ultimately slow down the disease progression and extend life. It is understood that a sympathetically mediated disease that may be treated with carotid body ablation may comprise elevated sympathetic tone, an elevated sympathetic/parasympathetic activity ratio, autonomic imbalance primarily attributable to central sympathetic tone being abnormally or undesirably high, or heightened sympathetic tone at least partially attributable to afferent excitation traceable to hypersensitivity or hyperactivity of a peripheral chemoreceptor (e.g., carotid body). In some important clinical cases where baseline hypocapnia or tachypnea is present, reduction of hyperventilation and breathing rate may be expected. It is understood that hyperventilation in the context herein means respiration in excess of metabolic needs on the individual that generally leads to slight but significant hypocapnea (blood $CO_2$ partial pressure below normal of approximately 40 mmHg, for example in the range of 33 to 38 mmHg).

Patients having CHF or hypertension concurrent with heightened peripheral chemoreflex activity and sensitivity often react as if their system was hypercapnic even if it is not. The reaction is often to hyperventilate, a maladaptive attempt to rid the system of $CO_2$, thus overcompensating and creating a hypocapnic and alkalotic system. Some researchers attribute this hypersensitivity/hyperactivity of the carotid body to the direct effect of catecholamines, hormones circulating in excessive quantities in the blood stream of CHF patients. The procedure may be particularly useful to treat such patients who are hypocapnic and possibly alkalotic resulting from high tonic output from carotid bodies. Such patients are particularly predisposed to periodic breathing and central apnea hypopnea type events that cause arousal, disrupt sleep, cause intermittent hypoxia and are by themselves detrimental and difficult to treat.

It is appreciated that periodic breathing of Cheyne Stokes pattern occurs in patients during sleep, exercise and even at rest as a combination of central hypersensitivity to $CO_2$, peripheral chemosensitivity to $O_2$ and $CO_2$ and prolonged circulatory delay. All these parameters are often present in CHF patients that are at high risk of death. Thus, patients with hypocapnea, CHF, high chemosensitivity and prolonged circulatory delay, and specifically ones that exhibit periodic breathing at rest or during exercise or induced by hypoxia are likely beneficiaries of the proposed therapy.

Hyperventilation is defined as breathing in excess of a person's metabolic need at a given time and level of activity. Hyperventilation is more specifically defined as minute ventilation in excess of that needed to remove CO2 from blood in order to maintain blood $CO_2$ in the normal range (e.g., around 40 mmHg partial pressure). For example, patients with arterial blood $PCO_2$ in the range of 32-37 mmHg can be considered hypocapnic and in hyperventilation.

For the purpose of this disclosure hyperventilation is equivalent to abnormally low levels of carbon dioxide in the blood (e.g., hypocapnia, hypocapnea, or hypocarbia) caused by overbreathing. Hyperventilation is the opposite of hypoventilation (e.g., underventilation) that often occurs in patients with lung disease and results in high levels of carbon dioxide in the blood (e.g., hypercapnia or hypercarbia).

A low partial pressure of carbon dioxide in the blood causes alkalosis, because CO2 is acidic in solution and reduced CO2 makes blood pH more basic, leading to lowered plasma calcium ions and nerve and muscle excitability. This condition is undesirable in cardiac patients since it can increase probability of cardiac arrhythmias.

Alkalemia may be defined as abnormal alkalinity, or increased pH of the blood. Respiratory alkalosis is a state due to excess loss of carbon dioxide from the body, usually as a result of hyperventilation. Compensated alkalosis is a form in which compensatory mechanisms have returned the pH toward normal. For example, compensation can be achieved by increased excretion of bicarbonate by the kidneys.

Compensated alkalosis at rest can become uncompensated during exercise or as a result of other changes of metabolic balance. Thus the invented method is applicable to treatment of both uncompensated and compensated respiratory alkalosis.

Tachypnea means rapid breathing. For the purpose of this disclosure a breathing rate of about 6 to 16 breaths per minute at rest is considered normal but there is a known benefit to lower rate of breathing in cardiac patients. Reduction of tachypnea can be expected to reduce respiratory dead space, increase breathing efficiency, and increase parasympathetic tone.

Therapy Example: Role of Chemoreflex and Central Sympathetic Nerve Activity in CHF Chronic elevation in sympathetic nerve activity (SNA) is associated with the development and progression of certain types of hypertension and contributes to the progression of congestive heart failure (CHF). It is also known that sympathetic excitatory cardiac, somatic, and central/peripheral chemoreceptor reflexes are abnormally enhanced in CHF and hypertension (Ponikowski, 2011 and Giannoni, 2008 and 2009).

Arterial chemoreceptors serve an important regulatory role in the control of alveolar ventilation. They also exert a powerful influence on cardiovascular function.

Delivery of Oxygen ($O_2$) and removal of Carbon Dioxide ($CO_2$) in the human body is regulated by two control systems, behavioral control and metabolic control. The metabolic ventilatory control system drives our breathing at rest and ensures optimal cellular homeostasis with respect to pH, partial pressure of carbon dioxide ($PCO_2$), and partial pressure of oxygen ($PO_2$). Metabolic control uses two sets of chemoreceptors that provide a fine-tuning function: the central chemoreceptors located in the ventral medulla of the brain and the peripheral chemoreceptors such as the aortic chemoreceptors and the carotid body chemoreceptors. The carotid body, a small, ovoid-shaped (often described as a grain of rice), and highly vascularized organ is situated in or near the carotid bifurcation, where the common carotid artery branches in to an internal carotid artery (IC) and external carotid artery (EC). The central chemoreceptors are sensitive to hypercapnia (high $PCO_2$), and the peripheral chemoreceptors are sensitive to hypercapnia and hypoxia (low blood $PO_2$). Under normal conditions activation of the sensors by their respective stimuli results in quick ventilatory responses aimed at the restoration of cellular homeostasis.

As early as 1868, Pflüger recognized that hypoxia stimulated ventilation, which spurred a search for the location of oxygen-sensitive receptors both within the brain and at various sites in the peripheral circulation. When Corneille Heymans and his colleagues observed that ventilation increased when the oxygen content of the blood flowing through the bifurcation of the common carotid artery was reduced (winning him the Nobel Prize in 1938), the search for the oxygen chemosensor responsible for the ventilatory response to hypoxia was largely considered accomplished.

The persistence of stimulatory effects of hypoxia in the absence (after surgical removal) of the carotid chemoreceptors (e.g., the carotid bodies) led other investigators, among them Julius Comroe, to ascribe hypoxic chemosensitivity to other sites, including both peripheral sites (e.g., aortic bodies) and central brain sites (e.g., hypothalamus, pons and rostral ventrolateral medulla). The aortic chemoreceptor, located in the aortic body, may also be an important chemoreceptor in humans with significant influence on vascular tone and cardiac function.

Carotid Body Chemoreflex:

The carotid body is a small cluster of chemoreceptors (also known as glomus cells) and supporting cells located near, and in most cases directly at, the medial side of the bifurcation (fork) of the carotid artery, which runs along both sides of the throat.

These organs act as sensors detecting different chemical stimuli from arterial blood and triggering an action potential in the afferent fibers that communicate this information to the Central Nervous System (CNS). In response, the CNS activates reflexes that control heart rate (HR), renal function and peripheral blood circulation to maintain the desired homeostasis of blood gases, $O_2$ and $CO_2$, and blood pH. This closed loop control function that involves blood gas chemoreceptors is known as the carotid body chemoreflex (CBC). The carotid body chemoreflex is integrated in the CNS with the carotid sinus baroreflex (CSB) that maintains arterial blood pressure. In a healthy organism these two reflexes maintain blood pressure and blood gases within a narrow physiologic range. Chemosensors and barosensors in the aortic arch contribute redundancy and fine-tuning function to the closed loop chemoreflex and baroreflex. In addition to sensing blood gasses, the carotid body is now understood to be sensitive to blood flow and velocity, blood Ph and glucose concentration. Thus it is understood that in conditions such as hypertension, CHF, insulin resistance, diabetes and other metabolic derangements afferent signaling of carotid body nerves may be elevated. Carotid body hyperactivity may be present even in the absence of detectable hypersensitivity to hypoxia and hypercapnia that are traditionally used to index carotid body function. The purpose of the proposed therapy is therefore to remove or reduce afferent neural signals from a carotid body and reduce carotid body contribution to central sympathetic tone.

The carotid sinus baroreflex is accomplished by negative feedback systems incorporating pressure sensors (e.g., baroreceptors) that sense the arterial pressure. Baroreceptors also exist in other places, such as the aorta and coronary arteries. Important arterial baroreceptors are located in the carotid sinus, a slight dilatation of the internal carotid artery 201 at its origin from the common carotid. The carotid sinus baroreceptors are close to but anatomically separate from the carotid body. Baroreceptors respond to stretching of the arterial wall and communicate blood pressure information to CNS. Baroreceptors are distributed in the arterial walls of the carotid sinus while the chemoreceptors (glomus cells) are clustered inside the carotid body. This makes the selective reduction of chemoreflex described in this application possible while substantially sparing the baroreflex.

The carotid body exhibits great sensitivity to hypoxia (low threshold and high gain). In chronic Congestive Heart Failure (CHF), the sympathetic nervous system activation that is directed to attenuate systemic hypoperfusion at the initial phases of CHF may ultimately exacerbate the progression of cardiac dysfunction that subsequently increases the extra-cardiac abnormalities, a positive feedback cycle of progressive deterioration, a vicious cycle with ominous consequences. It was thought that much of the increase in the sympathetic nerve activity (SNA) in CHF was based on an increase of sympathetic flow at a level of the CNS and on the depression of arterial baroreflex function. In the past several years, it has been demonstrated that an increase in the activity and sensitivity of peripheral chemoreceptors (heightened chemoreflex function) also plays an important role in the enhanced SNA that occurs in CHF.

Role of Altered Chemoreflex in CHF:

As often happens in chronic disease states, chemoreflexes that are dedicated under normal conditions to maintaining homeostasis and correcting hypoxia contribute to increase the sympathetic tone in patients with CHF, even under normoxic conditions. The understanding of how abnormally enhanced sensitivity of the peripheral chemosensors, particularly the carotid body, contributes to the tonic elevation in SNA in patients with CHF has come from several studies in animals. According to one theory, the local angiotensin receptor system plays a fundamental role in the enhanced carotid body chemoreceptor sensitivity in CHF. In addition, evidence in both CHF patients and animal models of CHF has clearly established that the carotid body chemoreflex is often hypersensitive in CHF patients and contributes to the tonic elevation in sympathetic function. This derangement derives from altered function at the level of both the afferent and central pathways of the reflex arc. The mechanisms responsible for elevated afferent activity from the carotid body in CHF are not yet fully understood.

Regardless of the exact mechanism behind the carotid body hypersensitivity, the chronic sympathetic activation driven from the carotid body and other autonomic pathways leads to further deterioration of cardiac function in a positive feedback cycle. As CHF ensues, the increasing severity of cardiac dysfunction leads to progressive escalation of these alterations in carotid body chemoreflex function to further elevate sympathetic activity and cardiac deterioration. The trigger or causative factors that occur in the development of CHF that sets this cascade of events in motion and the time course over which they occur remain obscure. Ultimately, however, causative factors are tied to the cardiac pump failure and reduced cardiac output. According to one theory, within the carotid body, a progressive and chronic reduction in blood flow may be the key to initiating the maladaptive changes that occur in carotid body chemoreflex function in CHF.

There is sufficient evidence that there is increased peripheral and central chemoreflex sensitivity in heart failure, which is likely to be correlated with the severity of the disease. There is also some evidence that the central chemoreflex is modulated by the peripheral chemoreflex. According to current theories, the carotid body is the predominant contributor to the peripheral chemoreflex in humans; the aortic body having a minor contribution.

Although the mechanisms responsible for altered central chemoreflex sensitivity remain obscure, the enhanced peripheral chemoreflex sensitivity can be linked to a depression of nitric oxide production in the carotid body affecting afferent sensitivity, and an elevation of central angiotensin II affecting central integration of chemoreceptor input. The enhanced chemoreflex may be responsible, in part, for the enhanced ventilatory response to exercise, dyspnea, Cheyne-Stokes breathing, and sympathetic activation observed in chronic heart failure patients. The enhanced chemoreflex may be also responsible for hyperventilation and tachypnea (e.g., fast breathing) at rest and exercise, periodic breathing during exercise, rest and sleep, hypocapnia, vasoconstriction, reduced peripheral organ perfusion and hypertension.

Dyspnea:

Shortness of breath, or dyspnea, is a feeling of difficult or labored breathing that is out of proportion to the patient's level of physical activity. It is a symptom of a variety of different diseases or disorders and may be either acute or chronic. Dyspnea is the most common complaint of patients with cardiopulmonary diseases.

Dyspnea is believed to result from complex interactions between neural signaling, the mechanics of breathing, and the related response of the central nervous system. A specific area has been identified in the mid-brain that may influence the perception of breathing difficulties.

The experience of dyspnea depends on its severity and underlying causes. The feeling itself results from a combination of impulses relayed to the brain from nerve endings in the lungs, rib cage, chest muscles, or diaphragm, combined with the perception and interpretation of the sensation by the patient. In some cases, the patient's sensation of breathlessness is intensified by anxiety about its cause. Patients describe dyspnea variously as unpleasant shortness of breath, a feeling of increased effort or tiredness in moving the chest muscles, a panicky feeling of being smothered, or a sense of tightness or cramping in the chest wall.

The four generally accepted categories of dyspnea are based on its causes: cardiac, pulmonary, mixed cardiac or pulmonary, and non-cardiac or non-pulmonary. The most common heart and lung diseases that produce dyspnea are asthma, pneumonia, COPD, and myocardial ischemia or heart attack (myocardial infarction). Foreign body inhalation, toxic damage to the airway, pulmonary embolism, congestive heart failure (CHF), anxiety with hyperventilation (panic disorder), anemia, and physical deconditioning because of sedentary lifestyle or obesity can produce dyspnea. In most cases, dyspnea occurs with exacerbation of the underlying disease. Dyspnea also can result from weakness or injury to the chest wall or chest muscles, decreased lung elasticity, obstruction of the airway, increased oxygen demand, or poor pumping action of the heart that results in increased pressure and fluid in the lungs, such as in CHF.

Acute dyspnea with sudden onset is a frequent cause of emergency room visits. Most cases of acute dyspnea involve pulmonary (lung and breathing) disorders, cardiovascular disease, or chest trauma. Sudden onset of dyspnea (acute dyspnea) is most typically associated with narrowing of the airways or airflow obstruction (bronchospasm), blockage of one of the arteries of the lung (pulmonary embolism), acute heart failure or myocardial infarction, pneumonia, or panic disorder.

Chronic dyspnea is different. Long-standing dyspnea (chronic dyspnea) is most often a manifestation of chronic or progressive diseases of the lung or heart, such as COPD, which includes chronic bronchitis and emphysema. The treatment of chronic dyspnea depends on the underlying disorder. Asthma can often be managed with a combination of medications to reduce airway spasms and removal of allergens from the patient's environment. COPD requires medication, lifestyle changes, and long-term physical rehabilitation. Anxiety disorders are usually treated with a combination of medication and psychotherapy.

Although the exact mechanism of dyspnea in different disease states is debated, there is no doubt that the CBC plays some role in most manifestations of this symptom. Dyspnea seems to occur most commonly when afferent input from peripheral receptors is enhanced or when cortical perception of respiratory work is excessive.

Surgical Removal of the Glomus and Resection of Carotid Body Nerves:

A surgical treatment for asthma, removal of the carotid body or glomus (glomectomy), was described by Japanese surgeon Komei Nakayama in 1940s. According to Nakayama in his study of 4,000 patients with asthma, approximately 80% were cured or improved six months after surgery and 58% allegedly maintained good results after five years. Komei Nakayama performed most of his surgeries while at the Chiba University during World War II. Later in the 1950's, a U.S. surgeon, Dr. Overholt, performed the Nakayama operation on 160 U.S. patients. He felt it necessary to remove both carotid bodies in only three cases. He reported that some patients feel relief the instant when the carotid body is removed, or even earlier, when it is inactivated by an injection of procaine (Novocain).

Overholt, in his paper Glomectomy for Asthma published in Chest in 1961, described surgical glomectomy the following way: "A two-inch incision is placed in a crease line in the neck, one-third of the distance between the angle of the mandible and clavicle. The platysma muscle is divided and the sternocleidomastoid retracted laterally. The dissection is carried down to the carotid sheath exposing the bifurcation. The superior thyroid artery is ligated and divided near its take-off in order to facilitate rotation of the carotid bulb and expose the medial aspect of the bifurcation. The carotid body is about the size of a grain of rice and is hidden within the adventitia of the vessel and is of the same color. The perivascular adventitia is removed from one centimeter above to one centimeter below the bifurcation. This severs connections of the nerve plexus, which surrounds the carotid body. The dissection of the adventitia is necessary in order to locate and identify the body. It is usually located exactly at the point of bifurcation on its medial aspect. Rarely, it may be found either in the center of the crotch or on the lateral wall. The small artery entering the carotid body is clamped, divided, and ligated. The upper stalk of tissue above the carotid body is then clamped, divided, and ligated."

In January 1965, the New England Journal of Medicine published a report of 15 cases in which there had been unilateral removal of the cervical glomus (carotid body) for the treatment of bronchial asthma, with no objective beneficial effect. This effectively stopped the practice of glomectomy to treat asthma in the U.S.

Winter developed a technique for separating nerves that contribute to the carotid sinus nerves into two bundles, carotid sinus (baroreflex) and carotid body (chemoreflex), and selectively cutting out the latter. The Winter technique is based on his discovery that carotid sinus (baroreflex) nerves are predominantly on the lateral side of the carotid bifurcation and carotid body (chemoreflex) nerves are predominantly on the medial side.

Neuromodulation of the Carotid Body Chemoreflex:

Hlavaka in U.S. Patent Application Publication 2010/0070004 filed Aug. 7, 2009, describes implanting an electrical stimulator to apply electrical signals, which block or inhibit chemoreceptor signals in a patient suffering dyspnea.

Hlavaka teaches that "some patients may benefit from the ability to reactivate or modulate chemoreceptor functioning." Hlavaka focuses on neuromodulation of the chemoreflex by selectively blocking conduction of nerves that connect the carotid body to the CNS. Hlavaka describes a traditional approach of neuromodulation with an implantable electric pulse generator that does not modify or alter tissue of the carotid body or chemoreceptors.

The central chemoreceptors are located in the brain and are difficult to access. The peripheral chemoreflex is modulated primarily by carotid bodies that are more accessible. Previous clinical practice had very limited clinical success with the surgical removal of carotid bodies to treat asthma in 1940s and 1960s.

What is claimed is:

1. A method of carotid septum ablation to treat at least one of heart failure and hypertension, comprising endovascularly positioning a distal region of a catheter within an internal jugular vein or one of its tributaries and proximate a carotid septum, the distal region comprising an ultrasound ablation transducer;

targeting carotid septum tissue for ablation with ablative ultrasound energy without targeting a carotid sinus by rotating the ultrasound ablation transducer within the jugular vein to aim the ablative ultrasound energy towards the carotid septum tissue and away from the carotid sinus; and directing the ultrasound ablation energy towards the carotid septum and away from the carotid sinus to ablate the carotid septum tissue with ablative ultrasound energy, to treat at least one of heart failure and hypertension.

2. The method of claim 1 wherein ablating the carotid body comprises heating carotid body tissue to greater than about 45 degrees C.

3. The method of claim 2 wherein the ablating step maintains the temperature of a wall of a vessel in which the ultrasound transducer is positioned at less than about 50 degrees C.

4. The method of claim 1 wherein ablating carotid septum tissue comprises causing cessation of carotid body activity as a result of the directed energy.

5. The method of claim 4 wherein ablating carotid septum tissue comprises causing a cessation of afferent nerve activity.

6. The method of claim 4 wherein the cessation of carotid body activity causes a reduction of sympathetic tone and blood pressure.

7. The method of claim 1 wherein ablating carotid septum tissue comprises directing ablation energy into an ablation zone that penetrates as deep as about 2 mm to about 10 mm into the carotid septum.

8. The method of claim 7 wherein ablating carotid septum tissue comprises directing ablation energy into an ablation zone that penetrates as deep as about 3 mm to about 8 mm into the carotid septum.

9. The method of claim 1 wherein the ablating step comprises directing ablation energy from the ultrasound transducer for about 5 to about 60 seconds.

10. The method of claim 1 wherein the ablating step comprises laterally directing ablation energy from the ultrasound transducer.

11. The method of claim 1 further comprising preventing the ultrasound transducer from contacting a wall of a blood vessel.

12. The method of claim 1 further comprising inflating an inflatable element in which the ultrasound transducer is disposed.

13. The method of claim 12 wherein the inflating step comprises inflating the inflatable element into stable contact with tissue to stabilize the position of the ultrasound transducer.

14. The method of claim 12 wherein the inflating step prevents the ultrasound transducer from contacting a vessel wall.

15. The method of claim 12 wherein inflating an inflatable element comprises inflating the inflatable element in the jugular vein or one of its tributaries.

16. The method of claim 12 wherein inflating comprises infusing cooling fluid into the inflatable element sufficient to maintain a wall of the inflatable element at less than 50 degrees C.

17. The method of claim 12 wherein inflating the inflatable element comprises leaking cooling fluid from within the inflatable element into the jugular vein or one of its tributaries.

18. The method of claim 1 further comprising monitoring the temperature of tissue proximate the ultrasound transducer.

19. The method of claim 1 further comprising emitting diagnostic energy towards at least one of an internal carotid artery, an external carotid artery, a common carotid artery, a carotid artery bifurcation, and a carotid septum.

20. The method of claim 19 further comprising determining a location of at least one anatomical landmark using the emitted diagnostic energy, and wherein at least one aspect of the ablating step is dependent on the determined location of the at least one anatomical landmark.

21. The method of claim 20 wherein the aspect of the ablating step that is dependent on the determined location of the at least one anatomical landmark is an orientation of the ultrasound transducer.

22. The method of claim 20 wherein the determining step comprises determining the location of at least an external carotid artery and an internal carotid artery.

23. The method of claim 20 wherein the determining step comprises determining the location of an external carotid artery and an internal carotid artery.

24. The method of claim 23 wherein the emitting step comprises emitting diagnostic energy from a first diagnostic transducer and emitting diagnostic energy from a second diagnostic transducer.

25. The method of claim 24 wherein the determining step comprises determining a location of a first anatomical landmark using the emitted diagnostic energy from the first diagnostic transducer, further comprising determining a location of a second anatomical landmark using emitted diagnostic energy from the second diagnostic transducer.

26. The method of claim 20 wherein a first anatomical landmark comprises an inner lumen of an internal carotid artery and a second anatomical landmark comprises an inner lumen of an external carotid artery.

27. The method of claim 26 further comprising orienting the ultrasound transducer towards space in between the external carotid artery and the internal carotid artery and between a carotid bifurcation and about 3 to about 15 mm cranial to the bifurcation.

28. The method of claim 27 wherein orienting the ultrasound transducer towards space in between the external carotid artery and the internal carotid artery occurs without further catheter movement based on the catheter location on which the ultrasound transducer is disposed.

29. The method of claim 26 wherein the ablating step is terminated if the orientation of the ultrasound transducer changes substantially during the ablating step.

30. The method of claim 26 further comprising orienting the ultrasound transducer towards space in between the external carotid artery and the internal carotid artery.

31. The method of claim 20 wherein the determining step comprises determining the location of a carotid bifurcation.

32. The method of claim 31 wherein the aspect of the ablating step that is dependent on the determined location is a position of the ultrasound transducer.

33. The method of claim 20 wherein the aspect of the ablating step that is dependent on the determined location of the at least one anatomical landmark is a position of the ultrasound transducer.

34. The method of claim 20 wherein the determining step comprises determining a location of a carotid septum, and the aspect of the ablating step that is dependent on the determined location is a position of the ultrasound transducer.

35. The method of claim 19 further comprising obtaining an indication of blood flow in at least one of an internal carotid artery, an external carotid artery, carotid bifurcation, and a common carotid artery using the emitted diagnostic energy and a received energy.

36. The method of claim 35 wherein the indication of blood flow includes an indication of arterial blood flow characterized by pulsations of blood flow higher than venous blood flow.

37. The method of claim 19 wherein emitting the diagnostic energy occurs from a location external to the patient.

38. The method of claim 19 wherein emitting the diagnostic energy and the directed energy occurs from within the jugular vein or one of its tributaries.

39. The method of claim 19 wherein emitting diagnostic energy comprises emitting Doppler energy.

40. The method of claim 39 wherein emitting Doppler energy comprises emitting pulsed Doppler energy.

41. The method of claim 40 wherein emitting pulsed Doppler energy comprises emitting pulsed Doppler energy that is configured to detect flow about 5 mm to about 15 mm away from an ultrasound transducer.

42. The method of claim 1 further comprising:
  positioning a diagnostic ultrasound transducer within the internal jugular vein or one of its tributaries and proximate the carotid septum; and
  obtaining a real-time image of an internal carotid artery and an external carotid artery with the diagnostic ultrasound transducer,
  wherein aiming the ablative ultrasound energy towards the carotid septum and away from the carotid sinus comprises, while visualizing the obtained real-time image of the internal carotid artery and external carotid artery, rotating the ultrasound ablation transducer to aim the ablative ultrasound energy between the imaged internal and external carotid arteries and away from the carotid sinus.

43. A method of carotid septum ablation to treat at least one of heart failure and hypertension, comprising:
  endovascularly positioning a distal region of a catheter within an internal jugular vein or one of its tributaries and proximate a carotid septum, the distal region comprising an ultrasound ablation transducer;
  targeting carotid septum tissue for ablation with ablative ultrasound energy without targeting a carotid sinus by reconfiguring the catheter to manipulate the wall of the jugular vein or one of its tributaries with the catheter; and
  ablating the carotid septum tissue with ablative ultrasound energy to treat at least one of heart failure and hypertension.

44. The method of claim 43 wherein reconfiguring the catheter to manipulate the wall of the jugular vein or one of its tributaries with the catheter moves the ultrasound ablation transducer closer to the carotid septum.

45. A method of carotid septum ablation to treat at least one of heart failure and hypertension, comprising:
  endovascularly positioning a distal region of a catheter within an internal jugular vein or one of its tributaries and proximate a carotid septum, the distal region comprising an ultrasound ablation transducer;
  targeting carotid septum tissue for ablation with ablative ultrasound energy without targeting tissue beyond a medial boundary of the septum, wherein targeting carotid septum tissue for ablation with ablative ultrasound energy without targeting tissue beyond a medial boundary of the septum comprises controlling the ablative ultrasound energy delivery parameters; and
  ablating the carotid septum tissue with ablative ultrasound energy using the ultrasound ablation transducer to treat at least one of heart failure and hypertension.

46. The method of claim 45 further comprising targeting carotid septum tissue for ablation with ablative ultrasound energy without targeting a carotid sinus by rotating the ultrasound ablation transducer within the jugular vein to aim the ablative ultrasound energy towards the carotid septum tissue and away from the carotid sinus; and
  directing the ultrasound ablation energy towards the carotid septum and away from the carotid sinus to ablate the carotid septum tissue with ablative ultrasound energy, to treat at least one of heart failure and hypertension.

* * * * *